US007722860B2

(12) United States Patent
Kappe et al.

(10) Patent No.: US 7,722,860 B2
(45) Date of Patent: May 25, 2010

(54) LIVE GENETICALLY ENGINEERED PROTOZOAN VACCINE

(75) Inventors: Stefan H. I. Kappe, Seattle, WA (US); Kai-Uwe C. Matuschewski, Berlin (DE); Ann-Kristin Mueller, Dossenheim (DE)

(73) Assignee: Seattle Biomedical Research Institute, Seattle, WA (US)

( * ) Notice: Subject to any disclaimer, the term of this patent is extended or adjusted under 35 U.S.C. 154(b) by 1022 days.

(21) Appl. No.: 11/165,586

(22) Filed: Jun. 22, 2005

(65) Prior Publication Data

US 2006/0121060 A1 Jun. 8, 2006

Related U.S. Application Data

(63) Continuation-in-part of application No. pct/us2004/043023, filed on Dec. 20, 2004.

(60) Provisional application No. 60/633,242, filed on Dec. 3, 2004.

(51) Int. Cl.
*A01N 63/00* (2006.01)
*A01N 65/00* (2006.01)
*A61K 48/00* (2006.01)
*A61K 39/38* (2006.01)
*A61K 39/00* (2006.01)
*A61K 39/015* (2006.01)

(52) U.S. Cl. .................. 424/93.1; 424/93.2; 424/93.21; 424/93.7; 424/184.1; 424/265.1; 424/268.1; 424/269.1

(58) Field of Classification Search ........................ None
See application file for complete search history.

(56) References Cited

U.S. PATENT DOCUMENTS

| 4,681,762 | A | 7/1987 | Oeschger et al. |
| 6,656,479 | B2 | 12/2003 | Brake et al. |
| 7,052,899 | B2 * | 5/2006 | Milhausen ............... 435/235.1 |

FOREIGN PATENT DOCUMENTS

| WO | WO 00/08165 A1 | 2/2000 |
| WO | WO 2004/026903 A2 | 4/2004 |
| WO | WO 2004/045559 A2 | 6/2004 |
| WO | WO2004/026903 A2 * | 4/2009 |

OTHER PUBLICATIONS

Butler, D., "Mosquito Production Mooted as Fast Track to Malaria Vaccine," *Nature* 425:437, Oct. 2, 2003.
Doolan, D.L., and S.L. Hoffman, "The Complexity of Protective Immunity Against Liver-Stage Malaria," *The Journal of Immunology* 165:1453-1462, 2000.
Fandeur, T., et al., "Protection of Squirrel Monkeys Against Virulent *Plasmodium Falciparum* Infections by Use of Attenuated Parasites," *Infection and Immunity* 60(4):1390-1396, Apr. 1992.
Guerin-Marchand, C., et al., "A Liver-Stage-Specific Antigen of *Plasmodium Falciparum* Characterized by Gene Cloning," *Nature* 329:164-167, Sep. 10, 1987.
Hoffman, S., "Save the Children," *Nature* 430:940-941, Aug. 19, 2004.
Hoffman, S.L., and D.L. Doolan, "Malaria Vaccines-Targeting Infected Hepatocytes," *Nature Medicine* 6(11):1218-1219, Nov. 2000.
Hoffman, S.L., et al., "Protection of Humans Against Malaria by Immunization With Radiation-Attenuated *Plasmodium Falciparum* Sporozoites," *The Journal of Infectious Diseases* 185:1155-1164, Apr. 15, 2002.
James, S., and L. Miller, "Malaria Vaccine Development: Status Report," Niaid.nih.gov, Jan. 5, 2001, <http://www.niaid.nih.gov/dmid/malaria/malariavac.htm> [retrieved Oct. 15, 2004].
Luke, T.C., and S.L. Hoffman, "Review Rationale and Plans for Developing a Non-Replicating, Metabolically Active, Radiation-Attenuated *Plasmodium Falciparum* Sporozoite Vaccine," *The Journal of Experimental Biology* 206:3803-3808, 2003.
Ménard, R., "Knockout Malaria Vaccine?" *Nature* 433:113-114, Jan. 13, 2005.
Mueller, A.-K., et al., "*Plasmodium* Liver Stage Developmental Arrest by Depletion of a Protein at the Parasite-Host Interface," *PNAS* 102(8):3022-3027, Feb. 22, 2005.
"Parasitic and Tropical Infections," *The Jordan Report*, National Institutes of Health, 2000, pp. 25-30.
Scheller, L., and A.F. Azad, "Maintenance and Protective Immunity Against Malaria by Persistent Hepatic Parasites Derived From Irradiated Sporozoites," *Proc. Natl. Acad. Sci. USA* 92:4066-4068, Apr. 1995.
Silvie, O., et al., "Effects of Irradiation on *Plasmodium Falciparum* Sporozoite Hepatic Development: Implications for the Design of Pre-Erythrocytic Malaria Vaccines," *Parasite Immunology* 24(4):221-223, Apr. 2002.
Suzuki, M., et al., "An Alternative Approach to Malaria Vaccine With a Permanent Attenuated Mutant From a High Virulence Plasmodium Berghei Strain," *Zentralbl. Bakteriol. Mikrobiol. Hyg.* 264(3-4):319-325, May 1987. (Abstract provided).
Kaiser, K., et al., "Differential transcriptome profiling identifies *Plasmodium* genes encoding pre-erythrocytig stage-specific proteins," *Molecular Microbiology*, 2004, pp. 1221-1232.

(Continued)

*Primary Examiner*—Vanessa L. Ford
(74) *Attorney, Agent, or Firm*—Christensen O'Connor Johnson Kindness PLLC

(57) ABSTRACT

The invention provides methods for inducing an immune response in a vertebrate host against a protozoan parasite, comprising administering to the host a live protozoan parasite that is genetically engineered to disrupt a stage-specific gene function that is required by the protozoan parasite to establish a secondary infection in the vertebrate host. Representative protozoan parasites belong to the phyla Apicomplexa and Kinetoplastida. The vertebrate host may be a mammal or a bird.

5 Claims, 2 Drawing Sheets

OTHER PUBLICATIONS

Figure 1:
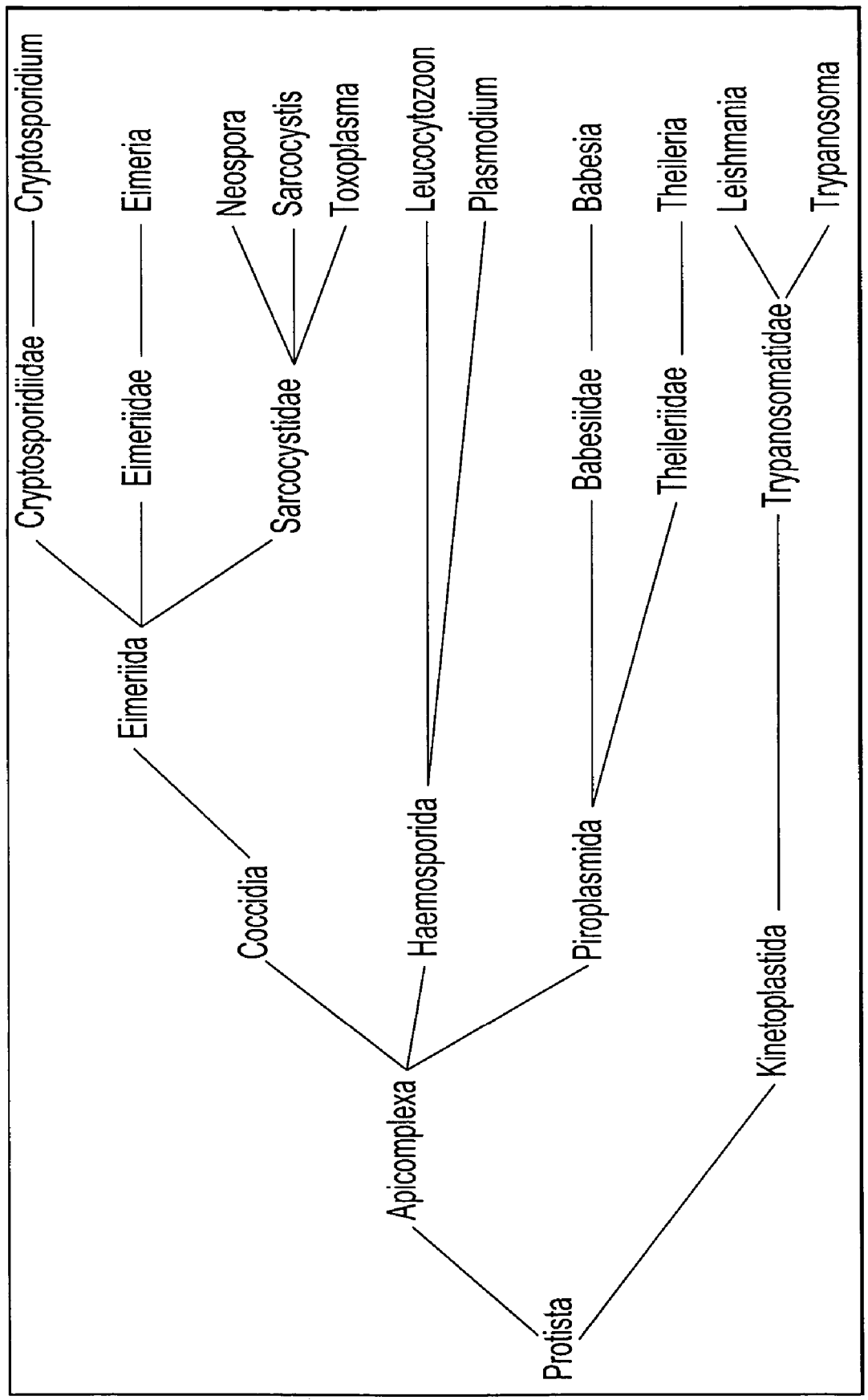

Kappe, S.H.I., et al., "*Plasmodium* Sporozoite Molecular Cell Biology," *Annu. Rev. Cell Dev. Biol.* 20:29-59, 2004.

Matuschewski, K., et al., "Infectivity-associated Changes in the Transcriptional Repertoire of the Malaria Parasite Sporozoite Stage," *The Journal of Biological Chemistry* 277(44):41948-41953, Nov. 2002.

Mueller, A.-K., et al., "Genetically modified *Plasmodium* parasites as a protective experimental malaria vaccine," *Nature* 433:164-167, Jan. 13, 2005.

Waters, A.P., et al., "Malaria Vaccines: Back to the Future?," *Science* 307:528-530, Jan. 28, 2005.

Worthey, E.A., and P.J. Myler, Invited review, "Protozoan genomes: gene identification and annotation," *International Journal for Parasitology* 35:495-512, 2005.

Good, M.F. "Towards a Blood-Stage Vaccine for Malaria: Are We Following All the Leads?" Nature Reviews 1:117-125, 2001.

Good, M.F., "Genetically Modified Plasmodium Highlights the Potential of Whole Parasite Vaccine Strategies," Trends in Immunology 26(6):295-297, 2005.

Mahanty, S., et al., "Progress in the Development of Recombinant and Synthetic Blood-Stage Malaria Vaccines," Journal of Experimental Biology 206:3781-3788, 2003.

Matuschewski, K., et al., "Infectivity-Associated Changes in the Transcriptional Repertoire of the Malaria Parasite Sporozoite Stage," Journal of Biological Chemistry 277(44):41948-41953, 2002.

Menard, R., et al., "Circumsporozoite Protein Is Required for Development of Malaria Sporozoites in Mosquitoes," Nature 385:336-340, 1997.

Menard, R., and C. Janse, "Gene Targeting in Malaria Parasites," Methods: A Companion to Methods in Enzymology 13:148-157, 1997.

Mueller, A.K., et al., "Genetically Modified Plasmodium Parasites as a Protective Experimental Malaria Vaccine," Nature 433:164-167, 2005.

Müller, A.K., et al., "Two Small Secretory Molecules Affect Development of Plasmodium Sporozoites in Hepatocytes," International Journal of Medical Microbiology 293 (Supp. 138):103 (abstract), 2004.

Sultan, A.A., et al., "TRAP Is Necessary for Gliding Motility and Infectivity of Plasmodium Sprozoites," Cell 90:511-522, 1997.

Waters, A.P., et al., "Malaria Vaccines: Back to the Future?" Science 307:528-530, 2005.

Cleary, M.D., et al., "Toxoplasma gondii Asexual Development: Identification of Developmentally Regulated Genes and Distinct Patterns of Gene Expression," Eukaryotic Cell 1(3):329-340, Jun. 2002.

* cited by examiner

LIVE GENETICALLY ENGINEERED PROTOZOAN VACCINE

CROSS-REFERENCES TO RELATED APPLICATIONS

This application is a continuation-in-part application of International Application No. PCT/US04/043023, filed Dec. 20, 2004; and also claims the benefit of U.S. Provisional Application No. 60/633,242, filed Dec. 3, 2004, both of which are incorporated herein by reference.

STATEMENT OF GOVERNMENT RIGHTS

The U.S. Government has a paid-up license in this invention and the right in limited circumstances to require the patent owner to license others on reasonable terms as provided for by the terms of RO1 A053709 This invention was made with government support under AI 053709 awarded by the National Institutes of Health. The government has certain rights in the invention.

FIELD OF THE INVENTION

This invention relates to live genetically modified protozoan organisms exemplified by the apicomplexan genus *Plasmodium*, and their use as immunospecific immunoeffectors for vaccination purposes.

BACKGROUND OF THE INVENTION

Malaria has a tremendous impact on human health, killing millions annually and the disease is a major impediment for social and economic development of nations in malaria-endemic areas, particularly in sub-Saharan Africa (Sachs & Malaney (2002) *Nature* 415:680-85). Malaria is a mosquito-borne disease that is transmitted by inoculation of the *Plasmodium* parasite sporozoite stage. *Sporozoites* invade hepatocytes (Kappe et al (2003) *Trends Parasitol.* 19:135-43), transform into liver stages, and subsequent liver stage development ultimately results in release of pathogenic merozoites (Shortt & Garnham (1948) *Nature* 161:126).

Because an effective "subunit" malaria vaccine has remained elusive and the complexity of the malaria parasite *Plasmodium* might preclude the successful development of such a vaccine, whole organism vaccine approaches against malaria have lately found renewed interest (Hoffman (2004) *Nature* 430:940-941). The feasibility of such a vaccine has been demonstrated in animal models and subsequently in humans by induction of sterile protective immunity through inoculation with irradiation-attenuated parasites (Nussenzweig et al. (1967) *Nature* 216:160-62; Hoffman et al. (2002) *J. Infect. Dis.* 185:1155-64). Liver stages are a prime malaria vaccine target because they can be completely eliminated by sterilizing immune responses, thereby preventing malaria infection (Hoffman & Doolan (2000) *Nat. Med* 6:1218-9). The recent availability of complete *Plasmodium* genome sequences (Gardner et al. (2002) *Nature* 419:498-511; Carlton et al. (2002) *Nature* 419:512-9) may now permit the development of live-attenuated parasites by more precise and defined genetic manipulations (WO 2004/045559 A2).

Using expression profiling, we identified genes that are specifically expressed during the pre-erythrocytic part of the parasite life cycle (Matuschewski et al. (2002) *J. Biol. Chem.* 277:41948-53; Kaiser et al. (2004) *Mol. Microbiol.* 51:1221-32). A number of pre-erythrocytic genes named UIS (up-regulated in infective sporozoites) also showed up-regulation in sporozoites when they gain infectivity for the mammalian host (Matuschewski et al. (2002) *J. Biol. Chem.* 277:41948-53).

Often overshadowed by *Plasmodium*, other organisms within the phylum Apicomplexa, as well as protozoan organisms within the phylum Kinetoplastida, cause significant diseases in humans and animals. For example, protozoan organisms within the genuses of *Toxoplasma, Neospora, Eimeria, Theileria, Babesia, Cryptosporidium, Sarcocystis, Leucocytozoon, Leishmania*, and *Trypansoma* all devastate susceptible vertebrate host populations and severely impact economic development in endemic regions. In general, these protozoan organisms are eukaryotic, unicellular, parasit that have a life cycle including at least two infective stages in a susceptible vertebrate host, one of which cause the secondary infection that is the hallmark of the protozoan disease.

There is a need in the art for vaccines that protect against protozoan diseases. The present invention addresses this need and others.

SUMMARY OF THE INVENTION

The invention provides methods for inducing an immune response in a vertebrate host against a protozoan parasite that causes a secondary infection and pathology in the vertebrate host. The host is vaccinated with a live protozoan parasite that is genetically engineered to disrupt the function of a stage-specific gene that is required by the protozoan parasite to establish a secondary infection in the vertebrate host. The vertebrate host may be mammalian or avian. Exemplary methods for disrupting the stage-specific parasite gene function may be disrupted include knockout, antisense, and RNA silencing techniques.

In a representative embodiment, the protozoan parasite is a *Plasmodium* organism and the vertebrate host is human. It has been shown by reverse genetics that selected individual genes, exemplified by UIS3 (up-regulated in infective sporozoites gene 3) and UIS4, are essential for early liver stage development: uis3(-) and uis4(-) sporozoites infect hepatocytes but are no longer able to establish blood stage infections in vivo and thus do not lead to disease. Immunization with either uis3(-) or uis4(-) sporozoites confers complete protection against infectious sporozoite challenge in a rodent malaria model. This protection is sustained and stage-specific. Thus, uis3(-) and uis4(-) sporozoites provide the first genetically attenuated whole organism malaria vaccines.

In related embodiments, the protozoan parasite belongs to another genus in the phylum Apicomplexa including, but not limited to, a genus selected from *Toxoplasma, Neospora, Eimeria, Theileria, Babesia, Cryptosporidium, Sarcocystis*, and *Leucocytozoon*. In another embodiment, the protozoan parasite belongs to a genus in the phylum Kineotoplastida, including, but not limited to, the genera *Leishmania* and *Trypanosoma*.

In some embodiments, the invention provides a method for inducing an immune response in a vertebrate host against a protozoan parasite, wherein the wild-type parasite undergoes a plurality of asexual multiplications in the host, including a first multiplication of a first parasite stage to produce a second parasite stage that is associated with a secondary infection in the host. The method comprises administering to the host a live parasite that is genetically engineered to disrupt expression of a parasite gene that is upregulated in the first parasite stage and that is essential for the first multiplication to produce a second parasite stage. In some embodiments, the plurality of asexual multiplications are intracellular multiplications. Thus, the first parasite stage may multiply within a first host cell to produce a second parasite stage that can multiply within the second host cell.

In other embodiments, the wild-type parasite undergoes a cellular transformation within the vertebrate host to produce a phenotypically distinct second parasite stage that is associated with secondary infection and pathology. Here, a parasite gene upregulated and essential for this cellular transformation is targeted for disruption.

The invention further provides a vaccine composition comprising a live protozoan parasite that is genetically engineered to disrupt a stage-specific gene function that is required by the protozoan parasite to establish a secondary infection and pathology in the vertebrate host. In addition, the invention provides the use of a vaccine composition comprising a live protozoan parasite that is genetically engineered to disrupt such a stage-specific gene function. The invention also provides for production of a vaccine composition, by suspending and packaging the subject engineered protozoan parasites in a suitable pharmaceutically acceptable carrier solution.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1 shows a categorization of the phyla Apicomplexa and Kinetoplastida in the kingdom Protista.

FIG. 2 depicts the primary structure of *Plasmodium* UIS3 proteins, as discussed in Examples I and 3. Predicted cleavable signal peptides and transmembrane spans are indicated with stippled and cross-hatched boxes, respectively. Amino acid identities of the *P. yoelii* and *P. falciparum* UIS3 orthologues (EAA22537 and PF13_0012, respectively) are indicated as percentage of identical residues compared with the *P. berghei* sequence.

FIG. 3 depicts the replacement strategy used to generate the uis3(-) parasite described in Example 1. The wild-type (WT) UIS3 genome locus is targeted with an EcoRI/HindIII-linearized replacement plasmid containing the 5' and 3' untranslated regions of the UIS3 open reading frame (ORF) and the *Toxoplasma gondii* dhfr/ts-positive positive selectable marker. Upon a double crossover event the UIS3 ORF is replaced by the selection marker. Replacement-specific test primer combinations are indicated by arrows, and expected fragments are shown as lines.

DETAILED DESCRIPTION OF THE PREFERRED EMBODIMENT

The invention provides a method for inducing an immune response in a vertebrate host against a protozoan parasite. The method comprises the step of administering to the host a live protozoan parasite that is genetically engineered to disrupt a stage-specific gene function that is required by the protozoan parasite to establish a secondary infection in the vertebrate host.

The term "protozoan parasite" generally refers to any protozoan organisms that is eukaryotic, unicellular, parasitic, and characterized by multiple infective stages within its vertebrate host. Exemplary parasitic protozoan organisms as described herein belong to the phylum Apicomplexa or the phylum Kinetoplastida. A taxonomic outline of the kingdom Protista including the phylum Apicomplexa and the phylum Kinetoplastida is shown in FIG. 1. Reclassification within the phylum Apicomplexa is quite common, as defining characteristics and new species are uncovered. In many instances, a grouping within the phylum does not have an official rank, such as the Piroplasmida. Sometimes, ranking is incomplete within the phylum. Some groupings lack a designated Class, while others have no assigned Order or Family classification (see, National Center for Biotechnology Information Taxonomy Browser (NCBI Taxonomy Browser). Apicomplexan parasites used in the methods of the invention include, but are not limited to, protozoan parasites that are members of the genera *Plasmodium, Toxoplasma, Neospora, Eimeria, Theileria, Sarcocystis*, and *Cryptosporidium.*

The phylum Kinetoplastida includes a particularly virulent family of parasitic protozoa, the Trypanosomatidae. This family includes the protozoan parasites *Trypanosoma* and *Leishmania*, which cause significant and serious disease throughout the world (see NCBI Taxonomy Browser). The various species and subspecies of *Trypanosoma brucei, Trypanosoma cruzi*, and *Leishmania*cause staggering losses in human life and productivity in regions of endemicity. Kinetoplastida parasites used in the methods of the invention include, but are not limited to, protozoan parasites of the genera *Trypanosoma* and *Leishmania.*

The term "infective stage" refers to a stage or form of a protozoan parasite within a vertebrate host. The vertebrate host may be a mammal or a bird, including, but not limited to, a human host, livestock (e.g., cattle, horses, sheep, goats, and pigs), companion animals (e.g., cats and dogs), oppossum, mice, gerbils, poultry (e.g., chickens, ducks, geese, and turkeys), and zoo animals. As described further below and shown in Table 1, the vertebrate host is generally first infected with a primary infective stage of the protozoan parasite. The primary infective stage of an apicomplexan protozoan parasite is typically referred to as a sporozoite, although for *Eimeria, Toxoplasma*, and *Neospora* organisms the vertebrate host is commonly infected by an oocyst that releases sporozoites. At some time after infection with the primary infective stage, at least one subsequent or secondary infective stage develops (referred to, for example, as a merozoite in *Plasmodium*, or a tachyzoite in Toxoplasma) and establishes a secondary infection of the vertebrate host. The transition between primary and secondary infective stages typically involves either an asexual division or a cellular transformation to a different protozoan phenotype.

The secondary infection with the protozoan parasite may be acute or chronic and is generally associated with the pathologic clinical manifestations of disease, that is, with most or all of the morbidity or mortality in the vertebrate host. Some of the pathologic clinical manifestations associated with secondary infection with exemplary protozoan parasites are shown in Table 1.

TABLE 1

Infective Stages of Protozoan Parasites and Secondary Infections

| Protozoan Parasite | Vertebrate Host | Primary Infective Stage | Secondary Infective Stage | Secondary Infection Pathologies |
|---|---|---|---|---|
| *Plasmodium* | Human | Sporozoite | Merozoite | Blood Stage Malaria |
| *Cryptosporidium* | Human, Livestock | Sporozoite | Merozoite | Diarrhea, Dehydration, Weight Loss, Fever, Nausea, Vomiting |
| *Eimeria* | Livestock, Poultry | Sporozoite | Merozoite | Coccidiosis (Severe Diarrheal Disease) |
| *Neospora* | Livestock, Dogs | Sporozoite | Tachyzoite | Abortion, Congenital Defects, Neurological Defects, High Fever, Lethargy, Paralysis, Encephalitis |
| *Sarcocystis* | Livestock, Cats | Sporozoite | Merozoite | Neurological Defects, Seizures, Depression, Muscular Atrophy, Paralysis |
| *Toxoplasma* | Mammals, Birds | Sporozoite | Tachyzoite | Abortion, Congenital Defects, Neurological Defects, Swollen Lymph Nodes, Myalgias, Ocular Damage |
| *Leucocytozoon* | Poultry | Sporozoite | Merozoite | Diarrhea, Ceccal Lesions |
| *Babesia* | Humans, Dogs, Livestock | Sporozoite | Merozoite | Redwater Fever, Blackwater Fever, Fever, Chills, Sweating, Myalgia, Fatigue, Hepatosplenomegaly, Hemolytic Anemia |
| *Theileria* | Livestock | Sporozoite | Merozoite | East Coast Fever, Corridor Disease, Tropical Theileriosis, Anemia, Fever, Mucocutaneous Bleeding, Jaundice, Lymph Node Enlargement, Ulceration, Splenomegaly Leukopenia, Cachexia, Dysentery |
| *Trypanosoma brucei* | Humans, Livestock | Metacyclics | Bloodstream Form | Human African Trypanosomiasis, Nagana |
| *Trypanosoma cruzi* | Humans, Cats, Dogs | Metacyclic Trypomastigotes | Amastigotes | Chagas Disease |
| *Leishmania* spp | Humans, Dogs | Promastigotes | Amastigotes | Visceral, Cutaneous, and Mucocutaneous Leishmaniasis |

1. *Plasmodium*

Within the phylum Apicomplexa, in the family Hemosporidia, is grouped the genus *Plasmodium*. *Plasmodium ovate, vivax*, and *falciparum* are the causative agents of malaria in humans. The social and economic impacts of malaria are devastating in endemic areas, which includes regions of Africa, Asia, Central and South America, and the Caribbean. Malaria is a vector-borne disease. Infectious *Plasmodium* sporozoites are introduced into human and animal hosts by bites from infected mosquitoes. Sporozoites rapidly invade hepatocytes, transform into liver stages (LS), and subsequent liver stage development ultimately results in the release of thousands of merozoites (Kappe et al. (2004) *Annu. Rev. Cell. Dev. Biol.* 20:29-59; Mota & Rodriguez (2004) *Cell. Microbiol.* 6(12):1113-8). Merozoites invade erythrocytes and implement the most injurious and often grave effects of malarial disease. Merozoites are also capable of re-initiating the erythrocytic cycle, thereby exacerbating illness and parasite burden (Kappe et al. (2003) *Trends Parasitol.* 19(3):135-43). Although anti-malarial drug treatments and pesticide sprays have heretofore limited disease progression and transmission, reported cases of malaria are expected to rise due to the emergence of drug-resistant parasites and a rise in pesticide-resistant mosquito populations (WHO (2005) Malaria Fact Sheet). Vaccine development has been hampered by parasite complexities and the logistics of vaccine production and storage. Immunity derived from irradiation-attenuated *Plasmodium* sporozoites was initially characterized in the 1940s, and research on the topic has provided much insight into the host immune response and vaccine requirements for lasting immunity (Luke & Hoffman (2003) *J. Exp. Biol.* 206 (Pt 21):3803-8). However, persistent problems with irradiated sporozoites remain, including the likelihood of breakthrough infection if sporozoites are under-irradiated and lack of efficacy if over-irradiated. Subunit or recombinant vaccination attempts have yielded some protection against, however this immunity is not lasting or complete.

2. *Toxoplasma*

The family Sarcocystidac includes several pathogenic parasites, including *Toxoplasma. Toxoplasma gondii* is the only identified species (NCBI Taxonomy Browser). Toxoplasmosis is a widespread illness, with very low host specificity-meaning the parasite can replicate within virtually any nucleated mammalian or avian cell (Charleston (1994)*N. Zealand J. Zool.* 21:67-81; Black & Boothroyd (2000) *Microbiol. Mol. Biol. Rev.* 64(3):607-23). While disease severity can range from mild to life threatening, those most at risk for serious illness and side effects are the immune compromised and developing fetuses (Innes (1997) *Comp. Immun. Microb. Infect. Dis.* 20(2): 131-8). Miscarriage, stillbirth, and severe congenital defects are a tragic result of maternal toxoplasmosis during pregnancy. Toxoplasmosis is also a leading cause of abortion in sheep, pigs, and goats, resulting in significant economic loss annually. Toxoplasmosis is also a major concern in biodiversity as well, as infection is generally fatal in marsupials, New and Old world monkeys (Black & Boothroyd (2000) *Microbiol. Mol. Biol. Rev.* 64(3):607-23). Chronic toxoplasmosis can result in encephalopathy, and recently, maternal toxoplasmosis has also been linked to schizophrenia in adult offspring (Brown & Schaefer (2005) *Am. J. Psychiatry* 162(4):767-73).

The sexual cycle of *Toxoplasma* occurs within cats, the definitive host, and parasitism is usually limited to the intestinal tract. The asexual cycle can continue nearly indefinitely in many intermediate hosts. Hosts can be infected in two ways: by accidental ingestion of oocysts shed in feline feces, or by consumption of meat or tissue chronically infected with toxoplasma bradyzoites. Mature oocysts are highly infectious and quite hardy to environmental conditions (Charleston (1994) *N. Zealand J. Zool.* 21:67-81; Black & Boothroyd (2000) *Microbiol. Mol. Biol. Rev.* 64(3):607-23). Oocyst consumption by intermediate hosts initiates the asexual life cycle, wherein sporozoites are released from oocysts. Sporozoites infect the host intestinal epithelium, and develop into rapidly growing tachyzoites. Acute infection ensues when tachyzoites rapidly disseminate throughout the entire body of the infected host, including the central nervous system. Following acute infection, tachyzoites differentiate into slow-growing bradyzoites and form tissue cysts, the hallmark of chronic infection. Tissue cysts are long lasting, and upon consumption of undercooked or raw meat of a chronically infected host, the asexual life cycle is continued in another host. Current drug therapy includes treatment with pyrimethamine and sulfonamide, however, these drugs are only effective against tachyzoites and do not treat the chronic bradyzoite stage. Long-term drug therapy is required, exposing the recipient to harmful side effects (Charleston (1994) *N. Zealand J. Zool.* 21:67-81; Black & Boothroyd (2000) *Microbiol. Mol. Biol. Rev.* 64(3):607-23). Vaccination is a viable and critical measure for disease prevention. There is currently an attenuated live vaccine for sheep available in New Zealand and the United Kingdom. This vaccine consists of a passage-attenuated strain that does not form tissue cysts. While this vaccine provides life long immunity, the median increase in lambing percentage in vaccinated animals is two to four percent (Charleston (1994) *N. Zealand J. Zool.* 21:67-81). While this is a significant increase, a vaccine with a more robust effect is desirable, given the cost and perceived risk associated with live vaccines (Brake (2002) *Intl. J. Parasitol.* 32:509-15).

3. *Neospora*

*Neospora* are biologically very similar to *Toxoplasma*, but cause a distinctively different disease. Like toxoplasma, neospora is widespread, and is capable of infecting many different types of warm-blooded mammalian cells (Dubey (2003) *Korean J. Parasitol.* 41(1):1-16). Infection with acute or chronic Neospora is a major cause of abortion in cattle, paralysis in dogs, and to a lesser extent abortion in sheep and goats. Young animals infected with *Neospora* will exhibit neurological symptoms such as ataxia and paralysis (Beckers (1997) *Mol. Biochem. Parasitol.* 89(2):209-23). The sexual cycle of Neospora occurs within dogs, and can cause a range of symptoms, especially in young pups (Buxton et al. (2002) *Trends Parasitol.* 18(12):546-52). While methods of transmission of *Neospora* are not as well studied as *Toxoplasma* (Hall et al. (2005) *Vet. Parasitol.* 128(3-4):231-41), transplacental transmission has been confirmed, and ingestion of fetal material (aborted fetus, placenta) and milk from seropositive cows, or ingestion of carcasses infected with bradyzoites also lead to infection. Ingestion of oocysts shed in dog feces is another route of transmission (Dubey (2003) *Korean J. Parasitol.* 41(1):1-16; Hall et al. (2005) *Vet. Parasitol.* 128(3-4): 231-41). Following ingestion of oocysts, tachyzoites rapidly invade host cells, and eventually develop into slower growing bradyzoites that encyst within tissue. Both tachyzoites and bradyzoites are found in the central nervous system and muscle of infected animals. Current methods of disease prevention include controlling access of dogs to feed, controlling access of all susceptible animals to fetal material and infected carcasses, culling seropositive animals, and not breeding seropositive animals (Romero et al. (2004) *Vet. Parasitol.* 123(3-4):149-59). These methods can be effective, but are impractical in herds that have a high prevalence of seropositive cows. Chemotherapeutic control is available, however the use of such drugs is restricted, and growing consumer awareness of residuals in beef is leading producers in different directions of disease prevention, including vaccination.

4. *Eimeria*

The many species of *Eimeria* parasites are found within the family Eimeriidae, and cause widespread disease throughout the world. *Eimeria* parasites are highly species specific and affect cattle, goats and sheep. Infection is most significant in avian populations, causing severe diarrhea, weight loss and ceccal lesions, often resulting in death (Augustine (2001) *Trends Parasitol.* 17(11):509-11; Allen & Fetterer (2002) *Clin. Microbiol. Rev.* 15(1):58-65). Infection with *Eimeria*, often referred to as coccidiosis, is a major cash burden in the poultry industry. Costs associated with poultry loss, lack of productivity and drug treatment are estimated to be well over $800 million annually (Augustine et al. (2001) *Trends Parasitol.* 17(11):509-11; Allen & Fetterer (2002) *Clin. Microbiol. Rev.* 15(1):58-65).

Coccidiosis is spread by the ingestion of oocysts, which become infectious or sporulated following incubation at ambient temperature and humidity. Upon consumption, sporozoites released from the oocysts rapidly invade the intestinal epithelia. Sporozoites then develop into merozoites, cause host cell rupture, and rapidly invade the next host cell. This cycle is repeated through 2-4 generations before gametogony. Unlike other apicomplexan organisms, the *Eimeria* asexual cycle does not continue indefinitely (Shirley (2000) *Intl. J. Parasitol.* 30:485-93; Augustine et al. (2001) *Trends Parasitol.* 17(11):509-1 1). Currently, anti-parasitic drugs and some vaccine strategies are used to control coccidiosis. However, there is a high occurrence of drug resistance in Eimeria (Augustine (2001) *Int. J. Parasitol.* 31(1):1-8; Min et al. (2004) *J. Vet. Sci.* 5(4):279-88). And with growing consumer distaste for residuals in meat products and eggs, poultry growers are forced to seek alternate routes of prevention (Greif et al. (2001) *Parasitol. Res.* 87:973-5; Gong et al. (2002) *J. Food Prot.* 65(4):688-91). Although recombinant vaccines are available, these do not provide cross species protection. This is critical, as there are at least five major species of *Eimeria* that cause disease in poultry alone: *tenella*, *acervulina*, *necatrix*, *brunette*, and *maxima*.

Live vaccines, including Immucox, Paracox, Livacox and Viracox (Eckert & Deplazes (1996) *Tierarztl. Prax.* 24(3): 322-9; Vermuelen et al. (2001) *Vet. Parasitol.* 100:13-20; Chapman et al. (2002) *Intl. J. Parasitol.* 32:617-629; Crouch et al. (2003) *Avian Pathol.* 32(3):297-304) have demonstrated efficacy, but pose some risks for poultry producers. Several of these vaccines contain live, wild type parasites, in low doses. Major concerns include the shedding of infective oocysts, stability of vaccine-strain attenuation, and cumbersome timing schedules for vaccinations. Also, infection with live, wild type vaccines results in low-grade infection, which adversely affects poultry growth for a duration of time post-vaccination. This is particularly undesirable in small-sized fowl with short growing periods. Recently vaccinated animals require separate feed and housing, as most poultry feed includes anti-coccidial compounds that interfere with immunization (Allen & Fetterer (2002) *Clin. Microbiol. Rev.* 15(1):58-65; Donald et al. (2002) *Eukaryotic Cell* 3(1):317-28; Gong et al. (2002) *J. Food Prot.* 65(4):688-91; Min et al. (2004) *J. Vet. Sci.* 5(4):279-88).

5. *Theileria*

*Theileria* is grouped with *Babesia* as a Piroplasmida. Theileriosis is a significant disease of cattle, sheep and goats in tropical and sub-tropical countries. Disease is commonly found from North Africa and southern Europe in the West, to India and China in the East (NCBI Taxonomy Browser; Burkot & Graves (2004) *Medical Entomology* (Eldridge & Edman, eds.), Kluwer Academic Publishers, pp. 187-230; Nagore et al. (2004) *Intl. J. Parasitol.* 34:1059-67). The introduction and cross-breeding of naive species of Western cattle, in particular Friesen, to improve cattle productivity has actually increased cattle morbidity due to theileriosis. Disease symptoms include anemia, leukopenia, cachexia, mucous membrane discharge, and dysentery. Susceptible animals often die within 15-25 days of acute infection if not treated (Criado-Fornelio et al. (2003) *Vet. Parasitol.* 113:189-201). Theileria is vector borne, and is transmitted by ticks. Sporozoites are released form the salivary glands of ticks and invade bovine lymphocytes. Infected lymphocytes are transformed by the schizonts stage to become lymphoblastoid, producing infected daughter cells. The next phase involves the release of erythrocyte-invading merozoites (Burkot & Graves (2004) *Medical Entomology* (Eldridge & Edman, eds.), Kluwer Academic Publishers, pp. 187-230; Nagore et al. (2004) *Intl. J. Parasitol.* 34:1059-67).

Methods of disease prevention include vector control by treatment with acaricides. This practice is expensive, harmful to the environment, and promotes vector resistance. Chemotherapeutic treatment of cattle is an option, however Halofuginone, parvaquone, and buparvaquone are expensive, and are often not manufactured where Theileriosis is endemic. An infection and treatment method is often used to prevent theileriosis (Criado-Fornelio et al. (2003) *Vet. Parasitol.* 113:189-201). Cattle are inoculated with *Theileria* and administered antibiotics (such as Tetracycline or Buparvaquone) simultaneously. This method is effective, however requires some expertise, poses some risk, and is costly. Subunit vaccines are in development, but live, passage-attenuated vaccines are the only type currently in use (Glass (2001) *Res. Vet. Sci.* 70:71-5; Marcotty et al. (2003) *Vaccine* 22:213-216). As with other passage-attenuated vaccines, vaccine stability and reversion to pathogenicity is always a major concern. It is not understood what entirely causes attenuation in passaged *Theileria*. Loss of matrix metalloproteinases (MMPs) is thought to be partially responsible, however other factors are thought to be involved in parasite attenuation (Hall et al. (1999) *Trop. Med. Intl. Health* 4(9):A78-A84).

6. *Babesia*

*Babesia*, along with *Theileria*, is grouped as a Piroplasmida. Unlike *Theileria, Babesia* does not have a pre-erythrocytic host cell, however there is some debate regarding *Babesia equi* first invading lymphocytes prior to erythrocytes (some groups have reclassified *B. equi* as *Theileria equi*, due to host cell specificity) (Gray et al. (2002) *Intl. J. Med. Microbiol. Suppl.* 33:108-111; Burkot & Graves (2004) *Medical Entomology* (Eldridge & Edman, eds.), Kluwer Academic Publishers, pp. 187-230). *Babesia* species are capable of infecting cattle, horses, dogs, pigs, and humans. Babesiosis occurs worldwide, but is most prevalent in the North Eastern United States and Europe through North Africa. While disease is rare in healthy humans, infection with *B. divergens* carries a mortality rate of 42%. Veterinary babesiosis is much more prevalent and incurs huge economic costs annually (Gray et al. (2002) *Intl. J. Med. Microbiol.* Suppl. 33:108-111; Zintl et al. (2003) *Clin. Microbiol. Rev.* 16(4):622-36; Burkot & Graves (2004) *Medical Entomology* (Eldridge & Edman, eds.), Kluwer Academic Publishers, pp. 187-230; Nagore et al. (2004) *Intl. J. Parasitol.* 34:1059-67). Peaks in parasitemia and disease incidence occur twice annually, once in the Spring and once in the Fall, illustrating the need for long lasting immunity.

Sporozoites develop in salivary glands of feeding ticks and when expelled, immediately attach to and invade host erythrocytes, other cell types or tissues are not affected. Sporozoites develop into multiple merozoites, wherein the host cell is lysed, and free merozoites invade additional erythrocytes, and exacerbate disease. Unlike other apicomplexan organisms, *Babesia* spp. are in direct contact with erythrocytes and not continuously enclosed in a parasitophorous vacuole. Fever, anemia, anorexia, depression, weakness and hemoglobinuria often follow in the host. Uptake by another tick continues the sexual cycle, followed by 2-3 rounds of asexual reproduction as well. Transovarial transmission of Babesia species is possible within the vector, hence all life cycle stages of ticks are potentially infectious (Gray et al. (2002) *Intl. J. Med. Microbiol.* Suppl. 33:108-111; Zintl et al. (2003) *Clin. Microbiol. Rev.* 16(4):622-36; Burkot & Graves (2004) Medical Entomology (Eldridge & Edman, eds.), Kluwer Academic Publishers, pp. 187-230

As with other vector-borne disease, control of babesiosis has relied heavily on tick control. However, an increase in acaricide resistant ticks has prompted control of Babesiosis at the parasite level (Burkot & Graves (2004) *Medical Entomology* (Eldridge & Edman, eds.), Kluwer Academic Publishers, pp. 187-230). Many of the most effective drugs against *Babesia* spp, have been withdrawn due to safety or residue problems (Brown (2001) *Vet. Parasitol.* 101:233-48; Alvarez et al (2004) *Ann. N.Y. Acad. Sci.* 1026:277-83). Vaccination with cultured exo-antigens does not provide adequate protection. Live vaccination has been attempted in some countries, but recent cross-species infections have raised concerns about this practice.

7. *Cryptosporidium, Sarcocystis*, and *Leucocytozoon*

*Cryptosporidium parvum* and *Cryptosporidium hominis* cause prolonged diarrheal disease in immunocompromised humans and livestock, and is particularly problematic in young calves. Ingestion of oocysts from contaminated water is the most common route of transmission, so immunization of animals is a possible method of preventing downstream human infection as well. Sporozoites are released from oocysts and rapidly infect intestinal epithelial cells. Current vaccine attempts include a freeze-thaw attenuated oocysts preparation. Complete human and bovine form sequences are available, and sporozoites can be cultured on biliary epithelial cells.

*Sarcocystis cruzi* and *neuroni* cause bovine, ovine, equine and porcine encephalopathy worldwide. These animals are aberrant intermediate hosts; the definitive host is the opossum. Only schizonts and merozoites are found in intermediate hosts.

*Leukocytozoon* cause disease in domesticated poultry, and are most problematic in Asian countries. Infection causes weight loss, poor egg production and death in chickens, ducks and turkeys. Currently, animals are treated with drugs, but residuals found in meat and eggs demonstrate the necessity for vaccine candidates. Killed as well as live sporozoite vaccine attempts are documented in literature, but these are not very effective.

8. *Trypanosoma*

The "lethargy that kills" has plagued sub-Saharan Africa for centuries. This early description of what is now termed African Trypanosomiasis (AT), aptly describes the insipid neurological disease caused by infection with *Trypanosoma brucei* (Stemberg (2004) *Parasite Immunol.* 26(11-12):469-76). Currently, over 60 million people in 36 different countries are susceptible to the potentially chronic and often fatal disease. Annually, it is believed over 500,000 are infected with *Trypanosoma brucei* subspecies (WHO (2001) African Trypanosomiasis Fact Sheet). *Trypanosoma brucei rhodesiense* is prevalent in the East African savannah plains, and often causes an acute and virulent disease. The West African bush is home to the *T. brucei* subspecies *gambiense*, which causes a chronic illness (Leder et al. (2001) *UpToDate* 2203). Humans remain refractory to *Trypanosoma brucei brucei*, however cattle and sheep are ravaged by infection with the parasite, in a condition referred to as nagana (WHO (2001) African Trypanosomiasis Fact Sheet). The loss of human life and the collapse of worker productivity and cattle crops due to African trypanosomiasis is devastating to endemic regions.

*Trypanosoma brucei* has a highly adaptable life cycle. As it is vector transmitted, the parasite is capable of surviving in both mammals and the tsetse fly. Beginning in the insect host, as the procyclic form, the parasite replicates rapidly (Hajduk (1984) *J. Protozool.* 31(1):41-7; Clayton & Hotz (1996) *Mol. Biochem. Parasitol.* 77(1):1-6). Following the procyclic stage of rapid growth is the non-proliferative metacyclic stage. An insect bite and blood meal transmits the parasite to the next host and the start of a new life stage, the bloodstream form. Initially slender within the bloodstream, the parasites adapt to the glucose- and nutrient-rich environment by gradually decreasing mitochondrial respiration, and eventually some cells take on a stumpy morphology (Clayton & Hotz (1996) *Mol. Biochem. Parasitol.* 77(1):1-6). An infected mammal is now a reservoir of *T. brucei*, and if bitten, the process can begin anew.

One bite by an infected tsetse fly is sufficient to transmit disease. A rubbery chancre forms at the bite site, and the organisms spread through lymphatic channels and within the bloodstream. The parasites reproduce in the bloodstream, but can later move to the central nervous system (CNS) causing inflammation in the brain, hence the descriptive neurological disease name, African Sleeping Sickness (Samulson (1995) *Infectious Diseases. Pathological Basis of Disease* (K. Robbins ed.) WB Saunders & Co., Philadephia, pp. 369-74; WHO (2001) African Trypanosomiasis Fact Sheet). The cardiovascular system can also be affected, with the development of myocardial inflammation. Subsequent myocarditis and CNS involvement can start within three to six weeks, followed by heart failure, convulsions and eventually coma and death. A rapid disease progression of six to nine months until death is typical of untreated T brucei rhodesiense infection. T brucei gambiense disease is a slower, chronic disease with bouts of fever and malaise potentially lasting for years before CNS involvement manifests (Samulson (1995) *Infectious Diseases. Pathological Basis of Disease* (K. Robbins ed.) WB Saunders & Co., Philadephia, pp. 369-74).

Typically, treatment of AT is most successful with the drug pentamidine, if there is no CNS involvement (Leder et al. (2001) *UpToDate* 2203). Pentamidine is most effective in gambiense infections, since CNS involvement occurs early in rhodesiense infections. If the CNS has been breached, the drug Melarsoprol is used. Both of these drugs carry significant side effects, particularly Melarsoprol, which is a highly toxic, potentially lethal, arsenical compound. Besides extreme toxicity, drug resistance to Melarsoprol has been reported in the Congo and Uganda. Eflornithine and Suramin are other potential drug therapy candidates (Leder et al. (2001) *UpToDate* 2203). The extreme toxicity of these drugs and resulting side effects are problematic, as death is often hastened by treatment (Nok (2003) *Parasitol. Res.* 90(1):71-9). Perhaps the greatest hurdle to these drug therapies is the considerable financial cost associated with the compounds, administration and patient support. Vector control is plagued with problems, due to toxicity of pesticides, and nomadic cultures of indigenous populations. There is a considerable and significant need for vaccines in the field.

The chronic and devastating disease caused by *Trypanosoma cruzi* was first characterized in the early 1900s by Carlos Chagas (Barret et al. (2003) *Lancet* 362(9394):1469-80). In endemic regions ranging from Northern Mexico and south through Argentina, it is estimated that 16-18 million people are infected with the parasite. Conservative estimates predict that another 11-40 million people are at risk of infection (WHO (2004) Chagas Disease).

*Trypanosoma cruzi* are also vector borne. The parasite is transmitted by a triatomine vector. Parasite epimastigotes replicate in the insect midgut, and then develop into metacyclic trypomastigotes. The insect then bites a mammalian host, takes a blood meal, and sheds parasite in feces. The parasites enter the mammalian host through wound, often assisted by scratching or rubbing at the site of the insect bite (Avila et al. (2003) *Genet. Mol. Res.* 2(1):159-68). Metacyclic trypomastigotes invade host cells, and differentiate into replicative amastigote forms. After multiplication, amastigotes differentiate into bloodstream trypomastigotes, which are released into the circulatory system, and infect new cells. A small sore will often develop at the site of bite. If bitten near the eyes, eyelids will often swell, a key indicator of infection known as Romana's sign (WHO (2004) Chagas Disease). The initial acute phase includes fever and swollen lymph nodes (Avila et al. (2003) *Genet. Mol. Res.* 2(1):159-68). The disease is particulary virulent in young children, and is often fatal. However in adults the course of illness has little to no symptoms for months to years. During this symptomless phase, parasites are invading and weakening host organs, including heart, intestines, esophagus. Fatality is often a result of cardiomyopathy, and upon autopsy, most victims of Chagas disease presented enlargement of several organs, including the spleen, heart, colon and esophagus. Parasites can also be transmitted through blood transfusions (Pomper et al. (2003) *Curr. Opin. Hematol.* 10(6):412-8), and congenitally from mother to fetus.

Drug therapy for infection includes nifurtimox and benznidazole, however, both drugs are proven to clear parasites only in the initial, acute phase of illness (Urbina & Docampo (2003) *Trends Parasitol.* 19(11):495-501). Long term therapy with nifurtimox and benznidazole to decrease parasite burden in chronic infections is not desirable, as the drugs can cause oxidative or reductive damage to host organs and tissue (Urbina & Docampo (2003) *Trends Parasitol.* 19(11):495-501). The best methods of controlling disease to date have included massive pesticide spraying regimes, screening blood supplies for contamination, and testing expectant mothers for infection (Schofield & Maudline (2001) *Int. J. Parasitol.* 31(5-6): 614-9). While all of these methods have made major improvements in preventing the transmission of disease, they are costly, and can be impractical. With development into regions of the Amazon, countless new reservoirs for insects and parasites are emerging. An effective vaccine for natives and travelers of endemics regions is greatly needed.

9. *Leishmania*

Leishmaniasis is a worldwide disease and is endemic in 88 countries. Human infections are found in 16 countries in Europe, including France, Italy, Greece, Malta, Spain and Portugal, as well as throughout Asia, Northern Africa, central and South America (WHO (2005) Leishmaniasis Home). Many mammals are potential host reservoirs, including rodents, foxes, jackals, but perhaps the most significant is the dog. Close human interactions with domesticated dogs are believed to be a significant source of human infection (Vanloubbeeck & Jones (2004) *Ann. N.Y Acad. Sci.* 1026:267-72). The parasite is transmitted by the bite of a sandfly, and the vector is difficult to control. Leishmaniaisis is of particular concern to travelers and military personnel stationed in endemic regions. There are many species and subspecies of Leishmania that cause disease, some of the most significant include *L. major, L. infantum, L. donovani, L. mexicana, L. braziliensis, L. chagasi,* and *L. amazonensis* (WHO (2005) Leishmaniasis Home).

Like *Trypanosoma brucei* and *cruzi, Leishmania* are highly adaptive and have several life stages. Within the insect, amastigotes transform in to the promastigote form. The promastigotes then migrate to the midgut of the fly, where they live extracellularly and multiply by binary fission. Promastigotes then move forward to the oesophagus and the salivary glands of the insect. When the sandlfy next feeds on a mammalian host, the *Leishmania* promastigotes are transferred to the host. Once in the host, the promastigotes are taken up by the macrophages where they revert to the amastigote form. Amastigotes multiply inside the macrophages, eventually leading to the lysis of the macrophages. (Vanloubbeeck & Jones (2004) *Ann. N.Y. Acad. Sci.* 1026:267-72). The released amastigotes are taken up by additional macrophages and so the cycle continues. Ultimately all the organs containing macrophages and phagocytes are infected, especially the spleen, liver and bone marrow (WHO (2005) Leishmaniasis Home).

Those infected may present a range of symptoms, as there are several forms of the disease, with varying ranges of severity. The most serious, and often fatal if untreated is visceral leishmaniasis (kala azar), with symptoms including fever, malaise, weight loss, anemia, swelling of the spleen, liver and lymph nodes. The most common manifestation is cutaneous leishmaniasis, resulting in multiple skin lesions and scarring. Mucocutaneous leishmaniasis, begins with skin ulcers which spread, and cause massive tissue destruction, especially of the nose and mouth and leaves victims horribly disfigured (Vanloubbeeck & Jones (2004) *Ann. N.Y. Acad. Sci.* 1026:267-72).

Drug therapy is limited to a few highly toxic compounds (Sundar & Rai (2002) *Curr. Opin. Infect. Dis.* 15(6):593-8), and evidence of drug resistance has narrowed an already small pool of candidate drugs (Murray (2004) *Am. J. Trop. Med. Hyg.* 71(6):787-94). Self-inoculation with Leishmania, termed "leishmaniazation" is an ancient immunization practice (Coler & Reed (2005) *Trends Parasitol.* 21(5):244-9). This method can provide some protection, but is not always effective against all forms of the disease. It is difficult to control the level of infection of the recipient. Leishmaniazation also creates open sores with infective parasites, and often scars the recipient. A safely attenuated live vaccine is greatly needed, as attempts at whole killed parasites and subunit vaccines have not yet proved efficacious (Vanloubbeeck & Jones (2004) *Ann. N.Y. Acad. Sci.* 1026:267-72).

In the methods of the invention, the protozoan parasite is genetically engineered to disrupt a stage-specific gene function that is required for the parasite to develop an infective stage that causes a secondary infection in the vertebrate host. The term "gene function" refers to a function provided by the gene and includes both protein-coding functions and non-protein coding functions. Many protozoan genes have been found to encode RNAs that do not code for proteins and that have direct roles in various cellular processes, such as DNA replication, splicing, RNA processing, regulation of translation and transcript abundance, and protein translocation (for review, see Worthey & Myler (2005) *Int. J. Parasitol.* 35:495-512). As described above, the subject protozoan parasites of the phylum Apicomplexa or the phylum Kinetoplastida have at least a first and a second infective stage in their vertebrate hosts, the second of which is responsible for establishing a secondary infection that causes significant disease. In some embodiments, the secondary infective stage is specific to the vertebrate host.

The term "stage-specific gene function" refers to the gene function that is required in one infective stage of the parasite for it to develop into a subsequent stage. For example, in *Plasmodium*, the term "liver-stage-specific gene function" or "LS-specific gene function" refers to a function that is required in liver stage parasites to ultimately produce infectious merozoites and establish the pathologic erythrocytic stage of the life cycle, but that is not required for entry into host hepatocytes or, preferably, maintenance of the parasite in asexual blood cell stages and production of infective sporozoites in mosquitoes. *Plasmodium* parasites in which an LS-specific function is disrupted may remain capable of invading hepatocytes, but cannot develop into merozoites that are capable of establishing a blood stage infection. For example, the disruption of an LS-specific gene function in a *Plasmodium* parasite may prevent the development of merozoites or prevent merozoites from leaving the liver or infecting erythrocytes.

The phrase "disrupt a stage-specific gene function" refers to interfering with an stage-specific gene function such as to completely or partially inhibit, inactivate, attenuate, or block that stage-specific gene function, for example, by gene disruption or influencing transcription, translation, protein folding, and/or protein activity. Of course, more than one stage-specific gene function can be disrupted as such redundancy may ensure an additional degree of protection against secondary infection. For example, double gene replacements can be created to disrupt two stage-specific gene functions.

A stage-specific gene function may be identified using routine methodology that is standard in the art. Candidate stage-specific gene functions may be identified, for example, by looking for genes whose expression is up-regulated in parasites of that stage, or by looking for homologues or orthologues of genes that have a stage-specific gene function in another protozoan parasite. For example, a stage-specific gene function in *Plasmodium* may be a gene that is expressed at higher levels in liver-stage parasites than, e.g., in the sporozoite population that emerges from mosquito mid-gut oocysts. Up-regulation of expression of such genes may also be observed in mature, infective salivary gland sporozoites (like in the UIS4 and UIS3 genes discussed in the Examples below). Well-known methods for differential transcriptional profiling, including, but not limited to, subtractive hybridization screens, differential display, and genome-wide microarray analyses, may be used for identifying genes whose expression is up-regulated in parasites of a specific stage. Such methods have been previously used to analyze infectivity-associated changes in the transcriptional repertoire of sporozoite-stage parasites (Matuschewski et al. (2002) *J. Biol. Chem.* 277:41948-53) and to identify *Plasmodium* genes that encode pre-erythrocytic stage-specific proteins (Kaiser et al. (2004) *Mol. Microbiol.* 51:1221-32). For example, suppression subtractive hybridization permits selective enrichment of differentially regulated cDNAs of high and low abundance through a combination of hybridization and polymerase chain reaction (PCR) amplification protocols that allow the simultaneous normalization and subtraction of the cDNA populations. Suppression subtractive hybridization has been used to analyze transcriptional differences between non-infective and infective sporozoites and to identity genes controlling infectivity to the mammalian host (Matuschewski et al. (2002) *J. Biol. Chem.* 277:41948-53). This procedure has permitted the identification of liver-stage (LS) up-regulated genes in *Plasmodium*, including but not limited to the UIS3 and UIS4 genes disrupted in the Examples below. Suppression subtractive hybridization of *Plasmodium* salivary gland sporozoites versus merozoites has also been used to identify stage-specific pre-erythrocytic transcripts (Kaiser et al. (2004) *Mol. Microbiol.* 51:1221-32). Differential expression of candidate stage-specific genes may be confirmed using methods that are standard in the art, including dot blots, reverse transcriptase PCR (RT-PCR), immunoblotting, immunofluorescence microscopy, and/or microarray expression analyses.

Once a candidate stage-specific gene function is identified by virtue of its up-regulated expression at the specific stage of interest, its function is analyzed, as further described below. One of skill in the art will appreciate that not all genes with a stage-specific gene function are necessarily genes whose expression is up-regulated at that stage. For example, *Plasmodium* genes whose expression is not up-regulated in LS forms may nevertheless possess an LS-specific gene function.

Another method for identifying candidate stage-specific gene functions is by looking for homologues of genes that are known to have a stage-specific gene function in another protozoan parasite or homologues of genes whose expression is up-regulated at a specific stage of interest in another protozoan parasite. As used herein, the term "homologue" refers to a gene, or a protein encoded by a gene, in one protozoan organism that has significant sequence identity over a large portion of the sequence to a gene, or protein encoded by a gene, in another protozoan organism. A homologue may be an orthologue. The term "orthologue" refers to the gene, or the protein encoded by a gene, in one protozoan organisms that has the highest degree of sequence identity within the genome or proteome of that protozoan organism to a gene, or a protein encoded by a gene, in another protozoan organism. Thus, orthologous sequences may be homologous sequences in different species that arose from a common ancestral sequence during speciation.

The identification of significant sequence identity is used to infer conservation of gene function (Altschul et al. (1994) *Nat. Genet.* 6:119-29; Bork et al. (1998) *J. Mol. Biol.* 283: 707-25; Grundy (1998) *J. Comput. Biol.* 5:479-91). Thus, the presence in one protozoan organism of a gene that is a homologue of a gene that has a stage-specific gene function in another protozoan organism suggests that the homologue also has a stage-specific function. For example, a *Toxoplasma* homologue of a *Plasmodium* stage-specific gene function may function as a *Toxoplasma* stage-specific gene. Similarly, a Toxoplasma homologue of a *Plasmodium* gene that is up-regulated at a specific stage of interest may function as a *Toxoplasma* stage-specific gene function.

Homologues of genes may be identified using methods that are standard in the art, including in vitro methods such as using hybridization or the Polymerase Chain Reaction, and in silico sequence comparison methods. For example, a homologue having significant sequence identity to a known stage-specific gene may be identified by using database search algorithms. The terms "identical" or percent "identity," in the context of two or more amino acid or nucleic acid sequences, refer to two or more sequences or subsequences that are the same or have a specified percentage of nucleotides or amino acids that are the same, when compared and aligned for maximum correspondence over a comparison window, as measured using one of the following sequence comparison algorithms or by manual alignment and visual inspection.

It is recognized that amino acid positions that are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. The scoring of conservative substitutions can be calculated according to, for example, the algorithm of Meyers & Millers (1988) *Computer Applic. Biol. Sci.* 4:11-17.

A "comparison window" includes reference to a segment of contiguous positions, such as between about 25 and about 600 positions, or between about 50 to 200 positions, or between about 100 and 150 positions, over which a sequence may be compared to a reference sequence of the same number of contiguous positions after the two sequences are optimally aligned. Methods of alignment of sequences for comparison are well-known in the art. Optimal alignment of sequences for comparison can be conducted, for example, by a local homology algorithm (Smith & Waterman (1981) *Adv. Appl. Math.* 2:482), by a global alignment algorithm (Needleman & Wunsch (1970) *J. Mol. Biol.* 48:443), by search for similarity methods (Pearson & Lipman (1988) *Proc. Natl. Acad. Sci. U.S.A.* 85:2444; Altschul et al. (1997) *Nucl. Acids Res.* 25(17):3389-402), by computerized implementations of these algorithms (e.g., GAP, BESTFIT, FASTA, and BLAST in the Wisconsin Genetics Software Package, Genetics Computer Group, 575 Science Dr., Madison, Wis.), typically using the default settings, or by manual alignment and visual inspection (see, e.g., Current Protocols in Molecular Biology (1994) Ausubel et al., eds.). For example, BLAST protein searches can be performed using the XBLAST program, score=50, wordlength=3 to obtain amino acid sequences that are more than 80% identical to the amino acid sequence of, for example, the protein encoded by *Plasmodium* UIS3. Additional searches that may be performed include BLASTP (Protein Query versus Protein Database), BLASTN (Nucleotide query versus Nucleotide Database), BLASTX (Nucleotide Query versus Protein database), TBLASTN (Protein Query versus Nucleotide Database, and TBLASTX (Nucleotide Query versus translated Nucleotide Database), for example, using default parameters. The statistical significance of a local alignment produced by BLAST is assessed with an E-value, calculated using the formal $E=Kmne^{-\lambda S}$, where m and n are the effective lengths of the query sequence and database, S is the nominal score of the alignment, and $\lambda$ and K are statistical parameters dependent on the scoring system used and the composition of the sequence being compared (Altschul et al. (1997) *Nucl. Acids. Res.* 25:3389-402).

One example of a useful algorithm implementation is PILEUP. PILEUP creates a multiple sequence alignment from a group of related sequences using progressive, pairwise alignments. It can also plot a dendrogram showing the clustering relationships used to create the alignment. PILEUP uses a simplification of the progressive alignment method of Feng & Doolittle (1987) *J. Mol. Evol.* 35:351-60. The method used is similar to the method described by Higgins & Sharp (1989) *CABIOS* 5:151-3. The multiple alignment procedure begins with the pairwise alignment of the two most similar sequences, producing a cluster of two aligned sequences. This cluster can then be aligned to the next most related sequence or cluster of aligned sequences. Two clusters of sequences can be aligned by a simple extension of the pairwise alignment of two individual sequences. A series of such pairwise alignments that includes increasingly dissimilar sequences and clusters of sequences at each iteration produces the final alignment. Another useful algorithm implementation is provided by Sequencher (see, e.g., Matuschewski et al. (2002) *J. Biol. Chem.* 277(44):41948-53, incorporated herein by reference, particularly at page 41949).

Accordingly, one method of identifying a homologue of a stage-specific gene is to use database search algorithms to compute pair-wise comparisons between the sequence of a known stage-specific gene and each of the sequences stored within a database to find all pairs of sequences that have a sequence identity above a defined threshold (Altschul et al. (1994) *Nat. Genet.* 6:119-29; Bork et al. (1998) *J. Mol. Biol.* 283:707-25). Frequently, a single, relatively non-stringent threshold (such as an E-value of about $10^{-6}$ or about $10^{-5}$) is used to determine whether two sequences are sufficiently related to be able to infer functional similarity. Thus, in some embodiments, a gene, or a protein encoded by a gene, in one protozoan organism is determined to be a homologue of a gene, or a protein encoded by a gene, in another protozoan organism if the statistical significance of the alignment has an E-value of $10^{-5}$ or lower, such as between $10^{-5}$ and $10^{-250}$, or between $10^{-10}$ and $10^{-50}$ using BLAST, or a corresponding measure of statistical significance using another search algorithm implementation. Descriptions of and links to databases of sequence information from protozoan organisms are provided in Worthey & Myler (2005) *Int. J. Parasitol.* 35:495-512 (see Table 1, incorporated herein by reference).

For example, the sequence of a gene that has a stage-specific function in *Plasmodium* or whose expression is up-regulated at a specific stage of interest in *Plasmodium* may be compared in silico to databases of genomic or cDNA sequence information from another protozoan parasite, such as *Toxoplasma*. Reciprocal comparisons of a candidate Toxoplasma gene identified in this manner to a *Plasmodium* sequence database may be used to confirm that the *Toxoplasma* gene is a orthologue of the *Plasmodium* gene. Exemplary methods for identifying homologues of genes that are known to have a stage-specific gene function in another protozoan parasite or homologues of genes whose expression is up-regulated at a specific stage of interest in another protozoan parasite are described in Examples 4-10.

Another method to find homologue is by identifying nucleic acid sequences that hybridize to a known sequence from another protozoan organism to form a heteroduplex with a $T_m$ that is within 20° C. (such as within 10° C. or within 5° C.) of that of a homoduplex of the known sequence. The melting temperature of a duplex is calculated using the formula:

$$T_M=81.5+16.6(\log_{10}[Na^+])+0.41(G+C)-600/l$$

where l is the length of the hybrid in basepairs (Sambrook et al. (1989) Molecular Cloning: A Laboratory Manual, 2d ed., Cold Spring Harbor Laboratory, Cold Spring Harbor, N.Y., page 9.51). This equation applies to the "reversible" $T_m$ that is defined by optical measurement of the hyperchromicity at $OD_{257}$. The melting temperature decreases 1.5° C. for every 1% decrease in sequence identity (Sambrook et al. (1989) Molecular Cloning: A Laboratory Manual, 2d ed., Cold Spring Harbor Laboratory, Cold Spring Harbor, N.Y., page 9.51).

Once a candidate stage-specific gene is identified by virtue of its being a homologue of a stage-specific gene function (or a candidate stage-specific gene function) in another protozoan parasite, its function is analyzed, as further described below. One of skill in the art will appreciate that not all genes with a stage-specific gene function in one protozoan parasite necessarily have homologues in another protozoan parasite, and vice versa.

Stage-specific gene functions may also be identified by analyzing the phenotype of parasites in which one or more gene functions have been disrupted. Similar phenotypic analyses are used to assess the function of candidate stage-specific genes functions. For example, several methods for disrupting gene functions in *Plasmodium* are well-known in the art and may be used in the practice of the invention. Such methods include, but are not limited to, gene replacement by homologous recombination, antisense technologies, and RNA interference. For example, methods of gene targeting for inactivation or modification of a *Plasmodium* gene by homologous recombination have been established (Thathy & Ménard (2002) Gene targeting in *Plasmodium berghei*, in *Methods in Molecular Medicine*, Vol. 72: Malaria Methods and Protocols (Doolan, ed.), Humana Press). Such methods were herein successfully used to disrupt LS-specific gene functions, as described in Examples 1 and 2. Antisense technology has also been successfully used for disrupting protozoan gene functions. For example, exogenous delivery of phosphorothioate antisense oligonucleotides against different regions of the *P. falciparum* topoisomerase II gene result in sequence-specific inhibition of parasite growth (Noonpakdee et al. (2003) *Biochem. Biophys. Res. Commun.* 302(4): 659-64). Similarly, transfection of an antisense construct to the *Plasmodium* falciparum clag9 gene, which had been shown to be essential for cytoadherence by targeted gene disruption, resulted in a 15-fold reduction in cytoadherence compared to untransfected control parasites (Gardiner et al. (2000) *Mol. Biochem. Parasitol.* 110(1):33-41).

Another exemplary technology that may be used in the practice of the invention to disrupt stage-specific gene functions is RNA interference (RNAi) using short interfering RNA molecules (siRNA) to produce phenotypic mutations in genes. RNAi has been used as a method to investigate and/or validate gene function in various organisms, including plants, *Drosophila*, mosquitoes, mice, and *Plasmodium* (see, e.g., Dykxhoorn et al. (2003) *Nat. Rev. Mol. Cell Biol.* 4:457-67; Reynolds et al. (2004) *Nat. Biotechnol.* 22:326-30; Heidel et al. (2004) *Nat. Biotechnol.* 22(12):1579-82; Kumar et al. (2002) *Malar. J.* 1(1):5; McRobert & McConkey (2002) *Mol. Biochem. Parasitol.* 119(2):273-8; Malotra et al. (2002) *Mol. Microbiol.* 45(5):1245-54; Mohmmed et al. (2003) *Biochem. Biophys. Res. Commun.* 309(3):506-11). In *Plasmodium*, RNAi has been used, for example, to demonstrate the essential role of a PPI serine/threonine protein phosphatase (PfPP1) from *P. falciparum* (Kumar et al. (2002) *Malar. J.* 1(1):5 (2002). RNAi has also been used to inhibit *P. falciparum* growth by decreasing the level of expression of the gene encoding dihydroorotate dehydrogenase (McRobert & McConkey (2002) *Mol. Biochem. Parasitol.* 119(2):273-8) and by blocking the expression of cysteine protease genes (Malotra et al. (2002) *Mol. Microbiol.* 45(5):1245-54). In the mouse malaria model, RNAi has been used to inhibit gene expression in circulating *P. berghei* parasites in vivo (Mohmmed et al. (2003) *Biochem. Biophys. Res. Commun.* 309(3): 506-1 1). These and other studies have demonstrated the use of RNAi as an effective tool for disrupting gene function in protozoan organisms.

The gene disruption approaches described above (for example, gene targeting by homologous recombination, antisense, and RNAi) have been used successfully to investigate the function of virtually all genes in an organism's genome. For example, the availability of sequenced genomes has enabled the generation of siRNA libraries for use in large-scale RNAi studies to screen for genes that are involved in various processes, such as developmental pathways or stages (see, e.g., Boutros et al. (2004) *Science* 303:832-5; Kamath et al. (2003) *Nature* 421:231-7). Such screens may be used in the practice of the invention to identify stage-specific gene functions in protozoan parasites, for example, LS-specific gene functions in *Plasmodium*. Assays that may be used for identifying stage-specific gene functions include, but are not limited to, phenotypic analyses such as the phenotypic assays described in Examples 1 and 2. The term "phenotypic analysis" includes all assays with vital recombinant parasites that are generated in a wild type, fluorescent or any other transgenic reporter background. Assays may be performed in vivo, with cultured cells, in vitro development assays or any other system that provides a read-out for development of parasites at that stage.

Interference with a stage-specific function may also be achieved by stage-specific overexpression of an inhibitory factor. This factor may be inserted by reverse genetics methods into a pseudogene, i.e., one that is not essential for parasite survival at any time point during the life cycle (Duraising et al. (2002) *Int. J. Parasitol.* 32(1):81-9). The inhibitory factor should not confer toxicity to the parasite but rather act in arresting development of the parasite at that stage. Such a factor may include, but is not limited to, inhibitors of cell-cycle progression and/or ubiquitin-mediated proteolysis, and/or factors that interfere with post-transcriptional control of gene-expression.

The engineered protozoan parasites in which a stage-specific gene function has been disrupted are typically grown in cell culture or animals, and harvested in an appropriate form (for example, as sporozoites in *Plasmodium*) for use in vaccines (see, e.g., Al-Olayan et al. (2002) *Science* 295:677-679).

The invention further provides a vaccine composition comprising a live protozoan parasite that is genetically engineered to disrupt a stage-specific gene function that is required by the protozoan parasite to establish a secondary infection and pathology in the vertebrate host. In addition, the invention provides the use of a vaccine composition comprising a live protozoan parasite that is genetically engineered to disrupt such a stage-specific gene function. The invention also provides for production of a vaccine composition, by suspending and packaging the subject engineered protozoan parasites in a suitable pharmaceutically acceptable carrier solution. Suitable pharmaceutically acceptable carriers include sterile water or sterile physiological salt solution, particularly phosphate buffered saline (PBS), as well known in the art.

Vaccines according to the invention may be administered by any suitable method of administration known in the art, including, but not limited to, intradermally, subcutaneously, intramuscularly, intraperitoneally, orally, jocularly (e.g., as an eye spray), and intravenously.

Dosage is empirically selected to achieve the desired immune response in the host. By "immune response" is meant an acquired and enhanced degree of protective immunity, preferably complete or sterile protection, against subsequent exposure to wild-type protozoan parasites. In the working examples described below, sterile protection was achieved following three vaccinations with 10,000 live genetically attenuated *Plasmodium* sporozoites per inoculation.

Some embodiments of the invention provide methods for inducing an immune response by administering live *Plasmodium* parasites that are genetically engineered to disrupt the function of an LS-specific gene. To generate genetically attenuated *Plasmodium* LS that are defective only in LS development, a stage-specific gene that plays an essential and exclusive role at this stage was disrupted. The gene is preferably not essential during the blood stage cycle given that *Plasmodium* is haploid and transfection is done with asexual blood stages and the mutant parasites are typically maintained as blood stages (Thathy & Ménard (2002) Gene targeting in *Plasmodium berghei*, in *Methods in Molecular Medicine*, Vol. 72: Malaria Methods and Protocols (Doolan, ed.), Humana Press). Transcription-profiling was previously used based on the prediction that infectious *Plasmodium* spzs residing in the mosquito salivary glands are uniquely equipped with transcripts required for hepatocyte invasion and subsequent development of the LS (Matuschewski et al. (2002) *J. Biol. Chem.* 277:41948-53). Next, transcripts that are specific for pre-erythrocytic and absent from blood cell stages were screened for (Kaiser et al. (2004) *Mol. Microbiol.* 51:1221-32). The combined screens identified two abundant salivary-gland-spz-enriched transcripts that are absent from blood stages, termed UIS3 and UIS4 (for upregulated in infectious spzs). Cell biological studies have shown that both encoded proteins locate to the parasitophorous vacuole, the parasite-derived organelle where replication and schizogony takes place (data not shown).

Gene knockouts using insertion and replacement strategies have revealed that both genes are necessary for LS development, as described below. Both proteins are normally expressed in spzs (data not shown), but uis3(-) and uis4(-) parasites develop normal spzs and these invade hepatocyte normally. However, uis3(-) and uis4(-) LS arrest in intermediate-LS development and do not produce late LS (data not shown). Therefore, both UIS3 and UIS4 have LS-specific gene functions. Remarkably, animals infected by natural bite or intravenously with doses of up to 10,000 spzs do not become patent, confirming that both genes play vital roles in successful completion of the *Plasmodium* life cycle (see Tables 1 and 2 below). Therefore, the first genetically attenuated LS has been successfully generated. Based on these discoveries, various other LS-up-regulated genes identified by microarray analysis are being tested for their importance in LS development. More LS-up-regulated genes are predicted to be essential for LS development (i.e., to possess LS-specific gene functions), especially uniquely expressed genes, given the remarkable capacity of the parasite to develop from a single spz to more than 10,000 daughter merozoites. Such LS-up-regulated genes can be similarly disrupted to produce additional live vaccine candidates, as described herein.

Exemplary methods for identifying and disrupting the function of a stage-specific gene function in other protozoan parasites are described in Examples 4-10.

In some embodiments, the invention provides a method for inducing an immune response in a vertebrate host against a protozoan parasite, wherein the wild-type parasite undergoes a plurality of asexual multiplications in the host, including a first multiplication of a first parasite stage to produce a second parasite stage that is associated with a secondary infection in the host. The method comprises administering to the host a live parasite that is genetically engineered to disrupt expression of a parasite gene that is upregulated in the first parasite stage and that is essential for the first multiplication to produce a second parasite stage that is responsible for the pathology that the immune response is designed to prevent or attenuate. Representative "first parasite stages" and the "second parasite stages" are the same as the primary infective stages and the secondary infective stages, respectively, in Table 1, above.

In some embodiments, the plurality of asexual multiplications are intracellular multiplications. Thus, the first parasite stage may multiply within a first host cell to produce a second parasite stage that can multiply within the second host cell. The "first host cell" and the "second host cell" generally refer to the cells infected by the first parasite stage and the second parasite stage, respectively. For example, in *Plasmodium*, the first host cell is a hepatocyte and the second host cell is an erythrocyte; in *Cryptosporidium*, the first host cell is an intestinal or respiratory epithelial cell and the second host cell is a digestive system epithelial cell; in *Eimeria*, the first host cell and the second host cell are intestinal epithelial cells; in *Neospora* and *Toxoplasma*, the first host cell is an intestinal epithelial cell and the second host cell is a cell of the central nervous system or the musculoskeletal system; in *Sarcocystis*, the first host cell is an intestinal epithelial cell and the second host cell is a cell of the central nervous system, the musculoskeletal system, or a vascular endothelial cell; in *Leucocytozoon*, the first host cell is a liver Kupfer cell and the second host cell is an erythrocyte, a parenchymal liver cell, or a brain, lung, or kidney lymphoid cell; in *Babesia*, the first host cell and the second host cell are erythrocytes; in *Trypanosoma cruzi*, the first host cell is a macrophage and the second host cell is a cardiac, glial, or intestinal cell; and in Leishmania, the first host cell is a macrophage and the second host cell is a macrophage or phagocyte.

In other embodiments, the protozoan parasite undergoes a phenotypic transformation and/or asexual reproduction within the vertebrate host. Thus, some protozoan parasites may not undergo a plurality of multiplications in the vertebrate host. Specifically, *Trypanosoma* and *Leishmania* parasites are transmitted to the vertebrate host as a non-replicative first parasite stage (e.g., metacyclics in *Trypanosoma* and promastigotes in *Leishmania*). For example, *Trypansoma brucei* parasites are transmitted from the insect host to the vertebrate host as metacyclic forms that travel through the lymphatic system to the bloodstream, where they transform into phenotypically distinct Long Slender (LS) bloodstream forms. The LS bloodstream forms circulate and amass in tissues such as the heart and brain to cause the characteristic pathologies of human African Trypanosomiasis and Nagana. Therefore, a first parasite stage may phenotypically transform into a second parasite without any cell division. The phenotypic transformation may occur intracellularly or extracellularly. Moreover, in some embodiments, the protozoan parasite does not multiply intracellularly within the vertebrate host. For example, *Trypansoma brucei* parasites multiply extracellularly.

Irrespective of whether the first parasite stage is a replicative stage, or whether the protozoan parasite multiplies intracellularly, a stage-specific gene function is disrupted that is upregulated in the first parasite stage and that is necessary for the transformation of the first parasite stage into the second parasite stage that is associated with secondary infection and pathology.

Methods for identifying genes that are upregulated in the first parasite stage and that are essential to produce the second parasite stage, and methods for disrupting the function of such genes are as herein and in the literature.

The following examples illustrate representative embodiments now contemplated for practicing the invention, but should not be construed to limit the invention.

EXAMPLE 1

This Example describes a method for inducing an immune response by administering live *Plasmodium* parasites that are genetically engineered to disrupt the function of the LS-specific gene, UIS3 (Mueller et al. (2005) *Nature* 433:164-7, which is hereby incorporated by reference; see also Ménard (2005) *Nature* 433:113-4; Waters et al. (2005) *Science* 307: 528-30).

Figure 2:
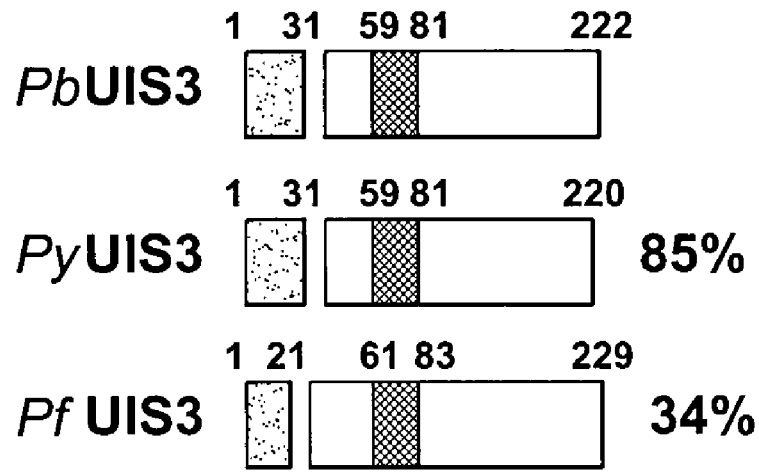

We hypothesized that inactivation of UIS genes for which expression is restricted to pre-erythrocytic stages could lead to attenuation of the liver stage parasite, without affecting the blood stages or mosquito stages. We focused on a gene called UIS3 that encodes a small conserved transmembrane protein (FIG. 2). UIS3 was expressed in infectious sporozoites (Kaiser et al. (2004) *Mol. Microbiol.* 51:1221-32) and we determined that it was also expressed after sporozoite infection of livers in vivo (data not shown). UIS3 of rodent malaria parasites (accession number EAA22537) and UIS3 of the human malaria parasite *P. falciparum* (Pfl3_0012) show 34% amino acid sequence identity (FIG. 2). Because the rodent malaria parasites such as *P. berghei* (Pb) are excellent models to study *Plasmodium* liver stage and pre-erythrocytic immunity we pursued investigation of UIS3 in this species.

Figure 3:
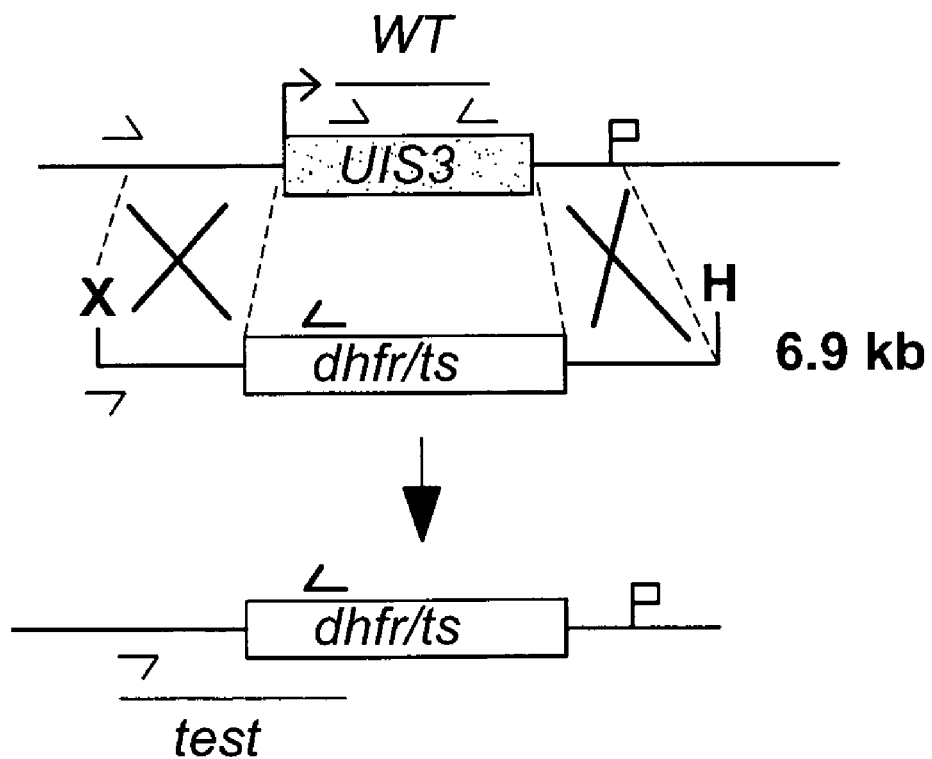

The endogenous PbUIS3 gene was deleted using an established replacement strategy (Thathy & Méard (2002) Gene targeting in *Plasmodium berghei*, in *Methods in Molecular Medicine*, Vol. 72: Malaria Methods and Protocols (Doolan, ed.), Humana Press) (FIG. 3). After transfection, parental blood stage parasites were used to obtain clonal parasite lines designated uis3(-) that contained exclusively the predicted locus deletion (data not shown). uis3(-) parasites showed normal asexual blood stage growth and normal transmission to the Anopheles mosquito vector (data not shown). Within the mosquito uis3(-) sporozoites developed normally in midgut oocycts and infected the salivary glands in numbers comparable to wildtype (WT) sporozoites (data not shown). Reverse transcriptase (RT)-PCR confirmed lack of UIS3 expression in uis3(-) sporozoites (data not shown). uis3(-) sporozoites showed typical gliding motility, a form of substrate-dependant locomotion that is critical for sporozoite transmission and infectivity (Sibley (2004) *Science* 304:248-53) (data not shown). They also retained their host cell invasion capacity of cultured hepatoma cells at levels comparable to WT parasites (data not shown).

Intracellular uis3(-) sporozoites initiated the typical cellular transformation process that leads to de-differentiation of the banana-shaped elongated sporozoite to a spherical liver trophozoite (Meis et al. (1983) *Nature* 302:424; Meis et al. (1985) *Cell Tissue Res.* 241:353-60) (data not shown). In marked contrast, uis3(-) parasites showed a severe defect in their ability to complete transformation into liver trophozoites (data not shown). Only a small fraction of uis3(-) parasites developed into spherical early liver stages, that in addition appeared consistently smaller than the corresponding WT forms. Consequently, mutant parasites lacked the capacity to progress to mature liver schizonts (data not shown). Based on this extreme developmental defect observed in vitro, we next tested if uis3(-) sporozoites had lost their capacity to progress through liver stage development and lead to blood stage infections in vivo. Indeed, intravenous injection of up to 100,000 uis3(-) sporozoites failed to induce blood stage parasitemia in young Sprague/Dawley rats which are highly susceptible to P. berghei sporozoite infections (data not shown). Control WT sporozoites induced blood stage parasitemia in rats between 3-4 days after injection.

Thus, the observed phenotypic characteristics of uis3(-) parasites, i.e., their ability to invade hepatocytes and their defect in complete liver stage development allowed us to test them as a whole organism vaccine in a mouse/sporozoite challenge model. We intravenously immunized mice with uis3(-) sporozoites using different prime-boost regimens and subsequently challenged the mice by intravenous injection of infectious WT sporozoites (Table 2). Protection was evaluated by blood smear to detect the development of blood stage parasitemia starting two days after sporozoite challenge, the most stringent readout for sterile protection against malaria infection. Priming with 50,000 uis3(-) sporozoites followed by 2 boosts with 25,000 uis3(-) sporozoites completely protected all immunized mice against a challenge with 10,000 WT sporozoites given 7 days after the last boost (Table 2). Complete sterile protection against the same sporozoite challenge dose was also achieved with a similar prime-2 boost protocol using 10,000 uis3(-) sporozoites (Table 2). We next immunized mice using the same prime-boost protocols but challenged with WT sporozoites 4 weeks after the last boost. None of the challenged mice developed blood stage infections and thus enjoyed protracted sterile protection (Table 2). Protracted protection was confirmed by a re-challenge experiment where protected animals were challenged again with a high inoculum of 50,000 infectious sporozoites after two months. All animals remained completely protected. Mice immunized with uis3(-) sporozoites were also completely protected against re-challenge by infectious mosquito bite (Table 2). To determine the level of protection with a reduced immunization dose we tested a prime-single boost protocol with 10,000 uis3(-) sporozoites. Seven out of ten animals enjoyed complete protection, while the remaining three animals became patent after a long delay in patency. Next, a subset of immunized mice was challenged by direct inoculation with blood stage parasites. All animals developed blood stage parasitemia two days after challenge, indicating that the observed protective immunity is not acting against blood stages and thus was specific against pre-erythrocytic stages. Finally, to evaluate a more vaccine-relevant delivery route we immunized mice subcutaneously using a prime-2 boost protocol with 50,000 uis3(-) and 25,000 uis3(-) sporozoites, respectively. All mice were completely protected against subsequent intravenous WT sporozoite challenge.

Our results show that it is possible to develop genetically modified malaria parasites that are completely attenuated at the liver stage, which normally establishes infection of the mammalian host after mosquito transmission. This attenuation was achieved by deletion of a single parasite gene, UIS3. Although UIS3 function remains unknown, uis3(-) parasites clearly lacked the ability to compensate for its loss. The protracted sterile protection against malaria that we observed after immunization with uis3(-) sporozoites in the mouse/sporozoite challenge model provides proof of principle that a genetically modified malaria vaccine is feasible. We identified a UIS3 orthologue (accession number PF13_0012) in the genome of the most lethal human malaria parasite P. falciparum. This will allow us to create a genetically attenuated uis3(-) human parasite that can be tested as a vaccine in human/sporozoite challenge models. Together our findings lead the way to the development of a genetically attenuated, protective whole organism malaria vaccine that prevents natural infection by mosquito bite.

Methods

*Plasmodium berghei* transfection. For replacement of PbUIS3 two fragments were amplified using primers: UIS3rep1for (5' GGGTACCCGCATTAGCATAACATCT-CATTGG 3') (SEQ ID NO: 1) and UIS3rep2rev (5' CAAGCTTGCTTTCATATATTTGTTATTTGTC 3') (SEQ ID NO: 2) for the 800 bp 3' fragment; and: UIS3rep3for (5' GGAATTCCCATATGTTTGTGTAACATC 3') (SEQ ID NO: 3) and UIS3rep4rev (5' CTCTAGAGTGTGCTTAAAT-GTTTCTTTAAAC 3') (SEQ ID NO: 4) for the 760 bp 5' fragment using *P. berghei* genomic DNA as template. Cloning into the *P. berghei* targeting vector (Thathy & Ménard (2002) Gene targeting in *Plasmodium berghei*, in *Methods in Molecular Medicine*, Vol. 72: Malaria Methods and Protocols (Doolan, ed.), Humana Press) resulted in plasmid pAKM19. To obtain clonal parasite populations, limited dilution series and i.v. injection of one parasite into 15 recipient NMRI mice each was performed. For RT-PCR analysis we dissected $6 \times 10^5$ uis3(-) and $6 \times 10^5$ WT salivary gland sporozoites and isolated polyA$^+$ RNA using oligo dT-columns (Invitrogen). For cDNA-synthesis and amplification we performed a two step-PCR using random decamer primers (Ambion) and subsequent standard PCR reactions.

Phenotypical analysis of uis3(-) parasites. *Anopheles stephensi* mosquito rearing and maintenance were under a 14 h light/10 h dark cycle, 75% humidity and at 28° C. or 20° C., respectively. For each experiment, mosquitoes were allowed to blood-feed for 15 min. on anaesthetized NMRI-mice that had been infected with wild-type *P. berghei* NK65 or the uis3(-) clone and were assayed for a high proportion of differentiated gametocytes and microgametocyte-stage parasites capable of exflagellation. Mosquitoes were dissected at days 10, 14, and 17 to determine infectivity, midgut sporozoite and salivary gland sporozoite numbers, respectively. For analysis of sporozoite motility, sporozoites were deposited onto precoated (3% BSA/RPMI 1640) glass coverslips, fixed for 10 min at RT with 4% paraformaldehyde, and incubated using primary antibody against *P. berghei* circumsporozoite protein (anti-PbCSP) (Potocnjak et al. (1980) *J. Exp. Med.* 151:1504-13). To detect liver stages in hepatocytes, $10^3$ Huh7 cells were seeded in eight chamber slides and grown to semi-confluency. *P. berghei* sporozoites were added, incubated 90 min. at 37° C., and washed off. After 8, 12, 15, 24, 36 and 48 h, LS were revealed using primary antibodies against the *P. berghei* heat shock protein 70 (HSP70) (Tsuji et al. (1994) *Parasitol. Res.* 8016-21). To analyze sporozoite invasion a double staining protocol with anti-CSP antibody was used (Renia et al. (1988) *J. Immunol. Methods* 112:201-5). To determine the infectivity of clonal sporozoite populations in vivo young Sprague-Dawley rats were injected intravenously with 100 microliter sporozoite suspension in RPMI 1640. Parasitemia of the animals was checked daily by Giemsa-stained blood smears. The appearance of a single erythrocytic stage represents the first day of patency.

Immunization and parasite challenge experiments. For all experiments female C57BL/6 mice (Charles River Laboratories) at the age of 50 to 80 days were used. For immunization, uis3(-) sporozoites were extracted from salivary glands from infected mosquitoes. Typically, a single infected mosquito contained 20,000 uis3(-) sporozoites. Sporozoites were injected in a volume of 100 microliters intravenously into the tail vein or subcutanously into the neck of animals. Animals were immunized with a single dose of 1 or $5×10^4$ uis3(-) sporozoites, followed by two boosts of either 1 or $2.5×10^4$ uis3(-) sporozoites administered i.v. or s.c. The first boost was given 14 days following the immunization, with a second boost following 7 days thereafter, or at time intervals indicated. One set of animals was immunized followed by a single boost with $1×10^4$ uis3(-) sporozoites each. The animals were then monitored for the parasitemia by daily blood smears. All animals remained blood stage parasite-negative after the first immunization and subsequent boosts. Animals were challenged 7 days up to 1 month after receiving the last boost of uis3(-) sporozoites by intravenous or subcutanous injection of either $5×10^4$ or $1×10^4$ infectious *P. berghei* WT sporozoites. For each set of experiments, at least three naive animals of the same age group were included to verify infectivity of the sporozoite challenge dose. In each naive animal, parasitemia was readily detectable at days three to five after injection by Giemsa-stained blood smears. Protected animals were monitored for at least 14 days and typically up to 1 month. A re-challenge study was performed for one immunization experiment two months after the first challenge with a single dose of $5×10^4$ infective *P. berghei* WT sporozoites. To test whether uis3(-) immunized mice were protected against re-challenge by natural transmission 10 protected and 5 naive control mice were exposed for 10 min to 10 highly infected mosquitoes that contained an average of 40,000 WT salivary gland sporozoites each. Successful blood-feeding was confirmed by mosquito dissection after the challenge experiment.

To confirm stage-specificity of protection, an additional experiment was performed with 10 mice that were fully protected against a challenge with infective sporozoites. All immunized mice and three naive control mice were challenged by intravenous injection of $5×10^4$ *P. berghei* WT blood stage parasites. All mice were fully susceptible to blood stage inoculations with no differences in patency.

Results

Table 2 below shows that C57Bl/6 mice immunized with *P. berghei* uis3(-) sporozoites are completely protected against a challenge with WT *P. berghei* sporozoites.

TABLE 2

Protection of C57B1/6 Mice Immunized With uis3(-) Sporozoites

| Exp. | Immunization #'s uis3(-) spz. | Boosts: 1st/2nd numbers (day) | Challenge dose (timepoint) | # Protected/ # Challenged (pre-patency) |
|---|---|---|---|---|
| I. | 50,000 | 25,000 (d.14)/ 25,000 (d.21) | 10,000 spz. (d.7) | 10/10 (no infection) |
|  | 10,000 | 10,000 (d.14)/ 10,000 (d.21) | 10,000 spz. (d.7) | 10/10 (no infection) |
|  | — | — | 10,000 spz. | 0/9 (d.3) |
|  | 50,000 | 25,000 (d.34)/ 25,000 (d.45) | 10,000 spz. (d.30) | 5/5 (no infection) |
| II. | 10,000 | 10,000 (d.34)/ 10,000 (d.45) | 10,000 spz. (d.30) | 5/5 (no infection) |
|  | — | — | 10,000 spz. | 0/6 (d.4.5) |
| IIII. | 50,000 | 50,000 (d.14)/ 10,000 (d.21) | 10 inf. mosq. (d.38) | 5/5 (no infection) |
|  | 10,000 | 10,000 (d.14)/ 10,000 (d.21) | 10 inf. mosq. (d.38) | 5/5 (no infection) |
|  | — | — | 10 inf. mosq. | 0/5 (d.3) |
| IV | 10,000 | 10,000 (d.14)/— | 10,000 spz. (d.7) | 7/10 (d.8) |
|  | — | — | 10,000 spz. | 0/5 (d.3) |
| V. | 50,000 | 25,000 (d.14)/ 25,000 (d.21) | 10,000 blood st. (d.30) | 0/5 (d.2) |
|  | 10,000 | 10,000 (d.14)/ 10,000 (d.21) | 10,000 blood st. (d.30) | 0/5 (d.2) |
|  | — | — | 10,000 blood st. | 0/3 (d.2) |
| VVI. | 50,000 s.c. | 25,000 (d.11) s.c./ 25,000 (d.18) s.c. | 10,000 spz. (d.23) | 5/5 (no infection) |
|  | 50,000 s.c. | 25,000 (d.11) s.c./ 25,000 (d.18) s.c. | 50,000 spz. (d.23) | 5/5 (no infection) |
|  | — |  | 10,000 spz. | 0/6 (d.4.5) |

Notes: Mice were immunized with *P. berghei* uis3(-) sporozoites. Mice were challenged with infectious *P. berghei* WT sporozoites or blood stages. Mice were from the same age group (50-80 days old) and sporozoites were from the same mosquito batch. Timepoints in column 4 indicate the day of challenge after the final boost. The pre-patent period is defined as the time until the first appearance of a single erythrocytic stage in Giemsa-stained blood smears. Five mice of the Exp. I. group were re-challenged with one dose of 50,000 WT sporozoites 2 months after the first challenge and remained protected.

EXAMPLE 2

This Example describes a method for inducing an immune response by administering live *Plasmodium* parasites that are genetically engineered to disrupt the function of the LS-specific gene, UIS4 (Mueller et al. (2005) *Proc. Natl. Acad. Sci. U.S.A.* 102(8):3022-7, which is hereby incorporated by reference).

Here, we disrupted another *Plasmodium* protein with a critical function for complete liver stage development. UIS4

(upregulated in infective sporozoites gene 4) is expressed exclusively in infective sporozoites and developing liver stages. Targeted gene disruption of UIS4 in the rodent model malaria parasite *Plasmodium berghei* generated knockout parasites that complete the malaria life cycle until after hepatocyte invasion. UIS4 knockout parasites transform into early liver stages. However, they are severely impaired in further liver stage development and can only initiate blood stage infections when inoculated at high sporozoite doses. Immunization with UIS4 knockout sporozoites completely protects mice against subsequent infectious wildtype sporozoite challenge. After sporozoite invasion of hepatocytes, UIS4 localizes to the newly formed parasitophorous vacuole membrane that constitutes the parasite-host cell interface and extends as a tubo-vesicular network into the hepatocyte cytoplasm. Together our data demonstrate that depletion of UIS4 results in attenuated liver stage parasites. Genetically attenuated liver stages may induce immune responses, which inhibit subsequent infection of the liver with wildtype parasites.

Methods

Generation of uis4(-) parasites: Given that UIS4 is expressed in sporozoites but not in blood stages, we were able to pursue a targeted gene disruption at the blood stages to study the importance of UIS4 for the *Plasmodium* pre-erythrocytic life cycle stages. The endogenous PbUIS4 gene was disrupted using the above-described insertion and replacement strategies (Thathy & Ménard (2002) Gene targeting in *Plasmodium berghei*, in *Methods in Molecular Medicine*, Vol. 72: Malaria Methods and Protocols (Doolan, ed.), Humana Press) (data not shown). The parental blood stage population from the successful transfection was used for selection of clonal parasite lines carrying the gene disruption. We obtained insertion/disruption clones designated uis4(-) and replacement clones designated uis4REP(-) that contained exclusively the predicted mutant locus. The correct replacement event was confirmed by insertion-specific PCR (data not shown). To confirm PbUIS4 deficiency of the mutant parasites we performed RT-PCR and cDNA amplification using polyA$^+$ RNA from salivary gland sporozoites as templates (data not shown). Moreover, Western blot analysis of uis4REP(-) sporozoites did not detect PbUIS4 (data not shown).

*Plasmodium berghei* transfection and genotypic analysis: For gene targeting of PbUIS4 a 582 bp fragment was amplified using primers UIS4INTfor (5' CGGAATTCATCATAT-TACTAATTTTCGGGGG 3') (SEQ ID NO: 5) and UIS4INTrev (5' TCCCCGCGGTTATTCCATGT-TATAAACGTTATTTCC 3') (SEQ ID NO: 6) using *P. berghei* genomic DNA as template. Cloning into the *P. berghei* targeting vector (13) resulted in plasmid pAKM15. Parasite transformation and selection was performed as described previously (Thathy & Ménard (2002) Gene targeting in *Plasmodium berghei*, in *Methods in Molecular Medicine*, Vol. 72: Malaria Methods and Protocols (Doolan, ed.), Humana Press). Integration-specific PCR amplification of the uis4(-) locus was achieved using the following primers: test1, *T. gondii* DHFR-TS for (5' CCCGCACGGACGAATCCA-GATGG 3') (SEQ ID NO: 7) and UIS4 test rev (5' CCCAAGCTTAGTTTGCATATACGGCTGCTTCC 3') (SEQ ID NO: 8); test 2, UIS4 test for (5' CGGAATTCTG-GATTCATTTTTTGATGCATGC 3' (SEQ ID NO: 9) and T7 (5' GTAATACGACTCACTATAGGC 3') (SEQ ID NO: 10). For replacement of PbUIS4 two fragments 1 kb and 600 bp were amplified using primers UIS4rep1 for (5' GAATTCTG-GATTCATTTTTTGATGCATGC 3') (SEQ ID NO: 11) and UIS4rep2rev (5' GGGGTACCTTTATTCAGACG-TAATAATTATGTGC 3') (SEQ ID NO: 12) for the 1 kb fragment and UIS4rep3for (5' AAAACTGCAGATAAT-TCATTATGAGTAGTGTAATTCAG 3') (SEQ ID NO:13) and UIS4rep4rev (5' CCCCAAGCTTAAGTTTG-CATATACGGCTGCTTCC 3') (SEQ ID NO: 14) for the 600 bp fragment using P berghei genomic DNA as template. Cloning into the hDHFR targeting vector (de Koning-Ward et al. (2000) *Mol. Biochem. Parasitol.* 106:199-212) resulted in plasmid pAKM17. To detect UIS4 expression in WT and mutant *P. berghei* parasites, 1×10$^5$ salivary gland sporozoites were dissolved in 10 microliters SDS sample buffer. UIS4 was visualized on Western blots using the polyclonal UIS4 antisera (Kaiser et al. (2004) *Mol. Microbiol.* 51:1221-32) and horseradish peroxidase-coupled anti-rabbit IgG secondary antibody (Amersham). For RT-PCR analysis we dissected 8×10$^5$ uis4(-), 8×10$^5$ uis4REP(-) and 4×10$^5$ WT salivary gland sporozoites and isolated polyA$^+$ RNA using oligo dT-columns (Invitrogen). For cDNA synthesis and amplification we performed a two step-PCR using random decamer primers (Ambion) and subsequent standard PCR reactions.

Phenotypic analysis of uis4(-) parasites: Anopheles stephensi mosquitoes were raised under a 14 h light/10 h dark cycle at 20° C., 75% humidity and were fed on 10% sucrose solution. Blood-feeding and mosquito dissection was as described (Sultan et al. (1997) *Cell* 90:511-22). The number of sporozoites per infected mosquito was determined in a hemocytometer. To analyze sporozoite motility, sporozoites were deposited onto precoated glass coverslips and incubated using primary antibody against *P. berghei* circumsporozoite protein (anti-PbCSP) (Sultan et al. (1997) *Cell* 90:511-22). Bound antibody was detected using Alexa Fluor 488-conjugated anti-mouse antibody (Molecular Probes). To detect liver stages in hepatocytes, *P. berghei* sporozoites were added to subconfluent hepatocytes, incubated 2 h at 37° C., and washed off. After 12, 24, 36 and 48 h, liver stages were revealed using primary antibodies against parasite heat shock protein 70 (HSP70) and a secondary antibody conjugated with Alexa Fluor 488 (Molecular Probes). To analyze sporozoite invasion, 3×10$^4$ salivary gland sporozoites were added to subconfluent HepG2 cells and incubated for 90 min at 37° C. The ratio between intracellular and extracellular parasites was visualized using a double staining protocol with the anti-CSP antibody (Renia et al. (1988) *J. Immunol. Methods* 112:201-5) and confocal microscopy. To determine the infectivity of clonal sporozoite populations in vivo, C57/B16 mice were injected intravenously or subcutaneously with 100 microliters sporozoite suspension of WT parasites or knockout parasites in RPMI 1640. Parasitemia of the animals was checked daily by examination of a Giemsa-stained blood smear. The appearance of a single erythrocytic stage represents the first day of patency.

Immunization and parasite challenge experiments: For all experiments female C57BL/6 mice (Charles River Laboratories) aged between 50 and 80 days were used. For immunizations, uis4REP(-) sporozoites were extracted from the salivary glands from infected mosquitoes. Sporozoites were injected in a volume of 100 microliters intravenously into the tail vein of the animals. Animals were immunized with a single dose of 10,000 or 50,000 uis4REP(-) sporozoites, followed by two boosts of either 10,000 or 25,000 uis4REP(-) sporozoites adminstered i.v. The first boost was given 14 days following the immunization, with a second boost following 14 days thereafter. The animals were then monitored for parasitemia by daily blood smears. Only those animals that remained blood stage parasite-negative after the first immunization and subsequent boosts were exposed to a challenge with WT sporozoites. Animals were challenged 10 days after receiving the last boost of uis4REP(-) sporozoites by intravenous injection. All challenges consisted of 50,000 infective *P. berghei* WT sporozoites. For both sets of experiments, 5 naive animals were included to verify infectivity of the sporozoite challenge dose. In each naive animal, parasitemia was readily detectable at day 3 after injection. Starting from day 3 after WT challenge, the uis4REP(-) sporozoite-immunized animals were examined for detectable parasitemia in Giemsa-stained blood smears. Animals did not show a detectable parasitemia within 50 days following the challenge and were considered completely protected.

Results

Results are shown in Table 3 below. Immunization with uis4REP(-) sporozoites confers sterile protection. The fact that a large proportion of mice remained blood stage negative after inoculation with uis4REP(-) sporozoites allowed us to test if immunization with these attenuated sporozoites would protect mice against WT sporozoite challenge. Therefore, we immunized C57/bl6 mice with 3 doses of 50,000 or 10,000 uis4REP(-) sporozoites and subsequently challenged the mice, which remained blood stage negative after immunization, with 50,000 infectious WT sporozoites (Table 3). None of the immunized mice developed blood stage infections after challenge and therefore enjoyed complete, sterile protection. Naive mice that were challenged with 50,000 WT sporozoites developed blood stage infections 3 days after inoculation.

Table 3 shows that C57B1/6 mice immunized with uis4REP(-) sporozoites are completely protected against a challenge with WT sporozoites.

TABLE 3

Protection of C57B1/6 Mice Immunized With uis4(-) Sporozoites

| Immunization (uis4REP(-) spz.) | Boosts (days after immun./# of spz.) | # Protected/# Challenged (prepatency) |
|---|---|---|
| 50,000 | $1^{st}$ (14/25,000), $2^{nd}$ (28/25,000) | 8/8 (no infection)[1] |
| none | none | 0/5 (day 3)[2] |
| 10,000 | $1^{st}$ (14/10,000), $2^{nd}$ (28/10,000) | 8/8 (no infection)[1] |
| none | none | 0/5 (day 3)[2] |

Notes:
[1] Immunized mice were challenged with 50,000 WT *P. berghei* sporozoites at day 38 after immunization. Mice were from the same age group and sporozoites were from the same mosquito batch. Blood smears were evaluated up to day 50 after challenge.
[2] Naive control mice were from the same age group and challenged with 50,000 WT *P. berghei* sporozoites.

Summary: Our findings demonstrate that malaria parasites harbor genes that are necessary only for successful completion of the pre-erythrocytic mammalian infection, within hepatocytes. We have shown that deletion of two genes individually effectively creates genetically attenuated malaria parasites that infect the liver of the mammalian host but are severely impaired in their ability to further progress through the life cycle and cause malaria disease. Other genes in the *Plasmodium* genome, which are critical for liver stage development, can be identified with the materials, methods, and procedures described herein.

Finally, we have shown here that immunization with UIS3 and UIS4 knockout sporozoites confers complete, sterile protection against subsequent infectious sporozoite challenge in a mouse model. This demonstrates the successful use of genetically attenuated *Plasmodium* parasites as live experimental vaccines. Genetically attenuated human *Plasmodium* parasites may be similarly prepared as whole organism vaccines against malaria.

EXAMPLE 3

This Example describes a representative method for making a UIS3-like knockout in *P. falciparum*.

The *P. falciparum* UIS3 gene is targeted for disruption by replacement via a well-established double-crossover recombination strategy (Thathy & Ménard (2002) Gene targeting in *Plasmodium berghei*, in Methods in Molecular Medicine, Vol. 72: Malaria Methods and Protocols (Doolan, ed.), Humana Press). The UIS3 locus is replaced by a fragment containing the 5' and 3' untranslated regions of the *P. falciparum* UIS3 open reading frame, each flanking the human dihydrofolate reductase (hdhfr) selectable marker. Sequence data for the *P. falciparum* UIS3 locus were obtained from the PlasmoDB database. The accession number for the coding sequence of *P. falciparum* UIS3 is PF13_0012 (12) and the location of the exon within chromosome 13 is 123930-124619 on the minus strand. The *P. falciparum* UIS3 rep1 fragment extends from nucleotides 124609-125594, and the rep2 fragment from 122872-123921.

PfUIS3 rep 1 and 2 fragments are amplified from *P. falciparum* 3D7 genomic DNA using Expand polymerase and the following primers: PfUIS3 rep1 forward 5'-GAG-TAATATAATGTGTAATGCATATGG-3' (SEQ ID NO:15) and reverse 5'-GAGACCTTCATTTCAAAAAGGAAG-3' (SEQ ID NO:16); PfUIS3 rep2 forward 5'-CAAAT-GAAAACTTGGAAATAATCAGACGAG-3' (SEQ ID NO:17) and reverse 5'-GTATTATGCTTAAATTG-GAAAAAAGTTTGAAG-3' (SEQ ID NO:18). The sizes of the rep1 and rep2 fragments amplified are 986 and 1051 base pairs, respectively. The PCR conditions are: one cycle of 94° C. for 3 min, followed by thirty cycles of 94° C. for 30 sec, 54.5° C. for 1 min, and 65° C. for 3 min.

The PCR products are digested and cloned into the pHTK (Duraising et al. (2002) Int. J. Parasitol. 32(1):81-9) vector. Rep1 was cloned into restriction sites BglII and SacII, and rep2 into EcoI and SfoI sites. The PfUIS3 replacement construct is sequenced to confirm correct cloning. Positive selection for transfected parasites carrying the dhfr gene is carried out with the drug WR99210. pHTK contains the gene for thymidine kinase, allowing for negative selection of parasites carrying the plasmid episomally.

A similar protocol may be used for making a knockout of any gene of interest in *P. falciparum* (for example, a UIS4-like gene, accession number NP_700638, PF10_0164), or for making a knockout of such LS-specific genes in other *Plasmodium* organisms. Genomic information, including genomic sequences, ESTs, annotations, automated predictions, SAGE tags, microarray data, mapping data, and open reading frames, for many Plasmodium organisms, including, for example, *P. falciparum, P. vivax, P. knowlesi, P. yoelii, P. chabaudi, P. reichenowi*, and *P. gallinaceum*, is readily available in public databases such as the National Center for Biotechnology Information, the Plasmodium Genome Database, and the Sanger Institute.

EXAMPLE 4

This Example describes a representative method for inducing an immune response in a vertebrate host against a *Toxoplasma* parasite by administering a live *Toxoplasma* parasite that is genetically engineered to disrupt the function of a stage-specific gene that is required by the parasite to establish a secondary infection in the vertebrate host.

Identification of Homologues of Plasmodium Genes in Toxoplasma: Toxoplasma and apicomplexan databases (see, e.g., ToxoDB and ApiDots) were analyzed by performing BLAST searches for homologues to UIS genes and genes expressed in sporozoite (S genes) identified in P. berghei (Matuschewski et al. (2002) J. Biol. Chem. 277:41948-53; Kaiser et al. (2004) Mol. Microbiol. 51(5):1221-32) and P. yoelii. Matches at a significance level of $E^{-5}$ were verified by reciprocal blast analysis on Plasmodium yoelii sequences. 7 Toxoplasma gondii orthologues or homologues of P. berghei UIS genes (UIS5, SEQ ID NO:19; UIS11, SEQ ID NO:20; UIS12, SEQ ID NO:21; UIS14, SEQ ID NO:22; UIS22, SEQ ID NO:23; UIS24, SEQ ID NO:24; and UIS30, SEQ ID NO:25) and 7 Toxoplasma gondii orthologues or homologues of P. berghei S genes (S1, SEQ ID NO:25; S8, SEQ ID NO:27; S9, SEQ ID NO:28; S13, SEQ ID NO:29; S15, SEQ ID NO:30; S18, SEQ ID NO:31; and S25, SEQ ID NO:32) were identified.

Amplification of Toxoplasma Genes: Sequence data derived from, for example, the BLAST searches, is used to design oligonucleotides for PCR amplification of stage-specific genes (e.g., homologues of Plasmodium UIS and S genes) from genomic DNA (gDNA) from Toxoplasma gondii. gDNA is extracted from either parasites in culture (Roos et al. (1994) Meth. Cell Biol. 45:27-63; Jerome et al. (1998) Infect. Immun. 66(10):4838-44; Ferguson (2004) Int. J. Parasitol. 34(3):347-60) or sporozoites isolated from experimentally infected cats (Speer et al. (1995) Mol. Biochem. Parasitol. 75:75-86; Striepen et al. (2002) Proc. Natl. Acad. Sci. U.S.A. 99(9):6304-9; Dumetre & Darde (2004) J. Microbiol. Meth. 56:427-30). Methods for extraction of genomic DNA are well known in the literature (Striepen et al. (2002) Proc. Natl. Acad. Sci U.S.A. 99(9):6304-9). Toxoplasma stage-specific genes are amplified by standard PCR protocols. PCR products are cloned into appropriate plasmids, and analyzed by automated sequencing methods. Homologue sequences are compared to sequences obtained from PCR amplification, and analyzed for similarity, motifs, or errors. Genes are then cloned into expression vectors, for the purpose of obtaining proteins for antibody production for later analysis and storage, using standard methods in the art.

Analysis of Toxoplasma Gene Expression: To verify expression of candidate stage-specific genes in different life stages, and to identify other differentially expressed genes similar to Plasmodium UIS and S genes, RNA is isolated from various life stages of sporozoites, and mRNA is purified using standard methods. RNA extraction from excysted Toxoplasma sporozoites is purified as previously described (Cleary et al. (2002) Eukaryot. Cell 1(3):329-40). cDNA is constructed and used for analysis by differential display (Dzierszinski et al. (2001) J. Mol. Biol. 309(5):1017-27), Suppression Subtractive Hybridization (SSH) (Diatchenko et al. (1996) Proc. Natl. Acad. Sci. U.S.A. 93(12):6025-30; Jin et al. (1997) Biotechniques 23(6):1084-6; Diatchenko et al. (1999) Meth. Enzymol. 303:349-80; Matuschewski et al. (2002) J. Biol. Chem. 277:41948-53; Kaiser et al. (2004) Mol. Microbiol. 51(5):1221-32), or microarray analysis (Cleary et al. (2002) Eukaryot. Cell 1(3):329-40).

cDNA populations are also generated from RNAs at different life cycle stages to analyze mRNA expression. cDNAs are separated by agarose gel electrophoresis, and transferred to membranes. Homologues of Plasmodium UIS and S genes, or other identified candidate stage-specific genes, are used as probes and hybridized to membrane-bound cDNAs (Matuschewski et al. (2002) J. Biol. Chem. 277:41948-53). Genes known to be differentially expressed in Toxoplasma are used as controls, including SAG1 (Speer et al. (1995) Mol. Biochem. Parasitol. 75:75-86; Ferguson (2004) Int. J. Parasitol. 34(3):347-60), which is expressed solely in tachyzoites; BAG1 (Speer et al. (1995) Mol. Biochem. Parasitol. 75:75-86; Ferguson (2004) Int. J. Parasitol. 34(3):347-60, a bradyzoite specific gene; GRA7 (Speer et al. (1995) Mol. Biochem. Parasitol. 75:75-86), which is expressed in all life stages including sporozoites, tachyzoites, merozoites and bradyzoites; and SPOROSAG (Radke et al. (2004) Mol. Microbiol. 52(1):93-105), a sporozoite specific gene.

Alternatively or additionally, mRNA expression is analyzed by dot-blotting specific genes directly on membranes, and hybridizing with labeled life-cycle stage specific cDNA populations (Matuschewski et al. (2002) J. Biol. Chem. 277: 41948-53). Desired genes are identified and prepared for knockout constructs. Gene expression is also assayed at the protein level by Western blot analysis of homogenized parasites, using life cycle stage-specific antibodies.

Construction Of Targeting Plasmids: Toxoplasma gondii is a very well studied organism, and conducive to classical genetic as well as molecular biological experimentation. Gene knockout by homologous recombination is well documented and effective (Roos et al. (1994) Meth. Cell Biol. 45:27-63; Boothroyd et al. (1995) in Molecular Approaches to Parasitology, Wiley-Liss, Inc., pp. 211-25; Bohne et al. (1998) Mol. Biochem. Parasitol. 92:291-301; Kim & Weiss (2004) Int. J. Parasitol. 34:423-32). Gene silencing by RNA interference (Al-Anouti et al. (2003) Biochem. Biophys. Res. Commun. 302(2):316-23; Blackman (2003) Protist 154:177-80), anti-sense RNA, and even ribozymes (Sheng et al. (2004) Int. J. Parasitol. 34:253-63), has been demonstrated in T gondii. Any of these methods may be used for disrupting a stage-specific gene function for parasite attenuation.

To design targeting plasmids for gene replacement, primers specific to Toxoplasma gondii homologues (Mueller et al. (2005) Nature 433:164-7; Mueller et al. (2005) Proc. Natl. Acad. Sci. U.S.A. 102(8):3022-7) and other candidate stage-specific genes (such as, for example, tachyzoite expressed genes, Kaiser et al. (2004) Mol. Microbiol. 51(5):1221-32) may be used to amplify genes and flanking sequences from genomic DNA. At this point, genes of interested may be cloned into protein expression plasmids, and protein may be purified to produce monoclonal or polyclonal antibodies using standard methods in the art. There are several selectable marker/reporter systems available, including cat (chloramphenicol resistance), DHFR (pyrimethamine resistance), HXGPRT, and ble (phleomycin resistance) (Roos et al. (1994) Meth. Cell Biol. 45:27-63; Boothroyd et al. (1995) in Molecular Approaches to Parasitology, Wiley-Liss, Inc., pp. 211-25; Messina et al. (1995) Gene 165:213-7). Constructs include gene of interest flanking sequences separated by reporter genes, all cloned into an appropriate plasmid backbone (Thathy & Ménard (2002) Gene targeting in Plasmodium berghei, in Methods in Molecular Medicine, Vol. 72: Malaria Methods and Protocols (Doolan, ed.), Humana Press). Plasmids are transformed in E. coli, and DNA extracted and purified. Plasmid vectors are analyzed by restriction digest and sequence analysis. If inserts are in proper orientation, DNA is prepared for electroporation.

Electroporation of T. gondii Tachyzoites: Tachyzoites can be maintained in many mammalian cell types, including CHO, HeLa, LM, MDBK, Vero, and 3T3 cells; and parasites tend to infect monolayers better than suspension culture (Roos et al. (1994) Meth. Cell Biol. 45:27-63; Boothroyd et al. (1995) in Molecular Approaches to Parasitology, Wiley-Liss, Inc., pp. 211-25). For general cell culture, parasites are often grown in Human Fibroblast Foreskin (HFF) cells in MEM, 10% with heat-inactivated newborn bovine serum, at 37° C. in humidified $CO_2$ incubator. Tachyzoite culture and maintenance is well documented in the literature. Tachyzoites are pelleted by centrifugation and resuspended into electroporation buffer, for example as previously described (Roos et al. (1994) *Meth. Cell Biol.* 45:27-63). Parasites are re-pelleted, at a concentration of approximately $3.3 \times 10^7$/mL in 300 microliters and are transferred to an electroporation cuvette (Roos et al. (1994) *Meth. Cell Biol.* 45:27-63). The cuvette is left undisturbed at room temperature for 15 minutes. Parasites are inoculated into a flask containing confluent HFF cells in 50 mL of medium with dialyzed serum. Other optimized methods for transfection may be used.

*T. gondii* Selection and Cloning: Drug selection is started either immediately or up to 24 hours post electroporation. Once parasites have depleted the host cell monolayer, tachyzoites are filter-purified and inoculated in 96-well plates for cloning by limiting dilution, under drug pressure. Drug dosage and duration are dependent upon the reporter system used (see, e.g., Roos et al. (1994) *Meth. Cell Biol.* 45:27-63; Boothroyd et al. (1995) in *Molecular Approaches to Parasitology*, Wiley-Liss, Inc., pp. 211-25; Messina et al. (1995) *Gene* 165:213-7; Bohne et al. (1998) *Mol. Biochem. Parasitol.* 92:291-301; Donald et al. (2002) *Eukarot. Cell* 3(1):317-28).

Phenotypic Analysis of *T. gondii*: To assess effects on sporozoites stages, tachyzoites are either fed to or injected into kittens. Feces is checked daily for shedding of oocysts, by Janeckso-Urbanyi flotation technique (Roos et al. (1994) *Meth. Cell Biol.* 45:27-63; Innes (1997) *Comp. Immun. Microb. Infect. Dis.* 20(2):131-8; Bohne et al. (1998) *Mol. Biochem. Parasitol.* 92:291-301; Jerome et al. (1998) *Infect. Immun.* 66(10):4838-44; Dumetre & Darde (2004) *J. Microbiol. Meth.* 56:427-30).

Oocysts are purified by sucrose flotation of cat feces, for additional purification, a cesium-chloride gradient may be used (Dumetre & Darde (2004) *J. Microbiol. Meth.* 56:427-30). Sporulated oocysts can be purified by centrifugal elutriation on a Beckman JE-6B elutriation system using a 4.8 mL Sanderson elutriation chamber (Dumetre & Darde (2004) *J. Microbiol. Meth.* 56:427-30) or an equivalent system. Oocysts are then pelleted, washed in PBS, resuspended in 10% Clorox in PBS for one hour, then pelleted again and washed in Hank's balanced salt solution. Oocysts are then vortexed with glass beads until sporocysts are released and then sporozoites excysted by treatment with iodixanol and purified by percoll gradient (Roos et al. (1994) Meth. Cell Biol. 45:27-63; Speer et al. (1995) *Mol. Biochem. Parasitol.* 75:75-86; Dumetre & Darde (2004) *J. Microbiol. Meth.* 56:427-30). Sporozoites are suspended in culture medium (Roos et al. (1994) *Meth. Cell Biol.* 45:27-63), and inoculated into cultured cells.

To ensure gene knockout effect, wild type and knockout tachyzoites and sporozoites are tested by RT-PCR analysis for transcript and western blot analysis for protein. RT-PCR will utilize previously produced oligonucleotides, and antibodies previously produced for Western Blot Analysis (Mueller et al. (2005) *Proc. Natl. Acad. Sci. U.S.A.* 102(8):3022-7). Wild type and knockout sporozoites are tested for motility, and attachment on semi-confluent HFF cells. These can be visualized by antibodies to sporozoite proteins, coupled with fluorescent secondary antibodies and visualized by fluorescent microscopy. Infectivity of sporozoites can be determined by injection of sporozoites directly into mice, rats or sheep (Innes (1997) *Comp. Immun. Microb. Infect. Dis.* 20(2):131-8; Blackman (2003) *Protist* 154:177-80). Sporozoite development into tachyzoites is monitored, as well as tachyzoite infectivity (Jerome et al. (1998) *Infect. Immun.* 66(10):4838-44).

Immunization and Challenge: A mouse model of *Toxoplasma* is available (Innes (1997) *Comp. Immun. Microb. Infect. Dis.* 20(2):131-8). Immunization experiments can also be conducted in either rats or sheep (Innes (1997) *Comp. Immun. Microb. Infect. Dis.* 20(2):131-8). Appropriate vaccine and boost dosages are determined from comparable studies of currently available live attenuated temperature-sensitive *Toxoplasma* vaccines. Methods of vaccination may include intravenous, subcutaneous as well as oral administration of oocysts, sporozoites or tachyzoites, in appropriate, immune-stimulating adjuvants. Animals are then challenged by either injection of sporozoites or feeding with infected rodents/tissue (Roos et al. (1994) *Meth. Cell Biol.* 45:27-63; Boothroyd et al. (1995) in *Molecular Approaches to Parasitology*, Wiley-Liss, Inc., pp. 211-25). Animal are then monitored for oocyst shedding and anti-Toxoplasma antibody production for several months, and re-challenged periodically.

EXAMPLE 5

This Example describes a representative method for inducing an immune response in a vertebrate host against a *Neospora* parasite by administering a live *Neospora* parasite that is genetically engineered to disrupt the function of a stage-specific gene that is required by the parasite to establish a secondary infection in the vertebrate host.

Identification of Homologues of *P. berghei* Genes in *Neospora: Neospora* and apicomplexan databases (see, e.g., ToxoDB; ApiDots; Li et al. (2004) *Nucl. Acids Res.* 32(Database Issue):D326-8) were analyzed by performing BLAST searches for homologues to UIS genes and genes expressed in sporozoite (S genes) identified in *P. berghei*(Matuschewski et al. (2002) *J. Biol. Chem.* 277:41948-53; Kaiser et al. (2004) *Mol. Microbiol.* 51(5):1221-32) and *P. yoelii*. Matches at a significance level of $E^{-5}$ were verified by reciprocal blast analysis on *Plasmodium yoelii* sequences. 2 *Neospora canium* orthologues of *P. berghei* UIS genes (UIS5, SEQ ID NO:33; and UIS24, SEQ ID NO:35) and 4 *Neospora canium*orthologues of *P. berghei* S genes (S6, SEQ ID NO:35; S8, SEQ ID NO:36; S13, SEQ ID NO:37; and S15, SEQ ID NO:38) were identified.

Amplification of *Neospora* Genes: Sequence data derived from, for example, the BLAST searches, is used to design oligonucleotides for PCR amplification of stage-specific genes (e.g., homologues of *Plasmodium* UIS and S genes) from genomic DNA (gDNA) from *Neospora caninum* or other species. gDNA is extracted from either parasites in culture, or sporozoites isolated from experimentally infected animals (Bell & Randford-Cartwright (2002) *Trends Parasitol.* 18(8):337-42; Risco-Castillo et al. (2004) *J. Parasitol.* 90(3):466-70; Ramamoorthy et al. (2005) *Vet. Parasitol.* 127:111-14). Methods for extraction of genomic DNA are well known in the literature (Donald et al. (2002) *Eukaryot. Cell* 3(1):317-28; Cho et al. (2004) *J. Parasitol.* 90(2):278-85). *Neospora* stage-specific genes are amplified by standard PCR protocols (Birkenheuer et al (2003) *J. Clin. Biol.* 41(9):4172-7; Siverajah et al. (2003) *Parasitol.* 126(Pt. 6):561-9), and products are cloned into appropriate plasmids, and analyzed by automated sequencing methods. Homologue sequences are compared to sequences obtained from PCR amplification, and analyzed for similarity, motifs, or errors. Genes are then cloned into expression vectors, for the purpose of obtaining proteins for antibody production for later analysis and storage, using standard methods in the art.

Analysis of *Neospora* Gene Expression: To verify expression of candidate stage-specific genes in different life stages, and to identify other differentially expressed genes similar to *Plasmodium* UIS and S genes, RNA is isolated from various life stages of sporozoites, and mRNA is purified by standard methods (Howe & Sibley (1997) *Methods* 13(2):123-33; Bell & Ranford-Cartwright (2002) *Trends Parasitol.* 18(8):337-42; Cho et al. (2004) *J. Parasitol.* 90(2):278-85). cDNA libraries are constructed (Ellis et al. (2002) *Parasitol.* 120 (Pt. 4):383-90) and used for analysis by differential display, Suppression Subtractive Hybridization (SSH) (Diatchenko et al. (1996) *Proc. Natl. Acad. Sci. U.S.A.* 93(12):6025-30; Jin et al. (1997) *Biotechniques* 23(6):1084-6; Diatchenko et al. (1999) *Meth. Enzymol.* 303:349-80; Matuschewski et al. (2002) *J. Biol. Chem.* 277:41948-53; Kaiser et al. (2004) *Mol. Microbiol.* 51(5):1221-32), or microarray analysis (Cleary et al. (2002) *Eukaryot. Cell* 1(3):329-40; (Boothroyd et al. (2003) *Trends Parasitol.* 19(10):470-6; Llinas & DeRisi (2004) *Curr. Op. Microbiol.* 7(4):382-7).

cDNA populations are also generated from RNAs at different life cycle stages to analyze mRNA expression (Ellis et al. (2002) *Parasitol.* 120 (Pt. 4):383-90). cDNAs are separated by agarose gel electrophoresis, and transferred to membranes. Homologues of *Plasmodium* UIS and S genes, and other identified candidate stage-specific genes, are used as probes and hybridized to membrane-bound cDNAs (Matuschewski et al. (2002) *J. Biol. Chem.* 277:41948-53). Genes known to be differentially expressed in *Neospora* are used as controls, including NcSAG, a tachyzoite specific protein (Tuney et al. (2002) *J. Parasitol.* 88(6):1095-9); NcBAG1, a bradyzoite specific protein (Vonlaufen et al. (2004) *Infect. Immun.* 72(1):576-83); and *Neospora* orthologues of SPOROSAG, a sporozoite-specific protein in *Toxoplasma* (Radke et al. (2004) *Mol. Microbiol.* 52(1):93-105).

Alternatively or additionally, mRNA expression is analyzed by dot-blotting specific genes directly on membranes, and hybridizing with labeled life-cycle stage specific cDNA populations (Matuschewski et al. (2002) *J. Biol. Chem.* 277: 41948-53). Desired genes are identified and prepared for knockout constructs. Gene expression is also assayed at the protein level by Western blot analysis of homogenized parasites, using life cycle stage-specific antibodies.

Disruption of *Neospora* Genes: Drawing on the similarities between *Neospora* and *Toxoplasma*, document methods of gene inactivation in *Neospora* using targeting vectors designed for *Toxoplasma* have been documented (Howe & Sibley (1997) *Methods* 13(2):123-33; Beckers et al (1997) *Mol. Biochem. Parasitol.* 89:209-23; U.S. Pat. No. 5,976,553; U.S. Pat. No.5,955,333). Flanking sequences and genes to *Neospora tachyzoite* or *Neospora* UIS and S homologues, and other candidate stage-specific genes, are amplified from genomic DNA with specifically designed primers (Mueller et al. (2005) *Nature* 433:164-7; Mueller et al. (2005) *Proc. Natl. Acad. Sci. USA.* 102(8):3022-7). Genes are cloned into protein expression vectors and protein is purified for antibody production for Western blot analysis or immunofluorescence studies. Flanking sequences are cloned into Toxoplasma and/ or Neospora expression vectors and transformed into *E. coli*. DHFR is a common selectable marker with very high efficiency, however, alternate selectable markers such as ble, or cat can be used (Howe & Sibley (1997) *Methods* 13(2):123-33). DNA is extracted, purified, and plasmid sequences are analyzed. DNA is prepared for electroporation using previously described methods (Howe & Sibley (1997) *Methods* 13(2):123-33). Drug selection is started either immediately or up to 24 hours post electroporation. Drug dosages are dependent on selectable marker chosen, but details are provided in the literature (U.S. Pat. No. 5,976,553).

Phenotypic Analysis of *Neospora*: Tachyzoites are used to infect fresh HHF monolayers and assayed for infectivity, motility and development.

Immunization and Challenge: Tachyzoites are used to infect an animal model, which can include gerbils, dogs, or cows (Buxton et al. (2002) *Trends Parasitol.* 18(12):546-52; Ramamoorthy et al. (2005) *Vet. Parasitol.* 127:111-14). Passage through dogs will yield infectious oocysts, which are isolated from feces as detailed in the literature. Oocysts are purified and used to infect a new animal (Innes et al. (2002) *Trends Parasitol.* 18(11):497-504). Vaccination prime and boost doses will follow those cited in the literature, and animals will be screened for the presence of anti-neospora antibodies and parasites in the blood (Fernandes et al. (2004) *Vet. Parasitol.* 123(1-2):33-40).

EXAMPLE 6

This Example describes a representative method for inducing an immune response in a vertebrate host against a Eimeria parasite by administering a live *Eimeria* parasite that is genetically engineered to disrupt the function of a stage-specific gene that is required by the parasite to establish a secondary infection in the vertebrate host.

Identification of Homologues of *P. berghei* Genes in *Eimeria*: *Eimeria* and apicomplexan databases (see, e.g., ToxoDB, ApiDots; Li et al. (2004) *Nucl. Acids Res.* 32(Database Issue): D326-8) were analyzed by performing BLAST searches for homologues to UIS genes and genes expressed in sporozoite (S genes) identified in *P. berghei* (Matuschewski et al. (2002) *J Biol. Chem.* 277:41948-53; Kaiser et al. (2004) *Mol. Microbiol.* 51(5):1221-32) and *P. yoelii*. Matches at a significance level of $E^{-5}$ were verified by reciprocal blast analysis on *Plasmodium yoelii* sequences. 6 *Elmeria tenella* orthologues of *P. berghei* UIS genes (UIS5, SEQ ID NO:39; UIS12, SEQ ID NO:40; UIS14, SEQ ID NO:41; UIS17, SEQ ID NO:42; UIS21, SEQ ID NO:43; and UIS24, SEQ ID NO:44) and 2 *Eimeria tenella* orthologues of *P. berghei* S genes (S8, SEQ ID NO:45; S15, SEQ ID NO:46) were identified.

Amplification of *Eimeria* Genes: Sequence data derived from, for example, the BLAST searches, is used to design oligonucleotides for PCR amplification of stage-specific genes (e.g., homologues of *Plasmodium* UIS and S genes) from *Eimeria tenella*. Oocysts are purified and sporozoites excysted as previously described (White & Radke (1997) *Methods* 13:158-70). Methods of genomic DNA extraction from various *Eimeria* life stages have also been described (Cai et al. (2003) *Gene* 321:39-46). *Eimeria* stage-specific genes are amplified by standard PCR methods and those previously described (White & Radke (1997) *Methods* 13:158-70). PCR products are cloned into appropriate plasmids, and analyzed by automated sequencing methods. Homologue sequences are compared to sequences obtained from PCR amplification, and analyzed for similarity, motifs, or errors. Genes are then cloned into expression vectors, for the purpose of obtaining proteins for antibody production for later analysis, and storage.

Analysis of *Eimeria* Gene Expression: To verify expression of candidate stage-specific genes in different life stages, and to identify other differentially expressed genes similar to *Plasmodium* UIS and S genes, RNA is isolated from various life stages of sporozoites and merozoites, and MRNA is purified by standard methods. RNA extraction from excysted *Eimeria* sporozoites, sporozoite-infected monolayers, and cultured merozoites is well detailed in the literature (Abrahamsen et al. (1995) *J. Parasitol.* 81(1):107-9; White & Radke (1997) *Methods* 13:158-70; Jean et al. (2001) *Gene* 262(1-2): 129-36). cDNA is constructed and used for analysis by differential display (Abrahamsen et al. (1993) *Mol. Biochem. Parasitol.* 57(1):1-14; Abrahamsen et al. (1995) *Mol. Biochem. Parasitol.* 71(2):183-91; Jin et al. (1997) *Biotechniques* 23(6):1084-6), Suppression Subtractive Hybridization (SSH) (Diatchenko et al. (1996) *Proc. Natl. Acad. Sci. U.S.A.* 93(12):6025-30; Jin et al. (1997) *Biotechniques* 23(6):1084-6; Diatchenko et al. (1999) *Meth. Enzymol.* 303:349-80; Matuschewski et al. (2002) *J. Biol. Chem.* 277:41948-53; Kaiser et al. (2004) *Mol. Microbiol.* 51(5):1221-32), or Representational Difference Analysis (cDNA-RDA). cDNA microarray technology may be employed as well (Howbrook et al. (2003) *Drug Discov. Today* 9(14):642-51; Rhodius & LaRossa (2003) *Curr. Opin. Microbiol.* 6(2):114-9; Llinas & DeRisi (2004) *Curr. Op. Microbiol.* 7(4):382-7).

cDNA populations are also generated from RNAs at different life cycle stages to analyze mRNA expression. cDNAs are separated by agarose gel electrophoreses, and are transferred to membranes. Homologues of *Plasmodium* UIS and S genes, or other identified candidate stage-specific genes, are used as probes and hybridized to membrane-bound cDNAs (Matuschewski et al. (2002) *J. Biol. Chem.* 277:41948-53). Genes known to be differentially expressed in *Eimeria* are used as controls, including DMZ8, a known merozoites specific protein (Abrahamsen et al. (1995) *Mol. Biochem. Parasitol.* 71(2):183-91); Eb25/50, a sporozoite specific gene (Abrahamsen et al. (1993) *Mol. Biochem. Parasitol.* 57(1):1-14); and MZ2.5 which is expressed in sporozoites and merozoites (White & Radke (1997) *Methods* 13:158-70).

Alternatively or additionally, mRNA expression is analyzed by dot-blotting specific genes directly on membranes, and hybridizing with labeled life-cycle stage specific cDNA populations (Matuschewski et al. (2002) *J. Biol. Chem.* 277: 41948-53). Desired genes are identified and prepared for knockout constructs. Gene expression is also assayed at the protein level by Western blot analysis of homogenized parasites, using life cycle stage-specific antibodies.

Constructs and Transfection: A system of transient transfection in Eimeria sporozoites has been established (Kelleher & Tomley (1998) *Mol. Biochem. Parasitol.* 67(1):1-10). Characterization of suitable promoters and reporter systems yields appropriate vectors for stable transfections. Recently, an *Eimeria* genome project was initiated and has providing much-needed sequence information (Augustine et al. (2001) *Trends Parasitol.* 17(11):509-11). Sequence from the database can be used to determine proper flanking sequences for candidate stage-specific genes for chromosomal integration for either homologous recombination or RNAi techniques. The DHFR locus is very commonly used as a selectable marker and is well characterized in the apicomplexan literature (Roos et al. (1994) *Meth. Cell Biol.* 45:27-63; Black & Boothroyd (2000) *Microbiol Mol. Biol. Rev.* 64(3):607-23). This selectable marker yields parasites resistant to the drug pyrimethamine. Several alternate markers are available, including SHble, or ble, which provide resistance to phleomycin. SHble fused with LacZ was successfully used as a selectable marker vector in a quail cell system (Messina et al. (1995) *Gene* 165:213-7; Molina et la. (1995) C. R. Acad. Sci. III. 318(10):1021-7). Addition of a GFP (green fluorescent protein) fusion to the reporter gene-plasmid construct would enables FACS sorting of transfectants and expedites cloning.

To design targeting plasmids for gene replacement, primers specific to *Eimeria* 6UIS or S gene homologues (Mueller et al. (2005) *Nature* 433:164-7; Mueller et al. (2005) *Proc. Natl. Acad. Sci. U.S.A.* 102(8):3022-7) and other candidate stage-specific genes may be used to amplify genes and flanking sequences from genomic DNA. At this point, genes of interested may be cloned into protein expression plasmids, and protein may be purified to produce monoclonal or polyclonal antibodies using standard methods in the art (U.S. Pat. No. 5,976,553; U.S. Pat. No. 5,955,333; U.S. Pat. No. 6,228, 649). Constructs include gene of interest flanking sequences separated by reporter genes, all cloned into an appropriate plasmid backbone (Thathy & Ménard (2002) Gene targeting in *Plasmodium berghei*, in *Methods in Molecular Medicine*, Vol. 72: Malaria Methods and Protocols (Doolan, ed.), Humana Press). Plasmids are transformed in *E. coli*, and DNA extracted and purified. Plasmid vectors are analyzed by restriction digest and sequence analysis. If inserts are in proper orientation, DNA is prepared for electroporation (Kelleher & Tomley (1998) *Mol. Biochem. Parasitol.* 67(1): 1-10).

Electroporation of *Eimeria*: Oocysts are purified from infected animals as previously described (White & Radke (1997) *Methods* 13:158-70). Sporozoites are excysted and purified by anion-exchange chromatography as previously described (White & Radke (1997) *Methods* 13:158-70; Kelleher & Tomley (1998) *Mol. Biochem. Parasitol.* 67(1):1-10). Merozoites are generated by infecting monolayers of MDBK (bovine kidney cells) with sporozoites and maintained as detailed in (Abrahamsen et al. (1995) *J. Parasitol.* 81(1):107-9; White & Radke (1997) *Methods* 13:158-70). Electroporation conditions are as previously described (Kelleher & Tomley (1998) *Mol. Biochem. Parasitol.* 67(1):1-10) and optimized as necessary. Drug selection is started either immediately or up to 24 hours post electroporation. Drug dosage and duration are dependent upon which reporter system is used.

Phenotypic Analysis of *Eimeria*: To assess effects on other life cycle stages, wild type and mutant sporozoites are passaged through chickens (or another animal model), and oocysts, sporocysts, sporozoites and merozoites are harvested and analyzed (White & Radke (1997) *Methods* 13:158-70). RT-PCR and western blot analysis of wild type and knockout *Eimeria* demonstrates gene disruption at both the transcript and protein level (White & Radke (1997) *Methods* 13:158-70). Sporozoites are tested for motility, on semiconfluent cells, and visualized by fluorescence microscopy using fluorescence-coupled secondary antibodies. Infectivity is determined by direct injection of sporozoites into appropriate animal model. Sporozoite development is carefully monitored.

Immunization and Challenge: Vaccination with oocysts, sporocysts or sporozoites (suspended in an appropriate adjuvant) can be administered orally (in feed or water) eye spray, subcutaneously, or in ovo in a chicken model system (Schering-Plough (2002) *Cocci-Forum*; Weber et al. (2003) *Poultry Sci.* 82(11):1701-7). If a sheep model is used, vaccination can be administered subcutaneously, as intravenous injection often results in animal mortality. Appropriate vaccine and boost dosages are modeled after current live attenuated vaccines (Barriga (1993) *Vet. Parasitol.* 55:29-55; Augustine et al. (2001) *Trends Parasitol.* 17(11):509-11; Brake (2002) *Int. J. Parasitol.* 32:509-15; Min et al. (2004) *J. Vet. Sci.* 5(4):279-88) and are optimized. Animals are then challenged by either direct injection, feeding or gavage, or exposure to infected animals or pens. Animals are monitored for oocyst shedding and anti-*Eimeria* antibody production for several days, and re-challenged periodically.

EXAMPLE 7

This Example describes a representative method for inducing an immune response in a vertebrate host against a Theileria parasite by administering a live *Theileria* parasite that is genetically engineered to disrupt the function of a stage-specific gene that is required by the parasite to establish a secondary infection in the vertebrate host.

Identification of Homologues of *Plasinodium* Genes in *Theileria: Theilera* and apicomplexan databases (available at the Wellcome Trust Sanger Institute, the TIGR database, and ApiDots) were analyzed by performing BLAST searches for homologues to UIS genes and genes expressed in sporozoite (S genes) identified in *P. berghei* (Matuschewski et al. (2002) *J. Biol. Chem.* 277:41948-53; Kaiser et al. (2004) *Mol. Microbiol.* 51(5):1221-32) and *P. yoelii*. Matches at a significance level of $E^{-5}$ were verified by reciprocal blast analysis on *Plasmodium yoelii* sequences. 6 *Theileria annulata* orthologues of *P. berghei* UIS genes (UIS5, SEQ ID NO:47; UIS11, SEQ ID NO:48; UIS22, SEQ ID NO:49; UIS23, SEQ ID NO:50; UIS24, SEQ ID NO:51; and UIS30; SEQ ID NO:52) and 4 *Theileria annulata* orthologues of *P. berghei* S genes (S5, SEQ ID NO:53; S13, SEQ ID NO:54; S18, SEQ ID NO:55; and S25, SEQ ID NO:56) were identified.

Amplification of *Theileria* Genes: Sequence data derived from, for example, the BLAST searches, is used to design oligonucleotides for PCR amplification of stage-specific genes (e.g., homologues of *Plasmodium* UIS and S genes) from genomic DNA (gDNA) from *Theileria parva, Theileria annulata*, and/or other strains of the parasite. gDNA is extracted as detailed in the literature (Katzer et al. (1994) *Mol. Biochem. Parasitol.* 67(1):1-10; Knowles et al. (1997) *Mol. Biochem. Parasitol.* 90(1):69-9; Caccio et al. (2000) *Int. J. Parasitol.* 30(11):1181-5; Nagore et al. (2004) *Int. J. Parasitol.* 34:1059-67; Nagore et al. (2004) *Vet. Parasitol.* 123(1-2):41-54) from parasites obtained from either cell culture, experimentally infected steer or ticks (Shkap & Pipano (2000) *Ann. N.Y. Acad. Sci.* 916:154-71; Shielsetal. (1992) *J. Cell Sci.* 101(Pt. 1):99-107; Shiels et al. (1998) Int. J. Parasitol. 28:1659-70; Schneider et al. (2004) Parasitol. Res. 94(6):405-15). *Theileria* stage-specific genes are amplified by standard PCR protocols. PCR products are cloned into appropriate plasmids, and analyzed by automated sequencing methods (Caccio et al. (2000) *Int. J. Parasitol.* 30(11):1181-5; Nagore et al. (2004) *Int. J. Parasitol.* 34:1059-67; Nagore et al. (2004) *Vet. Parasitol.* 123(1-2):41-54). Homologue sequences are compared to sequences obtained from PCR amplification, and analyzed for similarity, motifs, or errors. Genes are then cloned into expression vectors, for the purpose of obtaining proteins for antibody production for later analysis and storage, using standard methods in the art.

Analysis of *Theileria* Gene Expression: To verify expression of candidate stage-specific genes in different life stages, and to identify other differentially expressed genes similar to *Plasmodium* UIS and S genes, RNA is isolated from various life stages of sporozoites and merozoites, and mRNA is purified by standard methods (Somerville et al. (1998) *Vaccine* 16(6):569-75; Oura et al. (2001) *Exper. Parasitol.* 98:10-9). cDNA is constructed and used for analysis by differential display (Somerville et al. (1998) *Vaccine* 16(6):569-75; Oura et al. (2001) *Exper. Parasitol.* 98:10-9), Suppression Subtractive Hybridization (SSH) (Diatchenko et al. (1996) *Proc. Natl. Acad. Sci. U.S.A.* 93(12):6025-30; Jin et al. (1997) *Biotechniques* 23(6):1084-6; Diatchenko et al. (1999) *Meth. Enzymol.* 303:349-80; Matuschewski et al. (2002) *J. Biol. Chem.* 277:41948-53; Kaiser et al. (2004) *Mol. Microbiol.* 51(5):1221-32), or microarray analysis (Nene et al. (1992) *Mol. Biochem. Parasitol.* 51(1):17-27).

cDNA populations are also generated from RNAs at different life cycle stages to analyze mRNA expression. cDNAs are separated by agarose gel electrophoresis, and transferred to membranes. Homologues of *Plasmodium* UIS and S genes, and other identified candidate stage-specific genes, are used as probes and hybridized to membrane-bound cDNAs (Matuschewski et al. (2002) *J. Biol. Chem.* 277:41948-53). Genes known to be differentially expressed in *Theileria* will be used as expression controls and will include SPAG1 (Katzer et al. (1994) *Mol. Biochem. Parasitol.* 67(1):1-10) and p67 (Nene et al. (1992) *Mol. Biochem. Parasitol.* 51(1):17-27), which are sporozoite specific genes; hsp90 (Gerhards et al. (1994) *Mol. Biochem. Parasitol.* 68(2):235-46) and PIM (Nene et al. (1992) *Mol. Biochem. Parasitol.* 51(1):17-27), which are merozoite specific genes; and Tams (Gubbels et al. (2001) *Parasitol.* 123(Pt.6):553-61; Oura et al. (2001) *Exper. Parasitol.* 98:10-9), which is a major merozoite surface antigen.

Alternatively or additionally, mRNA expression is analyzed by dot-blotting specific genes directly on membranes, and hybridizing with labeled life-cycle stage specific cDNA populations (Matuschewski et al. (2002) *J. Biol. Chem.* 277:41948-53). Desired genes are identified and prepared for knockout constructs. Gene expression is also assayed at the protein level by Western blot analysis of homogenized parasites, using life cycle stage-specific antibodies.

Transfection and Targeting Vectors: Vectors for transfection into *Theileria annulata* sporozoites are constructed as previously described (Adamson et al. (2001) *Mol. Biochem. Parasitol.* 114:53-61). Using promoter sequences identified by Adamson et al, and any new potential promoter sequences now available from *Theileria* sequence databases (Davila et al. (2004) *Ann. N.Y. Acad. Sci.* 1026:41-6), vectors are constructed for gene replacement of target sporozoite-specific genes or *Theileria* homologues (U.S. Pat. No. 5,976,553; U.S. Pat. No. 5,955,333; U.S. Pat. No. 6,228,649). Primers designed to identify sporozoite/UIS homologues are used to amplify genes and flanking sequence from *Theileria* genomic DNA (Mueller et al. (2005) *Nature* 433:164-7; Mueller et al. (2005) *Proc. Natl. Acad. Sci. U.S.A.* 102(8):3022-7). Genes are cloned into protein expression vectors and protein purified for antibody production. Flanking sequences are cloned into targeting vectors along with appropriate selection markers including but not limited to CAT, or ble. Targeting vectors are transformed in competent *E. coli*, purified, and verified by sequence analysis. Sporozoite and bovine peripheral mononuclear cell (PBM) culture is well documented in the literature (Hall et al. (1999) *Trop. Med. Intl. Health* 4(9):A78-A84); Oura et al. (2001) *Exper. Parasitol.* 98:10-9; Schneider et al. (2004) *Parasitol. Res.* 94(6):405-15). Methods for transfection by lipid reagent and electroporation, with lipids providing greater yield of transfectants in sporozoites have also been described (Adamson et al. (2001) *Mol. Biochem. Parasitol.* 114:53-61). Both methods are employed for transfection and optimized. Drug selection is initiated at an appropriate time point post transfection. Cultures are cloned by limited dilution, and harvested for RNA and protein to verify gene knockout by RT-PCR and Western blot analysis.

Phenotypic Analysis of *Theileria*: Wild type and mutant sporozoites are passaged through a cow, and sporozoite development is analyzed. If merozoites are present, they are isolated and cultured for analysis. Sporozoite infectivity, motility and attachment are readily determined in vitro, on bovine PBMs. Passage through ticks yield oocysts, and provides insight into effects parasite life and sexual cycle.

Immunization and Challenge: Vaccine prime and boost doses with either sporozoites or oocysts are adjusted and modeled after published studies. Vaccines suspended in appropriate immune-stimulating adjuvants are administered via intramuscular or subcutaneous injections, or other routes yielding best immunity. Animals are screened for antibody production and infection upon challenge (Shkap & Pipano (2000) *Ann. N.Y. Acad. Sci.* 916:154-71; Barriga (1993) *Vet. Parasitol.* 55:29-55; Glass (2001) *Res. Vet. Sci.* 70:71-5; Marcotti et al. (2003) *Vaccine* 22:213-6). Challenge is by exposure to experimentally infected ticks, injection of infectious sporozoites, or exposure to endemic regions. Animals are also periodically re-challenged.

EXAMPLE 8

This Example describes a representative method for inducing an immune response in a vertebrate host against a *Babesia* parasite by administering a live *Babesia* parasite that is genetically engineered to disrupt the function of a stage-specific gene that is required by the parasite to establish a secondary infection in the vertebrate host.

Identification of Homologues of *Plasmodium* Genes in *Babesia*: *Babesia* and apicomplexan databases (available at the Wellcome Trust Sanger Institute and Apidots) are analyzed by performing BLAST searches for homologues to UIS genes and genes expressed in sporozoite (S genes) identified in *P. berghei* (Matuschewski et al. (2002) *J. Biol. Chem.* 277:41948-53; Kaiser et al. (2004) *Mol. Microbiol.* 51(5): 1221-32) and *P. yoelii*. Matches at a significance level of $E^{-5}$ are verified by reciprocal blast analysis on *Plasmodium yoelii* sequences.

Amplification of Babesia Genes: Parasites are obtained from either cell culture, from experimentally infected steer or ticks (Jones et al. (1997) *Int. J. Parasitol.* 27(12):1569-73; Schuster (2002) *Clin. Microbiol. Rev.* 15(3):365-73; Suarez et al. (2003) *Mol. Biochem. Parasitol.* 34:1177-84; Mosqueda et al. (2004) *Ann. N.Y. Acad. Sci.* 1026:222-31). Genomic DNA (gDNA) is extracted as detailed in the literature (Knowles et al. (1997) *Mol. Biochem. Parasitol.* 90(1):69-9; Nagore et al. (2004) *Int. J. Parasitol.* 34:1059-67; Nagore et al. (2004) *Vet. Parasitol.* 123(1-2):41-54). *Babesia* stage-specific genes are amplified by standard PCR protocols (Caccio et al. (2000) *Int. J. Parasitol.* 30(11):1181-5; Caccio et al. (2002) *Vet. Parasitol.* 106(4):285-92; Oliveira-Sequeira et al. (2005) *Int. J. Parasitol.* 35:105-111). PCR products are cloned into appropriate plasmids, and analyzed by automated sequencing methods. Homologue sequences are compared to sequences obtained from PCR amplification, and analyzed for similarity, motifs, or errors. Genes are then cloned into expression vectors, for the purpose of obtaining proteins for antibody production for later analysis and storage, using standard methods.

Analysis of *Babesia* Gene Expression: To verify expression of candidate stage-specific genes in different life stages, and to identify other differentially expressed genes similar to *Plasmodium* UIS and S genes, RNA is isolated from various life stages of sporozoites and merozoites, and mRNA is purified by standard methods detailed in the literature (Mosqueda et al. (2004) *Ann. N.Y. Acad. Sci.* 1026:222-31). cDNA is constructed and used for analysis by differential display (Dzierszinski et al. (2004) *J. Mol. Biol.* 309(5):1017-27), Suppression Subtractive Hybridization (SSH) (Diatchenko et al. (1996) *Proc. Natl. Acad. Sci. USA.* 93(12):6025-30; Jin et al. (1997) *Biotechniques* 23(6):1084-6; Diatchenko et al. (1999) *Meth. Enzymol.* 303:349-80; Matuschewski et al. (2002) *J. Biol. Chem.* 277:41948-53; Kaiser et al. (2004) *Mol. Microbiol.* 51(5):1221-32), or microarray analysis (Llinas & DeRisi (2004) *Curr. Op. Microbiol.* 7(4):382-7).

cDNA populations are also generated from RNAs at different life cycle stages to analyze mRNA expression. cDNAs are separated by agarose gel electrophoresis, and transferred to membranes. Homologues of *Plasmodium* UIS and S genes, and other identified candidate stage-specific genes, are used as probes and hybridized to membrane-bound cDNAs (Matuschewski et al. (2002) *J. Biol. Chem.* 277:41948-53). Genes known to be differentially expressed in Babesia will be used as controls, including erythrocyte specific genes such as EMA1 and EMA2 (Knowles et al. (1997) *Mol. Biochem. Parasitol.* 90(1):69-9), and genes expressed in both sporozoites and merozoites including RAP and RAP-1 (Vidotto et al. (1995) *Exp. Parasitol.* 81(4):491-500; Suarez et al. (2003) *Mol. Biochem. Parasitol.* 34:1177-84; Mosqueda et al. (2004) *Ann. N.Y. Acad. Sci.* 1026:222-31; Suarez et al. (2004) *Int. J. Parasitol.* 34:1177-84; hsp20 (Mosqueda et al. (2004) *Ann. N.Y. Acad. Sci.* 1026:222-31); and MSA1 and MSA2 (Florin-Christensen et al. (2002) *Infect. Immun.* 70(7):3566-75).

Alternatively or additionally, mRNA expression is analyzed by dot-blotting specific genes directly on membranes, and hybridizing with labeled life-cycle stage specific cDNA populations (Matuschewski et al. (2002) *J. Biol. Chem.* 277: 41948-53). Desired genes are identified and prepared for knockout constructs. Gene expression is also assayed at the protein level by Western blot analysis of homogenized parasites, using life cycle stage-specific antibodies.

Transfection and Gene Disruption: Gene are transfected into *Babesia* as previously described (Suarez et al. (2004) *Int. J. Parasitol.* 34:1177-84). Oligonucleotides of target genes are designed and used to amplify target gene sequences from genomic Babesia DNA (Mueller et al. (2005) *Nature* 433: 164-7; Mueller et al. (2005) *Proc. Natl. Acad. Sci. USA.* 102(8):3022-7). Identified full-length genes are cloned into protein expression plasmids, and expressed protein is purified and used for antibody production. Flanking sequence of target genes are used in gene replacement constructs, along with appropriate selectable markers, either dHFR as used by Suarez, or other suitable markers (U.S. Pat. No. 5,976,553; U.S. Pat. No. 5,955,333; U.S. Pat. No. 6,228,649). Plasmids are propagated in *E. coli*, purified, analyzed by restriction digest and sequence analysis. Plasmids are transfected into erythrocyte-stage parasites by electroporation, as described (Schuster (2002) *Clin. Microbiol. Rev.* 15(3):365-73; Suarez et al. (2004) *Int. J. Parasitol.* 34:1177-84). Different buffers are used for cell cultivation of different *Babesia* species, as has been previously described (Schuster (2002) *Clin. Microbiol. Rev.* 15(3):365-73; Mosqueda et al. (2004) *Ann. N.Y. Acad. Sci.* 1026:222-31). Initiating a primary culture involves obtaining blood from an infected cow. The blood is defibrinated, and grown in appropriate culture medium and antibiotics. There are two methods for cell growth, liquid suspension with agitation and growth in stationary layers of erythrocytes or MASP (microaerophilic stationary phase culture). The latter is preferred and is most convenient, particularly for experiments involving electroporation (Schuster (2002) *Clin. Microbiol. Rev.* 15(3):365-73). Cultures are diluted in 48-72 hour intervals with fresh medium and erythrocytes, detailed in the literature (Schuster (2002) *Clin. Microbiol. Rev.* 15(3):365-73). Erythrocyte stages are electroporated with both control and knockout plasmids of identified sporozoite/UIS genes (Suarez et al. (2004) *Int. J. Parasitol.* 34:1177-84). Knockouts and controls are passaged through *Bos taurus* steer, by intramuscular injection of infected erythrocytes (Brown (2001) *Vet. Parasitol.* 101:233-48; Alvarez et al. (2004) *Ann. N.Y. Acad. Sci.* 1026:277-83). *Boophilus microplus* ticks are allowed to feed on infected steer using skin patches, a technique documented in the literature. Adult female ticks are removed upon engorgement (Mosqueda et al. (2004) *Ann. N.Y. Acad. Sci.* 1026:222-31). Tick infection with *Babesia* is determined by the hemolymph test (Mosqueda et al. (2004) *Ann. N.Y. Acad. Sci.* 1026:222-31). Eggs and larvae are cultured as is described in the literature (Schuster (2002) *Clin. Microbiol. Rev.* 15(3):365-73). Ticks are macerated and separated by Percoll density gradients. Purified sporozoites are used immediately or frozen for storage. Purified sporozoites are used to confirm gene knockout effects at the level of transcription by RT-PCR with target gene primers, and at the protein level by Western blot analysis with target-gene derived antibodies.

Phenotypic Analysis of *Babesia*: Sporozoite motility, infectivity and ability to develop into erythrocyte stages is assessed by infecting a monolayer of erythrocytes with both control and knockout purified sporozoites.

Immunization and Challenge: Methods of vaccination and challenge with *Babesia* are well documented (Oliveira-Sequeira et al. (2005) *Int. J. Parasitol.* 35:105-111) and will be implemented in vaccine strategies. Animals will be monitored for infection and parasite development and immunity.

EXAMPLE 9

This Example describes a representative method for inducing an immune response in a vertebrate host against a *Cryptosporidium* parasite by administering a live *Cryptosporidium* parasite that is genetically engineered to disrupt the function of a stage-specific gene that is required by the parasite to establish a secondary infection in the vertebrate host.

Identification of Homologues of *Plasmodium* Genes in *Cryptosporidium*: *Cryptosporidium* databases (available at CryptoDB) were analyzed by performing BLAST searches for homologues to UIS genes and genes expressed in sporozoite (S genes) identified in *P. berghei* (Matuschewski et al. (2002) *J. Biol. Chem.* 277:41948-53; Kaiser et al. (2004) *Mol. Microbiol.* 51(5):1221-32) and *P. yoelii*. Matches at a significance level of $E^{-5}$ were verified by reciprocal blast analysis on *Plasmodiuni yoelii* sequences. 4 *Cryptosporidiurn parvum* orthologues of *P. berghei* UIS genes (UIS5, SEQ ID NO:57; UIS22, SEQ ID NO:58; UIS24, SEQ ID NO:59; and UIS30, SEQ ID NO:60) and 5 *Cryptosporidium parvum* orthologues of *P. berghei* S genes (S1, SEQ ID NO:61; S6, SEQ ID NO:62; S9, SEQ ID NO:63; S22, SEQ ID NO:64; and S25, SEQ ID NO:65) were identified.

Amplification of *Cryptosporidum* Genes: Parasites are obtained by purifying oocysts from the feces of known *Cryptosporidium*-infected animals, as detailed in the literature (Hijjawi et al. (2001) *Int. J. Parasitol.* 31(10):1048-55; Hijjawi et al. (2002) *Int. J. Parasitol.* 32(14):1719-26; Hijjawi et al. (2004) *Int. J. Parasitol.* 34(7):769-77). Purified oocysts are used to infect mice, and provide a pool of parasites to be used to develop an in vitro culture system. Eight days post inoculation, mice are processed, as previously described (Meloni & Thompson (1996) *J. Parasitol.* 82(5):757-62) and used to infect HCT-8 Cells, or in a host cell free system, as also previously described (Hijjawi et al. (2001) *Int. J. Parasitol.* 31(10:1048-55; Hijjawi et al. (2002) *Int. J. Parasitol.* 32(14):1719-26; Hijjawi et al. (2004) *Int. J. Parasitol.* 34(7):769-77). Genomic DNA (gDNA) is harvested as detailed in the literature (Moran et al. (1998) *Parasitology* 117(Pt. 1):31-7).

*Cryptosporidium* genes are amplified by standard PCR protocols. PCR products are cloned into appropriate plasmids, and analyzed by automated sequencing methods. Homologue sequences are compared to sequences obtained from PCR amplification, and analyzed for similarity, motifs, or errors. Genes are then cloned into expression vectors, for the purpose of obtaining proteins for antibody production for later analysis and storage, using standard methods. Genetic analysis is generally done in other apicomplexan organisms.

EXAMPLE 10

This Example describes a representative method for inducing an immune response in a vertebrate host against a *Trypanosoma* or *Leishmania* parasite by administering a live *Trypanosoma* or *Leishmania* parasite that is genetically engineered to disrupt the function of a stage-specific gene that is required by the parasite to establish a secondary infection in the vertebrate host.

Identification of Homologues of *Plasmodium* Genes in *Trypanosoma* and *Leishmania*: *Trypanosoma cruzi* databases (available at the TIGR database), *Trypanosoma brucci* databases (available at the TIGR database), and *Leishinania* databases (available at the Sanger Institute Pathogen Sequencing Unit database) were analyzed by performing BLAST searches for homologues to UIS genes and genes expressed in sporozoite (S genes) identified in *P. berghei* (Matuschewski et al. (2002) *J. Biol. Chem.* 277:41948-53; Kaiser et al. (2004) *Mol. Microbiol.* 51(5):1221-32) and *P. yoelii*. Matches at a significance level of $E^{-5}$ were verified by reciprocal blast analysis on *Plasmodium yoelii* sequences. 3 *Trypanosoma cruzi* orthologues of *P. berghei* UIS genes (UIS5, SEQ ID NO:66; UIS22, SEQ ID NO:67; and UIS24, SEQ ID NO:68) and 2 *Trypanosoma cruzi* orthologues of *P. berghei* S genes (S18, SEQ ID NO:69; and S25, SEQ ID NO:70); 3 *Trypanosoma brucei* orthologues of *P. berghei* UIS genes (UIS5, SEQ ID NO:71; UIS22, SEQ ID NO:72; and UIS24, SEQ ID NO:73) and 2 *Trypanosoina brucei* orthologues of *P. berghei* S genes (S18, SEQ ID NO:74; and S25, SEQ ID NO:75); and 2 *Leishmania major* orthotogues of *P. berghei* UIS genes (UIS24 SEQ ID NO:76; and UIS30, SEQ ID NO:77) and 1 *Leishmania major* orthologues of *P. berghei* S genes (S25, SEQ ID NO:78); were identified.

Amplification of *Trypanosoma* and *Leishmania* Genes: Sequence data derived from, for example, the BLAST searches, is used to design oligonucleotides for PCR amplification of stage-specific genes (e.g., homologues of *Plasmodium* UIS and S genes) from genomic DNA (gDNA) from *Trypanosoma* and *Leishmania* parasites grown in culture. Methods of parasite growth and maintenance, and gDNA extraction are as previously described (Brun & Lenni (1985) *Br. Med. Bull.* 41(2):122-9; Hirumi & Hirumi (1989) *J. Parasitol.* 75(6):985-9; Menz et al. (1991) *Mol. Biochem. Parasitol.* 47(1):101-8); Medina-Acosta & Cross (1993) *Mol. Biochem. Parasitol.* 59(2):327-9). *Trypanosoma* and *Leishmania* stage-specific genes are amplified by standard PCR protocols. PCR products are cloned into appropriate plasmids, and analyzed by automated sequencing methods. Homologue sequences are compared to sequences obtained from PCR amplification, and analyzed for similarity, motifs, or errors. Genes are then cloned into expression vectors, for the purpose of obtaining proteins for antibody production for later analysis and storage, using standard methods in the art.

Analysis of Trypanosoma and Leishmania Gene Expression: To verify expression of candidate stage-specific genes in different life stages, and to identify other differentially expressed genes similar to *Plasmodium* UIS and S genes, RNA is isolated from various life stages of parasites (e.g., procyclic, metacyclic and bloodstream forms in *T. brucei*, metacyclic trypomastigotes and amastigotes from *T. cruzi*, and promastigotes and amastigotes from *Leishmania*), and mRNA is purified by standard methods. cDNA is constructed and used for analysis by microarray analysis (Diehl et al. (2002) *Nucl. Acids Res.* 30(16):e79; Diehl et al. (2002) *Mol. Biochem. Parasitol.* 123(2):115-23; Boothroyd et al. (2003) *Trends Parasitol.* 19(10):470-6; Howbrook et al. (2003) *Drug Discov. Today* 9(14):642-51; Kopyants et al. (2004) *Mol. Biochem. Parasitol.* 136(1):71-86), RNA fingerprinting (Mathieu-Daude et al. (1998) *Mol. Biochem. Parasitol.* 92(1): 15-28), or Suppression Subtractive Hybridization (SSH) (Diatchenko et al. (1996) *Proc. Natl. Acad. Sci. U.S.A.* 93(12): 6025-30; Diatchenko et al. (1999) *Meth. Enzymol.* 303:349-80; Dost et al. (2004) *Parasitol. Res.* 94(2):134-40).

cDNA populations are also generated from RNAs at different life cycle stages to analyze mRNA expression. cDNAs are separated by agarose gel electrophoresis, and transferred to membranes. Homologues of *Plasmodium* UIS and S genes, and/or other identified candidate stage-specific genes, are used as probes and hybridized to membrane-bound cDNAs (Matuschewski et al. (2002) *J. Biol. Chem.* 277:41948-53). Genes known to be differentially expressed will be used as expression controls. These genes include, VSG or ESAG genes for bloodstream and PARP for procyclic forms in *T. brucei*, Met genes in trypomastigotes of *T. cruzi* (Krieger et al. (1999) *Mem. Inst. Oswaldo Cruz* 94(Supp. 1):165-8; Avila et al. (2001) *Mol. Biochem. Parasitol.* 117(2):169-77; Texeira & daRocha (2003) *Genet. Mol. Res.* 2(1):148-58), and amastigote specific A2 genes (Charest et al. (1996) *J. Biol. Chem.* 271(29):17-81-90) in *Leishmania*.

Alternatively or additionally, mRNA expression is analyzed by dot-blotting specific genes directly on membranes, and hybridizing with labeled life-cycle stage specific cDNA populations (Matuschewski et al. (2002) *J. Biol. Chem.* 277: 41948-53). Desired genes are identified and prepared for knockout constructs. Gene expression is also assayed at the protein level by Western blot analysis of homogenized parasites, using life cycle stage-specific antibodies.

Transfection and Targeting Vectors: Unlike the Apicomplexa, Trypanosomatida are diploid organisms, and require a different gene knockout strategy. Several vector and genetic manipulation options are available including homologous gene replacement and RNAi, and are detailed for each parasite in the literature: *T. cruzi* (Hariharan et al. (1993) *Mol. Biochem. Parasitol.* 57(1):15-30; Kelly et al. (1995) *Meth. Mol. Biol.* 47:349-59; Thomas & Gonzalez (1997) *Parasitol. Res.* 83(2):151-6; Norris (1998) *Infect. Immun.* 66(6):2460-5; Texeira & daRocha (2003) *Genet. Mol. Res.* 2(1):148-58); *T. brucei*, (Kelly et al. (1995) *Meth. Mol. Biol.* 47:349-59; Clayton & Hotz (1996) *Mol. Biochem. Parasitol.* 77(1):1-6; Texeira & darocha (2003) *Genet. Mol. Res.* 2(1):148-58; DaRocha et al. (2004) *Mol. Biochem. Parasitol.* 133(2):175-86); and *Leishmania* (Sbicego et al. (1998) *Mol. Biochem. Parasitol.* 94(1):123-6; Benzel et al (2000) *Mol. Biochem. Parasitol.* 111(1):77-86; Papdopoulou et al. (2002) *Infect. Immun.* 70(1):62-8; Yan et al. (2002) *Mol. Biochem. Parasitol.* 119 (2):217-23; DaRocha et al. (2004) *Mol. Biochem. Parasitol.* 133(2):175-86; Denise et al (2004) *FEMS Microbiol. Lett.* 235(1):89-94). Parasites are maintained as described in the literature, and generally, electroporation is the most efficient method of transfection (Kelly et al. (1995) *Meth. Mol. Biol.* 47:349-59). Selection of mutants is started shortly after cells have recovered from electroporation, and drug dosage and duration is dependent upon the reporter systems utilized in the chosen multi-step gene replacement strategy. To ensure gene knockout effect, wild type and knockout parasites are tested by RT-PCR analysis for transcript and Western blot analysis for protein. RT-PCR will utilize previously produced oligonucleotides, and antibodies previously produced for Western blot analysis (Mueller et al. (2005) *Proc. Natl. Acad. Sci. U.S.A.* 102(8):3022-7).

Phenotypic Analysis of *Trypanosoma* and *Leishmania*: Phenotypic analysis of mutant primary infective phases (procyclics, metacyclics, trypomastigotes) is conducted by microscopy, noting any alterations in motility or morphology (Mueller et al. (2005) *Nature* 433:164-7; Mueller et al. (2005) *Proc. Natl. Acad. Sci. U.S.A.* 102(8):3022-7). Mutants as well as wild type parasites are injected in appropriate doses into mice under selective drug pressure. Parasite development within the mammalian host is carefully analyzed through blood draws from infected mice, comparing wild type parasite and disease progression to mutants. If progression to the secondary infective phase is inhibited, appropriate prime and boost doses for immunization studies will be determined and tested in similar rodent models. Animals will be tested for parasite burden and immune response upon challenge.

Each of the references cited herein is hereby incorporated by reference.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for inducing an immune response in a vertebrate host against a protozoan parasite, comprising administering to the host a live protozoan parasite that is genetically engineered to disrupt a stage-specific gene function that is required by the protozoan parasite to establish a secondary infection in the vertebrate host.

2. The method of claim 1, wherein the protozoan parasite belongs to the phylum Apicomplexa.

3. The method of claim 2, wherein the protozoan parasite belongs to a genus selected from the group consisting of *Plasmodium, Toxoplasma, Neospora, Eimeria, Theileria, Babesia, Cryptosporidium, Sarcocystis*, and *Leucocytozoon*.

4. The method of claim 1, wherein the vertebrate host is a mammal or a bird.

5. The method of claim 1, wherein the live protozoan parasite is genetically engineered to delete a stage-specific gene function that is required by the protozoan parasite to establish a secondary infection in the vertebrate host.

* * * * *

SEQUENCE LISTING

<160> NUMBER OF SEQ ID NOS: 78

<210> SEQ ID NO 1
<211> LENGTH: 31
<212> TYPE: DNA
<213> ORGANISM: Plasmodium berghei

<400> SEQUENCE: 1
gggtacccgc attagcataa catctcattg g          31

<210> SEQ ID NO 2
<211> LENGTH: 31
<212> TYPE: DNA
<213> ORGANISM: Plasmodium berghei -continued

```
<400> SEQUENCE: 2
caagcttgct ttcatatatt tgttatttgt c                               31

<210> SEQ ID NO 3
<211> LENGTH: 27
<212> TYPE: DNA
<213> ORGANISM: Plasmodium berghei

<400> SEQUENCE: 3
ggaattccca tatgtttgtg taacatc                                    27

<210> SEQ ID NO 4
<211> LENGTH: 31
<212> TYPE: DNA
<213> ORGANISM: Plasmodium berghei

<400> SEQUENCE: 4
ctctagagtg tgcttaaatg tttctttaaa c                               31

<210> SEQ ID NO 5
<211> LENGTH: 31
<212> TYPE: DNA
<213> ORGANISM: Plasmodium berghei

<400> SEQUENCE: 5
cggaattcat catattacta attttcgggg g                               31

<210> SEQ ID NO 6
<211> LENGTH: 36
<212> TYPE: DNA
<213> ORGANISM: Plasmodium berghei

<400> SEQUENCE: 6
tccccgcggt tattccatgt tataaacgtt atttcc                          36

<210> SEQ ID NO 7
<211> LENGTH: 23
<212> TYPE: DNA
<213> ORGANISM: Plasmodium berghei

<400> SEQUENCE: 7
cccgcacgga cgaatccaga tgg                                        23

<210> SEQ ID NO 8
<211> LENGTH: 32
<212> TYPE: DNA
<213> ORGANISM: Plasmodium berghei

<400> SEQUENCE: 8
cccaagctta gtttgcatat acggctgctt cc                              32

<210> SEQ ID NO 9
<211> LENGTH: 31
<212> TYPE: DNA
<213> ORGANISM: Plasmodium berghei

<400> SEQUENCE: 9
cggaattctg gattcatttt ttgatgcatg c                               31

<210> SEQ ID NO 10
<211> LENGTH: 21
<212> TYPE: DNA
```

<213> ORGANISM: Plasmodium berghei

<400> SEQUENCE: 10
gtaatacgac tcactatagg c    21

<210> SEQ ID NO 11
<211> LENGTH: 29
<212> TYPE: DNA
<213> ORGANISM: Plasmodium berghei

<400> SEQUENCE: 11
gaattctgga ttcatttttt gatgcatgc    29

<210> SEQ ID NO 12
<211> LENGTH: 34
<212> TYPE: DNA
<213> ORGANISM: Plasmodium berghei

<400> SEQUENCE: 12
ggggtacctt tattcagacg taataattat gtgc    34

<210> SEQ ID NO 13
<211> LENGTH: 38
<212> TYPE: DNA
<213> ORGANISM: Plasmodium berghei

<400> SEQUENCE: 13
aaaactgcag ataattcatt atgagtagtg taattcag    38

<210> SEQ ID NO 14
<211> LENGTH: 34
<212> TYPE: DNA
<213> ORGANISM: Plasmodium falciparum

<400> SEQUENCE: 14
ccccaagctt aagtttgcat atacggctgc ttcc    34

<210> SEQ ID NO 15
<211> LENGTH: 27
<212> TYPE: DNA
<213> ORGANISM: Plasmodium falciparum

<400> SEQUENCE: 15
gagtaatata atgtgtaatg catatgg    27

<210> SEQ ID NO 16
<211> LENGTH: 24
<212> TYPE: DNA
<213> ORGANISM: Plasmodium falciparum

<400> SEQUENCE: 16
gagaccttca tttcaaaaag gaag    24

<210> SEQ ID NO 17
<211> LENGTH: 30
<212> TYPE: DNA
<213> ORGANISM: Plasmodium falciparum

<400> SEQUENCE: 17
caaatgaaaa cttggaaata atcagacgag    30

<210> SEQ ID NO 18
<211> LENGTH: 32

<212> TYPE: DNA
<213> ORGANISM: Plasmodium falciparum

<400> SEQUENCE: 18
gtattatgct taaattggaa aaagtttga ag                32

<210> SEQ ID NO 19
<211> LENGTH: 507
<212> TYPE: PRT
<213> ORGANISM: Toxoplasma gondii

<400> SEQUENCE: 19

```
Met Ser Arg Leu Ala Lys Val Ala Cys Ala Ala Pro Pro Cys Arg
1               5                  10                 15

Ala Ala Pro Phe Ser Ser Val Ser Ser Ser Ser Pro Ser Ser Pro
              20                  25                 30

Ser Pro Ser Ser Pro Ser Pro Pro Ser Ser Ser Ser Pro Ser Ser
              35                  40                 45

Gly Ser Gly Ala Phe Glu Ser Gly Gly Glu Ala Val Val Gly Ser Arg
        50                  55                 60

Pro Val Tyr Leu Asp Asn Gln Ala Thr Thr Val Gln Asp Pro Arg Val
65                  70                 75                  80

Thr Asp Ala Met Leu Pro Phe Leu Phe Asp Lys Phe Gly Asn Pro His
                85                  90                 95

Ser Ser Ser His Ala Val Gly Trp Glu Ala Asp Ala Ala Val Glu Lys
              100                 105                110

Ala Arg Lys Gln Val Ala His Leu Leu Gly Leu Asp Ala Ser Arg Ala
              115                 120                125

Arg Glu Ile Ile Phe Thr Ser Gly Ala Thr Glu Ser Asn Asn Leu Ala
        130                 135                140

Leu Lys Gly Ala Val His Tyr Tyr Cys Arg Gly His Pro Val Thr Phe
145                 150                 155                160

Arg Lys Ser Glu Lys Arg Gly Glu Thr Arg Ala Ala Ala Arg Ala Arg
                165                 170                175

Arg His Val Ile Thr Thr Gln Leu Glu His Lys Cys Ala Leu Gln Cys
              180                 185                190

Cys Arg Met Leu Gln Leu Glu Phe Ser Glu Ser Gln Gly Ala Arg Gly
              195                 200                205

Cys Asp Val Thr Tyr Leu Pro Val Lys Thr Asp Gly Leu Val Asp Leu
        210                 215                220

Glu Glu Leu Glu Lys Ala Ile Arg Pro Asp Thr Leu Leu Val Ser Val
225                 230                 235                240

Met Phe Val Asn Asn Glu Ile Gly Val Val Gln Asn Leu Glu Glu Ile
                245                 250                255

Gly Lys Ile Cys Lys Arg His Asp Ile Leu Phe His Thr Asp Ala Ala
              260                 265                270

Gln Gly Ala Gly Lys Leu Pro Ile Asp Val Asp Glu Met Gly Ile Asp
              275                 280                285

Leu Leu Ser Leu Ser Ser His Lys Ile Tyr Gly Pro Lys Gly Ile Gly
        290                 295                300

Ala Leu Phe Val Arg Ala Lys Asn Pro Arg Val Arg Leu Gln Pro Leu
305                 310                 315                320

Ile Asp Gly Gly Gly Gln Glu Arg Gly Leu Arg Ser Gly Thr Leu Ala
                325                 330                335

Thr Pro Leu Cys Val Gly Phe Gly Ala Ala Cys Glu Leu Ala Glu Lys
```

-continued

```
                340                 345                 350
Glu Met Glu Asn Asp Arg Arg His Val Ser Arg Leu Ala Arg Leu Leu
            355                 360                 365

Leu Asp Ser Val Arg Glu Gln Ile Pro Asp Ile Glu Val Asn Gly Ser
370                 375                 380

Leu Thr Ser Arg Tyr Pro Gly Asn Leu Asn Ile Ser Phe Thr Phe Val
385                 390                 395                 400

Glu Gly Glu Ser Val Leu Met Ser Ile Arg Asp Val Ala Ile Ser Ser
                405                 410                 415

Gly Ser Ala Cys Thr Ser Ala Ser Leu Glu Pro Ser Tyr Val Leu Arg
            420                 425                 430

Ala Leu Gly Val Gly Glu Glu Val Ala His Thr Ser Leu Arg Phe Gly
        435                 440                 445

Ile Gly Arg Phe Thr Arg Glu Glu Asp Val Arg Gln Cys Val Glu Arg
    450                 455                 460

Leu Val Lys Gln Ile His Arg Leu Arg Glu Leu Ser Pro Leu Tyr Glu
465                 470                 475                 480

Met Glu Met Ala Lys Arg Lys Ala Leu Ala Ser Gly Val Cys Pro Asn
                485                 490                 495

Asp Glu Thr Asp Gly Asn Ala Leu Ile Trp Thr
            500                 505

<210> SEQ ID NO 20
<211> LENGTH: 3934
<212> TYPE: PRT
<213> ORGANISM: Toxoplasma gondii

<400> SEQUENCE: 20

Met Ala Gly Gly Ser Met Gln Arg Ala Ala Arg Gln Ser Arg Gly Arg
1               5                   10                  15

Ser Gly Gly Arg Ala Gly Gly Gly Gly Glu Gly Ala Ser Gly Ser
            20                  25                  30

Leu Gly Asp Arg Gly Cys Ser Asp Thr Glu Glu Glu Arg Phe Trp Ile
        35                  40                  45

Glu Lys Asp Val Glu Phe Phe Ser Ala Ile Asn Pro Arg Leu Leu Ala
    50                  55                  60

Leu Leu His His His Lys Gln Ser Glu Ala Phe Leu Ser Ala Val
65                  70                  75                  80

Leu Pro Tyr Leu Arg Ser Arg Ser Arg Lys Asp Ala Ala Asp Ala Ala
                85                  90                  95

Gly Pro Ser Pro Arg Ser Glu Ala Ala Gln Ala Phe Ala Leu Arg Val
            100                 105                 110

Pro Val Arg Asp Phe Leu Arg Gln Asp Trp Thr Gly Glu Ile Gly
        115                 120                 125

Gly Ser Val Leu Ser Gly Ser Ala Glu Arg Arg Asp Arg Arg
    130                 135                 140

Arg Glu Glu Ile Ile Glu Arg Asp Ser Asp Pro Pro Lys Arg Val Ala
145                 150                 155                 160

Ser Ser Pro Pro Cys Arg Ser Arg Ser Val Glu Glu Asn Leu Thr Glu
                165                 170                 175

Arg Ala Ala Phe Ser Arg Asp Gly Arg Ser Ile Cys Ser Lys Asp Pro
            180                 185                 190

Gln Gly Ala Arg Glu Glu Val Ser Pro Ser Cys Asp Ser Leu Ser Ser
        195                 200                 205
```

```
Pro Val Arg Arg Ser Ser Ser Ala Ser Cys Leu Gly Ile Ser Gln Pro
    210                 215                 220

Val Ser Ser Glu Ala Gly Ser Glu Ala Gly Ser Ser Val Phe Ala
225                 230                 235                 240

Ser Gly Ala Thr Ala Val Ala Ala Gly Phe Ala Arg Thr Val Pro Thr
                245                 250                 255

Ser Ser Gly Lys Gly Ala Ala Ser Glu Gly Gly Glu Asn Ser Pro Arg
                260                 265                 270

Ser Glu Gly Gly Asn Ser Val Ser Ser Arg Val Cys Ser Ser Gln Gly
                275                 280                 285

Ser Ala Pro Ala Pro Val Val Gly Cys Gln Ala His Pro Ala Pro Ser
    290                 295                 300

Arg Leu Ser Gln Val Trp Pro His His Thr Gly Lys Ile Leu Leu Glu
305                 310                 315                 320

Arg Pro Ser Tyr Ser Gly Glu Thr Gly Arg Ile Ile Arg His Met Trp
                325                 330                 335

Pro Ala Thr Leu Leu Ala Asp Val Glu Pro Ser Ala Leu Cys Pro Pro
                340                 345                 350

Pro Leu Leu Arg Ser Lys Ala Ala Ala Asp Pro Lys Lys Lys Glu
                355                 360                 365

Asp Ser Arg Ala Tyr Val Arg Thr Gly Val Glu Lys Lys Asn Leu Glu
    370                 375                 380

Glu Ser Ser Arg Leu Ser Cys Gly Thr Glu Glu Thr Glu Ala Arg Gly
385                 390                 395                 400

Glu Ser Gln Lys Arg Ser Pro Asp Gly Gly Arg Ser Ser Gln Pro His
                405                 410                 415

Ser Ser Ser Val Ser Ala Asp Leu Lys Glu Thr Asn Arg Glu Thr Ala
                420                 425                 430

Glu Ser Gln Ala Asp Gly Ser Lys Thr Asp Ala Gly Leu Gly Leu Cys
    435                 440                 445

Ser Pro Trp Ser Glu Glu Thr Gly Lys Thr Glu Glu Lys Lys Asp
    450                 455                 460

Phe Glu Ser Gln Pro Cys Gly Asp Ala Gly Gly Arg Lys Asp Gly
465                 470                 475                 480

Glu Glu Asp Arg Gly Gly Glu Glu Thr Pro Gln Arg Ser Ser Gly Ala
                485                 490                 495

Val Lys Glu Glu Thr Asn Ala Ser Gly Glu Gly Arg Leu Pro Ser Gly
                500                 505                 510

Pro Gln Ser Pro Ser Lys His Leu Asp Gln Pro Gly Ser Ala Ala Trp
    515                 520                 525

Glu Ser Ser Asn Pro Arg Ile Leu Asn Gly Glu Thr Gly Ser Arg Asp
    530                 535                 540

Gly Glu Asp Ser Ser Ser Ser Cys Pro Glu Val Gly Thr Gln Gly Pro
545                 550                 555                 560

Arg Pro Thr Ser Arg Arg Ser Ser Val Glu Gly Arg Glu Arg Ser
                565                 570                 575

Ala Gly Leu Arg Ala Ala Ser Asp Asp Lys Thr Glu Lys Ser Glu Asp
                580                 585                 590

Ser Arg Glu Lys Glu Lys Asp Leu Gly Ala Pro Gln Pro Ser Lys Asp
    595                 600                 605

Ser Gln Glu Gly Gln Ala Ala Ser Val Glu Ala Thr Leu Gln Asn Thr
    610                 615                 620

Arg Thr Gly Ala Pro Ser Arg Ala Val Pro Thr Thr Val Leu Ser Gly
```

-continued

```
            625                 630                 635                 640
Val Lys Arg Glu Leu Glu Gln Asp Gly Asp Thr Gln Gly Pro Arg Cys
                    645                 650                 655

Gly Ala Arg Ser Pro Cys Arg Ala Ser Ala Thr Ser Pro Arg Asp Glu
                    660                 665                 670

Pro Met Ser Arg Pro Ala Gly Gln Thr Ser Ser Glu Lys Trp Lys Arg
                    675                 680                 685

Glu Glu Ala Phe Cys Leu Gln Val Ser Gln Asn Arg Ser Ile Phe Ser
                    690                 695                 700

Leu Val Pro Gly Ala Asn Asp Pro Ala Leu Leu Ala Ser Leu His Glu
705                 710                 715                 720

His Gln Leu His Ala His Leu Lys Tyr Gln Ser Arg Asp Leu Ser Val
                    725                 730                 735

Phe Ser His Ser Gly Asp Phe Lys Arg Ala Ala Ser Ala Arg Gly
                    740                 745                 750

Val Ser Arg Arg Ser Gly Gly Arg Arg Gly Thr Arg Leu Ala Ala Gly
                    755                 760                 765

Phe Asp Cys Glu Glu Thr Ala Glu Gly Asp Phe Ser Ser Gly Ser Leu
                    770                 775                 780

Ala Ser Ser Thr Pro Ser Pro Ala Ala Arg Ala Ala Gly Ala Arg
785                 790                 795                 800

Glu Arg Glu Arg Asn Arg Arg Gly Ser Asp Ser Asp Phe Thr Pro Ser
                    805                 810                 815

Arg Ser Glu Lys Gly Asp Ala Arg Gly Asp Arg Pro Ala Ala Ala Arg
                    820                 825                 830

Arg Arg Asp Gly Val Ser Gly Thr Val His Gln Lys Ala Gly Ser Gly
                    835                 840                 845

Ser Pro Gly Pro Ser Arg Ala Gly Arg Glu Glu Val Arg Ala Gly Gly
                    850                 855                 860

Arg Thr Pro Ser Gly Glu Arg Glu Pro Ala Gln Arg Ser Ser Ser Val
865                 870                 875                 880

Gly Arg Glu Ala Lys Ala Val Val Glu Gly Gly Glu Glu Asp Pro Asp
                    885                 890                 895

Glu Ala Gly Ala Asp Asp Leu Phe Val Pro Thr Val His Lys Lys Trp
                    900                 905                 910

Asn Gly Ser Met Arg Leu Pro Ala Phe Pro Thr Cys Arg Pro Pro Asp
                    915                 920                 925

Ala Phe Val Leu Ser Met Phe Val Pro Pro Asn Val Ser Pro Ala Asp
                    930                 935                 940

Phe Pro Glu Asp Thr Asn Ala Gln Gly Asp Val Ser Ala Phe Leu Ala
945                 950                 955                 960

Val Val Met Glu Ala Ala Thr Thr Thr Ala Ser Asp Trp Asp Ala His
                    965                 970                 975

Ala Asn Thr Phe Thr Pro His Asp Gly Tyr Asn Leu Ala Glu Lys Pro
                    980                 985                 990

Gly Asp Cys Gly Pro Val Arg Ala  Leu Gly Lys Val Ala  Ala Glu Arg
                    995                 1000                1005

Leu Gly  Ala Glu Arg Asn Arg  Gly Thr Glu Gly Leu  Gly Leu Val
    1010                1015                1020

Ser Arg  Glu Ala Cys Arg Gly  His Leu Leu Thr Thr  Ala Gly Ser
    1025                1030                1035

Cys Asp  Met Gln Glu Thr Ser  Arg Val Gly Ser Gly  Asp Ser Val
    1040                1045                1050
```

```
Ala Gln Val Glu Ala Glu Arg Arg Ala Gln Leu Glu Arg Ser Phe
1055                1060                1065

Ala Cys Glu Gly Ser Glu Ala Arg Pro Gly His Ala Arg Pro Val
1070                1075                1080

Ala Thr Glu His Pro Ser Ala Ser His Arg Arg Asp Leu Ser Lys
1085                1090                1095

Asp Gly Gly Leu Val Lys Thr Pro Gly Gly Arg Arg Arg Arg Arg
1100                1105                1110

Arg Ser Ser Ser Thr Gly Ser Gly Gly Glu Arg Thr Asn Ser Gly
1115                1120                1125

Asn Arg Arg Arg Leu Lys Asp Glu Lys Lys Arg Ser Ser Gly Thr
1130                1135                1140

Gly Ala Pro Val Ser Pro Gln Pro Arg Ser Ser Ser Gly Arg Phe
1145                1150                1155

Met Ser Arg Gln Ser Leu Thr Glu Val Ser Pro Ala Ala Pro Thr
1160                1165                1170

Ser Ser Lys Pro Arg Ala Ser Val Ser Pro Ser Ser Ser Leu Ala
1175                1180                1185

Leu Val Ser Ala Ser Pro Arg Lys Arg Pro Arg Arg Arg Leu Pro
1190                1195                1200

Leu Pro Thr Val Leu Ser Gly Pro Leu Pro Ala Trp Ile Asp Cys
1205                1210                1215

Ser Glu Arg Phe Pro Gly Pro Ala Pro Ile Val His Gly Pro Arg
1220                1225                1230

Gly Pro Ser Gly Pro Phe Asn Ala Gly Leu Ser Phe Ser Ala Ser
1235                1240                1245

His Gly Ser Cys Gly Gly Gln Ala Ser Gly Leu Gly Met Pro Gly
1250                1255                1260

Pro Cys Trp Gly Arg Pro Val Trp Pro Glu Thr Gly Ala Pro Phe
1265                1270                1275

His Ile Ser Gly Asp Glu Asp Pro Gly Arg Ala Gly Met Asn Gly
1280                1285                1290

Lys Arg Ala Leu Asp Lys Gly Ser Glu Thr Arg Gly Gly Lys Ala
1295                1300                1305

Ser Asp Glu Lys Arg Glu Gln Ser Gln Ala Glu Ser Glu Ala Arg
1310                1315                1320

Leu Pro Ser Ser Ser Thr Thr Asn Ala Ser Pro Pro Lys His Asp
1325                1330                1335

Pro Pro Cys Ser Ser Pro Pro Pro Ala Glu Arg Thr Gly Pro
1340                1345                1350

Arg Leu Glu Ala Glu Gly Met Arg Ser Ser His Ala Leu Phe Pro
1355                1360                1365

Pro Gly Gln Ser Tyr Gly Gly Leu Ser Pro Gly Thr Gln Ala Ser
1370                1375                1380

Gly Cys Ser Pro Ser Pro Gly Ala Leu Phe Ser Arg Ala Ser Pro
1385                1390                1395

Ala Gly Pro Ser Ser Pro Gly Ser Thr Ser Ser Gly Val His Pro
1400                1405                1410

Ser Gln Ser Phe Ala Ser Pro Pro Ser Ser Cys Pro Pro Phe Ala
1415                1420                1425

Phe Ser Gly Thr Gly Pro Ala Ala Pro Tyr Leu Ala Ser Gly Cys
1430                1435                1440
```

-continued

```
His Pro Cys Ser Phe Ser Val Arg Pro Ala Cys Gly Ala Ala
1445                1450                1455

Ala Ala Phe Ser Pro Ala Ser Pro Tyr Ala Pro Cys Arg Pro Cys
1460                1465                1470

Ala Tyr Leu Pro Gln Asp Ala Ser Ser Gly Pro Pro Pro Gln Ile
1475                1480                1485

Ser Gly Ser Ala Tyr Pro Gly Ala Ala Leu Leu Ser Pro Pro Ser
1490                1495                1500

Ser Ala Pro Pro Gly Pro Val Cys Ala Gly Pro Val Ser Glu Ala
1505                1510                1515

Phe Ser Ser Met Arg His Ser Phe Pro Ala Ala Cys Cys Pro Pro
1520                1525                1530

His Pro Cys Pro Pro Phe Ser Ser Cys Pro Pro Gly His Pro Gln
1535                1540                1545

Phe Cys Ala Pro Gly Asn Pro Phe Ser Ser Tyr Pro Ser Glu Met
1550                1555                1560

Ser Pro Phe Pro Glu Leu Gln Arg Phe Ser Ser Ala Pro Pro Pro
1565                1570                1575

Pro Cys Thr Ser Phe Asn Cys Pro Pro Pro Tyr Pro Pro Pro Ala
1580                1585                1590

Cys Phe Pro Pro Ala Pro Glu Ser Ser Ser Ser Val Ser Ser
1595                1600                1605

Ala Asp Phe Val Ala Ser Phe Ser Ser Ser Pro Gly Pro Cys Arg
1610                1615                1620

Arg Ala Ser Ser Ala Phe Ser Gly Ser Thr Ser Ser Glu Lys Ser
1625                1630                1635

Glu Glu Pro Pro Gly Val Ser Ser Cys Gln Asn Leu Gly Ser Asp
1640                1645                1650

Ala Thr His Pro Pro Cys Phe Ser Gly Pro Thr Tyr Pro Val Leu
1655                1660                1665

Gly Gly Pro Val Asp Thr Ala Phe Cys Arg Pro Pro Pro Ser Thr
1670                1675                1680

Ala Pro Pro Gly Ser Val Pro Phe Ala Ala Phe Pro Pro Phe Pro
1685                1690                1695

Cys Pro Pro Leu Leu Gly Leu Gly Pro Val Ala Glu Phe Glu Asp
1700                1705                1710

Arg Gly Pro Val Leu Arg Ser Phe Pro Phe Gly Pro Ala Ser Ser
1715                1720                1725

Pro Ala Tyr Leu Thr Leu Ser Leu Phe Pro Arg Pro Ser Leu Pro
1730                1735                1740

Ala Phe Pro Gly Ser Ser Ala Pro Phe Glu Pro Val Ser Arg Cys
1745                1750                1755

Ser Ser Phe Leu Pro Arg Gly Glu Leu Gln Thr Val Ser Ser Ser
1760                1765                1770

Pro Pro Glu Ser Val Ala Ser Cys Leu Pro Thr Pro Pro Pro Glu
1775                1780                1785

Ile Leu Val Pro Pro Phe Phe Gly Ala Gly Ser Ser Leu Lys Pro
1790                1795                1800

Phe Pro Pro Cys Cys Leu Tyr Pro Pro Glu Met Ala Glu Asn
1805                1810                1815

Phe Arg Tyr Ser Glu Lys Arg Lys Met Met Val Pro Ser Gly Val
1820                1825                1830

Arg Leu Glu Leu Leu Arg Ala Gln Met Thr Arg Val Asp Gly Leu
```

-continued

```
                1835                1840                1845

His Thr Phe Tyr Ala Asn Val Glu Thr Gly Lys Arg Phe Phe Gly
    1850                1855                1860

Glu Arg Ser Phe Phe Glu Ile Ala Lys Glu Asn Ala Arg Arg His
    1865                1870                1875

Asp Ala Gly Leu Gln Pro Leu Ser Leu Ser Pro Leu Thr Ser Asn
    1880                1885                1890

Ser Ala Thr Ala Phe Phe Met Ser Val Ala Pro Glu Thr Glu Ile
    1895                1900                1905

Pro Pro Ser Gly Ser Pro Asn Gly Pro His Thr Ala Pro Lys Lys
    1910                1915                1920

Thr Lys Ala Thr Lys Glu Asp Ser Glu Arg Glu Arg Glu Lys
    1925                1930                1935

Arg Glu Arg Glu Glu Arg Glu Lys Arg Glu Arg Asp Glu Glu Arg
    1940                1945                1950

Gly Arg Arg Asp Leu Glu Glu Lys Ile Arg Ile His Met Tyr Ser
    1955                1960                1965

Arg His Met Val Pro Ala Gly Ser Pro His Leu Ser Gly Ala His
    1970                1975                1980

Arg Leu Ile Pro Leu Pro Trp Gly Lys Arg Asp Ala Ser Arg Ser
    1985                1990                1995

Ser Pro Gln Glu Leu Glu Ile Arg Ala Arg Asp Gly Asp Cys Leu
    2000                2005                2010

His Ala Ser Thr Gly Ala Ser Ala Gly Val Gly Gly Pro Gln Glu
    2015                2020                2025

Lys Lys Gly Lys Thr Glu Asp Ala Gln Gly Glu Gln Leu Val Ser
    2030                2035                2040

Leu Glu Thr Ala Ala Glu Pro Glu Thr Gln Glu Lys Lys Glu Thr
    2045                2050                2055

Lys Ala Arg Gly Val Ala Gly Val Gly Pro Ser Ala Gln Ser Ala
    2060                2065                2070

Glu Thr Ala Ser Pro Ala Pro Glu Ala Ala Cys Asp Gly Gln Ser
    2075                2080                2085

Ala Glu Val Ser Pro Arg Gly Asp Ser Ala Ala Gly Arg Ala Glu
    2090                2095                2100

Thr Gly Pro Ala Cys Gly Val Thr Gly Glu Arg Arg Glu Val Asp
    2105                2110                2115

Arg Glu Ser Ala Gln Asp Glu Gly Lys Glu Thr Glu Val Lys Thr
    2120                2125                2130

Glu Gly Pro Glu Gly Ala Cys Glu Thr Glu Glu Phe Thr Gly Cys
    2135                2140                2145

Val Ser Val Glu Glu Gly Glu Gly Cys Gly Val Lys Glu Ile Thr
    2150                2155                2160

Glu Lys Ala Lys Glu Gly Cys Ala Ser Asp Thr Ala Asn Gly Gly
    2165                2170                2175

Thr Arg Arg Glu Leu Ser Glu Lys Glu Pro Gly Arg Asp Lys Asp
    2180                2185                2190

Arg Val Gly Met His Thr Pro Phe Ser Ser Glu Gly Gly Glu Lys
    2195                2200                2205

Glu Asn Arg Glu Glu Asn Gly Asp Asp Arg Glu Ser Ala Asp Pro
    2210                2215                2220

Phe Ser Leu Lys Glu Phe Asn Lys His Arg Gln Thr Ser Lys Pro
    2225                2230                2235
```

-continued

```
Val Gly Asp Val Ala Glu Pro Asp Arg Val Arg Glu Glu Asn Ala
    2240                2245                2250

Cys Pro Arg Glu Gln Ala Glu Ser Glu Ala Met Asp Val Asp Gly
    2255                2260                2265

Pro Glu Ala Arg Gly Glu Leu Pro Glu Gly Arg Lys Asp Phe Glu
    2270                2275                2280

Val Leu Ser Ser Arg Asn Ala Thr Glu Thr Ala Asp Phe Asp Thr
    2285                2290                2295

Arg Gln Asn Glu Lys Gln Lys Ala Lys Gly Thr Leu Val Thr Ser
    2300                2305                2310

Thr Ser Phe Gly Thr Glu Val Glu Asn Leu Leu Trp Arg Phe Ser
    2315                2320                2325

Ala Leu Met Asp Glu Lys Arg Ala Met Cys Ser Arg Leu Leu Met
    2330                2335                2340

Ser Ile Glu Arg Glu Lys Arg Pro Asp Trp Arg Ala Trp Ala Glu
    2345                2350                2355

Val Glu Asp Arg Met Leu Arg His Tyr Ile Glu Gln Ser Ala Lys
    2360                2365                2370

Ser Ser Leu Asp Thr Arg His Thr Tyr Thr Leu Thr Gln Gln Ser
    2375                2380                2385

Arg Asp Ile Leu Arg Leu Arg Val Ser Cys Ser Ser Ser Gly Arg
    2390                2395                2400

Leu Pro Pro Glu Trp Ala Glu Arg Ala Leu Cys Thr Val Cys Gly
    2405                2410                2415

Ser Gly Glu Asp Trp Asp Glu Asp Pro Ile Met Phe Cys Asp Gly
    2420                2425                2430

Cys Tyr Gln Pro Val His Phe Leu Cys Leu Gly His Lys Ala Val
    2435                2440                2445

Ser Ser Tyr Glu Glu Phe Val Lys Ala Ser Thr Thr Arg Arg Gln
    2450                2455                2460

Arg Arg Val Ala Gln Ala Gly Gly Asp Gln Gly Leu Ala Pro Ala
    2465                2470                2475

Thr Ala Arg Glu Arg Gly Ser Gly Pro Lys Arg Asp Lys Lys Lys
    2480                2485                2490

Ala Ala Glu Arg Ala Lys Glu Lys Lys Lys Gly Arg Gly Gly
    2495                2500                2505

Thr Gly Asp Leu Leu Ala Ser Gly Ala Phe Gly Ala Pro Ala Leu
    2510                2515                2520

Gly Ala Gly Ser Gly Asp Ala Pro Gly Ala Ser Arg Pro Ala Glu
    2525                2530                2535

Gly Asp Pro Ser Gly Pro Gly Ala Ser Pro Gly Asp Thr Gly His
    2540                2545                2550

Asn Thr Arg Arg Pro Val Cys Gly Ala Gly Gly Phe Ala Phe Arg
    2555                2560                2565

Glu Asp Glu Glu Glu Trp Leu Cys Pro Val Cys Glu Trp Leu Arg
    2570                2575                2580

Lys Gln Leu Pro Gln Leu Asp Asp Glu Leu Ala Leu Ala Ala Ile
    2585                2590                2595

Arg Leu Ala Ala Gly Pro Arg Ser His Ser Glu Ala Ala Glu Cys
    2600                2605                2610

Arg Gly Ser Tyr Val Gly Trp His Phe Glu Arg Leu Glu His Phe
    2615                2620                2625
```

-continued

Asp Ser Trp Val Lys Pro Gln Leu Leu Ala Leu Gln Tyr Gly Asp
    2630                2635                2640

Gly Arg Arg Arg Lys Gly Lys Gly Arg Leu Gln Val Asp Val Gly
    2645                2650                2655

Ala Pro Gln Gly Ser Arg Lys Asp Thr Arg Gln Gly Arg Lys Val
    2660                2665                2670

Ala Thr Gly Leu Gly Leu Pro Ser Gly Asp Ala Asp Ser Val Ser
    2675                2680                2685

Thr Leu Gln Ala His Ser Ala Tyr Ser Val Gln Glu Leu Leu Ala
    2690                2695                2700

Trp Pro Ala Val Arg Val Val Ala Asp Ala Gly Cys Leu Gly Pro
    2705                2710                2715

Asn Ala Gln Ser Ser Arg Ser Ser Thr Ser Arg Gly Ser Ala Ala
    2720                2725                2730

Arg Gly Pro Gly Thr Ala Gly Glu Thr Gly Gly Val Ala Gly Ser
    2735                2740                2745

Gly Gly Asp Gly Ser Gly Val Phe Arg Ala Glu Lys Asp Glu Glu
    2750                2755                2760

Asp Arg Gly Leu Lys Lys Pro Glu Leu Asp Glu Ser Gly Gly Arg
    2765                2770                2775

Pro Ser Ile Arg Gly Ala Gly Pro Lys Pro Cys Ile Ser Ser Leu
    2780                2785                2790

Ala Gln Thr Met Leu Gly Ala Arg Thr Leu Pro Val Trp Ala Thr
    2795                2800                2805

Asp Glu Glu Thr Gly Lys Gln Ser Cys Ser Arg Glu Gly Ser Val
    2810                2815                2820

Ala Gly Ser Lys Gly Gly Arg Leu Ala Ala Asp Gly Arg Arg Leu
    2825                2830                2835

Gly Gly Gly Glu Arg Ala Gly Asp Arg Cys Val Glu Pro Glu Glu
    2840                2845                2850

Asp Asp Ala Arg Arg Ala Lys Gly Asp Gly Asp Phe Ser Arg Asp
    2855                2860                2865

Ala Trp Thr Arg Gly Phe Arg Ser Gly Ser Glu Thr Gly Met Gly
    2870                2875                2880

Thr Ser Gly Lys Gly Ala Arg Glu Lys His Pro Val Ser Leu Val
    2885                2890                2895

Ala Pro Glu Asp Ala Thr Pro Ala Thr Asp Tyr Ile Arg Arg Val
    2900                2905                2910

Pro Tyr Ala Phe Ser Asp Ser Gly Asp Glu Gly Pro Ser Gly
    2915                2920                2925

Lys Asp Gly Asp Thr Pro Phe Phe Phe Cys Gln Tyr Thr Ala Gly
    2930                2935                2940

Ser Pro Thr Ala Ser Ser Pro Ser Ser Ala Ala His Arg Thr Pro
    2945                2950                2955

Ser Gln Glu Asp Asp Ser Gln Gly Gly Leu Phe Ser Gly Ser Ala
    2960                2965                2970

Phe Ser Pro Ser Ser Ala Ser Met Arg Ser Gly Ala His Ala Ser
    2975                2980                2985

Gly Gly Phe Ser Pro Asn Ser Ala Glu Pro Gly Ala Ser Leu Thr
    2990                2995                3000

Ser Lys His Tyr Cys Ser Lys Asp Pro Arg Arg Arg Cys Val Val
    3005                3010                3015

Arg Val Phe Pro Val Pro Gly Leu Ser Val Val Leu Arg Val Pro

-continued

```
             3020               3025               3030
Val Cys Ala Leu Cys Gly Tyr Asp Ala Phe Cys Arg Gly Gly Gly
        3035               3040               3045

Pro Ala Arg Lys Thr Glu Lys Lys Gly Val Trp Ala His Leu Arg
        3050               3055               3060

Cys Ala Leu Ser Leu Asn Ala Thr Val Met Asp Arg Val Ser Tyr
        3065               3070               3075

Glu Ala Asp Glu Ser Arg Ser Arg Leu Arg Cys Leu Phe Cys His
        3080               3085               3090

His Gln Gly Pro Ala Pro Gly His Cys Gly His Ala Gly Cys Gln
        3095               3100               3105

Arg Thr Tyr His Val Ser Cys Ala Thr Ala Thr Pro Gly Cys Met
        3110               3115               3120

Val Asp Trp Asp Met Gly Arg Pro Val Ile Phe Cys Ser Gln His
        3125               3130               3135

Ala Lys Asn Lys Ala Pro Thr Leu Ile Leu Arg Lys Phe Gln Ala
        3140               3145               3150

Asn Arg Glu Arg Glu Ala Val Lys Arg Arg Glu Glu Asp Leu Pro
        3155               3160               3165

Gly Glu Trp Lys Ile Gly Val Gly Lys Gly Arg Leu Gly Ile Ala
        3170               3175               3180

Leu Gln Ser Leu Leu Phe Pro Ser Tyr Asp Gly Leu Cys Asn Val
        3185               3190               3195

Phe Ser Asp Leu Leu Glu Val Pro Thr Leu Arg Leu Pro Thr Leu
        3200               3205               3210

Ser Pro Ala Glu Lys Lys Val Thr Ser Gln Gly Leu Glu Ala Leu
        3215               3220               3225

Ser Phe Pro Gly Ala Asp Pro Ala Leu Gly Ala Pro Arg Asp Glu
        3230               3235               3240

Ala Glu Ala Leu Glu Arg Arg His Arg Ala Gln Ser Arg Glu Glu
        3245               3250               3255

Lys Ala Thr Gly Val Asp Glu Gln Arg Arg Gly Asn Ala Gln Thr
        3260               3265               3270

Glu Asp Ala Ala His Arg Glu Lys Glu Lys Gly Arg Asn Leu
        3275               3280               3285

Glu Gly Ser Ser Val Ala Arg Gly Glu Ala Ser Gly Gly Gly
        3290               3295               3300

Pro Asp Glu Glu Glu Arg Phe Thr Arg Arg Leu Thr Trp Arg
        3305               3310               3315

Arg Arg Arg Val Ala Asp Ser Asp Ala Glu Asp Leu Glu Gly Lys
        3320               3325               3330

Glu Thr Lys Lys Lys Cys Pro Glu Glu Lys Ala Ala Gly Arg Thr
        3335               3340               3345

Ala Glu Gly Ala Asp Ala Ser Val Glu Thr Ser Arg Asp Cys Gly
        3350               3355               3360

Met Glu Gly Glu Ser Ala Ser Thr Ala His Ala Lys Gln Glu Val
        3365               3370               3375

Leu Asp Ala Gly Glu Leu Arg Arg Glu Thr Glu Gly Asp Ser Ser
        3380               3385               3390

Pro Pro Ser His Ser Pro Lys Asn Val Met Val Gly Glu Gly Val
        3395               3400               3405

Asp Asn Ser Arg Phe Pro Arg Ala Ser Leu Glu Glu Gln Glu Trp
        3410               3415               3420
```

-continued

```
Lys Lys Glu Lys Ala Glu Glu Lys Glu Arg Arg Asn Trp Glu Lys
3425                3430                3435

Pro Glu Val Ile Gln Ser Gly Leu Pro Ser Gly Glu Arg Glu Glu
3440                3445                3450

Val Cys Gln Ser Val Gly Ala Ala Ser Arg Glu Gln Gly Leu
3455                3460                3465

Ser Gly Ser His Ala Ala His Lys Glu Pro Gln Lys Glu Ala Glu
3470                3475                3480

Val Ser Cys Leu Ser Ser Thr Arg Asp Met Thr Arg Val Arg Glu
3485                3490                3495

Ala Arg Glu Glu Pro Thr Phe Glu Asn Arg Gly Lys Asn Asp Gln
3500                3505                3510

Thr Lys Pro Ala Glu Ala Glu Asp Arg Gly Asn Val Arg Val Asp
3515                3520                3525

Glu Phe Arg Leu Ser Arg Ser Pro Glu Asn Glu Ser Arg Leu Leu
3530                3535                3540

Ser Ser Leu Gln Lys Asp Arg Asp Glu Asp Lys Ile Glu Glu Ser
3545                3550                3555

Glu Asn Arg Leu Ala Gly Ala Arg Gly Thr Gly Glu Leu Arg Ser
3560                3565                3570

Asp Pro Thr Ser Ala Ser Ser Ser Ser Ala Val Asn Thr Val Ala
3575                3580                3585

Gly Ala Asp Pro Gly Arg Glu Val Glu Asn Val Val Ala Glu Asn
3590                3595                3600

Cys Ser Ser Pro Ser Ser Phe Pro Gly Gly Gln Asp Asp Thr Leu
3605                3610                3615

Ser Phe Val Leu Gln Glu Arg Glu Arg Ser Glu Ala Ala Ala Val
3620                3625                3630

Leu Gly Lys Ser Glu Ser Ala Thr Asp Ala Val Ala Gly Glu Gly
3635                3640                3645

Glu Gly Lys Glu Arg Ser Arg Gln Ser Pro Asn Gly Cys Gly Ala
3650                3655                3660

Gly Glu Glu Thr Arg Asp Asp Glu Ser Arg Leu Asp Arg Gln Ser
3665                3670                3675

Gly Ser Thr Thr Asp Ala Pro Pro Leu Phe Leu Pro Ser Gly Ser
3680                3685                3690

Ser Asp Leu Leu Ser Leu Pro Pro Ser Leu Arg Leu Gly Glu Thr
3695                3700                3705

Ala Gly Arg Cys Leu Pro Asn Gly Pro Ala Pro Pro Gly Glu Gly
3710                3715                3720

Val Ser Glu Pro Val Ser Ser Arg Val Gly Ser Val Leu Glu Gly
3725                3730                3735

Gly Thr Gly Ala Arg Arg Gly Glu Cys Val Ser His Ser Gln Ala
3740                3745                3750

Gly Thr Ser Arg Glu Gln Gly Gly Val Ser Arg Gly Glu Ser Asp
3755                3760                3765

Thr Ala Thr Pro Phe Ser Ser Gly Gly Glu Thr Gly Ala Ser His
3770                3775                3780

Ala Asp Glu Lys Pro Gln Arg Gly Pro His Ser Ser Leu Asn Phe
3785                3790                3795

Phe Ala Ala Leu Asp Leu Glu Gly Gly Arg Thr Gln Asn Ala Ala
3800                3805                3810
```

-continued

```
Pro Gly His Lys Gly Thr Leu Ala Ser Pro Thr Gly Val Ala Ala
    3815                3820                3825

Pro Phe Gly Asp Pro Leu Glu Asn Ser Pro Gln Asn Leu Phe Glu
    3830                3835                3840

Ala Asn Thr Ser Lys Ser Pro Phe Ser Pro Asp Gly Trp Gly Glu
    3845                3850                3855

Ala Ala Phe Phe Ser Ser Ala Ser Ser Phe Arg Ser Phe Ser Phe
    3860                3865                3870

Thr Ser Gly Asn Pro Pro Gly Ser Ser Ser Glu Pro Ala Ala Pro
    3875                3880                3885

Pro Arg Lys Arg Arg Gly Arg Pro Pro Leu Ser Arg Arg Ser Gln
    3890                3895                3900

Gly Ala Thr His Lys Asp Ala Val His Arg Gln Asp Arg Asp Arg
    3905                3910                3915

Val Ser Ser Tyr Leu Lys Met Ala Ala Gly Gly Gln Phe Ser Val
    3920                3925                3930

Leu

<210> SEQ ID NO 21
<211> LENGTH: 2074
<212> TYPE: PRT
<213> ORGANISM: Toxoplasma gondii

<400> SEQUENCE: 21

Met Val Asp Glu Asp Gly Gly Asp Ser Cys Arg Arg Gly Ser Arg Asp
1               5                   10                  15

Ile Gly Thr Glu Glu Ala Phe Arg Lys Gln Glu Phe Arg Ser Glu Ala
            20                  25                  30

Ala Val Gln Asn Met Arg Gly Ser Ala Trp Leu Cys Ala Gly Lys
        35                  40                  45

Ser Glu Phe Glu Leu Glu Ser Lys Glu Val Val Pro Pro Lys Gly Leu
    50                  55                  60

Ala Glu Asp Gly Val Gly Glu Val Ser Pro Gly Ala Arg Gly Thr Asp
65                  70                  75                  80

Thr Arg Val Glu Ala Pro Val Gly Glu Ala Arg Ala Ala Phe Val Glu
                85                  90                  95

Gly Asp Gly Glu Pro Glu Phe Asp Gln Val Phe Arg Gly Gly Ser Thr
            100                 105                 110

Gln Ser Val Arg Pro Trp Glu Ser Leu Gly Gly Asn Leu His Arg Gly
        115                 120                 125

His Glu Arg Asp Glu Asp Lys Glu Ser Gly Thr Thr Arg Arg Thr Ile
    130                 135                 140

Met Gly Leu Ser Glu Arg Pro Leu Asp Ala Ala Ser Lys Val Pro Cys
145                 150                 155                 160

Ala Asp Thr Gly Cys Asp Leu Pro Ser Phe Leu Phe Thr Ser Pro His
                165                 170                 175

Pro Leu Ala Ser Asp Val Pro Val Phe Arg Glu Glu Leu Ser Ser Cys
            180                 185                 190

Glu Asp Glu Gly Ala Gly Thr Met Gly Ser Pro His Ser Gly Cys Leu
        195                 200                 205

Ser Leu Ser Gln Asp Thr Thr Ala Pro Thr Tyr Ser Gly Asn Arg Gly
    210                 215                 220

Pro Ala Leu Val Ser Ser Ala Pro Ser Arg Ser Leu Asp Tyr Phe Ser
225                 230                 235                 240
```

```
-continued

Ile Ser Ser Ser Trp Gly Thr Ala Pro Ser Val Ser Gly Thr Pro Thr
            245                 250                 255

Ser Tyr Asn Leu Cys Ala Thr Lys Gly Arg Gln His Ala Leu Pro Pro
            260                 265                 270

Gly Gln Gly Ala Val Ala Tyr Leu Gly Ser Ser Gly Ser Ser Pro Ala
            275                 280                 285

Val Gly Phe Thr Ser Ser Phe Ser Arg His Met Pro Asp His Arg Pro
    290                 295                 300

Gly His Pro Ala Gln Gln Glu Thr Leu Gln His Gln Thr Ile Ser Glu
305                 310                 315                 320

Asp Phe Cys Phe Pro Glu Thr Phe Gln Pro Leu Pro Gln Asn Ala Ser
                325                 330                 335

Ala Leu Gly Phe Thr Asp Ser Gly Ala Glu Leu Lys Glu Arg Leu Pro
            340                 345                 350

Leu Pro Pro Pro Gly Ala Ala Glu Ala Ser Ala Ala Gln His Glu
            355                 360                 365

Ala Gly Gly Met Trp Ser Leu Gly Pro Gly Ala Ser Val Ala Gly Ala
    370                 375                 380

Ala Ala Ser Leu Ser Pro Pro Ser Ser Phe Gln Pro Ser Phe Pro Gly
385                 390                 395                 400

Thr Pro Gly His Pro Gly Ser Glu Ile Gln Ala Ala Gly Gly Val Gly
                405                 410                 415

Pro Phe Gly Arg Ser Pro Phe Ser Asp Glu Asn Gly Gly Asn Pro Leu
            420                 425                 430

Ala Val Ala Ser Pro Val Ser Cys Phe Pro Val Ala His Ala Arg His
            435                 440                 445

Pro Gly Asp Pro Gly Gly Ala Ser Ser Pro Arg Arg Ser Pro Ser Leu
            450                 455                 460

Val Ser Ser Ser Thr Thr Cys Pro Ser His Gly Thr Val Ser Ala Ala
465                 470                 475                 480

Ser Pro His Ser Arg Pro Thr Glu Ser Met Ser Pro Ala Phe Pro Tyr
                485                 490                 495

Ala Gly Ala Asn Leu Ser Ser Gly Leu Pro Pro Gly Leu Gly Gln Asn
            500                 505                 510

Leu Ala Asn Ile Val Ser Pro Leu Pro Leu Gln His Leu Leu Gln Leu
            515                 520                 525

Gly Ser Leu Ser Ser Ala Ile Gly Pro Ala Gly Phe Asp Arg Thr Val
    530                 535                 540

Pro Gly Thr Leu Gly Leu Pro Gly His Pro Leu Pro Asp Leu Ser Gln
545                 550                 555                 560

Leu Leu Gly Gly Ser Ser Leu Gly Val Asp Ser Ala Gly Thr Ser Asn
                565                 570                 575

Ala Gly Gly Gly Asp Arg Asp Asn Ser Ser Gly Ser Glu Ala Ser Met
            580                 585                 590

Lys Leu Ala Cys Ser Pro Leu Leu His Pro Ala Leu Arg Ser Ser Ala
            595                 600                 605

Cys Gly Leu Arg Pro Pro Ala Ser Ala Ser Arg Phe Ser Gly Val Gly
    610                 615                 620

Ala His Gly Asn Phe Cys Pro Pro Gly Gly Ser Glu Gly Val Pro Gln
625                 630                 635                 640

Gln Pro Gly Arg Thr Phe Val Gly Asn Ile Pro Pro Asp Ile Thr Arg
                645                 650                 655

Ala Ala Val Lys Arg Leu Ala Glu Arg Tyr Gly Thr Val Ile Gly Leu
```

-continued

```
              660                 665                 670
Glu Tyr Asp Pro Gln Pro Gly Arg Trp Ala Tyr Ala Tyr Ile Ile Phe
        675                 680                 685
Ala Thr Ser Thr Met Ala Asp Arg Ala Val Gly Ala Met His Gly Lys
    690                 695                 700
Arg Ala Phe Glu His Ala Glu Phe His Arg Leu Val Ser Cys Arg Cys
705                 710                 715                 720
Ala Lys Asp Phe Pro Leu Thr Arg Leu Pro Leu Thr Lys Met Asp Met
                725                 730                 735
Pro Cys Leu Asn Val Pro Ser Ser Asp Gly Leu Ala Thr Gly Gly Arg
            740                 745                 750
Gly Ser His Thr Pro Pro Arg Gly Val Asp Arg Met Leu Asp Gly Gln
        755                 760                 765
Leu Ser Ser Ser Ser Leu Ser Ser Ser Thr Leu Lys Pro Gly Trp Asn
    770                 775                 780
His Ala Asp Phe Ala Glu Gly Ser Gly Pro Thr Ser Ser Gly Thr Thr
785                 790                 795                 800
Ser Leu Ala Gly Gln Gly Asp Asn Gln Pro Asn Ala Ala Ala Gly Val
                805                 810                 815
Leu Ala Ala Leu Gly Ala Leu Gly Pro Val Ser Ala Ile Pro Gly Leu
            820                 825                 830
Arg Thr Val Gln Gly Lys Gly Cys Val Leu Asp Pro Gly Val Ile Gln
        835                 840                 845
Glu Gln Ala Arg Lys Thr Thr Phe Thr Leu Leu Arg Asp Gly Pro Pro
    850                 855                 860
Gly Ala Asn Leu Phe Ile Tyr Gly Ile Pro Ala Cys Trp Lys Glu Leu
865                 870                 875                 880
Glu Leu Met Ser Leu Ala Gly Gln Phe Gly His Val Val Gly Ile Arg
                885                 890                 895
Val Pro Pro Ala Ser Ser Val Val Gln Pro Ser Ser Asn Phe Pro Ser
            900                 905                 910
Gly Gly Pro Ile Gly Ser Ser Asn Thr Asn Ser Thr Leu Leu Ser Cys
        915                 920                 925
Cys Ser Tyr Asn Arg Gly Phe Gly Phe Val Ser Tyr Asp Asn Thr Ser
    930                 935                 940
Ala Ala Ile Glu Ala Phe Arg Gln Leu Ser Gly Leu Val Val Ala Gly
945                 950                 955                 960
Lys Ala Leu Lys Ile Gln Leu Lys Asn Gly Glu His Leu Leu Ala
                965                 970                 975
Ser Ala Leu Lys Thr Ile Ala Ser Asn Pro Ser Pro Ser Pro Ser Pro
            980                 985                 990
Ser Trp Ser Pro Ala Leu Ser Cys  Pro Met Met Trp Asp  Gly Pro Gly
        995                1000                 1005
Pro Gly  Ser Pro Phe Ile Ser  Thr Gly Leu Ser Thr  Ser Gly Gly
    1010                1015                 1020
Leu Pro  Ser Ala Arg Ser Trp  Cys Gly Gly Ser Thr  Cys Thr Thr
    1025                1030                 1035
Thr Val  Gly Ser Gly Pro Ala  Val Asn Val Ser Pro  Ala Ser Leu
    1040                1045                 1050
Ala Gln  Arg Gly Pro Gly Ser  Pro Gly Ala Pro Ala  Ala Gln Gln
    1055                1060                 1065
Leu Pro  Phe Pro Tyr Ser Val  Pro Glu Ser Pro Val  Gln Arg Phe
    1070                1075                 1080
```

-continued

```
Gly Ser Leu Pro Pro Ala Val Pro Thr Ala Leu Gly Gln Leu Gly
    1085                1090                1095

Gly Ser Phe Leu Gly Gly Ala Val Ala Gly Pro Gln Ser Ser Arg
    1100                1105                1110

Gly Gly Ala Gly Arg Val Thr Gly Ser Ala Ser Ser Pro Phe Met
    1115                1120                1125

Ser Ala Ala Ser Val Cys Ser Ser Thr Ser Ser Gly Pro Ala Gly
    1130                1135                1140

Ser Ser Arg Gly Gly Leu Gly Ser Val Gly Thr Phe Pro Thr Ser
    1145                1150                1155

Asp Pro Phe Leu Thr Val Thr Ala Ala Gly Leu Cys Ser Leu Leu
    1160                1165                1170

Ala Thr Ser Gly Val Gly Gly Lys Gly Gly Met Thr Met Gln Gln
    1175                1180                1185

Gln Leu Leu Leu Gln Gln Ala Phe Ser Thr Met Thr Leu Val Gln
    1190                1195                1200

Lys Gln Gln Leu Leu Leu Leu Thr Gln Ser Ser Gln Glu Thr
    1205                1210                1215

Ser Ala Pro Ser Gln Glu Glu Asn Lys Gly Glu Arg Gly Gly Ala
    1220                1225                1230

His Val Thr Val Asp Arg Gly Glu Ser Ser Gln Val Ala Val Phe
    1235                1240                1245

Arg Gly Pro Ser Val Ala Ser Ser Thr Ser Val Ile Pro Glu Ala
    1250                1255                1260

Gly Ser Gly Ala Lys Gly Pro Ser Val Ser Ser Gly Gly Thr His
    1265                1270                1275

Ser Phe Thr Leu Arg Asp Phe Leu Val Ala Ala Leu Ser Gln Gln
    1280                1285                1290

Pro Ser Lys Leu Ser Pro Thr Gln Gln Glu Ala Asp Asn Ser Val
    1295                1300                1305

Gly Ala Asn Gly Asn Pro Val Thr Leu Leu Gln His Met Arg Glu
    1310                1315                1320

Thr Ala Gln Gly Leu Pro Ala Pro Thr Ala Ser Ala Cys His Leu
    1325                1330                1335

Pro Pro Val Gly His Ser Thr Glu Gly Gly Asn Ala Val Ala Pro
    1340                1345                1350

Thr Asn Pro Leu Arg Asn Ser Gly Glu Lys Thr Arg Pro Pro Leu
    1355                1360                1365

Gln Gly Ser Ala Val Ser Pro Ser Gly Pro Gly Asp Asn Phe His
    1370                1375                1380

Met Gly Glu Trp Glu Ala Phe Ser Gly Gly Ser Asp Arg Leu Phe
    1385                1390                1395

Gly Thr Leu Leu Ser Gln Gln Asn Ser Leu Ala Phe Ser His Gln
    1400                1405                1410

Gly Lys Tyr Asp Thr Ser Leu Arg Phe Thr Val His Ser Ser Gly
    1415                1420                1425

Gly Ile Asn Glu Gly Ala Ala Thr Phe Phe Lys Thr Glu Leu Pro
    1430                1435                1440

Gly Asp Arg Pro Asp Ser Ile Asp Leu Ser Phe Leu Gln Thr Ala
    1445                1450                1455

Asp Gly Pro Arg Gln Lys Val Lys Ala Glu Met Thr Pro Ala Glu
    1460                1465                1470
```

-continued

```
Arg Ser Pro Ser Leu Ser Ala Glu Ala Phe Ser Pro Arg Arg Val
1475                1480                1485

Ser Leu Ala Arg Arg His Thr Lys Glu Glu Gly Met Ser Ser Thr
    1490                1495                1500

Gly Gly Ser Leu Asn Pro His Thr Arg Asp Val Ser Ala Ser Leu
    1505                1510                1515

Gly Ser Thr Ser Ala Leu Pro Ser Asp Phe Cys Leu Leu Ser Arg
    1520                1525                1530

Gly Lys Lys Gly Lys Phe Arg Asp Gln Cys Gly Thr Arg Ala Val
    1535                1540                1545

Ser Ser Pro Gln Ala Asp Glu Ala Asn Pro Ser Ser Ser Gly Ser
    1550                1555                1560

Asp Ser Leu Ala Ala Leu Lys Ala Gly Thr Arg Asp Ser Ala Ser
    1565                1570                1575

Lys Val Arg Glu Cys Gly Thr Ala Arg Thr Ile Val His Gln Leu
1580                1585                1590

Ala Gln Cys Val Ser Met Leu Ala Ser Pro Thr Gly Phe Phe Arg
1595                1600                1605

Lys His Glu Ala Glu Ala Trp Ser Val Glu Lys Ala Gly Gly Ala
1610                1615                1620

Gln Gly Glu Val Ser Gly Thr Gly Arg Ser Glu Glu Lys Leu Glu
1625                1630                1635

Asp Gly Phe Ala Asp Trp Asn Asp Arg Gly Arg Gly Asp Val Glu
1640                1645                1650

Glu Val Gln Lys Ala Glu Glu Ser Thr Pro Gly Glu Gly Cys Pro
1655                1660                1665

Ser Leu Pro Ile Pro Pro Met Phe Val Ser Trp Lys Gln Glu Thr
1670                1675                1680

Lys Gly Leu His Ala Glu Cys Ile Gly Gln Lys Thr Gly Asn Lys
1685                1690                1695

Asp Ala Lys Gln Trp Glu Asn Glu Thr Gly Gln Asn Ala Thr Thr
1700                1705                1710

Glu Ala Ala Gln Arg Gly Gly Gln Met Gly Val Arg Glu Gly Phe
1715                1720                1725

Val Arg Asp Lys Gly Glu Cys His Asn Ala Thr Ala Pro Gly Leu
1730                1735                1740

Gly Ala Glu Asp Ser Lys Arg Pro Leu His Ser Thr Gly Val Asp
1745                1750                1755

Ser Leu Ser Pro Ser Arg Gln Ala Ser Leu Glu Asp Ala Pro Ser
1760                1765                1770

Ser Met Ser Phe Phe Phe Ser Gly Ala Pro Ala Val Asn Lys Ala
1775                1780                1785

Ser Arg Glu Arg Gly Asp Cys Met Ser Ser Cys Gln Arg Pro Ser
1790                1795                1800

Ala Ala Leu Ser Ser Asn Leu Thr Gly Ala Pro Tyr Gly Ser Ala
1805                1810                1815

Pro Val Pro Pro Arg Leu Gly Arg Pro Glu Ala Asn Asp Glu Ala
1820                1825                1830

Thr Ala Ala Arg Pro Glu Leu Ala Lys Gly Leu Ser Leu Lys Arg
1835                1840                1845

Asp Glu Gly Glu Glu Thr Lys Glu Thr Thr Thr Ser Ser Ile Leu
1850                1855                1860

Glu Ala Ser Leu Lys Asp Ile Ala Asp Ala Ala Arg Arg Thr Glu
```

-continued

```
                    1865                1870                1875

Val Leu Gly Pro Leu Ala Gly Lys Ala Ser Gly Pro Ala Cys
        1880                1885                1890

Ala Thr Ser Pro Lys Arg Glu Arg Thr Ala Val Ser Gly Gly Leu
    1895                1900                    1905

Arg Ser Trp Pro Leu Gly Ser Ser Gly Ser Ser Thr His Gly Leu
    1910                1915                    1920

Ser Glu Glu Glu Gly Arg Ser Ser Gly Pro Ser Pro Pro Ser Cys
    1925                1930                    1935

Ser Pro Phe Leu Ser Glu Gln Asp Gly Val Pro Leu Ser Gln Arg
    1940                1945                    1950

Glu Ser Ser Pro Asn Val Lys Ser Val His Asp Phe Ser Asn Gly
    1955                1960                    1965

Gly Arg Asn Ala Val Ala Pro Pro Pro Thr Phe Lys Ala Ser
    1970                1975                1980

Gln Arg Arg Val Lys Arg Thr Asp Val Ser Met Leu Thr Ser Gly
    1985                1990                    1995

Gly Pro Gly Phe Leu Pro Pro Pro Ser Ser Gly Ile Asp Arg Glu
    2000                2005                    2010

Arg Arg Glu Gly Cys Ala Ala Ile Phe Ser Ser Leu Ala Ser Ser
    2015                2020                    2025

Ser Gln Gln Ala Ala Ala Gln Val Val Cys Gly Arg Gly Glu Gly
    2030                2035                    2040

Ala Ala Pro Lys Ser Ala Gly Pro Gly Pro Ser Leu Thr Pro Ala
    2045                2050                    2055

Ser Glu Glu Arg Ala Asp Asn Thr Arg Lys Gly Thr His Gly Phe
    2060                2065                    2070

Asp

<210> SEQ ID NO 22
<211> LENGTH: 1225
<212> TYPE: PRT
<213> ORGANISM: Toxoplasma gondii

<400> SEQUENCE: 22

Met Leu Glu Arg Arg Gly Thr Leu Arg Tyr Gly Ala Ala Arg Leu
1               5                   10                  15

Arg Gln Phe Gly Ser Arg Asp Ser Ile Leu Leu Ala Pro Ser Ser
            20                  25                  30

Arg Ser Met Ser Thr Ser Gly Phe Phe Leu Pro Ala Leu Pro Gly Glu
        35                  40                  45

Arg Ser Leu Ser Gly Asp Ser Glu Ala Pro Gln Asp Phe Asp Leu Glu
    50                  55                      60

Ala Ala Leu Arg Gly His Ser Arg Asn Pro Ala Arg Val Phe Pro Gly
65                  70                      75                  80

Glu Gly Asp Arg Arg Asp Gly Gly Asp Gly Gly Glu Lys Arg Glu Arg
                85                  90                      95

Ser Arg Gly Arg Gly Ser Leu Gly Thr Pro Arg Leu Ser Pro Ser Ser
            100                 105                 110

Phe Asp Ala Arg Glu Asp Phe Ser Gly Leu Ser Gly Arg Trp Gly Gln
        115                 120                 125

Arg Glu Asp Gly Phe Gly Ser Thr Gly Ala Ser Gly Arg Pro Pro Trp
    130                 135                     140

Val Gly Arg Lys Ser Arg Glu Gly Gly Arg Leu Ala Glu Met Thr Ala
```

-continued

```
            145                 150                 155                 160
        Ala Leu Ser Val Ala Thr Glu Glu Phe Ser Gly Asp Arg Glu Gln
                        165                 170                 175

Thr His Gly Trp Leu Thr Lys Ala Glu Thr Val Thr Gln Gly Asp Glu
                            180                 185                 190

Asp Leu Val Ser Ser Glu Thr Thr Tyr Ile Ala Met Leu Arg Glu Glu
                        195                 200                 205

Leu Trp Gln Ala Leu Ser Ala His Val Ala Met Trp Arg Arg Asp Lys
                    210                 215                 220

Ile Glu Ala Gly Leu Asn Cys Leu Glu Gln Ile Glu Trp Phe Trp Gly
        225                 230                 235                 240

Val Glu Gly Met His Lys Val Gln Glu Val Arg Ala Leu Val Lys Asp
                            245                 250                 255

Asn Lys Met Asp Ser Ala Gly Ala Val Ile Ser Ser Val Thr Ala Ser
                        260                 265                 270

Met Ser Ser Val Thr Gly Ser Met Gln Gly Arg Gln His Cys Phe Tyr
                    275                 280                 285

Val Leu Val Ala Val Pro Pro Tyr Thr Phe Arg Asn Ser Asp His Arg
                    290                 295                 300

Val Asn Leu Ala Ala Glu Leu Arg Arg Ile Ala Ser Lys Glu Gln Ser
        305                 310                 315                 320

Gln Asp Ser Ser Leu Val Tyr Arg Ile Val Glu Val Asp Ser Met Arg
                        325                 330                 335

Arg Ala Leu Leu Ala Ala Ile Val Asn Pro Asp Ile Leu Ala Val Val
                    340                 345                 350

Val Gln Asp Asn Val Pro Val Asp His Ser His Thr Ser Ser His Ala
                    355                 360                 365

Leu Val Gly Phe Glu Ala Phe Val Arg Gly Val Glu Met Phe Val Asp
                370                 375                 380

Ala Pro Val Ala Gln Met Arg Ala Gly Ala Pro Val Leu Ser Thr Phe
        385                 390                 395                 400

Val Arg Ser Val Ser Arg Cys Arg Gly Asn Val Asp Ile Phe Cys Val
                            405                 410                 415

Cys Thr Ala Met Gly Leu Ala Ser Leu Glu Pro Val Thr His Leu Val
                        420                 425                 430

Lys Arg Ala Phe Phe Pro Asn Asp Asp His Ser Asp Leu His Glu Ala
                    435                 440                 445

Ile Leu Ala Gly Val Arg Ser Lys Met Arg Cys Pro Phe Phe Glu Ala
                    450                 455                 460

Leu Arg Arg Tyr Ala Glu Arg Pro Ile Gly Val Phe His Ala Leu Ala
        465                 470                 475                 480

Ile Ser Arg Gly Asn Ser Val Arg Arg Ser Lys Trp Ile Gln Gly Leu
                        485                 490                 495

Ile Asp Phe Tyr Gly Val Asn Leu Phe Lys Ala Glu Ser Ser Ala Thr
                    500                 505                 510

Cys Gly Gly Leu Asp Ser Leu Leu Asp Pro His Gly Ser Leu Leu Asp
                    515                 520                 525

Ala Gln Asn Leu Ala Ala Arg Ala Tyr Asp Ala Ser Tyr Ala Phe Phe
                530                 535                 540

Val Thr Asn Gly Thr Ser Thr Ser Asn Lys Ile Val Leu Gln Ala Val
        545                 550                 555                 560

Leu Arg Pro Glu Asp Val Leu Val Asp Arg Asp Cys His Lys Ser
                        565                 570                 575
```

-continued

His His Tyr Gly Phe Val Leu Ala Gly Ser Ser Pro Cys Tyr Leu Asp
             580                 585                 590

Ala Tyr Pro Leu His Arg Phe Ser Met Tyr Gly Gly Val Pro Leu Asp
         595                 600                 605

Ser Ile Lys Arg Thr Leu Leu Ala Tyr Arg Ala Val Gly Arg Leu Glu
     610                 615                 620

Glu Val Lys Leu Leu Val Leu Thr Asn Cys Thr Phe Asp Gly Ile Val
625                 630                 635                 640

Tyr Asn Val Arg Arg Val Ile Glu Glu Cys Leu Ala Ile Ala Pro His
                 645                 650                 655

Leu Val Phe Leu Phe Asp Glu Ala Trp Phe Ser Tyr Ala Met Phe His
             660                 665                 670

Pro Ile Leu Lys Thr Arg Thr Ala Met His Ala Ala Asn Glu Ile Arg
         675                 680                 685

Arg Asp Leu Met Glu Gly Arg Tyr His Gln Leu Phe Glu Asp Leu Val
     690                 695                 700

Glu Thr Leu Gly Thr Asp Asp Leu Arg Ala Val Asp Ala Glu Thr Leu
705                 710                 715                 720

Ala Lys Thr Arg Leu Val Pro Asp Pro Arg Arg Met Arg Val Arg Val
                 725                 730                 735

Tyr Ala Thr His Ser Ile His Lys Ser Leu Thr Ala Leu Arg Gln Gly
             740                 745                 750

Ser Met Ile Leu Val Asn Asp Asp Leu Phe Glu Ser His Val His Thr
         755                 760                 765

Ala Phe Lys Glu Ala Tyr Tyr Thr His Met Ser Thr Ser Pro Asn Tyr
     770                 775                 780

Gln Ile Leu Ala Thr Leu Asp Val Gly Arg Ser Gln Met Glu Leu Glu
785                 790                 795                 800

Gly Tyr Gly Leu Val Glu Arg Gln Ile Glu Ala Ala Phe Phe Ile Arg
                 805                 810                 815

Arg Leu Leu Thr Arg Asp Leu Leu Val Arg Lys Tyr Phe Thr Val Leu
             820                 825                 830

Ser Pro Arg Asp Met Ile Pro Ser Ala Met Arg Lys His Ser Arg Glu
         835                 840                 845

Phe Leu Gly Glu Glu Ala Leu Gln Cys Glu Leu Thr Leu Gln Thr Leu
     850                 855                 860

Glu Gln Val Trp Leu Ser Asp Asp Glu Phe Val Leu Asp Pro Thr Arg
865                 870                 875                 880

Ile Thr Leu Phe Thr Gly Leu Ser Gly Leu Asp Gly Glu Thr Phe Lys
                 885                 890                 895

Val Lys Trp Leu Met Asp Lys Tyr Gly Val Gln Ile Asn Lys Thr Ser
             900                 905                 910

Arg Asn Ser Val Leu Phe Met Thr Asn Ile Gly Thr Thr Arg Ser Ser
         915                 920                 925

Cys Val Phe Leu Lys Ala Cys Ile Arg Ser Cys Ala Gln Glu Leu Glu
     930                 935                 940

Met His Arg Leu Leu Ser Ser Thr Arg Glu Leu Glu Glu Val Asn Asp
945                 950                 955                 960

Ala Val His Gly Leu Val Glu Glu Cys Pro Asp Leu Pro His Phe Ser
                 965                 970                 975

Ala Phe His Pro Val Phe Ala Lys Pro Ala Arg Val Cys Glu Ala Ala
             980                 985                 990

```
Arg Glu Asn Ala Ala Ala Glu Glu Pro Thr Gly Ala Ala Ala Asn Ala
        995                 1000                1005

Lys Gly Gly Asp Lys Lys Gly Asp Gly Lys Arg Glu Ala Ser Val
    1010                1015                1020

Asp Gly Glu Asp Ala Leu Ala Ser Leu Val Lys Asp Gly Asp Leu
    1025                1030                1035

Arg Ala Ala Phe Tyr Leu Ala Tyr Asp Glu Asn Asn Val Arg Tyr
    1040                1045                1050

Leu Ser Leu Arg Ser Ala Lys Glu Ala Ile Leu Lys Gly Lys Gln
    1055                1060                1065

Leu Val Ala Thr Thr Phe Val Ile Pro Tyr Pro Pro Gly Phe Pro
    1070                1075                1080

Val Ala Val Pro Gly Gln Val Leu Thr Val Ala Leu Val Asp Phe
    1085                1090                1095

Leu Leu Lys Leu Asp Val Lys Glu Ile His Gly Phe Asp Asp Lys
    1100                1105                1110

Leu Gly Phe Arg Leu Phe Lys Pro Gly Val Leu Thr Glu Lys Leu
    1115                1120                1125

Arg Glu Arg Gln Ser Ala Gly Ala Leu Arg Gly Thr Ser Val Glu
    1130                1135                1140

Gln Arg Leu Pro Pro Glu Thr Glu Thr Val His Val Ala Val Arg
    1145                1150                1155

Pro Pro Thr Ala Gly Thr Pro Gln Leu Ser Glu Glu Lys Lys Asp
    1160                1165                1170

Ala Ser Ser Asn Gly Val Val Ala Ala Ser Ala Asp Asp Pro Asp
    1175                1180                1185

Ser Lys Ile Ser Glu Lys Ser Gly Asn Ser Thr Asn Ala Thr Arg
    1190                1195                1200

Asn Ser Asp Ala Ala Ser Leu Ser Ser Arg Arg Asp Asp Gln
    1205                1210                1215

Glu Lys Arg Glu Ser Glu Thr
    1220                1225

<210> SEQ ID NO 23
<211> LENGTH: 521
<212> TYPE: PRT
<213> ORGANISM: Toxoplasma gondii

<400> SEQUENCE: 23

Met His Ser Leu His Ala Leu Pro Ala Cys Ala Pro Ser Asp Gln Leu
1               5                   10                  15

Val Gln Arg Ala Val Arg Arg Leu Gln Leu Asp Asn Ile Pro Asp Thr
            20                  25                  30

Leu Pro Cys Arg Thr Lys Glu Cys Leu Gln Val Arg Gln Phe Ile Arg
        35                  40                  45

Ser Ser Val Leu Gln Ser Gly Asn Gly Glu Val Leu Tyr Val Ser Gly
    50                  55                  60

Leu Pro Gly Thr Gly Lys Thr Ala Thr Val Gln Thr Val Arg Gly
65                  70                  75              80

Leu Gln Asp Glu Val Glu Gln Gly Ile Leu Pro Pro Phe Asp Val Val
                85                  90                  95

Asp Val Asn Ala Met Arg Leu Pro His Pro Asp Phe Leu Phe Ser Val
            100                 105                 110

Leu His Arg Arg Phe Phe Gly Thr Lys Ala Lys Ser Thr Gln Gln Ala
        115                 120                 125
```

```
Phe Ala Ala Leu Asp Arg Tyr Phe Thr Ser Ser Arg Val Arg Gly Glu
    130                 135                 140

Lys Ala Arg Gly Arg Gly Arg Asp Gly Glu Ala Ser Ser Gly Glu Asp
145                 150                 155                 160

Arg Glu Asp Gly Glu Glu Asn Tyr Phe Thr Tyr Cys Asp Ser Lys
                165                 170                 175

Gly Arg Arg Arg Gly Ala Ser Ser Gln Gly Asp Trp Ala Asn Arg Ile
                180                 185                 190

Val Arg Arg Gly Arg Asp Arg Arg Pro Cys Leu Leu Ile Val Asp Glu
            195                 200                 205

Val Asp Cys Leu Leu Thr Gln Lys Gln Arg Val Leu Tyr Thr Leu Phe
    210                 215                 220

Asp Trp Pro Thr Gln Arg Thr Ala Arg Leu Ile Val Val Gly Ile Ala
225                 230                 235                 240

Asn Thr Ile Asp Leu Pro Asp Arg Phe Leu Ser Ser Arg Cys Ala Ser
                245                 250                 255

Arg Val Gly Phe Gly Arg Leu Thr Phe Asn Pro Tyr Thr Arg Glu Gln
            260                 265                 270

Ile Glu Glu Ile Leu Leu Ala Arg Leu Gln Glu Cys Lys Tyr Leu Phe
        275                 280                 285

Asn Glu Ala Ala Ile Lys Val Cys Ala Arg Lys Val Ala Asn Phe Phe
    290                 295                 300

Gly Asp Leu Arg Arg Ala Leu Gln Pro Ala Asp Ile Ala Lys Ala Ala
305                 310                 315                 320

Asn Asp Leu Phe Asp Ser Pro Ile Lys Asp Ala Ile Thr Ala Leu Pro
                325                 330                 335

Trp Gly Leu Lys Leu Leu Leu Phe Ser Leu Leu Gln Ala Gln Arg Val
            340                 345                 350

Asp Gly Gly Gly Val Ser Leu Leu Gln Leu Arg Asp Arg Phe Gln Gly
        355                 360                 365

Ile Leu Met Ser Trp Gln Ser Gly Ala Cys Lys Thr Asp Ala Glu Gly
    370                 375                 380

Lys Gly Ala Gly Glu Glu Ala Glu Gly Asp Gly Pro Leu Arg Ala Ser
385                 390                 395                 400

Leu Ala Ser Thr Gln Ser Val Thr Tyr Asp Glu Leu Lys Thr Met Val
                405                 410                 415

Asp Val Leu Val Gln Leu Asn Val Val Arg Leu Gly Phe Tyr Leu Pro
            420                 425                 430

Arg Val Glu Ala Pro Ser Gly Ser Ala Ala Asp Cys Leu Pro Glu Glu
        435                 440                 445

Thr Ala Leu Pro Ser Leu Gln Arg Ser Ser Arg Pro Gly Glu Gly Gly
    450                 455                 460

Arg Ser Gln Thr Thr Ser Pro Gln Lys Arg Arg Asn Ala Ser Ala Ala
465                 470                 475                 480

Tyr Ala Ser Leu Gly Leu Ser Gln Gly Phe Gly Pro Leu Arg Val Asp
                485                 490                 495

Pro Val Val Asp Glu Leu Gly Gly Asp Met Gln Val Ala Ile Ala Val
            500                 505                 510

Pro Ser Ser Leu Pro Phe Leu Ser Gly
        515                 520

<210> SEQ ID NO 24
<211> LENGTH: 1456
```

<212> TYPE: PRT
<213> ORGANISM: Toxoplasma gondii

<400> SEQUENCE: 24

```
Met Gly Tyr Ala Asp Thr Phe Asp Ala Val Phe Gly Ser Ser Ala Gly
1               5                   10                  15

Ser Leu Ile Gly Ala Tyr Phe Ile Ser Arg Gln Leu Pro Tyr Glu Gly
            20                  25                  30

Thr Gln Ile Tyr Tyr Asp Trp Leu Pro Phe Met Gly Lys Lys Phe Leu
        35                  40                  45

Asp Leu Lys Arg Ile Gly Arg Gly Leu Gly Leu Gly Phe Leu Leu Asp
    50                  55                  60

Gly Asp Ile Ile Asp Phe Leu Ile Asn Lys Leu Gly Lys Pro Leu Leu
65                  70                  75                  80

Asn Leu Asp Val Leu Leu Lys Asp Ile Val Gln Glu Lys Gln Pro Leu
                85                  90                  95

Asp Trp Asp Lys Phe Lys Ala Asn Asp Ser Trp Gln Pro Leu Lys Val
            100                 105                 110

Trp Arg Arg Lys Val Ala Asn Phe Val Ser Gln Met Leu Met Ser Ile
        115                 120                 125

Asn Arg Ala Ile Ala Asp Gly Tyr Asp Gln Val Leu Val Leu Arg Ser
    130                 135                 140

Arg Pro Asp Gly Lys Arg Val Gly Arg Leu Gly Gly Ile Glu Ala Ala
145                 150                 155                 160

Val Ser Arg Ile Asn Tyr Val Trp Val Glu Asn Arg Leu Ala Arg Arg
                165                 170                 175

Phe Phe Ala Gly Lys His Lys Leu Arg His Val Tyr Glu Tyr Met Lys
            180                 185                 190

Gln Arg Gln His Arg Ile Arg Tyr Met Lys Asp Met Leu Met Leu Asn
        195                 200                 205

Glu Ala Thr Asn Arg His Ile Lys Leu Gln Val Ala Gly Leu Asp Gly
    210                 215                 220

Val Glu Lys Glu Gly His Ala Phe Ala Val Ala Leu Asp Pro Ser Thr
225                 230                 235                 240

Ala Glu Ile Ala Arg Ile Ser Met Thr Arg Lys His Ile Leu Glu Gly
                245                 250                 255

Val Arg Ala Gly Phe Ala Arg Leu Tyr Asp Val Ile Val Pro Asp Pro
            260                 265                 270

Gln Lys Arg Gly Arg Gly Tyr Glu Glu Ala Leu Lys Cys Cys Arg Gln
        275                 280                 285

Asp Arg Arg Asn Leu Pro Thr Leu Glu Ala Gln Asp Ser Leu Ile Arg
    290                 295                 300

Thr Leu Ala Thr Gly His Pro Asp Phe His Arg Ser His Glu Asn Cys
305                 310                 315                 320

Thr Phe Thr Glu Gly Phe Lys Asp Thr Tyr Pro Glu Asp Leu Leu Ala
                325                 330                 335

Asn Leu Leu Ala Ala Leu Leu Lys Lys Thr Asn Ile Asp Pro Asn Arg
            340                 345                 350

Ile Gln Asp Val Cys Ile Gly Asn Val Leu Gln Pro Gly Ala Gly Ala
        355                 360                 365

Leu Gly Thr Arg Ile Gly Met Leu Met Gly Gly Leu Pro Ala Ser Val
    370                 375                 380

Pro Val Asn Val Val Asn Arg Gln Cys Ser Ser Gly Leu Gln Ala Val
385                 390                 395                 400
```

```
Ala Asn Ile Val Ala Ala Ile Arg Gly Gly Phe Ile Asp Val Gly Ile
            405                 410                 415

Gly Gly Gly Val Glu Ser Met Ser His Phe Glu Met Met Lys Thr Leu
            420                 425                 430

Asn Pro Glu Lys Leu Ser Glu Arg Val Phe Gln Asp Glu Gln Ala Arg
            435                 440                 445

Asn Cys Leu Ile Pro Met Gly Leu Thr Ser Glu Ile Phe Gln Asn Val
            450                 455                 460

Ala Glu Lys Tyr Gly Ile Ser Arg Glu Ala Gln Asp Gln Leu Ala Lys
465                 470                 475                 480

Glu Thr His Glu Lys Cys Val Lys Ala Gln Glu Gln Gly Leu Phe Lys
            485                 490                 495

Glu Glu Ile Val Pro Leu Arg Val Lys Val Lys Asp Ala Asn Gly Val
            500                 505                 510

Glu Lys Glu Val Thr Val Asp Thr Asp Glu Gly Pro Arg Lys Gly Thr
            515                 520                 525

Thr Val Ala Asp Leu Ala Lys Leu Lys Pro Ala Phe Gln Ala His Gly
            530                 535                 540

Thr Thr Thr Ala Gly Asn Ser Ser Gln Val Ser Asp Gly Ala Ala Leu
545                 550                 555                 560

Val Leu Leu Ala Arg Arg Ser Thr Ala Glu Lys Leu Arg Leu Pro Ile
            565                 570                 575

Leu Ala Arg Phe Val Ala Phe Thr Val Val Gly Val Pro Pro Glu Ile
            580                 585                 590

Met Gly Ile Gly Pro Ala Phe Ala Ile Pro Ala Val Leu Glu Gln Ala
            595                 600                 605

Ser Leu Ser Met Asp Asp Ile Asp Ile Phe Glu Leu Asn Glu Ala Phe
            610                 615                 620

Ala Ser Gln Val Val Tyr Cys Val Asn Asn Leu Lys Ile Pro Lys Glu
625                 630                 635                 640

Lys Leu Asn Pro Lys Gly Lys Leu Leu Ser Ser Arg Thr Arg Asp Thr
            645                 650                 655

Gly Gly Gly Ile Ala Leu Gly His Pro Leu Gly Cys Thr Gly Ala Arg
            660                 665                 670

Gln Ile Ala Thr Leu Leu Pro Glu Leu Arg Arg Arg Lys Leu Arg Tyr
            675                 680                 685

Gly Val Val Ser Met Cys Val Gly Thr Gly Met Gly Ala Ala Ala Ile
            690                 695                 700

Ile Glu Asn Leu Leu Thr Asn Glu Asp His Asp Ser Ala Ala Ser Val
705                 710                 715                 720

Ala Arg Arg Val Pro Ala Gly Ser Pro Asp Ala Ala Gly Ser Glu Ala
            725                 730                 735

Leu Ala Gly Pro Ser Cys His Thr Ala Ala Asn Ser Thr Phe Leu Thr
            740                 745                 750

Asp Ser Leu His Val Ser Glu Ser Ala Val Pro Cys Gly Ala Ala Gln
            755                 760                 765

Thr Lys Asp Gly Ser Lys Leu Phe Val Pro Ala Glu Asp Asn Met Ala
            770                 775                 780

Asp Ser Pro Ala Val Gly Ile Asp Leu Gly Thr Thr Tyr Ser Cys Val
785                 790                 795                 800

Gly Val Trp Lys Asn Asp Ala Val Glu Ile Ile Ala Asn Asp Gln Gly
            805                 810                 815
```

-continued

```
Asn Arg Thr Thr Pro Ser Tyr Val Ala Phe Thr Asp Thr Glu Arg Leu
            820                 825                 830

Val Gly Asp Ala Ala Lys Asn Gln Val Ala Arg Asn Pro Glu Asn Thr
        835                 840                 845

Ile Phe Asp Ala Lys Arg Leu Ile Gly Arg Lys Phe Asp Pro Ser
    850                 855                 860

Val Gln Ser Asp Met Lys His Trp Pro Phe Lys Val Ile Ala Gly Pro
865                 870                 875                 880

Gly Asp Lys Pro Leu Ile Glu Val Thr Tyr Gln Gly Glu Lys Lys Thr
                885                 890                 895

Phe His Pro Glu Glu Val Ser Ala Met Val Leu Gly Lys Met Lys Glu
            900                 905                 910

Ile Ala Glu Ala Tyr Leu Gly Lys Glu Val Lys Glu Ala Val Ile Thr
        915                 920                 925

Val Pro Ala Tyr Phe Asn Asp Ser Gln Arg Gln Ala Thr Lys Asp Ala
    930                 935                 940

Gly Thr Ile Ala Gly Leu Ser Val Leu Arg Ile Ile Asn Glu Pro Thr
945                 950                 955                 960

Ala Ala Ala Ile Ala Tyr Gly Leu Asp Lys Lys Gly Cys Gly Glu Met
                965                 970                 975

Asn Val Leu Ile Phe Asp Met Gly Gly Gly Thr Phe Asp Val Ser Leu
            980                 985                 990

Leu Thr Ile Glu Asp Gly Ile Phe Glu Val Lys Ala Thr Ala Gly Asp
        995                 1000                1005

Thr His Leu Gly Gly Glu Asp Phe Asp Asn Arg Leu Val Asp Phe
    1010                1015                1020

Cys Val Gln Asp Phe Lys Arg Lys Asn Arg Gly Lys Asp Ile Ser
    1025                1030                1035

Thr Asn Ser Arg Ala Leu Arg Arg Leu Arg Thr Gln Cys Glu Arg
    1040                1045                1050

Thr Lys Arg Thr Leu Ser Ser Thr Gln Ala Thr Ile Glu Ile
    1055                1060                1065

Asp Ser Leu Phe Glu Gly Ile Asp Tyr Ser Val Ser Ile Ser Arg
    1070                1075                1080

Ala Arg Phe Glu Glu Leu Cys Met Asp Tyr Phe Arg Asn Ser Leu
    1085                1090                1095

Leu Pro Val Glu Lys Val Leu Lys Asp Ser Gly Ile Asp Lys Arg
    1100                1105                1110

Ser Val Ser Glu Val Val Leu Val Gly Gly Ser Thr Arg Ile Pro
    1115                1120                1125

Lys Ile Gln Gln Leu Ile Thr Asp Phe Phe Asn Gly Lys Glu Pro
    1130                1135                1140

Cys Arg Ser Ile Asn Pro Asp Glu Ala Val Ala Tyr Gly Ala Ala
    1145                1150                1155

Val Gln Ala Ala Ile Leu Lys Gly Val Thr Ser Gln Val Gln
    1160                1165                1170

Asp Leu Leu Leu Asp Val Ala Pro Leu Ser Leu Gly Leu Glu
    1175                1180                1185

Thr Ala Gly Gly Val Met Thr Lys Leu Ile Glu Arg Asn Thr Thr
    1190                1195                1200

Ile Pro Thr Lys Lys Ser Gln Thr Phe Thr Thr Tyr Ala Asp Asn
    1205                1210                1215

Gln Pro Gly Val Leu Ile Gln Val Tyr Glu Gly Glu Arg Ala Met
```

```
                1220                1225                1230

Thr Lys Asp Asn Asn Leu Leu Gly Lys Phe His Leu Asp Gly Ile
    1235                1240                1245

Pro Pro Ala Pro Arg Gly Val Pro Gln Ile Glu Val Thr Phe Asp
    1250                1255                1260

Ile Asp Ala Asn Gly Ile Met Asn Val Thr Ala Gln Asp Lys Ser
    1265                1270                1275

Thr Gly Lys Ser Asn Gln Ile Thr Ile Thr Asn Asp Lys Gly Arg
    1280                1285                1290

Leu Ser Ala Ser Glu Ile Asp Arg Met Val Gln Glu Ala Glu Lys
    1295                1300                1305

Tyr Lys Ala Glu Asp Glu Gln Asn Lys His Arg Val Glu Ala Lys
    1310                1315                1320

Asn Gly Leu Glu Asn Tyr Cys Tyr His Met Arg Gln Thr Leu Asp
    1325                1330                1335

Asp Glu Lys Leu Lys Asp Lys Ile Ser Ser Glu Asp Arg Asp Thr
    1340                1345                1350

Ala Asn Lys Ala Ile Gln Glu Ala Leu Asp Trp Leu Asp Lys Asn
    1355                1360                1365

Gln Leu Ala Glu Lys Glu Glu Phe Glu Ala Lys Gln Lys Glu Val
    1370                1375                1380

Glu Ser Val Cys Thr Pro Ile Ile Thr Lys Leu Tyr Gln Ala Gly
    1385                1390                1395

Ala Ala Ala Gly Gly Met Pro Gly Gly Met Gly Gly Met Pro Gly
    1400                1405                1410

Gly Met Gly Gly Met Pro Gly Gly Met Gly Gly Met Pro Gly Gly
    1415                1420                1425

Met Gly Gly Met Pro Gly Gly Met Gly Gly Met Pro Gly Ala Gly
    1430                1435                1440

Met Gly Gly Ser Gly Gly Pro Thr Val Glu Glu Val Asp
    1445                1450                1455

<210> SEQ ID NO 25
<211> LENGTH: 572
<212> TYPE: PRT
<213> ORGANISM: Toxoplasma gondii

<400> SEQUENCE: 25

Met Ser Glu Val Tyr Val His Glu Pro Ser Thr Arg Gly Lys Val Val
1               5                   10                  15

Leu His Thr Ser Leu Gly Asp Leu Asp Val Glu Leu Trp Ala Arg Glu
            20                  25                  30

Cys Pro Leu Ala Cys Arg Asn Phe Val Gln Leu Cys Leu Glu Gly Tyr
        35                  40                  45

Tyr Val Asn Thr Ile Phe His Arg Val Val Lys Asp Phe Ile Val Gln
    50                  55                  60

Gly Gly Asp Pro Thr Gly Thr Gly Arg Gly Gly Ala Asp Thr Thr Phe
65                  70                  75                  80

Asp Gly Lys Pro Phe Asp Val Glu Thr His Pro Arg Leu Lys Phe Arg
                85                  90                  95

Tyr Arg Gly Leu Val Gly Val Ala Asn Leu Gly Arg Ser Ser Lys Asp
            100                 105                 110

Ala Glu Asn Asp Glu Arg Gly Arg Ser Leu Gly Thr Asn Gly Asn Gln
        115                 120                 125
```

-continued

```
Phe Phe Ile Thr Leu Ala Arg Ala Asp Val Leu Asn Ala Tyr Thr
    130                 135                 140
Leu Phe Gly Lys Val Thr Gly His Thr Leu Tyr Asn Leu Met Lys Phe
145                 150                 155                 160
Asn Asp Leu Glu Val Gly Lys Glu Asp Arg Pro Met Thr Pro Pro Phe
                165                 170                 175
Ile Lys Ser Val Asp Val Leu Trp Asn Pro Phe Glu Asp Leu Val Pro
                180                 185                 190
Arg Arg Leu Pro Asp Ala Pro Pro Ala Gln Lys Asp Glu Arg Lys Arg
            195                 200                 205
Ala Arg Ala Ala Gly Gly Arg Thr Thr Glu Gly Arg Ala Arg Ser Gln
    210                 215                 220
Gly Ser Ala Leu Arg Glu Glu Ala Glu Ala Arg Ala Lys Leu
225                 230                 235                 240
Arg Lys Ala Asp Lys Lys Leu Leu Ser Phe Gly Asp Glu Glu Gly
                245                 250                 255
Ser Thr Pro Glu Thr Gly Lys Lys Leu Ser Ala His Asp Leu Leu Asp
                260                 265                 270
Asp Pro His Leu Leu Arg Asp Ser Trp Lys Pro Asp Arg Glu Gly Glu
            275                 280                 285
Arg Glu Arg Ala Glu Asp Asp Glu Glu Leu Glu Trp Gln Glu Glu
    290                 295                 300
Gln Lys Ala Arg Glu Thr Gly Pro Ser Val Leu Glu Gly Val Arg Ala
305                 310                 315                 320
Arg Leu Ala Ala Leu Ser Ser Arg Ser Glu Pro Thr Gly Asp Gly
                325                 330                 335
Gln Arg Gln Arg Arg Asp Arg Ser Arg Gly Tyr Glu Gly Arg Asp Ser
            340                 345                 350
Ala Cys Ser Ser Asp Ser Asp Ser Glu Gly Ala Glu Arg Arg Lys Ala
    355                 360                 365
Lys Arg Gly Arg Arg Ser Asp Ser Asp Asp Glu Arg Arg Thr His Val
    370                 375                 380
Asp Ala Leu Arg Leu Arg Thr Gly Val Gly Ser Ala Leu Gln Gly Ser
385                 390                 395                 400
His Ala Asp Arg Asn Lys Met Glu Asn Ser Asp Leu Met Thr Glu Ala
                405                 410                 415
Glu Lys Arg Arg Gln Phe Phe Leu Leu Lys Lys Asp Lys Gly Glu
                420                 425                 430
Gln Arg Arg Gln Asp Thr Thr Met Gln Lys Leu Glu Met Phe Thr Ala
    435                 440                 445
Gln Leu Arg Arg Leu Arg Thr Ser Ala Ala Pro Ala Asn Gly Phe Arg
    450                 455                 460
Glu Thr Val Ser Arg Gly Gly Val Ser Ala Ser Ser Arg Pro Gly Glu
465                 470                 475                 480
Asp Lys Arg Ser Gln Ala Glu Ala Gly Thr Leu Asn Ala Leu Leu Pro
                485                 490                 495
Asp Leu Asp Glu Val Asp Glu Ser Asp Gly Ser Trp Leu Asn Asn
                500                 505                 510
Gly Gly Leu Lys Phe Ala Val Asp Ser Ala Arg Ala Tyr Glu Leu Asp
            515                 520                 525
Glu Ala Arg Ala Ala Ser Val Val Phe Asp Pro Leu Lys Gly
    530                 535                 540
Met Ser Asp Glu Gln Phe Ala Gly Ala Ala Asp Phe Leu Lys Asp Arg
```

```
                545                 550                 555                 560

Val Met Cys Lys Arg Asp Ala Leu Arg Ser Phe Lys
                565                 570

<210> SEQ ID NO 26
<211> LENGTH: 553
<212> TYPE: PRT
<213> ORGANISM: Toxoplasma gondii

<400> SEQUENCE: 26

Met Asp Ser Pro Arg Thr Ala Leu Lys Leu Ala Arg Phe Cys Pro Ser
1               5                   10                  15

Pro Pro Gly Glu Gln Leu Gln Thr Asp Lys Arg Asn Lys Leu Thr Phe
            20                  25                  30

Asn Asn Phe Tyr Lys Thr Lys Leu Cys Pro Trp Tyr Ile Lys Gly Ser
        35                  40                  45

Cys His Trp Gly Ala Ser Cys Asn Tyr Ala His Thr Leu Ser Glu Gln
    50                  55                  60

Arg Glu Ala Val Asp Leu Thr Lys Thr Lys Leu Cys Pro Thr Trp Leu
65                  70                  75                  80

Arg His Ser Val Cys Arg Asn Pro Lys Cys Arg Tyr Ala His His Tyr
                85                  90                  95

Ser Glu Leu Arg Ala Thr Thr Asp Val Phe Lys Thr Ser Leu Cys Ser
            100                 105                 110

Phe Phe Val Lys Gly Ile Ser Cys Pro Met Glu Asn Arg Cys Arg Phe
        115                 120                 125

Ala His Gly Val His Glu Leu Arg Leu Arg Ala Lys Glu Gly His Gln
    130                 135                 140

Asn Gly Ser Ala Tyr Leu Asn Gln Lys Ala Ala Gln Ala Arg Ala Ala
145                 150                 155                 160

Met Ala Ala Ala Ser Ala Ala Ala Ala Arg Ala Ala Lys
                165                 170                 175

Ala Lys Ala Ala Ala Glu Ala Lys Ala Ala Ala Ala Ala Ile Ala
            180                 185                 190

Gly Leu Ala Glu Ala Ser Asn Ser Gly Cys Arg Ala Glu Ser Leu Ser
        195                 200                 205

Ser Pro Pro Val Ala Gln Val Leu Val Pro Val Arg Glu Gly Gly His
    210                 215                 220

Val Pro Leu Ser Cys Ala Val Leu Thr Ser Gly Ser Ser Ala Gln Pro
225                 230                 235                 240

Thr Ala Asp Asn His Leu Thr His Arg Gln Pro Thr Thr Gly Val Leu
                245                 250                 255

Thr Leu Asp Lys Lys Ser Gly Thr Trp Arg Pro Glu Met Ser Ala His
            260                 265                 270

Ala Pro Glu Phe Val Ser Arg Leu Ser Val Thr Pro Leu Tyr Pro Leu
        275                 280                 285

Leu Leu Ser Ala Asn Ala Ser Ala Pro Ser Phe Gly Gly Thr Gly Leu
    290                 295                 300

Glu Gly Thr Ile Glu Leu Leu Leu Gln Ser Leu Gln Cys Gln Ser Gly
305                 310                 315                 320

Asp Leu Ser Gly Asn Asn Ser Leu Gly Ser Met Thr Arg Pro Ile Thr
                325                 330                 335

Pro Gly Asn Gln Thr Ala Phe Val Ser Arg Glu Ser Gly Gln Gly Asn
            340                 345                 350
```

```
Ser Phe Asn Pro Arg Ala Thr Pro Phe Ser Pro Arg Glu Trp Cys Arg
        355                 360                 365

Lys His Gly Asn Gly Tyr Gln Val Ser Gly Asp Ser Leu Phe Pro Pro
    370                 375                 380

Gly Val Glu Pro Ala Ser Asp Asn Pro Leu Ser Ala Leu Asp Phe Ser
385                 390                 395                 400

Ser Leu Leu Ser Thr Val Ala Met Ala Ile Ala Ala Ser Pro Pro Gly
                405                 410                 415

Asp Met Lys Thr Asp Met Pro Met Glu Ala Phe Leu Pro Ala Ser Ala
                420                 425                 430

Gly Glu Ile Ala Ser Thr His Thr Leu Ser Thr Ser Trp Asn Pro Thr
            435                 440                 445

Gly Ser Gln Val Pro Cys Ser Ala His Leu Pro His Gly Leu Leu Arg
        450                 455                 460

Ser Ala Asp Ala Ser Leu Ser Ser Asp Gly Gln Thr Thr Ala Thr Gly
465                 470                 475                 480

Gly Glu Glu Ser Ser Phe Pro Leu Ala Ser Met Val Ser Ser Pro Ser
                485                 490                 495

Glu Gly Thr Gly Glu Asn Gly Thr Gln Ser Arg Thr Asp Ser Asn Ala
                500                 505                 510

Val Asn Leu Lys Val Cys Leu Gln Met Gln Thr Thr Asp Glu Thr Glu
            515                 520                 525

Gly Pro Ser Pro Ala Glu Ser Leu His Pro Val Thr Gly Ser Arg Gln
        530                 535                 540

Thr Thr Ala Ala Gly Ile Asp Tyr Glu
545                 550

<210> SEQ ID NO 27
<211> LENGTH: 769
<212> TYPE: PRT
<213> ORGANISM: Toxoplasma gondii

<400> SEQUENCE: 27

Met Arg Leu Gln Arg Glu Ala Val Phe Gly Leu Met Phe Ala Cys Gly
1               5                   10                  15

Met Trp Met Trp Pro Ser Glu Val Ala Gly Gly Trp Ser Ile Val
            20                  25                  30

Asp Ala Leu Arg Lys Arg Tyr Asp Thr Ser Arg Gly Gly Asp Ala Asn
        35                  40                  45

Gly Val Asp Thr Ser Gly Val Glu Asp Val Ile Gln Ser Glu Ser Ala
    50                  55                  60

Ile Gly Ala Ala Glu Gly Cys Thr Asn Gln Leu Asp Ile Cys Phe Leu
65              70                  75                  80

Ile Asp Ser Ser Gly Ser Ile Gly Ile Gln Asn Phe Arg Leu Val Lys
                85                  90                  95

Gln Phe Leu His Thr Phe Leu Met Val Leu Pro Ile Gly Pro Glu Glu
            100                 105                 110

Val Asn Asn Ala Val Val Thr Tyr Ser Thr Asp Val His Leu Gln Trp
        115                 120                 125

Asp Leu Gln Ser Pro Asn Ala Val Asp Lys Gln Leu Ala Ala His Ala
    130                 135                 140

Val Leu Asp Met Pro Tyr Lys Lys Gly Ser Thr Asn Thr Ser Asp Gly
145                 150                 155                 160

Leu Lys Ala Cys Lys Gln Ile Leu Phe Thr Gly Ser Arg Pro Gly Arg
                165                 170                 175
```

-continued

```
Glu His Val Pro Lys Leu Val Ile Gly Met Thr Asp Gly Glu Ser Asp
            180                 185                 190

Ser Asp Phe Arg Thr Val Arg Ala Ala Lys Glu Ile Arg Glu Leu Gly
        195                 200                 205

Gly Ile Val Thr Val Leu Ala Val Gly His Tyr Val Lys His Ser Glu
        210                 215                 220

Cys Arg Ser Met Cys Gly Cys Ser Gly Thr Ser Asp Asp Ser Pro
225                 230                 235                 240

Cys Pro Leu Tyr Leu Arg Ala Asp Trp Gly Gln Leu Ala Thr Ala Ile
            245                 250                 255

Lys Pro Met Leu Lys Glu Val Cys Lys Thr Leu Pro Gln Asp Ala Ile
            260                 265                 270

Cys Ser Asp Trp Ser Ala Trp Ser Pro Cys Ser Val Cys Gly Asp
            275                 280                 285

Gly Ser Gln Ile Arg Thr Arg Thr Glu Val Ser Ala Pro Gln Pro Gly
        290                 295                 300

Thr Pro Thr Cys Pro Asp Cys Pro Ala Pro Met Gly Arg Thr Cys Val
305                 310                 315                 320

Glu Gln Gly Gly Leu Glu Glu Ile Arg Glu Cys Ser Ala Gly Val Cys
                325                 330                 335

Ala Val Asp Ala Gly Cys Gly Val Trp Gly Glu Trp Ser Ala Trp Ser
            340                 345                 350

Ala Ser Cys Gly Asn Ala Thr Arg Lys Arg Glu Arg Thr Arg Tyr Asn
        355                 360                 365

Asp Pro Pro Gln Gly Ala Gly Arg Arg Cys Glu Asn Gln Asp Pro
        370                 375                 380

Pro Val Leu Gln Glu Gln Thr Glu Glu Ala Thr Leu Ala Pro Cys Ile
385                 390                 395                 400

Thr Ile Pro Pro Thr Pro Pro Glu Trp Ala Ala Trp Ser Asp Cys Thr
            405                 410                 415

Val Thr Cys Gly Gly Gly Asn Arg His Arg Val Arg Asn Ala Leu Pro
            420                 425                 430

Pro Gly Leu Gly Ser Gln Asn Gly Glu Ser Asp Glu Ser Leu Val Ser
        435                 440                 445

Lys Leu Trp Pro Gly Thr Asp Leu Arg Gln Glu Ala Cys Asn Thr
        450                 455                 460

Ser Pro Cys Pro Ile Asn Ala Thr Cys Gly Gln Phe Glu Glu Trp Ser
465                 470                 475                 480

Thr Cys Ser Val Ser Cys Gly Gly Gly Leu Lys Thr Arg Ser Arg Asn
            485                 490                 495

Pro Trp Asn Glu Asp Gln Gln His Gly Gly Leu Ser Cys Glu Gln Gln
        500                 505                 510

His Pro Gly Gly Arg Thr Glu Thr Ile Thr Cys Asn Pro Gln Ala Cys
        515                 520                 525

Pro Val Asp Glu Arg Pro Gly Glu Trp Ala Glu Trp Gly Glu Cys Ser
        530                 535                 540

Val Thr Cys Gly Asp Gly Val Arg Glu Arg Arg Gly Lys Ser Leu
545                 550                 555                 560

Val Glu Ala Lys Phe Gly Gly Arg Thr Ile Asp Gln Gln Asn Glu Ala
                565                 570                 575

Leu Pro Glu Asp Leu Lys Ile Lys Asn Val Glu Tyr Glu Pro Cys Ser
            580                 585                 590
```

```
Tyr Pro Ala Cys Gly Ala Ser Cys Thr Tyr Val Trp Ser Asp Trp Asn
            595                 600                 605

Lys Cys Val Cys Pro Met Gly Tyr Gln Ala Arg His Ala Ala Val Lys
        610                 615                 620

Phe Asp Tyr Arg Asn Lys Pro Cys Asp Leu Pro Thr Phe Glu Thr Lys
625                 630                 635                 640

Ala Cys Ser Cys Gly Glu Thr Asn Pro Val Pro Ser Glu Gly Thr Thr
                645                 650                 655

Pro Gly Ala Pro Gly Ala Thr Gly Pro Glu Gln Pro Asn Gln Arg Pro
            660                 665                 670

Leu Pro Glu Gly Ser Asp Glu Asn Glu Thr Pro Thr Asn Glu Glu Gly
        675                 680                 685

Glu Gln Ser Lys Glu Ser Gly Ser Gly Ile Ala Gly Ala Ile Ala
    690                 695                 700

Gly Gly Val Ile Gly Gly Leu Ile Leu Leu Gly Ala Ala Gly Gly Ala
705                 710                 715                 720

Ser Tyr His Tyr Tyr Leu Ser Ser Val Gly Ser Pro Ser Ala Glu
                725                 730                 735

Ile Glu Tyr Glu Ala Asp Asp Gly Ala Thr Lys Val Val Met Glu Glu
                740                 745                 750

Glu Lys Glu Thr Leu Val Pro Val Asp Asp Asp Ser Asp Met Trp Met
        755                 760                 765

Glu

<210> SEQ ID NO 28
<211> LENGTH: 256
<212> TYPE: PRT
<213> ORGANISM: Toxoplasma gondii

<400> SEQUENCE: 28

Met Ala Gln Gln Ser Gly Phe Cys Gln Pro Gly Ser Pro Val Asn
1               5                   10                  15

Gly Lys Asp Gln Ala Ser Leu Leu Arg Asn Arg Ile Val Glu Ile Pro
            20                  25                  30

Glu Ile His Val Val Glu Lys Leu Val Pro Lys Ile Gln Val Gln Asp
        35                  40                  45

Val Ile Arg Lys Val Pro Arg Thr Asp Ile Gln Trp Val Glu Lys Ile
    50                  55                  60

Val Glu Val Pro Gln Ile Gln Val Ile Glu Lys Ile Val Glu Val Pro
65                  70                  75                  80

Gln Val His Glu Ile Arg Arg Glu Val Pro Arg Val Glu Val Gln Glu
                85                  90                  95

Ile Val His Arg Val Pro Arg Tyr His Val Gln Asn Val Glu Lys Tyr
            100                 105                 110

Val Glu Ile Pro Gln Ile Gln Tyr Val Glu Lys Tyr Val Glu Val Pro
        115                 120                 125

Gln Ile Gln Glu Val Val Lys Phe Arg Glu Arg Val Glu Ile Val Glu
    130                 135                 140

Val Pro Val Glu Lys Ile Arg Glu Val Pro Arg Ile Glu Val Lys Val
145                 150                 155                 160

Val Glu Lys Ile Arg His Val Pro Gly Pro Ile Glu Tyr Ile Asp Val
                165                 170                 175

Pro Gln Glu Arg Ile Ile Glu Lys Pro Val Tyr Glu Thr Ile Glu Lys
            180                 185                 190
```

```
Ile Val Glu Val Pro Glu Val His Asp Val Val Glu Lys Pro Ile
            195                 200                 205

Met Val Pro Val Pro Gly Pro Glu Val Glu Val Pro Val Glu Val Pro
210                 215                 220

Val Tyr Tyr Asp Val Pro Glu Tyr Tyr Pro Gly Pro Thr Arg Val Ile
225                 230                 235                 240

Pro Val Glu Lys Glu Lys Leu Tyr Glu Lys Leu Val Glu Val Pro Val
            245                 250                 255

<210> SEQ ID NO 29
<211> LENGTH: 854
<212> TYPE: PRT
<213> ORGANISM: Toxoplasma gondii

<400> SEQUENCE: 29

Met Asp Arg Thr Leu Ser Pro Pro Val Glu His Ala Ser Arg Ala Gly
1               5                   10                  15

Ser Tyr Leu Pro Lys Leu Pro Phe Ala Gly Leu Phe Lys Ala Gly Phe
            20                  25                  30

Lys Val Ala Cys Leu Leu Val Gly Val Thr Leu Cys Val Val Gln Ile
        35                  40                  45

Leu Leu Leu Asp Ala Ala Gly Ser Lys Pro Tyr Glu Gln Lys His Ala
    50                  55                  60

Gly Leu Ser Tyr Arg Ser Phe Trp Arg Ser Ile Arg Pro His His Val
65                  70                  75                  80

Pro Thr Ala Ile Ala Gly Ser Leu Ala Gln Met Lys Asp Asp Glu Phe
                85                  90                  95

Asp Phe Asp Trp Asp Asp Glu Glu Tyr Asp Gly Gly Asn Ala Ala Asp
            100                 105                 110

Asp Glu Gln Ser Thr Asp Ala Glu Ser Asp Gly Asp Pro Asp Ala Leu
        115                 120                 125

Thr Met Thr Lys Gln Asp Ser Thr Asn Ala Phe Asn Val Asn Glu Lys
    130                 135                 140

Ser Tyr Val Ser Thr Thr Gln Asn Ala Arg Gln Ser Glu Gln Asp Phe
145                 150                 155                 160

Pro Thr Ser Ser Thr Ser Gly Phe Ser Asn Phe Gly Asn Val Gly Thr
                165                 170                 175

Pro Ala Trp Ala Arg Pro Gly Arg Gly Glu Ala Ala Pro Glu Pro Pro
            180                 185                 190

Ala Pro Val Asn Ser Ser Gly Gln Gly Pro Glu Pro Ala Phe Gly
        195                 200                 205

Ala Leu Arg Arg Ser Ile Asp Ala Ser Ala Pro Glu Ser Met Tyr Thr
    210                 215                 220

Arg Ala Val Glu Thr Ala Pro Ala Thr Asn Phe Leu Gly Val Gly Tyr
225                 230                 235                 240

Asp Ser Ile Lys Gly Asn Pro Ile Gly Asp Pro Asp Met Met Val Asp
                245                 250                 255

Pro Gly Leu Arg Ser Pro Ile Ile Val Phe Ser Phe Gln Gln Asp Pro
            260                 265                 270

Asp Gly Val Thr Asn Asp Leu Asn Tyr Leu Gln Pro Leu Gly Ala Phe
        275                 280                 285

Thr Arg Pro Phe Ser Ala Cys Arg Gln Ser Glu Asn Val Asn Glu Leu
    290                 295                 300

Asp Thr Leu Ser Asp Tyr Gln Lys Val Leu Ser Val Asp Ala Ala Leu
305                 310                 315                 320
```

-continued

His Gly Gly Asp Ser Leu Gly Ile Asn Ser Phe Ser Gly Ser Thr Gly
              325                 330                 335

Tyr Lys Glu Phe Ala Gln Asp Val Ser Ser Lys Ala Asn Lys Ser Phe
            340                 345                 350

Met Leu Lys Thr Tyr Cys Ile Arg Tyr Glu Ala Gly Leu Ala Gln Thr
        355                 360                 365

Asp Ser Phe Lys Trp Asn Tyr Thr Leu Ala Phe Asp Asp Ala Val Ala
    370                 375                 380

His Leu Pro Val Thr Phe Asp Gly Asn Glu Arg Asp Thr Pro Cys Ser
385                 390                 395                 400

Val Gln Gln Trp Arg Ala Asp His Met Ala Asp Gly Cys Gln Gln Thr
                405                 410                 415

Asn Ile Pro Ile Trp Met Ala Phe Ile Glu Gln Phe Gly Thr His Tyr
            420                 425                 430

Thr Ala Arg Leu Tyr Ala Gly Gly Lys Met Thr Tyr Gln Val Thr Met
        435                 440                 445

Lys Ser Ser Asp Val Lys Ala Leu Lys Lys Gly Val Asp Val Lys
    450                 455                 460

Ala Glu Val Lys Leu Met Leu Gly Gly Phe Ser Ala Gly Ala Ser Ser
465                 470                 475                 480

Gln Val Lys Thr Asn Gln Asp Ser Ala Ser Gln Leu Arg Ser Leu Asn
                485                 490                 495

Val Glu Lys Glu Ala Leu Val Ile Gly Gly Lys Pro Pro Ala Asp Val
            500                 505                 510

Ser Asp Pro Lys Ala Ile Ala Ala Trp Ala Asn Ser Val Asp Ala Leu
        515                 520                 525

Pro Met Pro Val Lys Leu Glu Leu Leu Pro Leu Gln Asn Leu Leu Pro
    530                 535                 540

Glu Asp Lys Arg Glu Ala Phe Thr His Ala Val Thr Tyr Tyr Ser Lys
545                 550                 555                 560

Ala Phe Gly Met Ser Ala Met Asp Val Gln Ser Leu Glu Gly Thr Ala
                565                 570                 575

Arg Ser Ile Gln Asp Val Leu Lys Asp Val Thr Gln Ile Ala Trp Ala
            580                 585                 590

Gly Ala Pro Pro Gly Tyr Ala Arg Cys Pro Arg Glu Gln Val Val Leu
        595                 600                 605

Phe Gly Phe Ala Met Arg Phe Asn Phe Lys Val Thr Ile Ser Asn Asn
    610                 615                 620

Leu Ala Asn Tyr His Ile Ala Pro Cys Thr Ala Gly Arg Glu Lys Cys
625                 630                 635                 640

Asp Gly Ile Gly Ala Glu Ala Ala Gly Asp Asp Glu Arg Ile Tyr
                645                 650                 655

Met Ala Cys Gly Pro Glu Val Val Asn Glu Phe Tyr Gln Val Val Ala
            660                 665                 670

Glu Thr Glu Ala Gly Glu Asn Val Ala Val Thr Cys Pro Glu Asp
        675                 680                 685

Thr Val Ile Ala Phe Gly Phe Gly Ile Ser Ile Gly Thr Gly Phe Tyr
    690                 695                 700

Ser Ser Glu Asn Thr Gln Val Glu Pro Cys Thr Ala Gly Gln Thr Arg
705                 710                 715                 720

Cys Thr Lys Ala Arg Thr Ser Asn Thr Val Lys Ser Tyr Val Trp Met
                725                 730                 735

Val Cys Ala Glu Lys Ser Phe Pro Gly Ile Ala Gln Leu Asn Asn Ile
            740                 745                 750

Ala Glu Val Gly Thr Arg Gly Lys Ala Asn Ser Arg Met Lys Asn Thr
            755                 760                 765

Asp Gly Ile Val Asn Val Ser Cys Gly Ala Asp Glu Arg Thr Leu Leu
        770                 775                 780

Gly Leu Ala Leu Glu Val His Thr His Met Pro Ser Val Arg Lys Ala
785                 790                 795                 800

Phe Lys Val Cys Thr His Asp Ser Asn Ser Cys Ala Leu Asn Gly Ala
                805                 810                 815

Gly Glu Gln Leu Thr Val Leu Tyr Val Asp Arg His Ala Leu Phe Gly
                820                 825                 830

Trp Ala Leu Cys Gly Arg Arg His Glu Glu Lys Ser His Val Ala Ser
            835                 840                 845

Asp Ile Ser Lys Gly Ala
            850

<210> SEQ ID NO 30
<211> LENGTH: 440
<212> TYPE: PRT
<213> ORGANISM: Toxoplasma gondii

<400> SEQUENCE: 30

Met Pro Thr Gly His Ala Ala Pro Cys Arg Ser Pro Gln Thr Ala
1               5                   10                  15

Ser Leu Leu Ala Gln Asp Ser Phe Leu Pro Lys Glu Lys Arg Gly Val
            20                  25                  30

Phe Phe Leu Asn Met Glu Arg Gln Ala Thr Cys Arg Tyr Asp Pro Leu
        35                  40                  45

Val Glu Val Pro Leu Pro Pro Gly Ile Val Ile Trp Thr Gln His Gln
    50                  55                  60

Tyr Tyr Asp Gly Ala Gly Trp Leu Ala Leu Pro Asp Arg Glu Lys Leu
65                  70                  75                  80

Glu Leu Lys Pro Thr Arg Trp Ser Asp Gly Arg Leu Arg Phe Leu Asp
                85                  90                  95

Pro Ile Asp Glu Leu Pro Glu Pro Phe Lys Ala Val Gln Ser Gly Lys
            100                 105                 110

Phe Asp Val Lys Cys Trp Lys Arg Gly Asp Cys Lys Leu Gly Ile Glu
        115                 120                 125

Gly Asp Lys Thr Val Phe Leu Lys Ser Pro Ile Ser Pro Asp Val Ala
    130                 135                 140

Val Tyr Val His Ala Glu Arg Leu Pro Thr Phe Pro Lys Ser Trp Lys
145                 150                 155                 160

Pro Leu Val Phe Ile Leu Asn Gln Ser Leu Ala Met Phe Arg Leu Thr
                165                 170                 175

Glu Asn Leu Cys Leu Leu Val Val Ala Glu Lys Asp Lys Thr Met Asn
            180                 185                 190

Ile Ser Cys Val Asp Tyr Asn Gly Gly Phe Ala Cys Thr His Pro Ser
        195                 200                 205

Thr Asn Met Val Val Ala Tyr Gly Ser Tyr Val Leu Lys Asn Phe Glu
    210                 215                 220

Lys Leu Pro Ser Cys Gln Ala Ile Pro Lys Met Leu Thr Ala Ser Gly
225                 230                 235                 240

Asp Trp Gly Phe Phe Val Gln Phe Tyr Pro Trp Gly Phe Phe Ile
                245                 250                 255

Pro Lys Ser Val Glu Leu Thr Arg Pro Gln Ala Val Leu Gly Ala Val
        260                 265                 270

Gly Met Gly Lys Lys Val Asp Thr Ile Gly Leu Val Phe His Pro Pro
        275                 280                 285

Asn Met Phe Ile Asn Val Lys Leu Asp Ile Pro Ala Lys Thr Thr Arg
        290                 295                 300

Ala Leu Gln Phe Gly Lys Asp Phe Gln Val Thr Ala Lys Lys Thr Ser
305                 310                 315                 320

Glu Thr Asp Ile Asp Val Phe Leu Val Ile Asp Gly Gln Leu Ala Lys
                325                 330                 335

Tyr Asn Tyr Ser Phe Asp Ile Arg Ile Asn Lys Pro Glu Arg Pro Lys
                340                 345                 350

His Thr Asp Asn Ile His Phe Lys Cys Ser Cys Asp Ala Glu Glu Lys
                355                 360                 365

Lys Lys Pro Asp Pro Lys Phe Lys Leu Ser Ala Cys Lys Asp Ser Val
        370                 375                 380

Ile Leu Leu Glu Gln Gly Cys Pro Ser Gly Asn Pro Asp Glu Gln Leu
385                 390                 395                 400

Val Ser Glu Gln Leu Ile Ala Cys Phe Asp Ala Glu Val Cys Leu Tyr
                405                 410                 415

Ser Thr His Pro Pro Ala Leu Lys Leu Cys Asp Ala Phe Thr Asp Val
                420                 425                 430

Ala Ile Arg Tyr Gln Arg Glu Ala
        435                 440

<210> SEQ ID NO 31
<211> LENGTH: 876
<212> TYPE: PRT
<213> ORGANISM: Toxoplasma gondii

<400> SEQUENCE: 31

Met Ser Thr Ser Arg Gly Asn Pro Phe Ala Tyr Val Ala Lys Thr Leu
1               5                   10                  15

Ala Gly Thr Glu Lys Thr Tyr Tyr Asp Ile Gly Ala Leu Gln Asp Asp
                20                  25                  30

Arg Leu Lys Thr Leu Pro Phe Ser Ile Arg Val Leu Leu Glu Ser Ala
            35                  40                  45

Val Arg Asn Cys Asp Gly Phe Ser Ile Lys Pro Glu Asp Val Gln Thr
        50                  55                  60

Ile Leu Asp Trp Gln Lys Ala Ser Gln Ala Gln Lys Glu Ile Pro Phe
65                  70                  75                  80

Met Pro Ala Arg Val Leu Leu Gln Asp Phe Thr Gly Val Pro Ala Val
                85                  90                  95

Val Asp Leu Ala Ala Met Arg Asp Ala Met Ala Arg Leu Gly Gly Pro
            100                 105                 110

Pro Ser Ser Ile Asn Pro Leu Val Asp Val Asp Leu Val Ile Asp His
        115                 120                 125

Ser Val Gln Val Asp Phe Ser Arg Ser Pro Glu Ala Phe Glu Lys Asn
    130                 135                 140

Leu Ala Lys Glu Met Glu Arg Asn Ser Glu Arg Phe Ser Phe Leu Lys
145                 150                 155                 160

Trp Gly Ser Thr Ala Phe Ser Asn Met Leu Ile Val Pro Pro Gly Ser
                165                 170                 175

Gly Ile Val His Gln Val Asn Leu Glu Tyr Leu Ala Arg Val Val Met

-continued

```
            180                 185                 190
Asp Lys Lys Val Gly Asp Arg Ala Val Leu Tyr Pro Asp Ser Leu Val
        195                 200                 205
Gly Thr Asp Ser His Thr Thr Met Ile Asn Gly Leu Gly Val Val Ala
    210                 215                 220
Trp Gly Val Gly Gly Ile Glu Ala Glu Ala Val Met Leu Gly Gln Gln
225                 230                 235                 240
Ile Ser Met Val Leu Pro Gln Val Val Gly Phe Glu Leu Thr Gly Gln
                245                 250                 255
Met Pro Pro Ser Val Thr Ala Thr Asp Leu Val Leu Thr Val Thr Asn
            260                 265                 270
Ile Leu Arg Lys Lys Gly Val Val Gly Lys Phe Val Glu Phe Tyr Gly
        275                 280                 285
Pro Gly Val Gln Thr Leu Thr Leu Ala Asp Arg Ala Thr Val Ala Asn
    290                 295                 300
Met Ala Pro Glu Tyr Gly Ala Thr Met Gly Phe Phe Pro Val Asp Glu
305                 310                 315                 320
Gln Thr Leu Arg Tyr Leu Lys Gln Thr Gly Arg Pro Asp Glu Lys Val
                325                 330                 335
Asp Leu Ile Glu Ala Tyr Thr Lys Ala Asn His Leu Phe Ala Ser Pro
            340                 345                 350
Ser Val His Ala Glu Ile Ala Phe Ser Asp Arg Val Ser Leu Asn Leu
        355                 360                 365
Ser Glu Leu Glu Pro Cys Val Ala Gly Pro Lys Arg Pro Gln Asp Arg
    370                 375                 380
Val Pro Leu Ser Glu Val Lys Glu Asp Phe Gln Val Ser Leu Arg Asn
385                 390                 395                 400
Pro Val Gly Phe Lys Gly Phe Gly Leu Ser Glu Gln Ala Glu Lys
                405                 410                 415
Lys Val Glu Met Thr Phe Arg Gly Lys Lys Tyr Thr Leu Thr His Gly
            420                 425                 430
Ser Val Val Ile Ala Ala Ile Thr Ser Cys Thr Asn Thr Ser Asn Pro
        435                 440                 445
Gly Val Ile Leu Gly Ala Ala Met Leu Ala Arg Asn Ala Leu Glu Lys
    450                 455                 460
Gly Leu Ser Val Pro Pro Tyr Ile Val Thr Thr Leu Ser Pro Gly Ser
465                 470                 475                 480
Arg Ala Val Thr Glu Tyr Leu Ala Arg Ser Gly Leu Leu Lys Asp Leu
                485                 490                 495
Glu Lys Leu Gly Phe Tyr Thr Ala Gly Tyr Gly Cys Met Thr Cys Ile
            500                 505                 510
Gly Asn Thr Gly Asp Phe Asp Pro Glu Val Ser Ala Ala Ile Ser Gln
        515                 520                 525
Gly Asp Leu Val Val Ala Ala Val Leu Ser Gly Asn Arg Asn Phe Glu
    530                 535                 540
Gly Arg Val His Pro Leu Thr Arg Ala Asn Phe Leu Ala Ser Pro Pro
545                 550                 555                 560
Leu Val Val Ala Tyr Ala Leu Ala Gly Arg Val Asp Phe Asp Phe Glu
                565                 570                 575
Glu Glu Pro Leu Gly Asn Asp Lys Glu Gly Asn Pro Val Phe Leu Arg
            580                 585                 590
Asp Ile Trp Pro Ser Arg Glu Gln Ile Ala Glu Val Glu Ala Lys Ala
        595                 600                 605
```

-continued

```
Leu Ser Ala Ser Ala Phe Val Lys Val Tyr Glu His Ile Thr Glu Gly
    610                 615                 620

Thr Pro Ala Trp Asn Ala Leu Lys Thr Ala Lys Ala Ser Asp Leu Phe
625                 630                 635                 640

Asp Trp Asp Glu Lys Ser Thr Tyr Ile His Asn Pro Pro Phe Phe Gln
                645                 650                 655

Thr Met Gln Lys Glu Pro Ala Pro Ile Glu Asp Ile Val Asp Ala Tyr
            660                 665                 670

Cys Leu Leu Asn Leu Gly Asp Ser Ile Thr Thr Asp His Ile Ser Pro
        675                 680                 685

Ala Gly Asn Ile Ala Val Asn Ser Pro Ala Ala Lys Tyr Leu Gln Ser
    690                 695                 700

Lys Gly Val Glu Arg Lys Asp Phe Asn Thr Tyr Gly Ala Arg Arg Gly
705                 710                 715                 720

Asn Asp Glu Ile Met Val Arg Gly Thr Phe Ala Asn Ile Arg Leu Val
                725                 730                 735

Asn Lys Leu Cys Pro Lys Asp Gly Pro Lys Ser Val His Val Pro Ser
            740                 745                 750

Gly Glu Val Leu Pro Val Tyr Asp Val Ala Met Lys Tyr Lys Ala Glu
        755                 760                 765

Arg Lys Pro Met Ile Val Leu Ala Gly Lys Glu Tyr Gly Ser Gly Ser
    770                 775                 780

Ser Arg Asp Trp Ala Ala Lys Gly Pro Tyr Leu Met Gly Val Lys Ala
785                 790                 795                 800

Ile Ile Ala Glu Ser Phe Glu Arg Ile His Arg Thr Asn Leu Val Gly
                805                 810                 815

Met Gly Ile Leu Pro Leu Gln Phe Gln Glu Gly Gln Asn Ala Glu Ser
            820                 825                 830

Leu Gly Leu Thr Gly Lys Glu Gln Phe Asn Ile Ser Leu Asn Lys Gly
        835                 840                 845

Glu Ile Ile Pro Gly Ser Leu Met Thr Val Lys Thr Ser Asp Gly Lys
    850                 855                 860

Ala Phe Asp Asp Asp Gly Thr Ala Gln Thr Ser Val
865                 870                 875

<210> SEQ ID NO 32
<211> LENGTH: 292
<212> TYPE: PRT
<213> ORGANISM: Toxoplasma gondii

<400> SEQUENCE: 32

Met Asp Ser Leu Gly Asn His Tyr Leu Thr Ala Ala Leu Asp Asp Thr
1               5                   10                  15

Arg Thr Ala Gly Leu Pro Ser Cys Thr Ser Ser Cys Ser Leu Ser Asp
            20                  25                  30

Ser Ile Thr Ala Gly Ser Glu Leu Pro Thr Ser Thr Ser Asp Ala Phe
        35                  40                  45

Phe Leu Asn Asp Glu Gly Asp Thr Glu Asp Phe Val Glu Asn Leu Arg
    50                  55                  60

Gln Gly Gln Ser Asn Val Leu Val Ala Val Arg Val Arg Pro Leu Gln
65                  70                  75                  80

Pro Lys Glu Thr Gln Ala Gly Cys Arg Gln Ile Val Arg Val Leu Gly
                85                  90                  95

Ser Lys Val Val Leu Leu Leu Asp Pro Gly Pro Ser Asn Gln Asp Asp
```

-continued

```
                100                 105                 110
Val Leu Arg Leu Lys Arg Ser Arg Glu Lys Arg Tyr Ala Phe Asp Tyr
            115                 120                 125

Ala Phe Asp Glu His Thr Asp Gln Gln Cys Val Tyr Glu Ser Thr Thr
        130                 135                 140

Lys Phe Leu Ile Asp Gly Val Leu Gln Gly Tyr Asn Ala Thr Ala Phe
145                 150                 155                 160

Ala Tyr Gly Ala Thr Gly Ala Gly Lys Thr Tyr Thr Met Leu Gly Ser
                165                 170                 175

Tyr Lys Gln Pro Gly Val Met Val Tyr Thr Leu Lys Glu Leu Phe Thr
            180                 185                 190

Arg Ile Glu Lys His Gly Glu Asn Lys Asp Phe Leu Val Lys Cys Ser
        195                 200                 205

Phe Leu Glu Ile Tyr Asn Glu Asn Val Arg Asp Leu Leu Asp Ile Arg
    210                 215                 220

Asn Glu Thr Cys Glu Val Arg Glu Asp Pro Gly Lys Gly Ile Ser Ile
225                 230                 235                 240

Ala Gly Ile Ser Glu Thr Glu Val Arg Thr Ala Glu Glu Ile Leu Ile
                245                 250                 255

Leu Leu Gln Thr Gly Asn Lys Asn Arg Thr Gln Glu Ser Thr Asp Ala
            260                 265                 270

Asn Gln Thr Ser Ser Arg Ser His Ala Ile Leu Gln Val Arg Arg Ala
        275                 280                 285

Val Lys Arg His
    290
```

<210> SEQ ID NO 33
<211> LENGTH: 296
<212> TYPE: PRT
<213> ORGANISM: Neospora caninum

<400> SEQUENCE: 33

```
Met Phe Leu Ser Val Glu Ser His Glu Thr Glu Gly Arg Ser Ala Ser
1               5                   10                  15

Pro Thr Pro Ala Ser Ser Arg Ser Pro Thr Asn Gly Pro Gln Thr Ala
            20                  25                  30

Leu Ser Leu Trp Thr Leu Pro Ala Ser Leu Ser Ser Tyr Leu Ser Ser
        35                  40                  45

Phe Pro Ser Ser Leu Ser Arg Ser Pro Lys Ala Ser Val Ser Ala Arg
    50                  55                  60

Arg Gly Thr Gly Glu Val Ala Ala Asp Arg Asp Gly Ala Lys Gln Gly
65                  70                  75                  80

Glu Ile Asp Glu Val Asn Ser His Ser Arg Gly Val Arg Phe Asp Leu
                85                  90                  95

Cys Arg Pro Gly Arg Asn Glu Asp Thr Ala Ala Asp Gly Pro Val Arg
            100                 105                 110

Gly Gly Thr Gln Arg Asn Ala Lys Glu Ala Met Ala Pro His Ser Asp
        115                 120                 125

Gly Val Gln Thr Gly Gly Thr Gly Thr Arg Asp Gly Gly Glu Val Ser
    130                 135                 140

Pro Phe Asp Lys Lys Pro Gly Glu Ser Tyr Ala Ala Tyr Ala Asp Arg
145                 150                 155                 160

Leu His Arg Arg Asp Gly Phe Ser Leu Tyr Phe Asp Asn Asn Ser Ser
                165                 170                 175
```

```
Thr Met Thr Asp Pro Arg Val Tyr Gln Glu Met Ala Pro Phe Phe Glu
        180                 185                 190

Cys Leu Phe Gly Asn Pro Gly Ser Ala His Glu Arg Gly Arg Ile Asn
        195                 200                 205

Lys Thr Ala Leu Glu Glu Ala Arg Val Arg Val Ala Arg Cys Leu Gly
    210                 215                 220

Val Ser Pro Ser Thr Val Ile Phe Thr Ser Gly Ala Thr Glu Asn Leu
225                 230                 235                 240

Asn Trp Ala Ile Lys Cys Gly Ala His Ala Gln Cys Arg Arg Gly Val
                245                 250                 255

Gly Arg His Ile Val Thr Thr Arg Val Glu His Pro Ala Val Leu Glu
                260                 265                 270

Ile Cys Lys Phe Leu Gln Glu Asp His Gly Phe Gly Val Ser Phe Cys
            275                 280                 285

Pro Val Asp Cys Phe Gly Phe Val
            290                 295

<210> SEQ ID NO 34
<211> LENGTH: 707
<212> TYPE: PRT
<213> ORGANISM: Neospora caninum

<400> SEQUENCE: 34

Pro Ser Arg Ala Leu Pro Phe Cys Ser Val Phe Pro Phe Ser Pro Pro
1               5                   10                  15

Ser Trp Cys Pro Phe Ser Phe Pro His Ala Leu Ser Arg Gly Tyr Phe
            20                  25                  30

Leu Phe Leu Lys Ser Arg Ile Asp Lys Met Ala Val Ala His Lys Leu
        35                  40                  45

Leu Ser Leu Leu Ala Leu Phe Cys Leu Val Gly Val Pro Thr Leu Arg
    50                  55                  60

Pro Val Ala Ala Asp Glu Ala Glu Glu Gly Gln Val Lys Asp Val Val
65                  70                  75                  80

Ile Gly Ile Asp Leu Gly Thr Thr Tyr Ser Cys Val Gly Val Tyr Arg
                85                  90                  95

His Gly Arg Val Asp Ile Ile Pro Asn Asp Gln Gly Asn Arg Ile Thr
            100                 105                 110

Pro Ser Tyr Val Ala Phe Thr Asp Asp Arg Lys Ile Gly Glu Ala
        115                 120                 125

Ala Lys Asn Glu Ala Thr Ile Asn Pro Thr Asn Thr Leu Phe Asp Val
    130                 135                 140

Lys Arg Leu Ile Gly Arg Arg Phe Asn Glu Lys Glu Val Gln Lys Asp
145                 150                 155                 160

Lys Gly Leu Leu Pro Tyr Glu Ile Ile Asn Lys Asp Gly Lys Pro Tyr
                165                 170                 175

Ile Arg Val Met Val Lys Gly Gln Pro Lys Val Leu Ala Pro Glu Glu
            180                 185                 190

Val Ser Ala Met Val Leu Thr Lys Met Lys Glu Thr Ala Glu Gln Phe
        195                 200                 205

Leu Gly Lys Glu Val Lys Asn Ala Val Val Thr Val Pro Ala Tyr Phe
    210                 215                 220

Asn Asp Ala Gln Arg Gln Ala Thr Lys Asp Ala Gly Ala Ile Ala Gly
225                 230                 235                 240

Leu Asn Val Ile Arg Ile Ile Asn Glu Pro Thr Ala Ala Ala Ile Ala
                245                 250                 255
```

```
Tyr Gly Leu Asp Lys Lys Asn Glu Lys Thr Ile Leu Val Tyr Asp Leu
            260                 265                 270
Gly Gly Gly Thr Phe Asp Val Ser Val Leu Val Ile Asp Asn Gly Val
            275                 280                 285
Phe Glu Val Leu Ala Thr Ala Gly Asp Thr His Leu Gly Gly Glu Asp
            290                 295                 300
Phe Asp Gln Arg Val Met Asp His Phe Ile Lys Val Lys Lys Lys
305                 310                 315                 320
Tyr Asp Lys Asp Leu Arg Thr Asp Lys Arg Ala Leu Gln Lys Leu Arg
                325                 330                 335
Arg Glu Val Glu Arg Ala Lys Arg Ala Leu Ser Ser Gln His Gln Ala
            340                 345                 350
Lys Val Glu Ile Glu Asn Leu Met Asp Gly Val Asp Phe Ser Glu Thr
            355                 360                 365
Leu Thr Arg Ala Lys Phe Glu Glu Leu Asn Ala Asp Leu Phe Gln Asn
        370                 375                 380
Thr Leu Lys Pro Val Lys Gln Val Leu Glu Glu Ala Asp Val Gln Lys
385                 390                 395                 400
Ser Gln Val Asp Glu Ile Val Leu Val Gly Gly Ser Thr Arg Ile Pro
                405                 410                 415
Lys Ile Gln Gln Leu Ile Lys Asp Phe Phe Asn Gly Lys Glu Pro Asn
            420                 425                 430
Arg Gly Ile Asn Pro Asp Glu Ala Val Ala Tyr Gly Ala Ala Val Gln
        435                 440                 445
Ala Gly Ile Leu Ser Gly Glu Gly Ala Gln Asp Met Val Leu Leu Asp
        450                 455                 460
Val Thr Pro Leu Thr Leu Gly Ile Glu Thr Ala Gly Gly Val Met Ala
465                 470                 475                 480
Lys Ile Ile Asn Lys Asn Thr Val Ile Pro Thr Lys Lys Thr Gln Thr
                485                 490                 495
Phe Ser Thr Tyr Ser Asp Asn Gln Ser Ala Val Leu Ile Gln Val Tyr
            500                 505                 510
Glu Gly Glu Arg Pro Met Thr Lys Asn Asn His Leu Leu Gly Lys Phe
            515                 520                 525
Glu Leu Thr Gly Ile Pro Pro Ala Pro Arg Gly Val Pro Gln Ile Glu
        530                 535                 540
Val Thr Phe Asp Val Asp Arg Asn Gly Ile Leu Ser Val Ser Ala Val
545                 550                 555                 560
Asp Lys Gly Thr Gly Lys Ser Glu Lys Ile Thr Ile Thr Asn Asp Lys
                565                 570                 575
Gly Arg Leu Thr Pro Glu Glu Ile Glu Arg Met Ile Ser Glu Ala Glu
            580                 585                 590
Lys Phe Ala Glu Glu Asp Lys Lys Val Lys Glu Arg Val Asp Ala Arg
        595                 600                 605
Asn Ala Leu Glu Gly Tyr Leu His Ser Met Lys Thr Thr Val Glu Asp
        610                 615                 620
Lys Asp Lys Leu Ala Asp Lys Ile Glu Glu Asp Lys Lys Thr Ile
625                 630                 635                 640
Leu Asp Lys Val Thr Glu Ala Gln Glu Trp Leu Asn Thr Asn Pro Asp
                645                 650                 655
Ala Asp Ala Glu Glu Thr Arg Asp Lys Leu Lys Asp Val Glu Ala Val
            660                 665                 670
```

```
Cys Asn Pro Ile Ile Ser Lys Val Tyr Gly Gln Thr Gly Gly Pro Gly
            675                 680                 685

Ala Gly Gly Ala Ala Gly Gly Ala Asp Asp Asp Asp Tyr Gly Gly His
        690                 695                 700

Asp Glu Leu
705

<210> SEQ ID NO 35
<211> LENGTH: 571
<212> TYPE: PRT
<213> ORGANISM: Neospora caninum

<400> SEQUENCE: 35

Cys Val Arg Leu Pro Ala Phe Cys Met Arg Arg Ala Glu Ala Ser His
1               5                   10                  15

Thr Phe His Asp Pro Ser Val Arg Ser Ile Asn Val Asp Leu Ala Leu
            20                  25                  30

Leu Ser Arg Ser Lys Arg Arg Asp Arg His Leu Tyr Val Trp Ser Phe
        35                  40                  45

Ala Thr Gly Trp Met Leu Arg Arg Leu Arg His Cys Gly Leu Leu Ser
    50                  55                  60

Leu Asn Gly Leu Gly Val Arg Arg Trp Arg Arg Arg Arg Ser Asn
65                  70                  75                  80

Gly Thr Thr Ser Thr His Arg Ser Asp Cys Ala Ala Arg Met Leu Ile
                85                  90                  95

Arg Ser Lys Arg Gly Gly Asp Met Ile Phe Arg Pro Ala Cys Pro Ala
            100                 105                 110

Ser Arg Gly Cys Thr Ala Val Pro Ser Leu Arg Ser Trp His Ser Arg
        115                 120                 125

Ile Ser Leu Leu Cys Gln Asn Phe Asp Arg Ala Leu His Gly Ser Gln
    130                 135                 140

Leu Asn Arg Leu Leu Leu Thr Ser Gly His Ala Ala Arg Arg Gln Arg
145                 150                 155                 160

Ile Ala Arg Met Ala Trp Arg Asp Asn Ala Phe His Ala Phe Leu Ala
                165                 170                 175

Ala Leu Val Val Gln Arg Lys Glu Phe Gly Val Thr His Ser Phe Leu
            180                 185                 190

Gly Asn Gly Val Phe Asn Gly Ala Leu His Val Asp Arg Asp Arg His
        195                 200                 205

Leu Leu Val Ala Gly Leu Asp Leu Gly Ala Lys Ile Phe Leu Asp Asn
    210                 215                 220

Leu Glu Phe Asp Arg Asp Gly Asn Ile Thr Val Asn Asp Leu Leu Asn
225                 230                 235                 240

Arg Asn Arg Ala Val Val Gly His Gly His Phe Asp Arg Leu Gly Asn
                245                 250                 255

Val Thr Val Leu Arg Gly His Asn Ile Ala Val Ser Val Leu Asp Val
            260                 265                 270

Gly Asp Phe Asp Asp Leu Leu His Ile Asn Asp Phe Leu His Asp His
        275                 280                 285

Arg Leu Arg His Leu Asp Asp Leu Phe Leu Leu Asn Asp Leu Asp Arg
    290                 295                 300

Leu Gln Arg Phe Leu Asn His Asn Val Ala Val Val His Leu Ala Asp
305                 310                 315                 320

Phe Asp Asn Leu Phe Leu Tyr Asn Phe Ala Arg Asp Arg Asn Asn Ala
                325                 330                 335
```

```
Phe Leu His His Asp Ala Trp Asn Leu Asp Asp Phe Leu Leu Val Asp
                340                 345                 350

Ile Leu Arg Asp Phe Asp Asp Phe Val Asn Asn Leu Asn Leu Arg His
            355                 360                 365

Leu Asp Asn Phe Leu Leu Val His Gly Leu Val Asp Val Ser Asp Ala
        370                 375                 380

Phe Leu Asp Asp Gly Leu Gly Asp Met Cys His Leu Leu Val His Asn
385                 390                 395                 400

Val Leu Arg His Leu Asp Asp Ser Val Asp Ile Leu His Leu Arg Asp
                405                 410                 415

Phe Asn Asp Ser Phe Leu Asp Phe Leu Leu Gln His Leu Asp Asn Ser
            420                 425                 430

Phe Leu Asp Lys Arg Leu Glu Asn Pro Ser Phe Ser Leu Gly Gly Asn
        435                 440                 445

Asn Ser Arg His Glu Ala Ala Ser Leu Ser Leu Leu Arg Leu Lys Ser
    450                 455                 460

Arg Ser Arg Ala Leu Leu Ala Leu Thr Gly Ser Ala Arg Leu Ala Ala
465                 470                 475                 480

Leu Arg Lys His Gly Asp Lys Glu Glu Asp Asn Phe Val Lys Glu Lys
                485                 490                 495

Gln Lys Asn Val Ser Thr Ala Lys Cys Lys Arg Thr Ser Val Thr Cys
            500                 505                 510

Phe Trp Ser Ala Cys Ala Arg Ser Pro Arg Glu Ile Phe Ser Val Arg
        515                 520                 525

Gly Arg Gly Val Phe Pro Gln Leu Lys Glu Glu Val Arg Asn Gly Lys
    530                 535                 540

Cys Leu Gly Leu Asp Arg Phe Arg Val Pro Leu Gln Lys Ile Cys Ala
545                 550                 555                 560

Lys Arg Asp Ala Pro Leu Asn Phe Glu Lys Gly
                565                 570

<210> SEQ ID NO 36
<211> LENGTH: 765
<212> TYPE: PRT
<213> ORGANISM: Neospora caninum

<400> SEQUENCE: 36

Met Gly Val Gln Arg Glu Ala Phe Phe Gly Leu Met Phe Ala Phe Gly
1               5                   10                  15

Leu Cys Leu Phe Pro Arg Glu Val Ala Gly Gly Arg Trp Gly Leu Met
            20                  25                  30

Asp Ile Phe Lys Arg Glu Pro Lys Ala Thr Ala Thr Ala Ser Asp Gly
        35                  40                  45

Glu Asp Thr Glu Gly Ser Ala Ile Thr Asp Leu Met Lys Ser Gly Gly
    50                  55                  60

Thr Ile Gly Ala Ala Glu Gly Cys Thr Ser Gln Leu Asp Ile Cys Phe
65                  70                  75                  80

Leu Val Asp Ser Ser Gly Ser Ile Gly Glu Ala His Tyr Glu Glu Val
                85                  90                  95

Lys Gln Phe Leu His Ala Phe Leu Ser Lys Leu Pro Ile Gly Asn Asp
            100                 105                 110

Glu Val Asn Thr Ser Leu Val Ile Phe Ser Thr Thr Val His Pro His
        115                 120                 125

Trp Ser Leu Arg Ala Asn Asn Ala Ser Asp Lys Glu Thr Ala Met Gln
```

-continued

```
            130                 135                 140
Asp Val Leu Thr Ile Pro Tyr His Gly Gly Thr Asn Thr Ala Ala
145                 150                 155                 160

Gly Leu Gln Thr Cys Asn Gln Met Leu Phe Asp Tyr Pro Arg Glu Glu
                165                 170                 175

Arg Gln Thr Val Pro Lys Leu Val Ile Ala Met Thr Asp Gly Glu Ser
                180                 185                 190

Asp Ser Asp Phe His Thr Val Asn Glu Ala Lys Val Ile Arg Glu Arg
                195                 200                 205

Gly Gly Ile Ile Thr Val Leu Ser Val Gly Met Tyr Val Asn His Asn
210                 215                 220

Glu Cys Arg Ser Met Cys Gly Cys Arg Asn Asp Ser Ser Pro Cys Pro
225                 230                 235                 240

Leu Tyr Leu Gln Thr Glu Trp Ser Gln Leu Leu Pro Ser Ile Ser Pro
                245                 250                 255

Ile Leu Lys Glu Val Cys Lys Thr Leu Pro Lys Asp Ala Val Cys Ser
                260                 265                 270

Glu Trp Ser Glu Trp Ser Pro Cys Ser Ala Thr Cys Gly Val Gly Thr
                275                 280                 285

Gln Gly Arg Thr Arg Gln Gln Leu Ser Pro Pro Ala Pro Gly Thr Pro
290                 295                 300

Thr Cys Pro Asp Cys Ile Pro Pro Met Gly Arg Ser Cys Glu Glu Gln
305                 310                 315                 320

Gly Gly Val Lys Glu Asn Arg Ser Cys Asp Ala Gly Thr Cys Ser Val
                325                 330                 335

Asp Ala Gly Cys Gly Thr Trp Gly Leu Trp Ser Glu Trp Ser Ser Ser
                340                 345                 350

Cys Gly Ala Ala Thr Arg Gln Arg Val Arg Glu Gly Tyr Asn Gln Pro
                355                 360                 365

Pro Pro Gln Gly Asp Gly Leu Leu Cys Glu Gln Gln Gln Pro Pro Val
                370                 375                 380

Glu Lys Ser Gln Thr Glu Gln Ala Gln Phe Ala Pro Cys Val Val Ile
385                 390                 395                 400

Pro Pro Thr Pro Pro Glu Trp Ser Ala Trp Ser Glu Cys Thr Ala Thr
                405                 410                 415

Cys Gly Gly Gly Thr Arg His Arg Ser Arg Asn Gly Leu Pro Pro Gly
                420                 425                 430

Thr Arg Ser Ala Asp Gln Asn Thr Glu Gln Lys Pro Glu Ser Asn Pro
                435                 440                 445

Trp Pro Gly Phe Asp Leu His Glu Gln Glu Ser Cys Asn Asn Ser Pro
450                 455                 460

Cys Pro Ile Asn Ala Thr Cys Gly Asp Phe Gly Glu Trp Ser Glu Cys
465                 470                 475                 480

Ser Val Ser Cys Gly Gly Leu Ser Gln Arg Ser Arg Asp Pro Trp
                485                 490                 495

Asn Asn Asp Gln Gln His Gly Gly Lys Ser Cys Met Gln Gln Tyr Pro
                500                 505                 510

Asn Gly His Thr Glu Lys Arg Ser Cys Asn Ala Gln Pro Cys Pro Val
                515                 520                 525

Asp Glu Glu Pro Gly Asp Trp Glu Glu Trp Gly Glu Cys Asn Val Thr
530                 535                 540

Cys Gly Gln Gly Glu Arg Thr Arg Arg Gly Arg Ser Val Ile Leu
545                 550                 555                 560
```

```
Pro Gln Tyr Gly Gly Arg Ser Ile Val Glu Gln Asn Lys Ser Leu Pro
                565                 570                 575
Glu Asn Glu Lys Ile Leu Leu Val Glu Thr Glu Thr Cys Ser Leu Pro
            580                 585                 590
Pro Cys Asp Ala Ser Cys Thr Phe Pro Trp Ser Asp Trp Ser Ser Cys
        595                 600                 605
Glu Gln Cys Glu Ala Gly Thr Gly Thr Gln Tyr Arg Asn Ser Ala Val
    610                 615                 620
Lys Phe Asp Tyr Arg Asn Lys Pro Cys Asp Phe Pro Thr Phe Gln Thr
625                 630                 635                 640
Gln Ser Cys Asp Cys Gly Glu Ala Val Pro Val Pro Ala Pro Pro Pro
                645                 650                 655
Ser Glu Gln Val Thr Pro Ser Ala Pro Tyr Asp Val Pro Glu Arg His
            660                 665                 670
Glu Glu Arg Glu Lys Asn Ala Gly Asp Glu Pro Lys Ser Glu Ser
        675                 680                 685
Glu Gly Val Pro Val Ala Ala Ile Ala Gly Ile Val Gly Gly Leu
    690                 695                 700
Ile Leu Leu Gly Ala Ala Gly Gly Ala Tyr Tyr Phe Gly Gly
705                 710                 715                 720
Gly Lys Ala Asn Glu Ser Leu Ala Glu Met Asp Phe Asp Val Asp Ser
                725                 730                 735
Gly Ala Thr Lys Val Val Met Glu Glu Lys Glu Thr Leu Val Pro
            740                 745                 750
Val Asp Asp Asp Ser Asp Met Trp Met Gly Ala Asp His
            755                 760                 765

<210> SEQ ID NO 37
<211> LENGTH: 209
<212> TYPE: PRT
<213> ORGANISM: Neospora caninum

<400> SEQUENCE: 37

Asp Tyr Gln Asn Glu Leu Ser Val Asp Ala Ser Leu Gln Gly Gly Asp
1               5                   10                  15
Pro Ile Gly Leu Asn Ser Phe Ser Ala Ser Ala Gly Tyr Arg Glu Phe
            20                  25                  30
Ala Lys Glu Val Ser Lys Lys Asp Thr Lys Thr Tyr Met Leu Arg Thr
        35                  40                  45
Tyr Cys Met Arg Tyr Glu Ala Gly Ile Ala Gln Gly Asp Gln Phe Lys
    50                  55                  60
Trp Asn Val Thr Leu Ala Phe Ala Ala Val Glu His Leu Pro Asp
65                  70                  75                  80
Thr Phe Glu Gly His Asn Pro His Cys Gly Cys Ser Pro Glu Gln Trp
                85                  90                  95
Arg Gln Asp Glu Ala Ala Asp Val Cys Ala Gly Ser Asn Ile Pro Thr
            100                 105                 110
Trp Ile Arg Phe Ile Glu Gln Phe Gly Thr His Tyr Leu Val Arg Leu
        115                 120                 125
Phe Ala Gly Gly Lys Met Thr Tyr Gln Val Thr Val Lys Arg Ser Glu
    130                 135                 140
Val Glu Lys Met Lys Lys Lys Gly Ala Asp Val Lys Ser Gln Leu Lys
145                 150                 155                 160
Met Gln Leu Val Gly Val Ser Gly Gly Gly Asn His Gly Val Ala Thr
```

```
                165                 170                 175
Thr Lys Asn Lys Ser Ser Asn Tyr Glu Met Asn Val Gln Lys Glu
            180                 185                 190

Thr Leu Val Ile Gly Gly Arg Pro Ala Asn Val Ser Asp Pro Gly
            195                 200                 205

Ala

<210> SEQ ID NO 38
<211> LENGTH: 439
<212> TYPE: PRT
<213> ORGANISM: Neospora caninum

<400> SEQUENCE: 38

Val Arg Pro Gln Pro Tyr Val Glu Gly Ala Ser Ser Arg Cys Arg
1               5                   10                  15

Gln Ile Pro Val Gly Ala Ser Ser Val Ser Cys Val Glu Ser Ser Gly
            20                  25                  30

Cys Arg Leu Phe Ser Phe Thr Met Glu Arg Leu Ser Thr Cys Arg Tyr
            35                  40                  45

Asp Pro Leu Thr Glu Val Pro Leu Pro Gly Ile Val Leu Trp Thr
50                  55                  60

Pro His Gln Tyr Tyr Asp Gly Ala Gly Trp Leu Ala Leu Pro Glu His
65                  70                  75                  80

Glu Lys Leu Gln Met Lys Pro Thr Arg Trp Ala Asp Gly Arg Leu Arg
                85                  90                  95

Phe Leu Asp Pro Ile Asp Glu Leu Pro Glu Pro Phe Lys Ala Val Gln
            100                 105                 110

Ser Gly Lys Phe Asp Val Lys Cys Trp Arg Arg Gly Asp Cys Lys Leu
            115                 120                 125

Gly Ile Glu Gly Asp Arg Thr Val Phe Leu Lys Ala Pro Ile Ser Pro
130                 135                 140

Glu Val Ala Val Tyr Val His Ala Asp Arg Leu Pro Ala Phe Pro Lys
145                 150                 155                 160

Thr Trp Lys Pro Leu Val Phe Ile Leu Asn Gln Ser Val Ala Met Phe
                165                 170                 175

Arg Leu Thr Glu Asn Leu Cys Leu Val Leu Val Val Glu Asn Asp Lys
            180                 185                 190

Thr Met Asn Ile Ser Cys Val Asp Tyr Asn Gly Gly Phe Ala Cys Thr
            195                 200                 205

His Pro Lys Thr Asn Met Val Val Ala Tyr Gly Ser Tyr Ile Val Lys
            210                 215                 220

Thr Phe Glu Lys Leu Ser Asn Cys Ala Ala Ile Pro Lys Met Val Thr
225                 230                 235                 240

Ala Ser Gly Asp Trp Gly Phe Phe Val Gln Phe Tyr Pro Trp Gly Phe
                245                 250                 255

Phe Phe Ile Pro Lys Ser Leu Glu Leu Thr Arg Pro Gln Ala Val Leu
            260                 265                 270

Gly Ala Val Gly Met Gly Lys Lys Val Asp Thr Ile Gly Leu Val Phe
            275                 280                 285

His Pro Pro Asn Met Phe Ile Asn Val Lys Leu Asp Leu Pro Ala Lys
290                 295                 300

Thr Thr Arg Ala Leu Gln Phe Gly Lys Asp Phe Gln Val Thr Ala Lys
305                 310                 315                 320

Lys Thr Ser Glu Thr Asp Ile Glu Ile Phe Leu Ile Ile Asp Gly Gln
```

```
                        325                 330                 335
Leu Ala Lys Tyr Asn Tyr Ser Phe Asp Ile Arg Asn Asn Lys Pro Glu
            340                 345                 350

Arg Pro Lys His Thr Asp Asn Ile His Phe Lys Cys Thr Cys Asp Ala
            355                 360                 365

Glu Glu Lys Lys Lys Pro Glu Pro Arg Phe Lys Leu Thr Ala Cys Lys
            370                 375                 380

Asp Ser Val Val Leu Glu Gln Gly Cys Pro Cys Gly Asn Pro Asp
385                 390                 395                 400

Glu Gln Leu Val Ser Glu Gln Val Ile Ala Phe Phe Asp Ala Glu Val
            405                 410                 415

Cys Leu Tyr Tyr Thr His Pro Pro Ala Leu Lys Leu Cys Asp Ala Phe
            420                 425                 430

Thr Asp Val Val Phe Arg Glu
            435

<210> SEQ ID NO 39
<211> LENGTH: 309
<212> TYPE: PRT
<213> ORGANISM: Eimeria tenella

<400> SEQUENCE: 39

Ala Ser Thr Val Ala Ala Val Leu Gly Leu Pro Pro Ser Arg Ser Arg
1               5                   10                  15

Glu Ile Val Phe Thr Ser Gly Ala Thr Glu Ser Asn Asn Leu Ala Thr
            20                  25                  30

Lys Gly Leu Val Arg Phe Tyr Glu Gln Gln Gln Ala His Lys Gln His
            35                  40                  45

Leu Leu Gln Gln Gln Gly Lys Gln Glu Pro Gly Lys Pro Arg Lys Ser
        50                  55                  60

His Ile Ile Thr Thr Gln Ile Glu His Lys Cys Val Leu Gln Cys Cys
65                  70                  75                  80

Arg Leu Leu His Leu Glu Trp Gln Gln Ser Gly Gly Ala Ser Gly Ala
                85                  90                  95

Glu Val Thr Phe Leu Pro Val Ser Ala Asp Gly Leu Val Ser Ala Ala
            100                 105                 110

Ala Val Ala Ala Ala Ile Arg Pro Glu Thr Leu Leu Val Ser Val Ile
            115                 120                 125

His Val Asn Asn Glu Ile Gly Val Val Gln Asp Leu Arg Glu Ile Gly
        130                 135                 140

Arg Val Cys Arg Glu Lys Gly Val Phe Phe His Thr Asp Ala Ser Gln
145                 150                 155                 160

Gly Phe Gly Lys Val Pro Leu Asn Val Asp Glu Met Asn Ile Asp Leu
                165                 170                 175

Leu Ser Val Ser Gly His Lys Ile Tyr Gly Pro Lys Gly Val Gly Ala
            180                 185                 190

Leu Phe Val Arg Ala Arg Arg Pro Lys Val Arg Leu Ala Pro Ile Ile
            195                 200                 205

Asp Gly Gly Gly Gln Glu Arg Gly Met Arg Ser Gly Thr Leu Pro Thr
        210                 215                 220

Pro Ile Ile Val Gly Leu Gly Lys Ala Ala Ser Leu Ala Leu Glu Cys
225                 230                 235                 240

Met Asp Ser Asp Arg Arg His Val Glu Arg Met Ala Arg Leu Leu Leu
                245                 250                 255
```

```
His Arg Leu Gln Gln Leu Pro His Ile Thr Val Asn Gly Ser Leu
              260                 265                 270

Asn Arg Tyr Leu Trp Asn Ser Asn Ile Ser Leu Ser Phe Val Glu
          275                 280                 285

Gly Glu Ser Leu Leu Met Ser Met Gly Asp Val Ala Met Ser Ser Gly
      290                 295                 300

Ser Ala Cys Thr Ser
305

<210> SEQ ID NO 40
<211> LENGTH: 78
<212> TYPE: PRT
<213> ORGANISM: Eimeria tenella

<400> SEQUENCE: 40

Pro Pro Gly Ala Asn Leu Ile Val Phe His Ile Pro Asn Asp Trp Asn
1               5                   10                  15

Asp Val Asp Leu Ile Gln His Tyr Gln His Phe Gly Asp Ile Ala Ser
                20                  25                  30

Ala Arg Ile Gln Arg Asp Val Glu Gly Arg Ser Thr Gly Gly Phe Val
            35                  40                  45

Ser Phe Ala Asp Gln Thr Ser Ala Val His Ala Ile Arg Gly Met His
        50                  55                  60

Gly Tyr Leu Val Gly Gly Lys His Leu Lys Ala Gln Leu Lys
65                  70                  75

<210> SEQ ID NO 41
<211> LENGTH: 166
<212> TYPE: PRT
<213> ORGANISM: Eimeria tenella

<400> SEQUENCE: 41

Ala Ser Thr Arg Glu Arg Glu Arg Glu Arg Glu Arg Glu Arg
1               5                   10                  15

Glu Leu Pro Asp Phe Ser Gly Phe His Pro Ala Phe Ser Gln Val Pro
                20                  25                  30

Leu Gln Pro Met Ser Thr Lys Ile Gly Asn Ser Asp Lys Gln Arg Gly
            35                  40                  45

Asp Gly Thr Pro Val Glu Thr Pro Thr Ser Val Asp His Gly Ser Ser
        50                  55                  60

Asp Ser Ser Ile His Cys Glu Ala Cys Ile Arg Asp Gly Asp Val
65                  70                  75                  80

Arg Glu Pro Phe Tyr Leu Ser Tyr Asp Glu Glu Asn Val Glu Tyr Tyr
                85                  90                  95

Ser Leu Lys Glu Ala Ile Glu Leu Ile Arg Asn Gly Arg Val Leu Val
            100                 105                 110

Gly Ser Thr Phe Ile Ile Pro Tyr Pro Pro Gly Phe Pro Ile Ser Val
        115                 120                 125

Pro Gly Gln Ile Leu Ser Glu Ala Ile Val Glu Phe Met Ile Lys Ile
    130                 135                 140

Asp Val Lys Glu Ile Pro Gly Phe Asp Pro Gln Leu Gly Leu Arg Cys
145                 150                 155                 160

Phe Lys Glu Ser Leu Leu
                165

<210> SEQ ID NO 42
<211> LENGTH: 186
```

```
<212> TYPE: PRT
<213> ORGANISM: Eimeria tenella

<400> SEQUENCE: 42

Thr Leu Asn Pro Arg Gln Met Ala Leu Tyr Ser Gly Gln Gln Lys Glu
1               5                   10                  15

Thr Leu Glu Leu Ala Ala Ala Leu Val Arg Leu Gly Pro Leu Asp Ala
            20                  25                  30

Val Asn Glu Ser Leu Ala His Ala Ala Leu Cys Pro Ser Ile Glu
        35                  40                  45

Gly Leu Leu Arg Asp Arg Cys Gln Gly Ile Pro Glu Leu Val Val Asp
50                  55                  60

Pro Ala Ala Gly Lys Tyr Phe Ile Ala Ser Tyr Phe Asn Lys Leu Lys
65                  70                  75                  80

Asn Ser Phe Arg Ser Pro Trp Thr Asp Thr Trp Leu Pro Pro Ile Ser
                85                  90                  95

Asp Ala Ser Lys Pro Ala Pro His Leu Arg Gln Leu Glu Gln Gln Phe
            100                 105                 110

Asn Ala Ala Tyr Asn Ser Tyr Arg Asp Ala His Tyr Gly Gly Gly Val
        115                 120                 125

Ser Ser Val Tyr Ala Trp Pro Leu Gln Ser Gln Asp Gly Phe Ala Ala
130                 135                 140

Ala Phe Leu Leu Leu Lys Glu Ala Pro Val Asp Glu Pro Leu Leu Pro
145                 150                 155                 160

Leu Cys Phe Phe Thr His Arg Leu Glu Val Thr Leu Thr Ala Thr Asn
                165                 170                 175

Ala His Tyr Lys Leu His Ser Thr Leu Leu
            180                 185

<210> SEQ ID NO 43
<211> LENGTH: 166
<212> TYPE: PRT
<213> ORGANISM: Eimeria tenella

<400> SEQUENCE: 43

Gly Phe Arg Val Gly Val Cys Val Gln Ser Lys Ala Gln Ala Ser Leu
1               5                   10                  15

Asp Ala Ala Leu Thr Arg Lys Ala Val Gly Leu Arg Arg Ala Ser Asp
            20                  25                  30

Ser Glu Asp Asp Thr Arg Lys Asn Lys Met Ala Asn Ala Gln Gln Ser
        35                  40                  45

Leu Phe Asp Asp Glu Leu Gly Leu Glu Arg Gln Lys Lys Arg Leu
50                  55                  60

Lys Ser Phe Leu Lys Asp Lys Asn Asn Ser Lys Gly Lys Thr Asn Glu
65                  70                  75                  80

Tyr Ile Asp Ser Ala Leu Ser Leu Gly Asn Leu Arg Gln Glu Ala Val
                85                  90                  95

Thr Trp Asp Phe Glu Glu Gly Glu Arg Ser Asp Asp Glu Gly Gly Glu
            100                 105                 110

Ala Pro Gln Asp Ala Lys Glu Asn Ala Ala Glu Thr Leu Glu Ala Asp
        115                 120                 125

Pro Val Glu Ser Glu Thr Asp Asp Pro Glu Asp Pro Leu Thr Ser
130                 135                 140

Phe Gly Gln Lys Met Lys Asn Leu Leu Glu Lys Ala Arg Asp Glu Glu
145                 150                 155                 160
```

Ala Asp Ala Glu Leu His
            165

<210> SEQ ID NO 44
<211> LENGTH: 677
<212> TYPE: PRT
<213> ORGANISM: Eimeria tenella

<400> SEQUENCE: 44

Met Arg Gly Ala Val Ala Leu Ser Ala Arg Ala Leu Trp Ala Ala
1               5                   10                  15

Ala Val Pro Pro Gln Pro Arg Gly Pro Pro Lys Glu Gln Arg Val Phe
                20                  25                  30

Ser Ala Val Arg Thr Ala Ala Val Gly Thr Leu Ser Ser Leu Ala Gly
            35                  40                  45

Arg Arg Gly Phe Ser Gly Val Arg Gly Asp Val Val Gly Ile Asp Leu
    50                  55                  60

Gly Thr Thr Asn Ser Cys Val Ala Val Met Glu Gly Ser Gln Pro Lys
65                  70                  75                  80

Val Leu Glu Asn Ser Glu Gly Met Arg Thr Thr Pro Ser Val Val Ala
                85                  90                  95

Phe Thr Lys Asp Gly Gln Arg Leu Val Gly Val Ala Lys Arg Gln
                100                 105                 110

Ala Ile Thr Asn Pro Glu Asn Thr Phe Phe Ser Thr Lys Arg Leu Ile
            115                 120                 125

Gly Arg Ser Phe Asp Glu Ala Ile Ala Lys Glu Arg Lys Ile Leu
    130                 135                 140

Pro Tyr Lys Val Ile Arg Ala Asp Asn Gly Asp Ala Trp Val Glu Gly
145                 150                 155                 160

Trp Gly Lys Lys Tyr Ser Pro Ser Gln Ile Gly Ala Phe Val Leu Met
                165                 170                 175

Lys Met Lys Glu Thr Ala Glu Ser Tyr Leu Gly Arg Asp Val Asn Gln
                180                 185                 190

Ala Val Ile Thr Val Pro Ala Tyr Phe Asn Asp Ser Gln Arg Gln Ala
            195                 200                 205

Thr Lys Asp Ala Gly Lys Ile Ala Gly Leu Asp Val Leu Arg Ile Ile
    210                 215                 220

Asn Glu Pro Thr Ala Ala Leu Ala Tyr Gly Met Glu Lys Glu Asp
225                 230                 235                 240

Gly Arg Thr Ile Ala Val Tyr Asp Leu Gly Gly Gly Thr Phe Asp Val
                245                 250                 255

Ser Ile Leu Glu Ile Leu Gly Gly Val Phe Glu Val Lys Ala Thr Asn
                260                 265                 270

Gly Asn Thr Ser Leu Gly Gly Glu Asp Phe Asp Gln Lys Val Leu Gln
            275                 280                 285

Phe Leu Val Asn Glu Phe Lys Lys Glu Gly Ile Asp Leu Ser Lys
    290                 295                 300

Asp Arg Leu Ala Leu Gln Arg Leu Arg Glu Ala Ala Glu Thr Ala Lys
305                 310                 315                 320

Ile Glu Leu Ser Ser Lys Leu Ser Thr Glu Ile Asn Leu Pro Phe Ile
                325                 330                 335

Thr Ala Asp Gln Ser Gly Pro Lys His Leu Gln Val Ser Leu Ser Arg
                340                 345                 350

Ala His Leu Glu Glu Leu Val Gly Ala Leu Leu Gln Gln Ser Ile Glu
            355                 360                 365

```
Pro Cys Glu Lys Cys Ile Arg Asp Ala Gly Val Gln Lys Ala Asp Leu
        370                 375                 380

Ser Asp Val Ile Leu Val Gly Gly Met Thr Arg Met Pro Lys Val Ala
385                 390                 395                 400

Glu Val Val Lys Asn Ile Phe His Lys Glu Pro Ser Lys Gly Val Asn
                405                 410                 415

Pro Asp Glu Ala Val Ala Ala Gly Ala Ala Ile Gln Ala Gly Val Leu
            420                 425                 430

Lys Gly Glu Ile Lys Asp Leu Leu Leu Asp Val Cys Pro Leu Ser
        435                 440                 445

Leu Gly Ile Glu Thr Leu Gly Gly Val Phe Thr Arg Leu Ile Asn Arg
    450                 455                 460

Asn Thr Thr Ile Pro Thr Lys Lys Ser Gln Ile Phe Ser Thr Ala Ala
465                 470                 475                 480

Asp Asn Gln Thr Gln Val Gly Ile Lys Val Tyr Gln Gly Glu Arg Glu
                485                 490                 495

Met Ala Ser Ala Asn Lys Leu Leu Gly Gln Phe Asp Leu Val Gly Ile
            500                 505                 510

Pro Pro Ala Pro Arg Gly Val Pro Gln Ile Glu Val Thr Phe Asp Val
        515                 520                 525

Asp Ala Asn Gly Ile Met Asn Ile Ser Ala Val Asp Lys Ser Thr Ala
530                 535                 540

Lys Arg Gln Gln Ile Thr Ile Gln Ser Gly Gly Leu Ser Glu Ala
545                 550                 555                 560

Gln Ile Lys Gln Met Val Glu Asp Ala Glu Arg Phe Lys Asp Glu Asp
                565                 570                 575

Gln Arg Gln Lys Asp Leu Val Ala Ala Lys Asn Glu Ala Glu Thr Leu
            580                 585                 590

Val Tyr Ser Val Glu Lys Gln Ile Ser Asp Leu Lys Asp Lys Ile Ser
        595                 600                 605

Ala Glu Asp Lys Thr Asp Leu Glu Ser Arg Ile Gln Glu Leu Arg Ser
    610                 615                 620

Ala Leu Val Glu Gly Glu Leu Glu Thr Ile Arg Ser Arg Val Lys Ala
625                 630                 635                 640

Leu Gln Glu Leu Ser Trp Lys Val Ser Gln Gln Ala Tyr Ser Gln Ser
                645                 650                 655

Asn Asn Thr Ser Ala Asp Gly Asp Ser Ser Ser Thr Ser Ser Gly Asp
            660                 665                 670

Ser Ser Ser Lys Pro
        675

<210> SEQ ID NO 45
<211> LENGTH: 734
<212> TYPE: PRT
<213> ORGANISM: Eimeria tenella

<400> SEQUENCE: 45

Val Ile Phe Leu Ile Ser Tyr Ser Ser Phe Tyr Pro Val Pro Leu
1               5                   10                  15

Ser Cys Ile Ile Pro Ala Met Ala Pro Leu Pro Arg Arg Arg Leu Ala
                20                  25                  30

Pro Cys Arg Ala Leu Ser Leu Leu Val Gly Leu Leu Ala Ala Ser Phe
            35                  40                  45

Ala Phe Ser Ser Leu Gln Pro Gly Ala Thr Thr Ser Ser Gly Gln Asp
```

```
            50                  55                  60
Gln Val Cys Thr Ser Leu Leu Asp Val Met Leu Val Val Asp Glu Ser
 65                  70                  75                  80

Gly Ser Ile Gly Thr Ser Asn Phe Arg Lys Val Arg Gln Phe Ile Glu
                     85                  90                  95

Asp Phe Val Asn Ser Met Pro Ile Ser Pro Glu Asp Val Arg Val Gly
                    100                 105                 110

Leu Ile Thr Phe Ala Thr Arg Ser Lys Val Arg Trp Asn Leu Ser Asp
                115                 120                 125

Pro Lys Ala Thr Asn Pro Ser Leu Ala Ile Ser Ala Ala Arg Ser Leu
130                 135                 140

Ser Tyr Ser Thr Gly Val Thr Tyr Thr His Tyr Gly Leu Gln Asp Ala
145                 150                 155                 160

Lys Lys Leu Leu Tyr Asp Thr Asn Ala Gly Ala Arg Asn Asn Val Pro
                165                 170                 175

Lys Leu Val Leu Val Met Thr Asp Gly Ala Ser Asn Leu Pro Ser Gln
                180                 185                 190

Thr Arg Ser Ser Ala Ala Leu Arg Asp Ala Gly Ala Ile Val Val
        195                 200                 205

Val Leu Gly Val Gly Ser Gly Val Asn Ser Ser Glu Cys Arg Ser Ile
210                 215                 220

Ala Gly Cys Ser Thr Ser Asn Cys Pro Arg Tyr Leu Gln Ser Asn Trp
225                 230                 235                 240

Ser Asn Val Thr Gln Gln Val Asn Gly Ile Ile Lys Ala Ala Cys Lys
                245                 250                 255

Asp Leu Ala Lys Asp Ala Val Cys Ser Glu Trp Ser Glu Tyr Gly Pro
                260                 265                 270

Cys Val Gly Glu Cys Gly Lys Glu Gly Val Gln Thr Ser Thr Arg Val
            275                 280                 285

Glu Ile Ser Pro Gln Lys Pro Gly Ser Pro Cys Pro Thr Cys Glu
        290                 295                 300

Ala Pro Arg Gly Arg Ser Cys Ala Glu Gln Pro Pro Gly Leu Thr Arg
305                 310                 315                 320

Thr Gln Pro Cys Thr Met Pro Val Cys Lys Thr Asp Ala His Cys Gly
                325                 330                 335

Glu Phe Gly Ala Trp Ser Glu Trp Ser Thr Thr Cys Gly Thr Ala Thr
                340                 345                 350

Arg Lys Arg Gln Arg Glu Gly Tyr Asn Ser Pro Ala Ala Gly Gly
        355                 360                 365

Gly Leu Ser Cys Met Glu Gln Asn Pro Pro Lys His Glu Phe Glu Val
    370                 375                 380

Glu Thr Val Gln Lys Ser Pro Cys Pro Val Gln Gln Pro Gly Pro
385                 390                 395                 400

Trp Ser Glu Trp Thr Glu Cys Ser Ala Thr Cys Gly Gly Gly Thr Lys
                405                 410                 415

His Arg Glu Arg Glu Gly Leu Pro Gln Glu Gly Glu Leu Tyr Gly Gly
            420                 425                 430

Gln Thr Leu Glu Gln Gln Gly Ile Ala Val Arg Glu Thr Ala Ser Cys
            435                 440                 445

Ser Glu Asn Pro Cys Pro Ile Asp Ala Thr Cys Gly Glu Trp Thr Glu
        450                 455                 460

Tyr Ser Ala Cys Ser Arg Thr Cys Gly Gly Gly Thr Gln Glu Arg Lys
465                 470                 475                 480
```

```
Arg Glu Pro Trp Leu Asp Asn Ala Gln His Gly Gly Arg Thr Cys Met
                485                 490                 495

Glu Gln Tyr Pro Asp Gly Pro Ile Ser Val Arg Glu Cys Asn Thr Gln
            500                 505                 510

Pro Cys Pro Val Asp Glu Val Val Gly Asp Trp Glu Asp Trp Gly Gln
        515                 520                 525

Cys Ser Glu Gln Cys Gly Gly Lys Arg Thr Arg Asn Arg Gly Pro
    530                 535                 540

Ser Lys Gln Glu Ala Met Phe Gly Gly Lys Thr Val Ala Gln Gln Asn
545                 550                 555                 560

Ala Glu Leu Pro Glu Gly Glu Lys Ile Glu Val Val Gln Glu Glu Gly
                565                 570                 575

Cys Asn Glu Val Pro Cys Gly Pro Cys Thr Leu Pro Phe Ser Glu Trp
                580                 585                 590

Thr Glu Cys Glu Ser Cys Ser Gly His Arg Thr Arg Glu Ser Ala Val
            595                 600                 605

Ala Phe Asp Tyr Thr Asp Arg Met Cys Ser Gly Asp Thr His Glu Val
        610                 615                 620

Gln Ser Cys Glu Glu Tyr Cys Ser Gln Asn Ala Gly Gly Gly Ala Gly
625                 630                 635                 640

Gly Asp Gly Gly Ala Gly Gly Thr Gly Gly Ser Gly Glu Glu Glu
                645                 650                 655

Gly Lys Glu Glu Ser Ser Gly Phe Pro Thr Ala Ala Val Ala Gly Gly
                660                 665                 670

Val Ala Gly Gly Val Leu Ala Ile Ala Ala Gly Ala Gly Ala Phe Tyr
                675                 680                 685

Gly Leu Ser Gly Gly Ser Ala Ala Ala Thr Glu Ala Gly Ala Glu
            690                 695                 700

Val Met Thr Glu Ala Gly Thr Ser Asn Ala Ala Glu Val Glu Lys Glu
705                 710                 715                 720

Ser Leu Ile Ser Ala Gly Glu Gln Ser Glu Met Trp Ala Ser
                725                 730

<210> SEQ ID NO 46
<211> LENGTH: 316
<212> TYPE: PRT
<213> ORGANISM: Eimeria tenella

<400> SEQUENCE: 46

Arg Val Asp Leu Ser Phe Ile Phe Ser Ile Ser Val Phe Arg Tyr Ile
1               5                   10                  15

Leu Gln Leu Glu Ile Ser Ala Thr Gly Arg Asp His Ser Val His Cys
                20                  25                  30

His Arg Ile Leu Cys Val Glu Arg Phe Ala His Thr Thr Pro Gln Gln
            35                  40                  45

Ser Ser Arg Gly Ala Ala Ala Pro Asp Thr Met Glu Ala Val Asn Lys
        50                  55                  60

Leu Phe Ser Cys Arg Phe Glu Pro Leu Val Glu Pro Val Pro Glu
65                  70                  75                  80

Lys Ala Val Val Trp Thr Ser Lys Asn Tyr Tyr Asp Gly Ser Gly Trp
                85                  90                  95

Val Gly Leu Ala Asp Gly Glu Lys Leu Ser Leu Lys Pro Thr Leu Phe
            100                 105                 110

Ala Asp Asn Arg Leu Leu Phe Leu Glu Pro Val Glu Gly Val Cys Glu
```

```
            115                 120                 125
Ala Phe Ser Ser Val Gln Ser Gly Lys Tyr Asp Val Lys Cys Trp Ser
130                 135                 140

Lys Leu Gly Cys His Leu Gly Ile Glu Gly Asp Gln Asn Val Phe Leu
145                 150                 155                 160

Ser Thr Pro Lys Leu Lys Glu Val Ala Val Tyr Ser His Pro Glu Arg
                165                 170                 175

Leu Pro Ala Phe Pro Lys Ser Trp Lys Pro Leu Leu Phe Thr Leu Asn
            180                 185                 190

Ser Ser Val Ile Thr Phe Arg Leu Thr Asp Thr Leu Cys Leu Val Val
        195                 200                 205

Thr Ile Asp Glu Ser Lys Thr Thr Lys Val His Cys Val Asp Tyr Asn
210                 215                 220

Gly Gly Phe Ala Leu Ser His Pro Ala Ser Asp Ser Ala Leu Ala Tyr
225                 230                 235                 240

Gly Ser Leu Ala Val Lys Gly Phe Glu Ala Leu Pro His Cys Glu Val
                245                 250                 255

Ile Pro Arg Val Thr Ser Ala Ala Gly Glu Trp Gly Phe Phe Val Gln
            260                 265                 270

Leu Phe Gln Trp Gly Ser Phe Val Pro Lys Ala Val Asp Leu Thr
        275                 280                 285

Arg Pro Ser Ser Phe Leu Gly Lys Ser Asp Ala Tyr Gly Pro Thr Gly
290                 295                 300

Arg Thr Arg Ala Pro Leu Arg Ser Ala Ile Arg Phe
305                 310                 315

<210> SEQ ID NO 47
<211> LENGTH: 795
<212> TYPE: PRT
<213> ORGANISM: Theileria annulata

<400> SEQUENCE: 47

Met Lys Phe Phe Cys Arg Asn Glu Phe Ile Lys Ser Ile Asn Cys Phe
1               5                   10                  15

Val Ser Arg Tyr Tyr Ser Ile Ser Ile Asp Ile Gln Gly Gln Phe Lys
                20                  25                  30

Thr Ser Cys Gly Lys Lys Thr Tyr Asn Arg Val Tyr Leu Asp Asn Gln
            35                  40                  45

Ala Thr Thr Cys Val Asp Pro Arg Val Leu Asp Ser Met Met Pro Tyr
50                  55                  60

Leu Thr His Ala Phe Gly Asn Pro His Ser Arg Thr His Ser Tyr Gly
65                  70                  75                  80

Trp Glu Ala Glu Lys Ala Val Glu Thr Ala Arg Ala Asp Val Ala Asn
                85                  90                  95

Leu Ile Asn Cys Glu Ser Lys Asn Val Ile Phe Thr Ser Gly Ala Thr
            100                 105                 110

Glu Ser Asn Asn Leu Ala Ile Lys Gly Ser Lys Ser Phe Tyr Gly Arg
        115                 120                 125

Leu Val Glu Ser Pro Gly Lys Ser Lys Asn His Val Ile Thr Thr
130                 135                 140

Gln Ile Glu His Lys Cys Val Leu Gln Cys Cys Arg Gln Leu Glu Asn
145                 150                 155                 160

Glu Gly Tyr Ser Val Thr Tyr Leu Lys Pro Asp Lys Tyr Gly Met Ile
                165                 170                 175
```

-continued

```
Leu Pro Asp Leu Val Arg Lys Asn Ile Arg Pro Glu Thr Phe Leu Cys
        180                 185                 190

Ser Val Ile His Val Asn Asn Glu Ile Gly Val Ile Gln Asn Ile Ser
        195                 200                 205

Glu Ile Gly Arg Ile Cys Lys Glu His Lys Val Ile Phe His Thr Asp
        210                 215                 220

Ala Ala Gln Ser Phe Gly Lys Leu Pro Ile Asp Leu Lys Asn Leu Asp
225                 230                 235                 240

Val Asp Leu Leu Ser Ile Ser Gly His Lys Ile Tyr Gly Pro Lys Gly
                245                 250                 255

Val Gly Ala Leu Phe Val Arg Thr Lys Pro Arg Ile Arg Leu Gln Pro
            260                 265                 270

Ile Ile Asp Gly Gly Gly Gln Glu Arg Gly Leu Arg Ser Gly Thr Leu
        275                 280                 285

Pro Thr Ala Leu Val Val Gly Leu Gly Thr Ala Ala Lys Ile Ala Lys
        290                 295                 300

Met Glu Met Lys Arg Asp Gln Leu His Met Glu Asn Leu Phe Phe Lys
305                 310                 315                 320

Leu Tyr Asn Gly Leu Ser Ala Ile Asp His Val Ser Ile Asn Gly Ser
                325                 330                 335

Ile Lys Pro Gly Glu Arg Tyr Phe Gly Asn Leu Asn Met Ser Phe Glu
            340                 345                 350

Phe Ile Glu Gly Glu Ser Leu Leu Met Ser Leu Ser Asn Phe Ala Leu
        355                 360                 365

Ser Ser Gly Ser Ala Cys Thr Ser Ala Ser Leu Glu Pro Ser Tyr Val
        370                 375                 380

Leu Arg Ser Leu Asp Val Ser Glu Glu Leu Ala His Thr Ser Ile Arg
385                 390                 395                 400

Phe Gly Leu Gly Arg Phe Thr Met Glu Ser Glu Val Asp Met Ala Leu
                405                 410                 415

Glu Ser Ile Thr Lys Val Val Glu Lys Leu Arg Asn Leu Ser Pro Leu
            420                 425                 430

Tyr Glu Ile Leu Glu Lys Lys Met Tyr Lys Tyr Asp Pro Glu Val
        435                 440                 445

Pro Leu Val Lys Ile His Ile Gly Lys Trp Ile Phe Arg Cys Leu Gly
        450                 455                 460

Cys Asn Ser Lys Glu Gln Asp Glu Thr Glu Tyr Ile Asp Leu Ser Lys
465                 470                 475                 480

Ile Lys Asn Val Asp Glu Val Leu His Ile Asn Asp Leu Ile Val Ser
                485                 490                 495

Lys Pro Glu Leu Tyr Val Glu Thr Pro Lys Ser Tyr Tyr Val Thr Arg
            500                 505                 510

Lys Leu Asp Asn Cys Glu Ser Glu Lys Phe Gly Gly Val Lys Pro Thr
        515                 520                 525

Thr Ala Ile Pro Ile Gln Asn Gln Trp Pro Ser Glu Thr Ser Ser Glu
        530                 535                 540

Asn Ser Thr Pro Asn Gln Ile Leu Ile Lys Glu Phe Ser Ser Lys Asn
545                 550                 555                 560

Gln Lys Arg Asp Gly Lys Asp Asn Tyr Thr Glu Asn Asn Lys Ile Val
                565                 570                 575

Val Gln Leu Ser Asn Ile Thr Gly Phe Leu Glu Lys Glu Ser Asp Lys
            580                 585                 590

Gln Leu Thr Ile Ser Glu Ser Ile Ala Ile Ala Glu Lys Ile Tyr Gln
```

```
                595                 600                 605
Asn Glu Lys Arg Gln Ile Met Asn Leu Gly Lys Ala Glu Asn Gln Asp
            610                 615                 620

Ser Lys Ser Thr Asn Tyr Val Glu Ser Asp Lys Ile Lys Tyr Met Glu
625                 630                 635                 640

Phe Asn Asn Pro Phe Glu Met Lys Glu Ile Asp Glu Lys Tyr Thr Leu
                645                 650                 655

Ser Arg Lys Glu Ser Pro Asn Ser Ile Ile Thr Asn Glu Asn Tyr Lys
            660                 665                 670

Lys Glu Thr Lys Arg Gly Lys Leu Ser His Ile Cys Asp Val Ser Asp
            675                 680                 685

Asp Ser Asp Glu Asp Glu Glu Ser Leu Ala Ser Arg Val Trp Asn Met
690                 695                 700

Phe Met Lys Val Ser Ser Ala Gly Asn Asn Asp Asp Gln Gln Val Arg
705                 710                 715                 720

Asn Arg Lys Gln Ile Asn Asn Asn Met Thr Lys Glu Arg Phe Lys Ser
                725                 730                 735

Lys Ile Pro Leu Glu Asn Glu Glu Lys Ile Asn Arg Gly Glu His Ile
            740                 745                 750

Trp Lys Gly Asn Gly Lys Asp Lys Gly Val Ile Asn Glu Lys Gln Trp
            755                 760                 765

Ile Lys Glu Asn Tyr Lys Val Ser Ser Gly Glu Ala Leu Glu Ile Val
            770                 775                 780

Glu Gly Thr Ile Arg Lys Ile Asn Asn Leu Leu
785                 790                 795

<210> SEQ ID NO 48
<211> LENGTH: 2323
<212> TYPE: PRT
<213> ORGANISM: Theileria annulata

<400> SEQUENCE: 48

Met Ser Thr Glu Ser Gln Gln Thr Lys Glu Pro Ser Gln Glu Glu
1               5                   10                  15

Arg Phe Trp Asn Asp Phe Asp Arg Gln Tyr Phe Ser Ser Pro His Pro
            20                  25                  30

Ser Leu Val Leu Cys Leu Lys Asn His Ile Trp His Thr Arg His Ile
        35                  40                  45

Ser Ser Lys Ile Thr Lys Tyr Leu Ser Ser Lys Gly Thr Val Lys Lys
    50                  55                  60

Asn Leu Lys Lys Asn Asn Thr Ile His Leu Arg Ser Val Lys Phe Pro
65                  70                  75                  80

Leu Arg Leu Ser Ser Thr Asp Lys Thr Leu Phe Asn Pro Ile Val Asn
            85                  90                  95

Pro Thr Thr Asp Gly Ile Phe Arg Tyr Phe Ser Ser Thr Ser Leu
                100                 105                 110

Ser Ser Glu Gln Phe Gln Gly Leu Leu Glu Asn Asp Asn Val Tyr Lys
        115                 120                 125

Pro Leu Val Ser Pro Lys His Asp Ser Asn Gln Arg Leu Pro Thr Ile
    130                 135                 140

Tyr Ser Ser Pro Leu Pro Asp Ala Ile His Leu Thr Leu Tyr Val Pro
145                 150                 155                 160

Lys Val Ser Pro Lys Thr Asp Ser Asp Lys Lys Glu Lys Glu Lys Asp
                165                 170                 175
```

-continued

```
Lys Pro Lys Leu Pro Asp Lys Ser Lys Asp Glu His Lys Glu Lys Lys
            180                 185                 190
Glu Lys Glu Asp Thr Gln Lys Leu Asp Glu Val Glu Ala Ile Asn Asn
            195                 200                 205
Phe Val Asp Ser Phe Lys Ser Leu Gln Leu Leu Lys Asn Gln Glu Val
210                 215                 220
Pro Gln Ile Ile Ser Gly Pro Asn Pro Ser Trp Phe Val Lys Gly Lys
225                 230                 235                 240
Gly Arg Phe Lys Lys Gly Val Asp Leu Gly Pro Lys Tyr Lys Lys Cys
            245                 250                 255
Asp Lys Leu Val Lys Asn Pro His Gly Leu Leu Ser Asp Pro Val Trp
            260                 265                 270
Gln His Phe Asn Thr Asn Tyr Val Asn Val Pro Val Lys Gly Asn Asp
            275                 280                 285
Asn Met Phe Ser Tyr Asp Asp Asn Thr Arg Asn Gln Asn Lys Val Ala
            290                 295                 300
Asn Lys Thr Lys Thr Asn Glu His Glu Asp Ile Lys Asp Gly Thr Asp
305                 310                 315                 320
Leu Leu Asn Tyr His Asn Met Cys Asp Met Asn Thr Cys Arg Val Asp
            325                 330                 335
Tyr Ser Pro Leu Leu Phe Thr Phe Val Ser Ser Lys Arg Ser Leu Leu
            340                 345                 350
Cys Lys Arg Cys Leu Gly Phe Pro Lys Leu Phe Cys Asn Leu Cys Lys
            355                 360                 365
Asn Leu Lys Gly Ser Ser Thr Ala Ile Phe Ser Ser Gln Tyr Ile Ser
            370                 375                 380
Asp Glu Lys Tyr His Met Thr Tyr Asn Leu Leu Asp Leu Phe Lys Leu
385                 390                 395                 400
Arg Ser Asn Thr Asp Asp Cys Ile Gln Thr Phe Tyr Val Asn Pro Tyr
            405                 410                 415
Lys Gly Met Tyr Asn Asn Gln Pro Asn Phe Ser Val Leu Asn Asn Asp
            420                 425                 430
Asp Leu Gln Ser Lys Glu Glu Asp Asp Thr Ser Leu Ile Tyr Asn
            435                 440                 445
Tyr Ile Gln Thr Leu Glu Ser Leu Asn Ala Val Phe Asn Asn Leu Leu
            450                 455                 460
Asn Arg Ile Ala Asn Glu Tyr Lys Pro Asp Thr Ser Lys Trp His Asp
465                 470                 475                 480
Ile Glu Ser Lys Met Leu Glu Thr Tyr Ile Glu Gln Tyr Asn Asn Lys
            485                 490                 495
Thr Leu Asp Asn Arg Tyr Thr Tyr Ser Val Gln Arg Gln Ser Leu Asp
            500                 505                 510
Val Leu Leu Leu Arg Leu Lys Val Asn Lys Ser Ser Asp Leu Pro Ser
            515                 520                 525
Thr Trp Thr Asp Arg Ala Leu Cys Ser Ile Cys Gly Thr Asp Glu Asp
            530                 535                 540
Trp Asp Asp Asp Pro Ile Leu Phe Cys Asp Cys Cys Tyr Ile Pro Met
545                 550                 555                 560
His Phe Cys Cys Leu Gly Tyr Lys Pro Gly Thr Leu Thr Asp Ile Lys
            565                 570                 575
Gln Lys Leu Asn Val Asn Lys Phe His Arg Leu Asn Phe Tyr Asn His
            580                 585                 590
Leu Ala Asn Asn Ile Glu Arg Pro Val Lys Lys Ile Lys Leu Asp Lys
```

```
            595                 600                 605
Leu Asp Asp Tyr Met Asp Met Asp Glu Asp Glu Trp Tyr Cys Pro Val
    610                 615                 620
Cys Thr Tyr Leu Met Glu Gln Leu Val Phe Leu Asp Glu Asn Leu Val
625                 630                 635                 640
Met Thr Ala Ile Arg Asn Ile Ala Gly Pro Lys Thr Gln Gln His Leu
                645                 650                 655
Glu Met Ile Asn Glu Asn Tyr Thr Ser His Lys Val Asp Asn Ala Thr
            660                 665                 670
Ser Lys Ser Lys Asp Asn Lys Thr Gly Asn Thr Lys Pro Asn Asp Gln
        675                 680                 685
Ser Lys Gln Ser Lys Asp Asn Arg Val Ser Glu Asn Ala Ser Val Lys
    690                 695                 700
Ala Lys Asp Asp Ile Phe Lys Arg Lys Leu Pro Ile Ile Leu Gly Phe
705                 710                 715                 720
Asp Tyr Asp Asn Pro Ser Glu Arg Ser Phe Ile Thr Val His Pro Ser
                725                 730                 735
Asn Gln Asn Asn Ile Ser Ser Leu Glu Lys Leu Lys Gly Asp Lys Glu
            740                 745                 750
Ser Leu Asn Glu Thr Ser Asn Glu Lys Lys Leu Glu Lys Leu Ser Ile
        755                 760                 765
Leu Asn Leu Tyr Asn Gly Lys Lys Glu Ser Val Met Phe Asn Gln Asn
    770                 775                 780
Asn Val Ser Asp Pro Lys Ile Phe Cys Lys Asn Leu Leu Ser Lys Lys
785                 790                 795                 800
Gly Leu Tyr Phe Glu Asn Asn Phe Trp Leu Leu Leu Ser Arg Ala Asn
                805                 810                 815
Leu Thr Gly Ile Gln Glu Tyr Leu Asn Tyr His Thr Tyr Glu Glu Leu
            820                 825                 830
Tyr Leu Ser Arg Leu Val Gln Gln Asp Lys Leu Ile Gln Ser Thr Lys
        835                 840                 845
Tyr Ser Pro Lys Lys Arg Ser Asn Ser Ile Thr Ser Lys Ser Ser Ser
    850                 855                 860
Ser Arg Ser Leu Ser Leu Asn Ser Leu Lys Asp Ser Val Pro Val Lys
865                 870                 875                 880
Glu Asp Glu Pro Pro Thr Lys Ser Lys Lys Glu Pro Glu Thr Gln
                885                 890                 895
Leu Lys Lys Glu Lys Asp His Ser Leu Asp Glu Pro Ser Leu Lys
            900                 905                 910
Lys Gln Glu Leu Lys Ser Ala Gln Asn Ile Asn Cys Lys Asn Pro Leu
        915                 920                 925
Lys Lys Met Tyr Leu Ser Leu Asp Leu Lys Leu Leu Ser Gln Ser Thr
    930                 935                 940
Asn Phe Thr Leu Asn Lys Asn Gly His Glu Thr Val Gln Lys Asn Lys
945                 950                 955                 960
Asn Gly His Glu Thr Val Pro Lys Asn Lys Asn Gly His Glu Thr Val
                965                 970                 975
Gln Lys Asn Lys Asn Ser Met Lys Lys Glu His Glu Lys Lys Glu Asn
            980                 985                 990
Gly Lys Lys Asp Leu Gly Glu Val  Tyr Leu Val Ile Lys  Val Pro Val
        995                 1000                1005
Cys Ile  Phe Cys Gly Phe Asp  Ala Phe Ile Pro Gly  Gly Gly Pro
    1010                1015                1020
```

```
Met Lys Arg Thr Ser Asn Ser Gly Thr Trp Gly His Ile Lys Cys
    1025                1030                1035

Ala Leu Ala Asn Glu Cys Thr Ile Glu Pro Asp Glu Ile Asn Tyr
    1040                1045                1050

Gly Thr Phe Leu Pro Lys Ile Lys Ala Leu Lys Cys Ile Phe Cys
    1055                1060                1065

Asn Ile Trp Ser Thr Ser Val Ile Gln Cys Ser Tyr Gly Asn Cys
    1070                1075                1080

Cys Lys Ala Phe His Val Pro Cys Ser Ser Ser Pro Asn Cys
    1085                1090                1095

Leu Phe Thr Trp Asp Thr Asn Gly Lys Pro Asp Val Leu Cys Pro
    1100                1105                1110

Ile His Ser Lys Gly Leu Ala Pro Thr Ser Leu Leu Arg Lys Leu
    1115                1120                1125

Gln Ile Arg Leu Ser Leu Asn Lys Asp Lys Asp Gly Lys Glu Arg
    1130                1135                1140

Ser Asp Tyr Asp Lys Thr Ser His Pro Tyr Ser Leu Thr Glu Lys
    1145                1150                1155

Asn Lys Glu Lys Lys Glu Lys Ser Lys His Glu Lys Gln Thr Glu
    1160                1165                1170

Lys Ile Asp Lys Arg Arg Ala Asp Arg Glu Lys Tyr Lys Ile Glu
    1175                1180                1185

Gly Gln Asn Asp Lys Val Tyr Lys Pro Lys Leu Glu Glu Lys Thr
    1190                1195                1200

Lys Glu Arg Asp Ser Gly Asn Lys Lys Gly Ser Arg Asp Ala Ile
    1205                1210                1215

Asp Asn Ile Cys Val Asn Glu Asn Leu Tyr Leu Asn His Phe Leu
    1220                1225                1230

Arg Pro Asn Tyr Ser Asn Leu Thr Lys Leu Leu Glu Leu Leu Leu
    1235                1240                1245

Asn Glu Lys Val Gly Thr Ile Phe Gln Ser Asn Met Ser Ser Asn
    1250                1255                1260

Tyr Tyr Lys Thr Glu Val Met Pro Arg Tyr Ala Ser Ile Val Ser
    1265                1270                1275

Asn Val Thr Ser Asp Arg Ser Thr Thr Arg Ser Val Ser Asn Lys
    1280                1285                1290

Phe Tyr Asn Met Asp Asp Leu Ser Ser Asn Glu Asp Asp Met Ser
    1295                1300                1305

Leu Leu Lys Glu Phe Asp Arg Glu Tyr Asp Glu Cys Val Pro Asn
    1310                1315                1320

Leu Val Thr Pro Ile Ser Val His Thr Asn Ser Asn Thr Asp Ser
    1325                1330                1335

Thr Phe Ser Leu Asn Ser Asp Lys Leu Ser Arg Gln Asn Ser Thr
    1340                1345                1350

Ser Ser Gln Asn Thr Ser Asp Ser Ala Ala Val Asp Thr Ser Ser
    1355                1360                1365

Asn Met Asp Ile Ser Ser Arg Val Asn Ser Thr Lys Ser Glu Glu
    1370                1375                1380

Ser Asp His Ser Gly Thr Asp Lys Ser Asn Thr Phe Asp Tyr Gln
    1385                1390                1395

Leu Pro Asp Glu Glu Leu Glu Thr Asp Asp Asp Leu Val Leu Ser
    1400                1405                1410
```

-continued

```
Arg Lys Ser Thr Leu Ile Glu Asn Gln Glu Thr Val Glu Gln Asn
1415                1420                1425

His Thr Glu Gly Lys Cys Pro Leu Asn Asn Ile Asn Lys Asn Asn
1430                1435                1440

Cys Phe Trp Cys Cys Leu Gly Phe Asp Leu Lys Asn His Asn Arg
1445                1450                1455

His Val Phe Asp Asp Lys Thr Pro Ser Ser Lys Met Ile Leu Ser
1460                1465                1470

Ile Leu Tyr Asn Asn Asn His Ser Asn Val Asn Ala Ile Lys Ser
1475                1480                1485

Ile Ile Asn Ser Lys Tyr Glu Ser Ala Glu Lys Asn Glu Thr Asn
1490                1495                1500

Thr Ser Lys Pro Gln Thr Lys Leu Lys Asn Asp Glu Asn Gly Glu
1505                1510                1515

Lys Lys Ser Thr Lys Thr Lys Thr Lys Glu Asp Asn Arg Glu Glu
1520                1525                1530

Phe Lys Ile Pro Trp Ser Ile Leu Ser Asn Ile Ile Ile Asp Asn
1535                1540                1545

Val Val Asp Asp Lys Ile Asn Thr Phe Ile Asn Gly Asp Leu Val
1550                1555                1560

Asn Asn Asn Lys Leu Val Lys Lys Asn Asp Phe Leu Val Gln Lys
1565                1570                1575

Met Ala Ser Glu Ala Leu Val Arg Leu Phe Asn Thr Phe Glu Pro
1580                1585                1590

Asp Ser Ser Met Phe Val Val Lys Thr Leu Phe Ser Ile Leu Lys
1595                1600                1605

His Val Asp Phe Ile His Glu Ile Asp Asp Leu Tyr Gly Tyr Asn
1610                1615                1620

Asn Leu Tyr Phe Cys Asn Pro Ser Pro Ser Ile Asp Asn Tyr Met
1625                1630                1635

Ser Ser Asp Lys Leu Leu Asp Lys Arg Leu Asp Leu Ile Lys Pro
1640                1645                1650

Arg Ile Asn Asn Ala Ile Pro Lys Leu Asn Ser Ile Ser Pro Leu
1655                1660                1665

Ser Asp Gln Ser Arg Gln Ile Asn Gly Glu Ser Asn Thr Asn Gln
1670                1675                1680

Asn Tyr Ser Ala Arg Ser Asp Asn Val Gln Leu Asn Gly Met Asn
1685                1690                1695

Lys Asn His Lys Lys Thr Gln Met Gln Ser Gln Pro Gln Ile Gln
1700                1705                1710

Val Gln Asp Gln Asn Leu Leu Ser Phe Ile Gln Thr Thr Asn Ser
1715                1720                1725

Ser Lys Pro Leu Asn Leu Pro Glu Ser Leu Ser Lys Met Ala Pro
1730                1735                1740

Leu Ile Lys Asp Ile Phe Asn Lys Asp Lys Thr Glu Arg Leu Asn
1745                1750                1755

Asn Pro Ile Thr Gln Leu Asn Arg Val Val Pro Thr Thr Asn Thr
1760                1765                1770

Ile Thr Pro Thr Asn Thr Met Asp Lys Asn Lys Thr Thr Asp Gly
1775                1780                1785

Val Asn Ile Phe Asn Ser Leu Asn Asn Asn Ala Ser Glu Val Asn
1790                1795                1800

Gly Asn Asp Gln Lys Asp Arg Asp Ala Lys Lys Ala Leu Lys Glu
```

-continued

```
              1805                1810                1815
Arg  Ile  Phe  Asn  Met  Leu  Lys  Gln  Val  Asn  Gln  Val  Glu  Ile  Ile
              1820                1825                1830

Lys  Met  Asp  Lys  Ser  Leu  Leu  Pro  Asn  Ser  Ile  Leu  Arg  Lys  Tyr
              1835                1840                1845

Ile  Asn  Asn  Lys  Lys  Ile  Thr  Ile  Cys  Lys  Val  Cys  Leu  Glu  Phe
              1850                1855                1860

Lys  Tyr  Ile  Glu  Asn  Asp  Ile  Asp  Asn  Asn  Lys  Arg  Lys  Arg  Asn
              1865                1870                1875

Ile  Tyr  Asn  Glu  Ser  Tyr  Arg  Lys  Cys  Ile  Asn  Cys  Asn  Val  Glu
              1880                1885                1890

Val  Cys  Asn  Ser  Cys  Leu  Ser  Val  Asn  Lys  Thr  Asp  Phe  Glu  His
              1895                1900                1905

Leu  Thr  Asn  Ser  Ser  Thr  Met  Ile  Ile  Gly  Asp  Tyr  Ile  Gly  Gln
              1910                1915                1920

Asp  Val  Asp  Asp  Phe  Tyr  Phe  Ser  Cys  Ile  Arg  Cys  Lys  Glu  Phe
              1925                1930                1935

Ser  Glu  Asn  Leu  Gln  Met  Pro  Leu  Leu  Asn  Cys  Val  Leu  Cys  Ser
              1940                1945                1950

Arg  Tyr  Asp  Gly  Leu  Met  Leu  Lys  Ile  Asn  Ser  Lys  Leu  Leu  Ser
              1955                1960                1965

Phe  Val  Pro  Ser  Arg  Thr  Ser  Phe  Trp  Asn  Asn  Tyr  Ser  Tyr  Val
              1970                1975                1980

His  Leu  Val  Cys  Leu  Glu  Trp  Leu  Tyr  Trp  Ser  Lys  Asn  Ala  His
              1985                1990                1995

Asn  His  Ser  Lys  Lys  Leu  Asn  Lys  Thr  Ile  Phe  Glu  Gln  Asn  Cys
              2000                2005                2010

Asn  Tyr  Cys  Gly  Ile  Gln  Thr  Gly  Ala  Thr  Val  Thr  Cys  Ser  Asn
              2015                2020                2025

Thr  Thr  Cys  Ile  Ser  Lys  Phe  His  Pro  Ser  Cys  Ala  Ala  Phe  Leu
              2030                2035                2040

Gly  Cys  Lys  Ile  Asp  Val  Gly  Lys  Lys  Asn  Glu  Ser  Leu  Ile  Gly
              2045                2050                2055

Val  Lys  Arg  Ala  Leu  Cys  Leu  Arg  His  Thr  Leu  Ile  Ser  Ile  Cys
              2060                2065                2070

Arg  Thr  Ser  Leu  Ser  Glu  Arg  Lys  Phe  Met  Val  Ala  Pro  Ser  Tyr
              2075                2080                2085

Leu  Tyr  Glu  Val  Leu  Val  Asn  Asn  Asn  Tyr  Phe  Thr  Ser  Phe  Phe
              2090                2095                2100

Arg  Gly  Val  Tyr  Leu  Ser  Pro  Asn  Cys  Ile  Asn  Asn  Arg  Thr  Lys
              2105                2110                2115

Leu  Thr  Thr  Arg  Phe  Lys  Ile  Lys  Lys  Lys  Ser  Arg  Ser  Leu  Asp
              2120                2125                2130

Tyr  Lys  Asn  Asn  Leu  Ser  Ile  Met  Lys  Met  Ala  Ser  Tyr  Ile  Asn
              2135                2140                2145

Tyr  Gly  Leu  Ile  Ile  Asn  Lys  Thr  Pro  Gln  Met  Tyr  Asp  Leu  Thr
              2150                2155                2160

Ile  Ser  Glu  Ala  Ile  Ala  Arg  Asp  Arg  Leu  Ile  Gln  Gly  Met  Asn
              2165                2170                2175

Tyr  Ile  Phe  Tyr  Gln  Gln  Lys  Ser  Pro  Asn  His  Ile  Asn  Phe  Tyr
              2180                2185                2190

Asn  Gln  Ser  Tyr  Lys  Glu  Ser  Lys  Glu  Asn  Ser  Ile  Lys  Asp  Ile
              2195                2200                2205
```

-continued

```
Lys Asn Ile Ile Thr Leu Ile Lys Asn Gly Leu Leu Lys Pro Ile
    2210                2215                2220

Gln Gly Ser Lys Arg Gly Arg Lys Pro Lys Ser Leu Asp Gly Ser
    2225                2230                2235

Asp Val Asp Lys Arg Arg Lys Met Ser Met Glu Glu Ile Leu Arg
    2240                2245                2250

Tyr Ala His Ser Gly Ile Leu Asp Asn Gly Asp Tyr Tyr Cys Pro
    2255                2260                2265

Val Cys Phe Ser Ile Tyr Phe Glu Asn Ser Pro Gly Leu Pro Gly
    2270                2275                2280

Asp Glu Leu His Trp Ile Gly Cys Asp Lys Cys Glu Arg Trp Phe
    2285                2290                2295

His Phe Val Cys Ala Gly Val Trp Val Asp Phe Arg Asp Lys Asp
    2300                2305                2310

Ser Trp Tyr Cys Tyr His Cys Ser Asn Ala
    2315                2320

<210> SEQ ID NO 49
<211> LENGTH: 681
<212> TYPE: PRT
<213> ORGANISM: Theileria annulata

<400> SEQUENCE: 49

Met Met Lys Val Leu Arg Ser Ser Gly Arg Thr Lys Arg Thr Tyr
1               5                   10                  15

Asp Asp Asp Thr Ile Ser Ser Pro Leu Thr Glu Gln Ile Lys Gly Ile
                20                  25                  30

Lys Gly Ile Lys Arg Thr Lys Thr Lys Asp Glu Asp Glu Ala Tyr Thr
            35                  40                  45

Tyr Val Arg Asp Pro Tyr Gly Asp Val Ile Ala Asn Val Asn Gly Lys
        50                  55                  60

Lys Phe Tyr Arg Ser Ala Leu Ile His Asp Glu Ile Ile Ser Ile Tyr
65                  70                  75                  80

Asp Ser Val Asp Val Leu Arg Thr Ser Asn Lys Ser Lys Asn Val Arg
                85                  90                  95

Glu Ser Asn Leu Ala Lys Ile Ser Ala Ile Tyr Val Asp Thr Asn Gly
                100                 105                 110

Lys Leu Met Ala Glu Val Ser Phe Tyr Phe Asp Ser Gly Glu Glu Ile
            115                 120                 125

Pro Asn Thr Asp Asn Ser Gln Ile Ser Pro Lys Ile Leu Phe Asp Asn
        130                 135                 140

Asn Phe Asn Lys Trp Lys Gly Phe Thr His Val Asn Glu Val Val Ala
145                 150                 155                 160

Tyr Asn Lys Phe Glu Asp Val Glu Ile Glu Thr Phe Asp Glu Lys Val
                165                 170                 175

Asn Val His Ala Ser Lys Glu Glu Tyr Leu Asn Glu Ile Asn Ser Gly
                180                 185                 190

Gly Asp Glu Glu Ile Asn Val Phe Cys Asn Tyr Ile Cys Tyr His Glu
            195                 200                 205

Asn His Ser Ile Leu Pro Phe Asn Ile Asn Thr Asp Trp Glu His Ile
        210                 215                 220

Met Val Glu Ser Ser Lys Tyr His Ser Ile Tyr Tyr Pro Lys Met Val
225                 230                 235                 240

Tyr Lys Glu Glu Ser Ile Val Glu Pro Leu Ser Pro Glu Leu Thr Leu
```

-continued

```
                245                 250                 255
Gln Leu Asn Ser Asn Glu Lys Ile Leu Gly Arg Glu Glu Ala Glu
                260                 265                 270
Lys Ile Arg Thr Phe Met Glu Thr Asn Ile Lys Gln Gly Gly Thr Gly
                275                 280                 285
Gln Ile Leu Tyr Ile Ser Gly Val Pro Gly Thr Gly Lys Thr Glu Thr
                290                 295                 300
Val Lys Met Val Ser Lys Glu Leu Ile Ser Lys Leu Lys Gly Gln
305                 310                 315                 320
Ile Pro Trp Phe Asp Leu Ile Glu Ile Asn Ala Val His Leu Ser Lys
                325                 330                 335
Pro Asn Glu Leu Tyr Arg Val Phe Tyr Asn Lys Leu Phe Ala Lys Pro
                340                 345                 350
Ala Pro Ile Ser His Ser Tyr Asp Glu Leu Asp Lys Tyr Phe Asn Asn
                355                 360                 365
Asn Thr Thr Pro Cys Ile Leu Ile Val Asp Glu Ala Asp Tyr Ile Val
                370                 375                 380
Thr Lys Thr Gln Lys Val Leu Phe Asn Leu Phe Asp Leu Pro Cys Lys
385                 390                 395                 400
Lys Asn Ser Lys Phe Ile Leu Ile Ile Ser Asn Thr Met Asp Leu
                405                 410                 415
Asn Tyr Lys Met Lys Ser Ser Ile Gln Ser Arg Leu Gly Phe Gly Ser
                420                 425                 430
Leu Val Phe Lys Pro Tyr Arg Tyr Gln Gln Ile Gln Val Ile Glu
                435                 440                 445
Ser Lys Leu Gly Lys His Ser Pro Ile Asp Pro Val Ala Leu Gln Leu
                450                 455                 460
Cys Ala Arg Arg Val Thr Asn Tyr Ser Gly Asp Met Arg Lys Ala Leu
465                 470                 475                 480
Gln Ile Cys Lys Leu Ala Ile Lys Glu Ser Asn Gly Glu Lys Ile Thr
                485                 490                 495
Val Tyr Ser Ile Thr Val Phe Arg Tyr Gly Val Arg Phe Thr Ala Thr
                500                 505                 510
Asn Thr Leu Pro Val Val Gln Gln Pro Asp Ser Pro Ser Pro Gln Lys
                515                 520                 525
Gly Phe Gln Leu Val Ser Glu Met Ser Arg Ile Ser Asn Met Val Leu
                530                 535                 540
Asn Ser Ser Ile Ser Asp Ala Leu Gln Tyr Val Ser Val Gly Met Lys
545                 550                 555                 560
Cys Leu Leu Val Ala Ile Ile Leu Val Leu Lys Gln Val Gln Leu Ser
                565                 570                 575
Ile Ala Pro Ala Val Gln Val Tyr Asn Thr Phe Arg Gly Met Met Thr
                580                 585                 590
Val Leu Lys Pro Glu Leu Glu Asn Val Cys Lys Asp Ser Phe Lys His
                595                 600                 605
Leu Leu Ile Ser Ser Leu Asn Asn Gly Val Ile Ser Leu Glu Pro Thr
                610                 615                 620
Val Phe Ser Ser Phe Ser Leu Thr Asp Lys Lys Val Lys Val
625                 630                 635                 640
Phe Glu Glu Ile Asn Glu Asp Leu Gly Asp Val Gly Ile Thr Phe Gln
                645                 650                 655
Ile Asp Ile Gly His Leu Ile Thr Ala Leu Ala Lys Asp Pro Tyr Trp
                660                 665                 670
```

```
Gln Ser Lys Leu Glu Thr Ile Asn His
        675                 680
```

<210> SEQ ID NO 50
<211> LENGTH: 319
<212> TYPE: PRT
<213> ORGANISM: Theileria annulata

<400> SEQUENCE: 50

```
Met Lys Lys Tyr Ile Leu Glu Glu Leu Leu Thr Glu Tyr Glu Gln Asn
1               5                   10                  15

Asn Glu Ile Asn Asn Asn Glu Asp Glu Ala Tyr Gln Gln Tyr Ser
            20                  25                  30

Trp Glu Leu Asp Val Asp Lys Ser Trp Glu Gln Leu Ile Glu Lys Asp
        35                  40                  45

Gly Ile Leu Gln Phe Ile Lys Pro Gln Thr Lys Ile Tyr Gln Glu Phe
    50                  55                  60

Asp Ile Asp Tyr Asn Thr Asn Leu Lys Gln His Asn Val Asp Ile Ile
65                  70                  75                  80

Tyr Lys Arg Gly Ile Ile Arg Phe Val Thr Val Phe Trp Ser Ile Met
                85                  90                  95

Ile Leu Phe Asp Met Ser Glu Gln Met His Glu Met Asp Phe Lys Pro
            100                 105                 110

Asp Arg Leu Tyr Cys Ala Phe Asn Ser Leu Lys Glu Phe Met Asn Val
        115                 120                 125

Leu Tyr Gly Ser Gly Pro Ile Thr Gln Val Gly Ile Ile Val Met Arg
    130                 135                 140

Asn Lys Ile Cys Asn Val Ile Thr Gln Phe Gly Thr Asn Pro Asp Glu
145                 150                 155                 160

Gln Met Glu Leu Leu Ser Asn Ile Leu Lys Asp Gly Pro Glu Gly Ser
                165                 170                 175

Ser Ser Leu Gln Asn Gly Leu Glu Met Cys Leu Lys Ile Met Cys Glu
            180                 185                 190

Leu Pro Tyr Tyr Met Thr Arg Glu Ile Leu Ile Ile Phe Gly Ser Asn
        195                 200                 205

Lys Thr Leu Asp Pro Gly Asn Ile Leu Ile Thr Leu Asp Lys Leu Lys
    210                 215                 220

Gln Asn Phe Ile Thr Val Asn Cys Ile Ser Leu Ser Pro Glu Leu Tyr
225                 230                 235                 240

Ile Leu Lys Gly Cys Gly Ile Phe Met Val Ser Pro Pro Asp Ile Ser
                245                 250                 255

Arg Ala Phe His His Leu Ile Pro Pro Lys Ser Phe His Lys Ile Glu
            260                 265                 270

Arg Asn Ile Asn Cys Ser Gly Cys Asn Leu Asn Ile Glu Ile Gly Tyr
        275                 280                 285

Glu Cys Gln Asn Cys Gln Gly Ile Phe Cys Glu Tyr Cys Asp Lys Tyr
    290                 295                 300

Ile His Gln Asp Leu His Gln Cys Pro Ile Cys Leu Phe Gln His
305                 310                 315
```

<210> SEQ ID NO 51
<211> LENGTH: 681
<212> TYPE: PRT
<213> ORGANISM: Theileria annulata

<400> SEQUENCE: 51

-continued

```
Met Lys Ser Leu Ser Arg Leu Tyr Ser Ile Phe His Ser Ser Arg Cys
1               5                   10                  15

Ser Leu Glu Leu Ser Asn Lys Leu Ser Thr Ile Ser Gly Ile Thr Thr
            20                  25                  30

Met Leu Asp Ser Leu Arg Ile Gly Ser Arg Arg Gly Ile Phe Thr Thr
        35                  40                  45

Ser Gly Arg Phe Ala Lys Val Gln Gly Asp Val Val Gly Ile Asp Leu
    50                  55                  60

Gly Thr Thr Asn Ser Cys Val Ala Ile Met Glu Gly Ser Thr Pro Lys
65                  70                  75                  80

Val Ile Glu Asn Ala Glu Gly Ala Arg Thr Thr Pro Ser Ile Val Ala
                85                  90                  95

Phe Thr Asp Asp Gly Gln Arg Leu Val Gly Val Val Ala Lys Arg Gln
            100                 105                 110

Ala Val Thr Asn Pro Glu Asn Thr Val Phe Ala Thr Lys Arg Phe Ile
        115                 120                 125

Gly Arg Lys Phe Asp Asp Pro Glu Thr Lys Lys Glu Gln Ser Thr Leu
    130                 135                 140

Pro Tyr Lys Ile Val Arg Ser Ser Asn Asn Asp Ala Trp Ile Glu Ala
145                 150                 155                 160

Gln Asn Lys Gln Tyr Ser Pro Ser Gln Ile Gly Ala Tyr Ile Leu Ala
                165                 170                 175

Lys Met Lys Glu Thr Ala Glu Ser Tyr Leu Gly Arg Thr Val Ser Lys
            180                 185                 190

Ala Val Ile Thr Val Pro Ala Tyr Phe Asn Asp Ser Gln Arg Gln Ala
        195                 200                 205

Thr Lys Asp Ala Gly Lys Ile Ala Gly Leu Glu Val Leu Arg Ile Ile
    210                 215                 220

Asn Glu Pro Thr Ala Ala Ala Leu Ala Phe Gly Met Asp Lys Asn Asp
225                 230                 235                 240

Gly Lys Thr Ile Ala Val Tyr Asp Leu Gly Gly Gly Thr Phe Asp Val
                245                 250                 255

Ser Ile Leu Glu Ile Leu Gly Gly Val Phe Glu Val Lys Ala Thr Asn
            260                 265                 270

Gly Asn Thr Ser Leu Gly Gly Glu Asp Phe Asp Gln Arg Ile Leu Asn
        275                 280                 285

Tyr Leu Val Glu Glu Phe Lys Lys Ser Asn Gly Ile Asp Leu Lys Lys
    290                 295                 300

Asp Lys Leu Ala Leu Gln Arg Leu Arg Glu Ser Ser Glu Ser Ala Lys
305                 310                 315                 320

Ile Glu Leu Ser Thr Lys Thr Gln Thr Glu Ile Asn Leu Pro Phe Ile
                325                 330                 335

Thr Ala Asp Gln Ser Gly Pro Lys His Leu Leu Ile Lys Leu Ser Arg
            340                 345                 350

Ser Lys Leu Glu Gln Leu Thr Ser Glu Leu Leu Glu Gly Thr Val Asp
        355                 360                 365

Pro Cys Lys Lys Cys Leu Lys Asp Ala Gly Val Asn Ala Ser Glu Leu
    370                 375                 380

Asn Asp Val Ile Leu Val Gly Gly Met Thr Arg Met Pro Lys Val Thr
385                 390                 395                 400

Glu Val Val Lys Asn Ile Phe Gly Lys Glu Pro Ser Lys Ala Val Asn
                405                 410                 415
```

```
Pro Asp Glu Ala Val Ala Met Gly Ala Ala Ile Gln Ala Gly Val Leu
            420                 425                 430

Lys Gly Glu Ile Lys Asp Leu Leu Leu Leu Asp Val Cys Pro Leu Ser
            435                 440                 445

Leu Gly Ile Glu Thr Leu Gly Gly Val Phe Thr Arg Leu Ile Asn Arg
            450                 455                 460

Asn Thr Thr Ile Pro Thr Lys Lys Ser Gln Ile Phe Ser Thr Ala Ala
465                 470                 475                 480

Asp Asn Gln Thr Gln Val Gly Ile Lys Val Tyr Gln Gly Glu Arg Gly
                485                 490                 495

Met Ala Ala Asp Asn Gln Leu Leu Gly Gln Phe Asp Leu Val Gly Ile
            500                 505                 510

Pro Pro Ala Pro Arg Gly Val Pro Gln Ile Glu Val Thr Phe Asp Val
            515                 520                 525

Asp Ala Asn Gly Ile Met Asn Ile Ser Ala Val Asp Lys Ser Thr Gly
            530                 535                 540

Lys Arg Gln Glu Ile Thr Ile Gln Ser Ser Gly Gly Leu Ser Glu Glu
545                 550                 555                 560

Glu Val Glu Lys Met Val Lys Glu Ala Ser Asn Tyr Lys Glu Gln Asp
                565                 570                 575

Glu Arg Arg Lys Glu Leu Val Asp Val Arg Asn Glu Ser Glu Ser Leu
            580                 585                 590

Leu Tyr Ser Val Glu Lys Gln Leu Thr Asp Leu Lys Asp Lys Val Ser
            595                 600                 605

Ser Ser Glu Leu Asp Gln Leu Arg Thr Leu Ser Thr Ser Leu Lys Glu
            610                 615                 620

Val Leu Ser Ser Asp Asp Val Ser Ala Ile Lys Asp Lys His Lys Gln
625                 630                 635                 640

Leu Gln Glu Leu Ser Trp Lys Val Ser Gln Ala Ala Tyr Ser Lys Ser
                645                 650                 655

Asn Thr Gly Ala Thr Ser Ala Asn Thr Ser Glu Asn Thr Asn Thr Ser
            660                 665                 670

Asn Glu Glu Asn Asp Thr His Asn Lys
            675                 680

<210> SEQ ID NO 52
<211> LENGTH: 426
<212> TYPE: PRT
<213> ORGANISM: Theileria annulata

<400> SEQUENCE: 52

Met Ser Glu Val Tyr Ser Leu Glu Pro Ser Cys Lys Gly Arg Val Val
1               5                   10                  15

Val Asn Thr Ser Leu Gly Glu Leu Asp Ile Arg Leu Trp Ser Ser His
            20                  25                  30

Cys Pro Lys Ala Cys Arg Asn Phe Val Gln Leu Cys Met Glu Gly Tyr
            35                  40                  45

Tyr Asn Asn Cys Ile Phe His Arg Val Ile Pro Asn Phe Met Val Gln
            50                  55                  60

Thr Gly Asp Pro Ser Gly Thr Gly Asn Gly Gly Glu Ser Ile Tyr Gly
65                  70                  75                  80

Glu Pro Phe Glu Asn Glu Ile Val Ser Arg Leu Lys Phe Arg Asn Arg
                85                  90                  95

Gly Met Val Ala Met Ala Asn Thr Gly Gly Lys Cys Ser Asn Met Ser
            100                 105                 110
```

```
Gln Phe Phe Ile Thr Leu Asp Arg Ser Asp Phe Leu Asn Gly Lys Tyr
            115                 120                 125

Thr Leu Phe Gly Lys Val Glu Gly Asn Ser Ile Tyr Asn Leu Leu Lys
        130                 135                 140

Ile Gly Lys Ser Glu Val Asp Lys Asn Asp Arg Pro Ile Asp Pro Pro
145                 150                 155                 160

Lys Ile Leu Ser Cys Tyr Val Val Glu Asn Pro Phe Asp Asp Ile Val
                165                 170                 175

Pro Arg Leu Leu Gln Leu Ser Glu Pro Glu Glu Lys Gln Glu Glu
            180                 185                 190

Glu Val Thr Thr Gln Thr Lys Asp Lys Arg Leu Leu Ser Phe Leu
        195                 200                 205

Asp Ser Asp Asp Glu Glu Asp Gln Ser Val Lys Ile Lys Ser Ala His
    210                 215                 220

Asp Leu Leu Gln Asp Lys Ser Leu Ser Lys Thr Ser Val Gln Ile Lys
225                 230                 235                 240

Glu Thr Pro Lys Ser Asp Gln Pro Asp Glu Pro Ala Thr Ala Glu Glu
                245                 250                 255

Leu Glu Asp Ile Glu Asp Glu Val Asn Glu Glu Val Glu Asp Leu Asn
            260                 265                 270

Glu Glu Asp Glu Met Arg Lys Lys Glu Ile Asn Glu Leu Glu Lys Lys
        275                 280                 285

Leu Ile Asp Asn Lys Asp Asp Leu Tyr Asn Arg Lys Lys Lys Lys Lys
        290                 295                 300

Thr Lys His Asp Pro Lys Glu Thr Leu Glu Arg Leu Ala Leu Phe Thr
305                 310                 315                 320

Lys Lys Leu Gly Glu Ile Ser Lys Asn Glu Lys Leu Ala Asn Lys Gln
                325                 330                 335

Pro Glu Thr Asp Glu Asp Met Ser Asp Gly Ser Trp Phe Ala Gly Thr
            340                 345                 350

Lys Leu Gln Phe Ser Ile Asp Ser Asn Arg Ala Tyr Ala Tyr Asp Ala
        355                 360                 365

Gly Arg Asp Thr Val Phe Leu Ala Leu Asn Phe Ile Val Gln Leu Asp
    370                 375                 380

Val Tyr Asp Pro Leu Lys Gly Lys Asp Lys Leu Asn Ser Ile Lys
385                 390                 395                 400

Asn Ile Arg Arg Asn Val Phe Leu Asp Tyr Leu Thr Gln Glu Phe Leu
                405                 410                 415

Val Asn Asn Asn Tyr Ser Cys Leu Ser Arg
            420                 425

<210> SEQ ID NO 53
<211> LENGTH: 1337
<212> TYPE: PRT
<213> ORGANISM: Theileria annulata

<400> SEQUENCE: 53

Met Arg Ile Asn Ser Leu Ile Thr Asn Thr Trp Lys Leu Cys Phe Leu
1               5                   10                  15

Cys Met Leu Ser Ser Lys Phe Ser Leu Ser Leu Arg Phe Asn Pro Asp
            20                  25                  30

Val Ser Asn Lys Arg Val Ile Ser Arg Leu Glu Leu Phe Asn Pro Glu
        35                  40                  45

Ser Thr Gly Gly Pro Ser Phe Ala Glu Ile Gly Gly Phe Phe Ile Pro
```

-continued

```
                50                    55                    60
Thr Pro Ile Leu Asp Lys Ser Gly Asn Asn Ser Tyr Ser Tyr Leu Gln
 65                    70                    75                    80

His Ser Thr Thr Ser Leu Gly Val Asp His Asp Val Val Lys Leu Ser
                    85                    90                    95

Lys Glu Ser Leu Lys Phe Arg Asn Val Glu Gly Leu Ile Lys Glu Lys
                   100                   105                   110

Pro Leu Thr Leu Ile Val Gly Thr Tyr Gly Ser Arg Phe Asp Met
                   115                   120                   125

Leu Phe Glu Lys Ile Val Ser Lys Asp Asn Lys Phe Glu Phe Ser
130                   135                   140

Leu Pro Lys Gly Thr Phe Tyr Ile Lys Thr Glu Gly Ser Gly Tyr Phe
145                   150                   155                   160

Leu Pro Gly Val Lys Val Val Leu Pro Cys Lys Leu Lys Phe Cys
                   165                   170                   175

Pro Phe Val Asn Asp Ser Phe Lys Asp Ser Ile Ala Val Glu Leu Ala
                   180                   185                   190

Lys Asp Asp Gly Ser Ile Tyr Thr Tyr Asn Trp Lys Leu Gln Asp Glu
                   195                   200                   205

Ser Gln Phe Gly Val Glu Ser Ile Asn Arg Ile Pro Gln Asp Glu Ala
                   210                   215                   220

Ser Ile Leu Ser Pro Ser Ser Thr Val Val Ser His Val Asp Ala Ser
225                   230                   235                   240

Asp Ala Ser Ala Lys Leu Lys Leu Leu Phe Gly Ile Glu Leu His Gly
                   245                   250                   255

Val Trp Gly Ser Glu Tyr Ala Asn Arg Leu Leu Ser Val Phe Leu Lys
                   260                   265                   270

Phe Asp Phe Leu Asn Arg Glu Asn Ser Pro Asn Pro Lys Lys Gln Lys
                   275                   280                   285

Trp Leu Leu Thr Asp Glu Ser Leu Tyr Pro Gln Asp Ile Glu Ile Ile
                   290                   295                   300

Lys Asn Val Val Asp Arg Asn Gly Ser Arg Asn Lys Asn Gln Asn Val
305                   310                   315                   320

Val Glu Asp Thr Glu Tyr Glu Gln Ile Val Lys Ile Ser Arg Glu Ala
                   325                   330                   335

Phe Lys Tyr Ser Val Lys Gln Ala Ile Asp Lys Lys Asn Gly Phe
                   340                   345                   350

Tyr Phe Ser Arg Arg Leu Tyr Lys Ser Val Ile Arg Ala Ile Cys Leu
                   355                   360                   365

His Asn Pro Glu Asn Met Lys Arg Leu Phe Lys Asp Ala His Asn Val
                   370                   375                   380

Val Ile Leu Glu Pro Phe Glu Leu Glu His Met Ile Arg Ala Lys Asn
385                   390                   395                   400

Ser Phe Thr His Tyr Pro Ser Ser His Tyr Gln Ser Trp Phe Lys His
                   405                   410                   415

Pro Glu Glu Leu Ile Glu Ile Leu Thr Ser Trp Arg Glu Tyr Pro Ser
                   420                   425                   430

Gly Leu His Lys Val Asn Gly Leu Arg Tyr Phe Leu Arg Arg Gln Asp
                   435                   440                   445

Gly Met Val Asn Pro Glu Gln Pro Thr Ala Pro Ala Ile Ala Tyr Pro
                   450                   455                   460

Arg Gly Pro Asn Ser Asp Ser Tyr Ile Glu Phe Met Glu Ser Gly Phe
465                   470                   475                   480
```

```
His Asn Tyr His Asp Val Ser Gln Leu Ile Leu His Glu Ile Gly His
            485                 490                 495

Phe Ile His Phe Asn Thr Val Pro Glu Asp Leu Lys Thr Lys Trp Ile
            500                 505                 510

Glu Leu Gly Gly Trp Tyr Glu Asp Pro Lys Asp Pro Asp Gly Trp Ser
            515                 520                 525

Thr Arg Lys Gln Thr Glu Phe Val Ser Ala Tyr Ser His Gln Lys Asn
            530                 535                 540

Pro Gly Glu Asp Phe Ala Ser Thr Leu Ala Asp Tyr Val Leu Asn Pro
545                 550                 555                 560

Lys Leu Val Arg Ser Arg Ala Leu Gln Lys Phe Met Phe Ile Lys Asp
            565                 570                 575

Asn Ile Met Gly Gly Val Tyr Tyr Leu Val Lys Ala Ser His Glu Phe
            580                 585                 590

Lys Val Leu Asn Leu Gly Asn Ala Asp Tyr Phe Tyr Pro Gly Arg Leu
            595                 600                 605

Ser Glu Ile Asn Val Val Val Asn Gly Lys Val Asn Glu Pro Lys Lys
            610                 615                 620

Val Lys Leu Thr Phe Lys Leu Leu Asn Lys Arg Asn Ala Gln Gly Glu
625                 630                 635                 640

Asp Ser Asp Thr Cys Ala Lys Lys Ile Thr Phe Arg Leu Phe Ser Glu
            645                 650                 655

Ile Gly Thr Phe Glu Asp Ile Val Leu Lys Ser Asn Thr Gly Cys Ser
            660                 665                 670

His Val Leu Glu Thr Glu Ile Thr Ile Asn Gln Met Lys Lys Arg Gly
            675                 680                 685

Val Trp Thr Thr Asp Gln Ile Val Thr Asp Asp Lys Gly Leu Gln
            690                 695                 700

Arg Phe Val Gly Ser Ala Asp Phe Gly Leu Arg Val Trp Ile Asn Asn
705                 710                 715                 720

Gly Ser Glu Asp Phe Gln Asp Pro Arg Ala Leu Thr Asn Ser Val Ser
            725                 730                 735

Leu Ala Leu Val Lys Lys Gly Asp Glu Glu Ala Val Arg Val Gly Trp
            740                 745                 750

Leu Val Val Asp Asp Ser Glu Leu Arg Lys Lys Asn Ala Gly Tyr Ala
            755                 760                 765

Ala Ile Asn Gly Asn Ser Asn Asn Gln His Ser Met Gly Ala Tyr Ser
            770                 775                 780

Arg Phe Asp Asn Ser Asp Ser Thr Pro Asn Asn Phe Trp Arg Lys Asp
785                 790                 795                 800

Val Trp Ser Gly Ala Arg Lys Val Pro Leu Glu Phe Cys Ser Leu Asn
            805                 810                 815

Ser Pro Asp Ile Lys Asn Ser Leu Ser Asp Pro Asn Ile Lys Phe Asn
            820                 825                 830

Thr His Lys Leu Gly Gly Leu Asp Asn Phe Glu Gly Leu Thr Ser Asp
            835                 840                 845

Gln Val Ser Ser Gly Ser Phe Asn Cys Phe Arg Val Ala Val Asn Ile
            850                 855                 860

Pro Ile Ser Lys Ser Ser Arg Thr Gly Asp Tyr Phe Leu Thr Gln Ile
865                 870                 875                 880

Val Thr Tyr Asp Ser Ala Gly Asn Ser Gln Leu Leu Gln Trp Pro Gln
            885                 890                 895
```

-continued

Lys Thr Gly Pro Phe Ile Thr Tyr Thr Ser Ser Asn Pro Asn Pro Asp
            900                 905                 910

Asn Ser Pro Pro Thr Val Lys Asp Ile Arg Val Thr Ser Arg Pro Ser
        915                 920                 925

Asn Pro Asn Ser Pro Asn Gly Glu Thr Leu Val Glu Ile Ser Phe Asn
    930                 935                 940

Leu Cys Asp Ser Gly Ser Gly Ile Ser Ser Leu Ser Ala Ser Leu Arg
945                 950                 955                 960

Asp Pro Phe Gly Ala Thr Phe Ile Leu Tyr Pro Ser Trp Ser Lys Thr
                965                 970                 975

Glu Gly Cys Gln Lys Ile Val His Thr His Val Leu Pro Lys Gly Ser
            980                 985                 990

Ile Pro Gly Ile Trp His Leu Asn Lys Ile Tyr Ala Gln Asp Phe Ala
        995                 1000                1005

Gly Asn Glu Leu Ser Ala Asp Leu Thr Glu Leu Leu Thr Leu Ser
    1010                1015                1020

Ser Cys Ser Val Leu Asp Gly Cys Lys Thr Thr Cys Tyr Leu
    1025                1030                1035

Val Lys Pro Ile Asn Lys Asn Arg Pro Ser Val Gly Ala Ile Lys
    1040                1045                1050

Asn Asn Pro Asn Ser Asn Gly Arg Thr Val Ile Lys Gly Leu Val
    1055                1060                1065

Arg Ser Lys Ser Tyr Ala Thr Ile Pro Ser Thr Leu Glu Ile Gly
    1070                1075                1080

Asp Phe Leu Asp Ser Ala Met Lys Arg Leu Asn Pro Phe Asn Leu
    1085                1090                1095

Lys Ser Phe Phe Gln Lys Tyr Asp His Ile Ile Tyr His Arg Phe
    1100                1105                1110

Leu Arg Ser Ile Thr Arg Ile Pro Pro Leu Thr Gly Phe Tyr Val
    1115                1120                1125

Leu Leu Ser Thr Ile Thr Ala Phe Val Ser Tyr Phe Phe Asn Asp
    1130                1135                1140

Asn Leu Pro Phe Ser Trp Met Lys Phe Asp Leu Asp Arg Val Leu
    1145                1150                1155

Lys Gly Glu Val Trp Arg Leu Phe Thr Pro Tyr Phe Leu Tyr Gly
    1160                1165                1170

Gln Leu Trp Ile Asn His Tyr Met Leu Ser Val Ser Asn Leu Asn
    1175                1180                1185

Tyr Met Ala Asn Val Glu Leu Ala His Ile Asn Lys Pro Glu Lys
    1190                1195                1200

Phe Ile Glu Phe Leu Ala Phe Gly Val Leu Thr Leu Ser Ala Tyr
    1205                1210                1215

Ser Phe Leu Glu Ala Tyr Phe Ser Lys Lys Tyr Leu Pro Gln Ser
    1220                1225                1230

Ala Val Thr Tyr Asp Asn Met Ala Phe His Phe His Val Phe Val
    1235                1240                1245

Leu Tyr Phe Trp Ser Arg Ile Asn Glu Gly Gln Arg Val Glu Cys
    1250                1255                1260

Met Asp Phe Ser Ile Pro Ala Glu Tyr Ile Pro Tyr Leu Phe
    1265                1270                1275

Ile Leu Gln Asn Leu Ile Phe Tyr Asn Ser Gly Leu Thr Ser Asp
    1280                1285                1290

Phe Val Ala Leu Leu Phe Ser Tyr Ala Tyr Phe Thr Leu Phe Ser

```
               1295                1300                1305
Asn Lys Lys Thr Cys Pro Ile Phe Arg Gly Phe Lys Thr Ser Cys
    1310                1315                1320

Leu Arg Arg Leu Tyr Leu Lys Phe Arg Asp Glu Met Gln Tyr
    1325                1330                1335

<210> SEQ ID NO 54
<211> LENGTH: 1113
<212> TYPE: PRT
<213> ORGANISM: Theileria annulata

<400> SEQUENCE: 54

Met Ser Ile Met Val Val Leu Thr Gly Asn Cys Ser Cys Leu Gly Glu
1               5                   10                  15

Arg Glu Arg Asn Cys Leu Lys Asn Asn Lys Cys Val His Thr Trp Leu
            20                  25                  30

Tyr Thr Ile Phe Leu Val Asn Leu Thr Met Pro Ala Leu Val Gly Trp
        35                  40                  45

Asp Ile Asn Gly Val Leu Tyr Gln Ile Ile Lys Ile Leu Leu Ser Val
    50                  55                  60

Cys Lys Ala Leu Leu Trp Glu Ser Arg Arg Lys Asp Lys Glu Ser Pro
65                  70                  75                  80

Lys Val Gly Ile Lys Ser Asn Ser Gly Lys Glu Leu Lys Glu Phe Leu
                85                  90                  95

Asn Glu Lys Arg Lys Gln Lys Ser Tyr Asn Lys Asn Phe Tyr Pro Asn
            100                 105                 110

Asn Lys Gln Gly Gly Arg Arg Ala Ser Ser Ser Phe Leu Glu Arg Gly
        115                 120                 125

Ser Arg Ser Lys Asn Glu Lys Glu Leu Thr Gln Ile Arg Gln Lys Leu
    130                 135                 140

Ala Lys Asp Arg Phe Gln Gln Lys Gln Ala Ile Tyr Ser Asp Gly Lys
145                 150                 155                 160

Ser Ala His Ile Gln Asn Asn Phe Ser Asn Asn Thr Lys Asp Tyr Asn
                165                 170                 175

Thr Val Gly Leu Ile Leu Asp His Arg Phe His His Glu Lys His Glu
            180                 185                 190

Asp Asp Met Gly Pro Tyr Tyr His Asp Thr Glu Asp Leu Asp Asp Tyr
        195                 200                 205

Glu Glu Glu Glu Glu Asn Glu His Asp Asn Val Glu Leu Asp Asp Gly
    210                 215                 220

Tyr Tyr Asp Gly Tyr Phe Leu Asp Asp Glu Asp Phe Glu Glu Glu
225                 230                 235                 240

Leu Arg Arg Arg Lys Ile His Arg Asn Lys Pro Asn Arg Thr Ser Tyr
                245                 250                 255

Ile Gln Leu Asn Asn Arg Asp Gln Ser Asn Glu Thr Ile Pro Lys Tyr
            260                 265                 270

Arg Lys Gly Asn Lys Ser Ser Gly Leu Leu Asn Thr Ile Met Asn Thr
        275                 280                 285

Pro Ile Arg Gln Pro Asn Pro Leu Ile His Pro Ser Asp Gly Leu Glu
    290                 295                 300

His Asp Ser Ser Asn Ser Lys Glu His Glu Asn Gly Glu Asp Leu Glu
305                 310                 315                 320

Glu Asn Thr Tyr Asp Asp Leu Asn Leu Phe Pro Leu Leu Asp Asp Glu
                325                 330                 335
```

-continued

```
Lys Asn Lys Thr Val Gly His Ser Glu Asp Lys Ile Asp Asn Ser Ile
            340                 345                 350

Thr Glu Lys Leu Glu Lys Pro Lys Pro Lys Gln His Asn Pro Asn
        355                 360                 365

Lys Leu Pro Glu Asn Ser Leu Glu Asp Gly Asp Asn Tyr Ser Thr Leu
        370                 375                 380

Glu Pro Asn Pro Val Asn Asn Lys Leu Asn His Lys Glu Ser Asn Lys
385                 390                 395                 400

Val Glu Pro Ser Pro Val Val Lys Glu Asp Glu Asp Asp Lys Ser
                405                 410                 415

Asp Pro Ala Ser Met Asp Asp Lys Pro Phe Phe Gln Lys Asn Phe Lys
                420                 425                 430

Asp Lys Trp Thr Glu Asn Met Asp Ser Ile Asp Leu Asn Ile Glu Pro
            435                 440                 445

Asp His Met Lys Ser Met Lys Gln Leu Gly Gly Asp Phe Gly Asp Glu
        450                 455                 460

Phe Pro Glu Ile Glu Gly His Ile Lys Arg His Ser Glu Arg Thr His
465                 470                 475                 480

Glu Val Glu Ser Gly Ser Thr Arg Arg Val Thr Asn Ser Glu Asp Phe
                485                 490                 495

Arg Asp Pro Ser Leu Asp Trp Asn Asn Ser Gly Leu Ala Ala Ser Met
                500                 505                 510

Arg Tyr Leu Gly Ser Gly Tyr Asp Ile Ile Phe Gly Asn Pro Leu Gly
            515                 520                 525

Asp Pro Val Val Met Met Asp Gln Gly Tyr Arg Asn Pro Val Ile Lys
        530                 535                 540

Leu Asn Trp Glu Asp Glu Tyr Leu Asn Lys Asp Gly Ala Asn Leu Lys
545                 550                 555                 560

Glu Pro Arg Gly Ser Trp Ile Arg Pro Glu Tyr Ser Cys Arg Gln Ser
                565                 570                 575

Glu Thr Ile Asp His Val Asn Thr Val Asp Asp Phe Lys Lys Glu Leu
            580                 585                 590

Ser Val Asp Ala Gln Ala Ser Tyr Gly Ile Pro Tyr Phe Phe Ser Phe
        595                 600                 605

Ser Ala Ser Thr Gly Tyr Lys Asn Phe Val Lys Ser Thr Ala Ser Asn
        610                 615                 620

Lys Val Arg Thr Tyr Ile Thr Lys Thr Tyr Cys Leu Arg Tyr Val Gly
625                 630                 635                 640

Gly Ile Val Asp Tyr His Ser Leu Glu Thr Thr Glu Glu Phe Lys Lys
                645                 650                 655

Ala Val Ala Ala Leu Pro Asp Arg Phe Asp Ser His Arg Cys Thr Leu
                660                 665                 670

Asp Met Phe Lys Ser Asn Glu Asp Asp Pro Met Cys Ala Glu Asn Val
            675                 680                 685

Trp Pro Trp Met Gln Phe Ile Lys Met Phe Gly Thr His Phe Thr Thr
        690                 695                 700

Ile Val His Leu Gly Gly Lys Ile Thr His Gln Val Gln Ile Asp Lys
705                 710                 715                 720

Thr Asp Val Leu His Met Gln Gln Ser Gly Val Asn Val Asp Leu Ala
                725                 730                 735

Val Lys Ala Thr Ile Ser Pro Ser Phe Val Asp Ser Leu Glu Val Gly
                740                 745                 750

Thr Thr Thr Asn Thr Glu Lys Gly Ser Val Ser Leu Ser Asn Asn Leu
```

-continued

```
                755                 760                 765
Lys Tyr Glu Lys Gln Val Leu Val Ile Gly Gly Asp Gly Leu Val Asp
            770                 775                 780

Ser Lys Asp Val Asn Ser Leu Asn Asn Trp Ala Arg Glu Leu Tyr Lys
785                 790                 795                 800

Arg Pro Met Pro Ile Lys Ile Lys Leu Glu Ser Ile Lys Thr Leu Leu
                805                 810                 815

Gly Asp Lys Lys Asp Leu Phe Asp Glu Ala Leu Arg Phe Tyr Ser Glu
            820                 825                 830

Thr Tyr Gly Val Ser Pro Asp Glu Ile Tyr Lys Lys Tyr Gly Lys Glu
            835                 840                 845

Phe Gly Ile Ala Ser Ala Ile Glu Lys Gly His Gln Ile Val Tyr Ser
        850                 855                 860

Gly Asn Lys Ser Gly Ser Ala Val Cys Pro Asn Lys Thr Val Ile Ile
865                 870                 875                 880

Met Gly Phe Ser Leu Ser Ile Val Lys Lys Asn Leu Val Gly Lys
                885                 890                 895

Asn Val Phe Ser Leu His Ile Thr Gln Cys Pro Val Gly Glu Glu Lys
            900                 905                 910

Cys Ile Val Ser Ser Asp Asn Pro Met Ser Glu Ser Arg Ile Trp Ala
        915                 920                 925

Ile Cys Gly Glu Asp Thr Ile Pro Leu Leu Asn Gln Gln Thr Ser Ser
        930                 935                 940

Lys Leu Asp Glu Pro Ala Val Ala Ser Cys Pro Ala Gly Tyr Ser Ile
945                 950                 955                 960

Ala Tyr Gly Phe Ala Leu Ser Val Pro Lys Gly Asn Val Thr Leu Ser
                965                 970                 975

Thr Asp Ser Tyr Ala Cys Arg Pro Gly Thr Gln Ser Cys Thr His Glu
            980                 985                 990

Ser Thr Asp Lys Ser Ala Thr Asn Ala Val Trp Ile Ala Cys Val Glu
            995                 1000                1005

Asn Gly Ala Pro Gln Leu Thr Glu Ile Ser Asn His Val Val Ser
    1010                1015                1020

Thr Ser Ser Arg Tyr Cys Ser Asn Lys Thr Lys Asp Asn Lys Tyr
    1025                1030                1035

Asp Asp Asn Ser Cys Pro Ile Asn Ser Lys Leu Ile Ala Gly Trp
    1040                1045                1050

Ser Met Glu Phe Ser Glu Thr Asp Asn Asn Ser Asn Lys Ile Glu
    1055                1060                1065

Lys Cys Ser Lys Gly Thr Phe Gly Cys Lys Val Asp Gln Leu Met
    1070                1075                1080

Lys Thr Glu Asn Lys Cys Arg Ser His Tyr Ser Trp Ile Ser Cys
    1085                1090                1095

Leu His Glu Glu Gly Ala Cys Ser Thr Glu Lys Thr Glu Ser Thr
    1100                1105                1110
```

<210> SEQ ID NO 55
<211> LENGTH: 929
<212> TYPE: PRT
<213> ORGANISM: Theileria annulata

<400> SEQUENCE: 55

```
Met Leu Val Ser Phe Gly Glu Lys Leu Gly Leu Lys Ser Gly His Ser
1               5                   10                  15
```

-continued

```
Val Leu Arg Gln Met Lys Asn Phe Ser Ser Arg Pro Asn Pro Phe
             20                  25                  30
Glu Lys Val Lys Lys Thr Leu Ala Gly Thr Asn Lys Lys Tyr Phe Ser
         35                  40                  45
Leu Arg Asp Leu Lys Asp Pro Arg Leu Phe Glu Leu Pro Phe Ser Ile
     50                  55                  60
Arg Val Leu Leu Glu Ala Ala Val Arg Asn Cys Asp Glu Phe Ser Thr
 65                  70                  75                  80
Thr Ser Asn Asp Val Glu Lys Ile Leu Gly Trp Ala Lys Asn Ser Leu
                 85                  90                  95
Asn Gln Thr Glu Ile Pro Phe Ile Pro Ser Arg Val Leu Leu Gln Asp
             100                 105                 110
Phe Thr Gly Val Pro Thr Ile Val Asp Leu Ala Ala Met Arg Asp Phe
         115                 120                 125
Val Ala Lys Ser Gly Lys Asp Pro Thr Arg Ile Asn Pro Leu Val Pro
    130                 135                 140
Val Asp Leu Val Ile Asp His Ser Val Gln Val Asp Phe Ser Arg Asp
145                 150                 155                 160
Ser Lys Ala Leu Ala Leu Asn Gln Glu Thr Glu Met Asn Arg Asn Ser
                165                 170                 175
Glu Arg Phe Arg Phe Leu Lys Trp Gly Ala Gln Thr Phe Lys Asn Thr
            180                 185                 190
Leu Ile Val Pro Pro Gly Ser Gly Ile Val His Gln Val Asn Leu Glu
        195                 200                 205
Phe Leu Ala Arg Cys Leu Phe Asp Lys Asn Asp Val Leu Tyr Pro Asp
    210                 215                 220
Ser Val Val Gly Thr Asp Ser His Thr Thr Met Ile Asn Gly Leu Gly
225                 230                 235                 240
Val Val Gly Trp Gly Val Gly Gly Ile Glu Ala Glu Ala Thr Met Leu
                245                 250                 255
Gly Gln Pro Ile Ser Met Leu Leu Pro Gln Val Val Gly Phe Glu Leu
            260                 265                 270
Val Gly Lys Pro Ser Glu Asn Val Phe Ser Thr Asp Val Val Leu Ala
        275                 280                 285
Val Thr Ser Leu Leu Arg Ser Gly Ala Gly Val Gly Lys Phe Val
    290                 295                 300
Glu Phe Phe Gly Glu Gly Val Lys Tyr Leu Ser Leu Ala Asp Arg Ala
305                 310                 315                 320
Thr Ile Ala Asn Met Ala Pro Glu Tyr Gly Ala Thr Val Gly Phe Phe
                325                 330                 335
Pro Ile Asp Gln Leu Thr Leu Asp Tyr Leu Leu Gln Thr Gly Arg Pro
            340                 345                 350
Asn Glu Lys Val Asp Leu Leu Glu Arg Tyr Ser Lys Glu Asn Leu Leu
        355                 360                 365
His Thr Ser Thr Ser Glu Ala Gly Ser Ile Lys Tyr Ser Thr Val Val
    370                 375                 380
Arg Leu Asp Leu Ser Thr Leu Thr Pro Ser Ile Ala Gly Pro Lys Arg
385                 390                 395                 400
Pro Gln Asp Asn Ile Pro Leu His Leu Val Lys Thr Lys Tyr Ser Glu
                405                 410                 415
Leu Leu Thr Ser Lys Asp Thr Lys Gly Tyr Gly Leu Asp Thr Leu Ser
            420                 425                 430
Asn Lys Val Lys Phe Thr Tyr Lys Gly Asn Glu Tyr Glu Leu Asp Asn
```

-continued

```
            435                 440                 445
Gly Ser Val Val Ile Ala Ser Ile Thr Ser Cys Thr Asn Thr Ser Asn
            450                 455                 460
Pro Ser Val Met Leu Ala Ala Gly Leu Leu Ala Lys Asn Ala Val Glu
465                 470                 475                 480
His Gly Leu Ser Val Lys Pro Tyr Ile Lys Thr Ser Leu Ser Pro Gly
                    485                 490                 495
Ser Lys Thr Val Thr Arg Tyr Leu Glu Leu Ser Gly Leu Ile Gly Tyr
                500                 505                 510
Leu Glu Lys Leu Gly Phe Tyr Ile Ala Gly Tyr Gly Cys Met Thr Cys
            515                 520                 525
Ile Gly Asn Ser Gly Glu Leu Asp Pro Glu Val Thr Glu Ala Ile Leu
            530                 535                 540
Asn Asn Lys Leu Val Val Ser Ser Val Leu Ser Gly Asn Arg Asn Phe
545                 550                 555                 560
Glu Gly Arg Val His Pro His Thr Arg Ala Asn Phe Leu Ala Ser Pro
                    565                 570                 575
Pro Leu Val Val Ala Phe Ala Leu Ala Gly Asn Val Asn Phe Asp Leu
                580                 585                 590
Met Ser Glu Pro Leu Gly Val Ser Ser Lys Thr Gly Lys Pro Val Phe
            595                 600                 605
Leu Asn Asp Leu Leu Pro Ser Lys Glu Val Ser Ser Leu Glu Ala
            610                 615                 620
Gln Phe Val Lys Ala Ser Leu Phe Asn Glu Val Tyr His Asn Ile Thr
625                 630                 635                 640
Glu Gly Ser Asp Ser Trp Arg Lys Leu Asn Ser Pro Lys Ser Glu Leu
                    645                 650                 655
Tyr Pro Trp Glu Glu Leu Ser Thr Tyr Ile Gln His Pro Pro Tyr Phe
                660                 665                 670
Lys Gly Met His Leu Asp Lys Leu Asn Glu Val Lys Pro Ile Lys Asp
            675                 680                 685
Ala Arg Val Leu Leu Leu Gly Asp Ser Ile Thr Thr Asp His Ile
            690                 695                 700
Ser Pro Ala Gly Asn Ile Ala Lys Asn Ser Pro Ala Ala Arg Phe Leu
705                 710                 715                 720
Met Glu Asn Gly Val Glu Gln Lys Asp Phe Asn Ser Tyr Gly Ser Arg
                    725                 730                 735
Arg Gly Asn Asp Lys Val Met Ser Arg Gly Thr Phe Ala Asn Ile Arg
                740                 745                 750
Ile Asn Asn Leu Leu Cys Pro Gly Gln Gly Pro Asn Thr Val His Phe
            755                 760                 765
Pro Thr Asn Lys Leu Met Ser Val Tyr Asp Ala Ser Glu Leu Tyr Gln
770                 775                 780
Lys Glu Asn Thr Pro Leu Val Val Ala Gly Lys Glu Tyr Gly Thr
785                 790                 795                 800
Gly Ser Ser Arg Asp Trp Ala Ala Lys Gly Pro Leu Leu Gly Val
                    805                 810                 815
Lys Ala Ile Leu Ala Glu Ser Phe Glu Arg Ile His Arg Thr Asn Leu
                820                 825                 830
Val Gly Cys Gly Ile Leu Pro Leu Gln Phe Leu Asp Gly Gln Asn Ala
            835                 840                 845
Thr Thr Leu Asn Leu Ser Gly Asn Leu His Phe Ser Phe Gln Asn Leu
            850                 855                 860
```

Thr Gly Thr Glu Lys Phe Thr Val Gln Leu Gly Asn Asp Val Glu Pro
865                 870                 875                 880

Gly Ser Leu Val Arg Val Thr Thr Asp Thr Gly Leu Ser Phe Asp Thr
            885                 890                 895

Lys Cys Arg Ile Asp Thr Gln Ile Glu Val Phe Leu Pro Leu Ile Ile
            900                 905                 910

Phe Ile Phe Arg Val Ser Thr Thr Asn Thr Val Glu Tyr Tyr Asn Met
            915                 920                 925

Phe

<210> SEQ ID NO 56
<211> LENGTH: 429
<212> TYPE: PRT
<213> ORGANISM: Theileria annulata

<400> SEQUENCE: 56

Met Asn Glu Ser Leu Phe Val Arg Tyr Tyr Arg Lys Ile Asn Asp Asn
1               5                   10                  15

Pro Glu Pro Leu Arg Leu Phe Ile Tyr Cys Ser Ser Val Phe Ile Arg
            20                  25                  30

Leu Ala Leu Ile Ala Tyr Ser Ser Phe His Asn Leu Lys Phe Asp Val
            35                  40                  45

Lys Tyr Thr Asp Ile Asp Tyr Leu Val Phe Ser Asp Ala Ser Lys Leu
50                  55                  60

Val Leu Ala Gly Lys Ser Pro Tyr Leu Arg His Thr Tyr Arg Tyr Thr
65                  70                  75                  80

Pro Ile Leu Ser Tyr Leu Met Val Phe Asn His Tyr Leu Phe Asn Asp
            85                  90                  95

Phe Gly Lys Leu Leu Phe Thr Val Ser Asp Leu Leu Val Gly Leu Ala
            100                 105                 110

Ile Glu Lys Thr Leu Ser Ala Ser Ser Asp Leu Lys Lys Tyr Leu Leu
            115                 120                 125

Ser Ala Leu Trp Leu Leu Asn Pro Phe Val Ile Ala Ile Ser Ser Arg
130                 135                 140

Gly Asn Ala Asp Thr Ile Ile Cys Leu Ile Ile Ile Ser Ser Ile Tyr
145                 150                 155                 160

Phe Leu Lys Arg Gly His Ile Ser Val Ser Ala Leu Leu Phe Gly Leu
            165                 170                 175

Ser Val His Phe Lys Leu Tyr Pro Val Ile Tyr Ala Leu Pro Val Val
            180                 185                 190

Phe His Leu Tyr Ser Arg Glu Leu Val Cys Cys Trp Leu Asn Phe Arg
            195                 200                 205

Lys Phe Leu Met Lys Leu Pro Leu Leu Leu Ile Thr His Ile Asn Phe
210                 215                 220

Lys Gln Ile Arg Phe Ala Ile Leu Ser Phe Leu Ser Phe Ala Phe Phe
225                 230                 235                 240

Thr Tyr Leu Thr Phe Tyr Leu Tyr Gly Phe Glu Ser Ile Tyr Glu Ser
            245                 250                 255

Tyr Leu Tyr His Tyr Val Arg Lys Asp His Arg His Asn Phe Ser Leu
            260                 265                 270

Tyr Phe Asn Leu Met Tyr Tyr Ile Val Asp Thr Asn Met Asn Leu Asn
            275                 280                 285

Leu Phe Val Ser Phe Val Pro Gln Val Phe Cys Phe Leu Ile Phe Ser
            290                 295                 300

```
Leu Val Ala Phe Val Asp Leu Thr Leu Ser Leu Phe Leu Met Thr Ile
305                 310                 315                 320

Ser Phe Val Ser Leu Asn Lys Val Leu Thr Ser Gln His Phe Leu Trp
                325                 330                 335

Trp Ile Cys Leu Leu Pro Leu Val Leu Ser Lys Ile Asn Leu Asn Phe
                340                 345                 350

Gly Asn Leu Arg Tyr Phe Leu Leu Ser Val Ala Ser Val Phe Val Phe
                355                 360                 365

Lys Phe Phe Trp Leu Phe Cys Gly Tyr Arg Gln Glu Phe Leu Gly Tyr
                370                 375                 380

Ser Ser Phe Asn Glu Val Cys Gly Gly Leu Ile Tyr Cys Leu Asp Val
385                 390                 395                 400

Val Phe Ile Asn Ile Pro Cys Gly Leu Pro His Ala Cys Arg Met Asp
                405                 410                 415

Ser Asn Ile Gln Phe Leu Gln Gln Ile Asp Lys Glu Asn
                420                 425

<210> SEQ ID NO 57
<211> LENGTH: 423
<212> TYPE: PRT
<213> ORGANISM: Cryptosporidium parvum

<400> SEQUENCE: 57

Met Ile Val His Arg Tyr Cys Arg Gln Trp Ala Pro Ser Val Val Arg
1               5                   10                  15

Gly Ile Ser Lys Leu Ala Phe Phe Ser Ser Met Ser Ser Ile Ala Lys
                20                  25                  30

Lys Arg Pro Ala Tyr Phe Asp Tyr Gln Ala Thr Thr Pro Val Asp Pro
                35                  40                  45

Arg Val Leu Asp Lys Met Met Pro Phe Phe Thr Glu Lys Phe Gly Asn
                50                  55                  60

Ser His Ser Arg Thr His Gly Tyr Gly Trp Glu Ala Glu Glu Ala Val
65              70                  75                  80

Glu Asn Ala Arg Thr Asn Ile Ala Asn Leu Ile Lys Cys Leu Pro Lys
                85                  90                  95

Glu Ile Ile Phe Thr Ser Gly Ala Thr Glu Ser Asn Asn Thr Ile Ile
                100                 105                 110

Arg Gly Val Cys Asp Ile Tyr Gly Asp Ile Glu Asn Lys Lys Asn His
                115                 120                 125

Ile Ile Thr Thr Gln Ile Glu His Lys Cys Val Leu Ser Thr Leu Arg
                130                 135                 140

Glu Leu Glu Leu Lys Gly Phe Arg Val Thr Tyr Leu Lys Val Asn Asn
145                 150                 155                 160

Lys Gly Leu Ile Ser Leu Glu Glu Leu Glu Lys Ser Ile Ile Pro Gly
                165                 170                 175

Glu Thr Ile Leu Ala Ser Ile Met His Val Asn Asn Glu Ile Gly Val
                180                 185                 190

Ile Gln Pro Met Asn Leu Ile Gly Glu Ile Cys Lys Lys Tyr Asn Val
                195                 200                 205

Leu Phe His Ser Asp Val Ala Gln Gly Leu Gly Lys Ile Asn Ile Asp
                210                 215                 220

Val Asp Lys Trp Asn Ala Asp Phe Leu Ser Leu Ser Ala His Lys Val
225                 230                 235                 240

Tyr Gly Pro Lys Gly Ile Gly Ala Phe Tyr Ile Arg Ser Lys Pro Arg
```

-continued

```
                245                 250                 255
Arg Arg Ile Lys Pro Leu Ile Phe Gly Gly Gln Glu Arg Gly Met
            260                 265                 270

Arg Ser Gly Thr Met Pro Val Pro Leu Ala Val Gly Phe Gly Glu Ala
        275                 280                 285

Cys Lys Ile Ala Ser Ser Glu Met Asn Ser Asp Ser Ile His Val Lys
        290                 295                 300

Ser Leu Tyr Asp Lys Leu Tyr Lys Gly Ile Thr Thr Gln Leu Pro Asp
305                 310                 315                 320

Val Glu Leu Asn Gly Cys Gly Val Asn Arg Met Phe Gly Asn Leu Asn
                325                 330                 335

Leu Ser Phe Thr Gly Val Glu Gly Ser Leu Met Met Lys Leu Tyr
            340                 345                 350

Ser Leu Ala Leu Ser Ser Gly Ser Ala Cys Thr Ser Ala Ser Leu Glu
            355                 360                 365

Pro Ser Tyr Val Leu Arg Ala Ile Gly Val Gly Glu Asp Val Ala His
        370                 375                 380

Thr Ser Ile Arg Phe Gly Leu Gly Arg Phe Thr Lys His Glu Asp Val
385                 390                 395                 400

Asp Lys Ala Val Lys Glu Ile Val Glu Ser Val Thr Leu Leu Arg Lys
                405                 410                 415

Met Ser Pro Leu Trp Asp Ser
            420

<210> SEQ ID NO 58
<211> LENGTH: 396
<212> TYPE: PRT
<213> ORGANISM: Cryptosporidium parvum

<400> SEQUENCE: 58

Met Ser Ser Gly Ser Asn Arg Thr Gln Leu Ser Gly Asp Ser Leu Asp
1               5                   10                  15

Gly Ile Gln Gly Thr Thr Gly Ser Lys Glu Ile Ser Asp Leu His Trp
            20                  25                  30

Ser Lys Arg Pro Lys Lys Val Leu Pro Cys Arg Glu Lys Glu His Glu
        35                  40                  45

Glu Ile Thr Leu Val Leu Lys Thr Ser Ile Leu Asn Glu Gly Gly Gly
    50                  55                  60

Val Leu Phe Ile Ala Gly Leu Pro Gly Thr Gly Lys Thr Ala Thr Val
65                  70                  75                  80

Leu Asn Thr Leu Asp Met Leu Glu Thr Glu Met Asn Leu Ser Asn Lys
                85                  90                  95

Asn Gln Ser Lys Ile Ser Val Cys Tyr Ile Asn Ala Leu His Leu Ser
            100                 105                 110

Ser Pro Asp His Phe Tyr Arg Thr Phe Leu Gln Lys Leu Asn Gly Ala
        115                 120                 125

Asn Thr Trp Ala Pro Asn Lys Glu Ala Cys Tyr Thr Ser Leu Asp Lys
    130                 135                 140

Tyr Leu Lys Ala Lys Gly Ser Pro Ile Thr Ile Leu Val Ile Asp Glu
145                 150                 155                 160

Ile Asp Trp Leu Gln Lys Asn Gly Thr Ser His Ser Thr Met Glu Gly
                165                 170                 175

Ser Asn Asn Ser Leu Leu Tyr Thr Leu Ile Asp Trp Pro Phe Gln Lys
            180                 185                 190
```

-continued

Asn Thr Lys Leu Ile Ile Ala Ile Ala Asn Thr Met Asp Leu Pro
            195                 200                 205

Glu Arg Leu Ile Pro Arg Cys Thr Ser Arg Cys Gly Tyr Ala Arg Val
    210                 215                 220

Asn Phe Thr Pro Phe Ser Val Glu Asp Met Ile Thr Ile Leu Asn Asp
225                 230                 235                 240

Arg Val Lys Tyr Phe Ser Pro Gly Leu Pro Asp Ile Asn Ile Glu Thr
                245                 250                 255

Cys Asp Lys Asn Asp Gln Gly Arg Arg Leu Ser Pro Arg Ile Arg Asn
            260                 265                 270

Lys Asn Lys Asn Lys Asn Ile Glu Thr Leu Gln Glu Asp Leu Glu Ser
        275                 280                 285

Val Phe Cys His Lys Ala Val Glu Phe Cys Ala Arg Arg Ile Ala Gln
    290                 295                 300

Gln Ser Ser Asp Val Arg Arg Ala Leu Gln Val Leu His Arg Ala Trp
305                 310                 315                 320

Glu Ile Cys Lys Gln Glu Phe Glu Gln Ala Lys Asn Ser Lys Ile Asp
                325                 330                 335

Lys Ser Asn Lys Ser Asn Lys Lys Leu Gln Val Gln Ile Pro His Val
            340                 345                 350

Gln Ala Ala Cys Arg Glu Val Leu Leu Asn Asn Val Ser Ile Asn Leu
        355                 360                 365

Val Glu Thr Leu Pro Leu Ser Tyr Lys Val Phe Leu Ala Ser Leu Ile
    370                 375                 380

Leu Glu Leu Glu Phe Lys His Lys Met Glu Leu Glu
385                 390                 395

<210> SEQ ID NO 59
<211> LENGTH: 274
<212> TYPE: PRT
<213> ORGANISM: Cryptosporidium parvum

<400> SEQUENCE: 59

Lys Ser Ser Asn Arg Arg Ile Thr Gly Asp Ile Ile Gly Ile Asp Leu
1               5                   10                  15

Gly Thr Thr Asn Ser Cys Thr Ala Ile Leu Glu Gly Thr Gln Pro Lys
            20                  25                  30

Val Leu Glu Asn Ser Glu Gly Met Arg Thr Thr Pro Ser Val Val Ala
        35                  40                  45

Phe Ser Glu Asp Gly Gln Arg Leu Val Gly Val Ala Lys Arg Gln
    50                  55                  60

Ala Ile Thr Asn Pro Glu Asn Thr Val Tyr Ala Thr Lys Arg Leu Ile
65                  70                  75                  80

Gly Arg Arg Tyr Glu Glu Ala Ile Lys Lys Glu Gln Gly Ile Leu
                85                  90                  95

Pro Tyr Lys Ile Val Arg Ala Asp Asn Gly Asp Ala Trp Val Glu Ala
            100                 105                 110

Arg Gly Glu Arg Tyr Ser Pro Ser Gln Ile Gly Ala Phe Ile Leu Glu
        115                 120                 125

Lys Met Lys Glu Thr Ala Glu Thr Tyr Leu Gly Arg Gly Val Lys His
    130                 135                 140

Ala Val Ile Thr Val Pro Ala Tyr Phe Asn Asp Ser Gln Arg Gln Ala
145                 150                 155                 160

Thr Lys Asp Ala Gly Ser Ile Ala Gly Leu Asn Val Thr Arg Ile Ile
                165                 170                 175

```
Asn Glu Pro Thr Ala Ala Ala Leu Ala Tyr Gly Met Glu Lys Ala Asp
            180                 185                 190

Gly Lys Thr Ile Ala Val Tyr Asp Leu Gly Gly Thr Phe Asp Ile
        195                 200                 205

Ser Ile Leu Glu Ile Leu Gly Val Phe Glu Val Lys Ala Thr Asn
        210                 215                 220

Gly Asn Thr Ser Leu Gly Gly Glu Asp Phe Asp Gln Arg Ile Leu Asn
225                 230                 235                 240

Lys Leu Ser Arg Ala Lys Tyr Glu Glu Leu Val Asp Asp Leu Leu Lys
                245                 250                 255

Lys Thr Ile Ser Pro Ser Glu Lys Cys Ile Arg Asp Ser Gly Ile Pro
                260                 265                 270

Lys Glu

<210> SEQ ID NO 60
<211> LENGTH: 100
<212> TYPE: PRT
<213> ORGANISM: Cryptosporidium parvum

<400> SEQUENCE: 60

Met Ser Val Arg Ile Ile Thr Asn Tyr Gly Asp Leu Lys Phe Glu Leu
1               5                   10                  15

Phe Cys Ser Gln Cys Pro Lys Ala Cys Lys Asn Phe Leu Ala Leu Ser
                20                  25                  30

Ala Ser Gly Tyr Tyr Lys Asn Thr Ile Phe His Lys Asn Ile Lys Gly
            35                  40                  45

Phe Ile Ile Gln Gly Gly Asp Pro Thr Gly Thr Gly Lys Gly Gly Glu
        50                  55                  60

Ser Ile Tyr Gly Arg Tyr Phe Asp Asp Glu Ile Tyr Pro Glu Leu Lys
65                  70                  75                  80

Tyr Asp Arg Arg Gly Ile Leu Ser Met Ala Ser Lys Gly Ala Ser Lys
                85                  90                  95

Lys Pro Asn Thr
            100

<210> SEQ ID NO 61
<211> LENGTH: 200
<212> TYPE: PRT
<213> ORGANISM: Cryptosporidium parvum

<400> SEQUENCE: 61

Lys Arg His Leu Lys Lys Ile Met Ala Gln Phe Tyr Lys Thr Lys Lys
1               5                   10                  15

Cys Pro Trp Phe Ala Val Gly Arg Cys Arg Met Asp Lys Glu Cys Asn
                20                  25                  30

Trp Ala His Ser Ile Asp Glu Leu Arg Pro Ser Val Asp Leu Thr Arg
            35                  40                  45

Thr Lys Leu Cys Glu Ile Gln Leu Lys Glu Gly Ile Cys Arg Asn Pro
        50                  55                  60

Gln Cys Arg Tyr Ala His Ser Arg Lys Glu Leu Arg Ala Thr Ser Asp
65                  70                  75                  80

Leu Phe Lys Thr Ser Leu Cys Val Tyr Trp Ile Lys Gly Ser Cys Val
                85                  90                  95

Val Gly Asp Ser Cys Arg Tyr Ala His Gly Ile Glu Glu Leu Arg Ser
            100                 105                 110
```

```
Lys Pro Gln Lys Gly Glu Phe Ile Pro Leu Asp Val Glu Thr Leu Pro
            115                 120                 125

Val Pro Ile Gln Lys Ile Thr Asn Gln Arg Gln Asp Leu Ser Met Asn
        130                 135                 140

Phe Asp Gly Lys Asn Ile Phe Asn Asp Ser Arg Leu Tyr His Pro Tyr
145                 150                 155                 160

Asn Ala Val Ser Thr Thr Ser Ser Leu Gly Ser Ile Asn Lys Phe Gly
                165                 170                 175

Ser Asp Ser Ile Asp Lys Ser Phe Glu Gly Met Pro Ser Leu Val Ser
            180                 185                 190

Ser Leu Phe Asn Thr Glu Ser Ser
            195                 200

<210> SEQ ID NO 62
<211> LENGTH: 991
<212> TYPE: PRT
<213> ORGANISM: Cryptosporidium parvum

<400> SEQUENCE: 62

Asn Glu Asn Ile Ser Asn Gln Gly Gln Glu Ile Ser Arg Asn Gly Asn
1               5                   10                  15

Phe Glu Ile Ile Asp Asn Gly Lys Ser Glu Asn Ser Lys Glu Ile
            20                  25                  30

Ile Leu Glu Lys Cys Arg Val Lys Val Ser Ser Asp Gly Val Tyr Glu
        35                  40                  45

Ser Leu Pro Val Glu Arg Lys Ser Ile Asp Ala Lys Ser Ser Glu Lys
    50                  55                  60

Ala Ser Asp Lys Ile Gln Gly Asp Thr Val Phe Glu Val Leu Pro Arg
65                  70                  75                  80

Ser Glu Ser Asn Ala Asp Ala Ser Tyr Asn Lys Ala Gly Asp Phe Val
                85                  90                  95

Asn Asp Ile Gly Ile Phe Glu Ser Leu Pro Lys Ser Thr Ser Asp Ala
            100                 105                 110

Asp Tyr Lys Tyr Asn Glu Arg Val Asp Ile Thr Gln Asp Arg Ile Val
        115                 120                 125

Phe Glu Val Leu Pro Arg Ser Asp Asn Ile Val His Tyr Asp Asn Asp
    130                 135                 140

Thr Ser Asn Glu Ser Ser Ile Lys Val Asn Glu Met Ile Lys Lys Lys
145                 150                 155                 160

Glu Ser Glu Leu Asn Asn Ile Leu Lys Glu Gln Lys Ile Asp Gly Asp
                165                 170                 175

Ile Thr Ser Arg Asn Gly Asn Ile Glu Asn Asp Pro Thr Leu Gly Leu
            180                 185                 190

Ser Ile Tyr Asn Glu Glu Ser Val Ser Pro Pro Ser Glu Thr Ser Met
        195                 200                 205

Thr Ile Phe Glu Asn Leu Pro Ile Lys Lys Glu Asn Ile Asp Ile Asp
    210                 215                 220

Asn Glu Phe Gln Ser Asn Ser Ile Leu Ser Asp Asn Ile Ile Glu
225                 230                 235                 240

Asn His Gln Ser Ile Phe Glu Thr Ala Asn Leu Ser Arg Ser Asn Ser
                245                 250                 255

Ser Ser His Ile Ser Ser Leu Lys Asp Gly Glu Glu Ala Glu Arg Leu
            260                 265                 270

Thr Ser Asn Glu Val Ser Glu His Ser Glu Ile Ser Asn Asp Glu Cys
        275                 280                 285
```

-continued

```
Glu Lys Asp Leu Lys Ser Asn Phe Glu Leu Asn Asn Gln Leu Ile Thr
            290                 295                 300
Asp Phe Asn Gln Asp Val Lys Thr Gln Asp Lys Lys Glu Leu Ser Pro
305                 310                 315                 320
Gln Val Glu Ser Lys Ala Asn Leu Asn Ile Val Asn Ser Glu Lys
                325                 330                 335
Ser Val Phe Glu Val Val Pro Ser Glu Gln Ser Arg Ala Asp Ile Gly
                340                 345                 350
Tyr Asn Ser Lys Ile Pro Leu Ser Phe Asp Glu Arg Thr Val Phe Glu
                355                 360                 365
Ser Lys Pro Val Ala Asn Ser Asn Ala Asp Val Ser Tyr Asn Ser Lys
            370                 375                 380
Val Gly Ile Thr Lys Ala Glu Glu Arg Ser Val Phe Glu Ser Cys Pro
385                 390                 395                 400
Ile Thr Asp Ser Lys Ala Asp Val Ser Tyr Asn Ser Lys Phe Gln Pro
                405                 410                 415
Arg Lys Asp Glu Lys Ile Ile Phe Glu Ser Asn Pro Ile Ala Asn Ser
                420                 425                 430
Asn Ala Asp Val Gly Tyr Asn Thr Lys Ile Gly Leu Glu Arg Gln Glu
            435                 440                 445
Lys Ser Thr Tyr Glu Ser Ile Pro Thr Ile Gly Val Val Ala Asp Val
            450                 455                 460
Ser Tyr Lys Ser Lys Ala Gln Thr Asn Ser Gly Asn Glu Lys Ser Ile
465                 470                 475                 480
Phe Glu Ser Val Pro Ile Ser Asn Ser Ile Ala Asp Val Ser Tyr Asn
                485                 490                 495
Ser Lys Ser Gln Pro Ile Lys Glu Glu Lys Val Val Phe Glu Ser Ile
            500                 505                 510
Pro Ser Glu Asn Cys Lys Ile Asp Val Ser Tyr Asn Ser Lys Leu Asp
            515                 520                 525
Leu Lys Gly Gln Glu Lys Ser Val Phe Glu Ser Asn Pro Met Met Thr
            530                 535                 540
Ser Asn Ala Asp Val Gly Tyr Asn Ser Lys Pro Glu Ile Asn Leu Asn
545                 550                 555                 560
Glu Lys Ser Val Phe Glu Ser Val Pro Ser Asn Ile Ser Lys Ala Asp
                565                 570                 575
Val Ser Tyr Asn Ser Lys Ile Thr Asn Thr Ser Glu Lys Ser Ile Phe
                580                 585                 590
Glu Ser Glu Pro Ile Lys Asn Val Asn Ile Asp Val Ser Tyr Asn Ser
            595                 600                 605
Lys Leu Asp Leu Lys Gly Gln Glu Lys Ser Val Phe Glu Ser Asn Pro
            610                 615                 620
Met Met Thr Ser Asn Ala Asp Val Gly Tyr Asn Ser Lys Pro Glu Ile
625                 630                 635                 640
Asn Leu Asn Glu Lys Ser Val Phe Glu Ser Val Pro Thr Asn Ile Ser
                645                 650                 655
Lys Ala Asp Val Ser Tyr Asn Ser Val Val Ala Asn Thr Ser Glu Lys
                660                 665                 670
Thr Ile Phe Glu Ser Glu Pro Arg Arg Asn Ser Val Ala Asp Val Ser
            675                 680                 685
Tyr Asn Ser Ser Leu Ile Pro Ile Ser Lys Asp Glu Lys Thr Val Phe
            690                 695                 700
```

-continued

```
Glu Ser Asn Pro Asn Val Asp Ser Lys Ala Asp Val Ser Tyr Asn Ser
705                 710                 715                 720

Lys Ile Glu Leu Lys Lys Asp Glu Lys Phe Val Phe Glu Ser Asn Pro
            725                 730                 735

Asn Val Asp Ser Asn Ala Asp Val Ser Tyr Asn Ser Lys Leu Gln Pro
        740                 745                 750

Arg Lys Asp Glu Lys Phe Ile Phe Glu Ser Asn Thr Thr Val Asn Ser
    755                 760                 765

Lys Ala Asp Val Ser Tyr Asn Ser Lys Ser Glu Pro Lys Met Asn Glu
770                 775                 780

Lys Ser Val Phe Glu Ser Ser Pro Ile Leu Ser Ser Val Ala Asp Val
785                 790                 795                 800

Gly Tyr Asn Thr Lys Gly Val Gly Met Thr Gln Glu Lys Ser Val Tyr
            805                 810                 815

Glu Ser Val Pro Ile Ser Lys Ser Lys Ile Asp Ala Gly Tyr Asp Thr
        820                 825                 830

Lys Leu Asp Phe Thr His Glu Asn Asn Lys Thr Ile Phe Glu Ser Asn
    835                 840                 845

Pro Ser Cys Glu Ser Ile Ala Asp Val Gly Tyr Asn Ser Lys Ile Glu
850                 855                 860

Thr Arg Thr Glu Glu Lys Ser Val Tyr Glu Ser Asn Tyr Asp Lys Val
865                 870                 875                 880

Ser Lys Ala Asp Ala Arg Tyr Asn Ser Asp Ser Ser Gln Ile Tyr Pro
            885                 890                 895

Pro Glu Lys Met Val Tyr Glu Ser Thr Pro Val Val Gly Leu Ala Val
        900                 905                 910

Asp Ala Arg Phe Ala Asp Gln Asn Asn Thr Asn Glu Glu Lys Gln Thr
    915                 920                 925

Val Phe Val Ser Leu Pro Arg Ser Glu Ser Val Phe Asp Ala Ser Tyr
930                 935                 940

Ser Leu Asn Asn Glu Tyr Arg Gln Glu Lys Thr Ile Phe Glu Ser Val
945                 950                 955                 960

Pro Asn Thr Lys Gly Ile Arg Ile Asp Ala Arg Ser Ser Asp Thr Ser
            965                 970                 975

Glu Ile Met Asn Phe Gln Ser Lys Thr Val Phe Glu Ser Val Pro
        980                 985                 990
```

<210> SEQ ID NO 63
<211> LENGTH: 260
<212> TYPE: PRT
<213> ORGANISM: Cryptosporidium parvum

<400> SEQUENCE: 63

```
Met Ser Asp Arg Asn Val Glu Asp Asn Glu Asn Asp Ser Phe Ile Pro
1               5                   10                  15

Gln Asp Cys Cys Ser Ser Asn Pro Arg Ile Val Glu Asp Ser Asn Gln
            20                  25                  30

Asp Ser Val Ser Ser Pro Gly Gly Asn Ala Gln Ile Val Thr Val Pro
        35                  40                  45

Leu Val Gln Glu Val Asn Val Arg Asp Arg Ile Ile Glu Val Pro Glu
    50                  55                  60

Val His Ile Thr Gln Lys Ile Arg Gln Lys Val Ile Val Lys Asp Val
65                  70                  75                  80

Ile Arg Lys Val Pro Lys Gln Glu Ile Gln Tyr Val Asp Lys Phe Val
            85                  90                  95
```

```
Glu Val Pro Glu Val Arg Ile Val Asp Lys Phe Val Ser Lys Pro Val
            100                 105                 110

Thr Lys Tyr Val Glu Arg His Val Pro Lys Val Glu Val Arg Glu Ile
        115                 120                 125

Val Lys Glu Ile Pro Lys Ile Glu Ile Gln Tyr Val Glu Lys Ile Val
    130                 135                 140

Glu Val Pro Glu Ile Arg Val Val Asp Lys Ile Val Glu Ile Pro Thr
145                 150                 155                 160

Ile Lys His Val Ile Lys Glu Val Pro Lys Ile Glu Ile Lys Glu Ile
                165                 170                 175

Gln Val Glu Lys Ile Val Lys Val Pro Lys Ile Glu Ile Lys Gln Ile
            180                 185                 190

Glu Lys Glu Arg Lys Val Leu Gly Pro Val Glu Tyr Ile Asp Ile Pro
        195                 200                 205

Ile Glu Lys Ile Ile Leu Lys Pro Asn Pro Gln Ile Ile Glu Lys Ile
    210                 215                 220

Val Gln Val Pro Ile Pro Lys Glu Val Glu Ile Glu Val Pro Val Tyr
225                 230                 235                 240

Asn Pro Asp Ile Arg Asp Thr Val Glu Ile Glu Val Asp Asn Tyr Tyr
                245                 250                 255

Thr Val Glu Lys
            260

<210> SEQ ID NO 64
<211> LENGTH: 450
<212> TYPE: PRT
<213> ORGANISM: Cryptosporidium parvum

<400> SEQUENCE: 64

Met Leu Ile Ile Ile Glu Tyr Ile Ser Glu Val Asn Pro Glu Leu Ile
1               5                   10                  15

Phe Glu Phe Gln Lys Tyr Ser Lys Ser Ser Ile Gln Ser Asn Asn Asn
            20                  25                  30

Asn Met Ile Glu Met Leu Asn Ile Phe Asn Asn Glu Leu Leu Gln Asn
        35                  40                  45

Thr Ser Thr Cys Phe Gln Glu Tyr Leu Ser Asp Leu Leu Ser Ile Thr
    50                  55                  60

Glu Lys Ser Lys Leu Ile Leu Ser Ser Tyr Ile Thr Ser Asn Asn Ser
65                  70                  75                  80

Asp Thr Glu Lys Gln Lys Ser Asn Ile Asn Ile Glu Glu Asn Gln Ser
                85                  90                  95

Ile Gln Phe Lys Asp Lys Asn Gln Asn Asp Glu Asn Val Val Lys Ile
            100                 105                 110

Asn Asn Gln Ser Asp Ile Lys Arg Lys Pro Asn Tyr Met Arg Pro Thr
        115                 120                 125

Arg Leu Ser Glu Ile Arg Arg Gln Asn Ser Arg Lys Ser Ile Asn Glu
    130                 135                 140

Lys Val His Ser Lys Phe Glu Glu Gly Val Asn Thr Ser Thr Ser Val
145                 150                 155                 160

Phe Thr Thr Ala Asn Thr Asn Ser Asn Thr Asn Ile Ile Asn Thr
                165                 170                 175

Thr Ser Thr Thr Asn Asn Thr Thr Asn Ile Thr Asn Asn Asn Thr
            180                 185                 190

Thr Asn Asn Asn Asn Ser Asn Asn Asn Asn Ser Asn Ser Lys Asn Thr
```

-continued

```
                195                 200                 205
Val Leu Gly Gln Val Lys Ala Asn Ile Gln Lys Asp Pro Glu Lys Glu
    210                 215                 220

Met Ile Lys Asp Asn Glu Lys Asn Pro Ser Ser Leu Lys Asn Asp Gln
225                 230                 235                 240

Asn Lys Lys Asn Arg Phe Arg Asn Leu Ser Thr Lys His Leu Ile Asp
                245                 250                 255

Ser Lys Glu Asn Asn Glu Met Leu Asn Asn Ser Val Ser Asn Asp Asn
            260                 265                 270

Leu Ser Lys Asn Pro Thr Ile Ile Asn Thr Asn Asn Ser Ile Asn Tyr
        275                 280                 285

Asn Ser Tyr Asp Glu Asn Lys Phe Ile Asn Glu Lys Asn Asn Leu Lys
    290                 295                 300

Thr Ile Leu Asn Ile Leu Glu Glu Lys Ser Lys Ser Gln Val Val Asn
305                 310                 315                 320

Lys Val Asn Phe Asp Asp Glu Leu Phe Asn Ile Ile Ser Glu Leu Asp
                325                 330                 335

Lys Ile Asn Phe Lys Asn Gln Asn Asn Glu Asn Asp Ile Ser Thr Asn
            340                 345                 350

Ile Ser Glu Asp Phe Ser Gln Asn Ile Tyr Ser Asn Asn Lys Ser Asp
        355                 360                 365

Asn Asp Lys Asp Phe Gln Tyr Gln Asp Glu Asn Ile Asn Asp Glu Thr
    370                 375                 380

Tyr Leu Gln Val Asn Asn Ile Lys Ser His Leu Asp Pro Tyr Asp Trp
385                 390                 395                 400

Tyr Tyr Ser Ser Asn Asn Glu Asn Gly Asp Asn Glu Asn Val Gln
                405                 410                 415

Met Thr Thr Lys Leu Asn Lys Leu Ser Pro Lys Thr Val His Thr Asn
                420                 425                 430

Asn Glu Lys Val Thr Gln Leu Ile Ser Leu Ser Glu Asn Asp Asp Asn
            435                 440                 445

Asn His
    450

<210> SEQ ID NO 65
<211> LENGTH: 350
<212> TYPE: PRT
<213> ORGANISM: Cryptosporidium parvum

<400> SEQUENCE: 65

Val Phe Thr Asp Ala Ala Lys Ala Val Leu Gln Gly Lys Ser Pro Tyr
1               5                   10                  15

Thr Arg His Thr Tyr Arg Tyr Thr Pro Leu Leu Ala Tyr Ile Ala Ser
                20                  25                  30

Ile Asn Ile Ile Phe Lys Met Glu Ile Leu Ser Lys Leu Leu Phe Cys
            35                  40                  45

Ala Val Asn Ile Leu Ser Gly Lys Ile Leu Glu Trp Leu Leu Ile Leu
        50                  55                  60

Leu Asp Val Asp Asn Glu Thr Lys Ile Lys Gly Ser Val Thr Leu Arg
65                  70                  75                  80

Arg Phe Leu Ile Ser Thr Trp Leu Leu Asn Pro Phe Pro Val Val Ile
                85                  90                  95

Ala Ala Arg Gly Ser Ala Asp Ile Ile Pro Ser Ile Leu Val Leu Ile
                100                 105                 110
```

```
Thr Ile Tyr Phe Leu Met Lys Ala Lys Tyr Asp Ser Phe Asn Asn Lys
            115                 120                 125

Ile Asn Ile Ile Ile Ser Ala Phe Phe Phe Gly Leu Ser Val His Phe
        130                 135                 140

Lys Leu Tyr Pro Val Ile Tyr Gly Phe Pro Phe Ile Phe Phe Ile Asn
145                 150                 155                 160

Pro Asn Tyr Leu Lys Lys Asp Arg Ser Leu Phe Trp Tyr Ile Leu Asn
                165                 170                 175

Leu Pro Ile Lys Ile Phe Thr Thr Leu Asn Ile Asp Gln Leu Ile Phe
                180                 185                 190

Gly Leu Val Ser Phe Ser Thr Ile Val Ser Leu Ile Ser Phe Phe Tyr
            195                 200                 205

Tyr Leu Tyr Gly Trp Glu Phe Leu Tyr Glu Thr Tyr Leu Tyr His Ala
        210                 215                 220

Ile Arg Lys Asp His Arg His Asn Phe Ser Val Phe Phe Tyr Leu Phe
225                 230                 235                 240

Tyr Leu Thr Met Tyr Ser Val Lys Glu Val Leu Ala Ser Asn Phe Val
                245                 250                 255

Tyr Lys Ala Leu Pro Tyr Ile Ala Ser Ile Pro Gln Met Phe Leu Val
                260                 265                 270

Ala Leu Ser Gly Ile Ser Leu Val Arg Glu Gly Glu Cys Ile Met Ala
            275                 280                 285

Ile Phe Cys Gln Thr Val Leu Phe Val Ala Phe Asn Lys Val Cys Thr
        290                 295                 300

Ser Gln Tyr Phe Leu Trp Trp Phe Ile Leu Phe Pro Leu Ala Leu Arg
305                 310                 315                 320

Val Tyr Leu Thr Asn Asn Ile Ala Gln Leu Asp Glu Ser Lys Gly Ile
                325                 330                 335

Ile His Ser Ala Ser Ala Ser Phe Thr Pro Ile Leu Ile Ser
            340                 345                 350

<210> SEQ ID NO 66
<211> LENGTH: 446
<212> TYPE: PRT
<213> ORGANISM: Trypanosoma cruzi

<400> SEQUENCE: 66

Met Phe Arg Gly Val Cys Gly Leu Leu Gly Ala Ala Lys Ala Thr Pro
1               5                   10                  15

Thr Ala Ala Ala Ser Val Thr Ser Thr Ala Ala Thr Ala Gly
            20                  25                  30

Val Ser Ser Gly Gly Ser Val Arg Ser Ser Thr Cys Asp Thr Arg
            35                  40                  45

Pro Leu Tyr Leu Asp Phe Gln Ala Thr Thr Pro Leu Asp Pro Arg Val
50                  55                  60

Leu Asp Arg Met Leu Pro Tyr Leu Thr Glu Arg Tyr Gly Asn Pro His
65                  70                  75                  80

Ser Arg Thr His Arg Tyr Gly Trp Thr Ala Glu Asp Ala Val Glu Lys
                85                  90                  95

Ala Arg Ala Glu Val Ala Asp Leu Ile Gly Thr Ser Pro Lys Gly Val
            100                 105                 110

Phe Phe Thr Ser Gly Ala Thr Glu Ser Asn Asn Ile Ala Ile Lys Gly
        115                 120                 125

Val Ala Tyr Tyr Asn Lys Ser Lys Lys Asn His Ile Ile Thr Leu Gln
    130                 135                 140
```

-continued

Thr Glu His Lys Cys Val Leu Asp Ser Cys Arg Tyr Leu Glu Met Asp
145                 150                 155                 160

Gly Phe Glu Val Thr Tyr Leu Pro Val Glu Lys Asn Gly Leu Val Asn
                165                 170                 175

Leu Gln Lys Ile Glu Glu Ala Ile Arg Pro Thr Thr Ala Leu Val Ser
            180                 185                 190

Cys Met Tyr Val His Asn Glu Ile Gly Val Ile Gln Pro Ile Ser Glu
        195                 200                 205

Ile Gly Asn Leu Cys Arg Asn Lys Lys Val Leu Phe His Thr Asp Ala
    210                 215                 220

Ala Gln Ala Leu Gly Lys Val Ser Ile Asp Val Glu Arg Asp Asn Ile
225                 230                 235                 240

Asp Leu Met Ser Leu Ser Ser His Lys Ile Tyr Gly Pro Lys Gly Cys
                245                 250                 255

Gly Ala Leu Tyr Met Arg Arg Arg Pro Arg Val Arg Val Arg Ser Pro
                260                 265                 270

Val Ser Gly Gly Gly Gln Glu Arg Gly Val Arg Ser Gly Thr Val Ala
            275                 280                 285

Thr Ala Gln Val Val Gly Met Gly Ala Ala Cys Ala Ile Ala Lys Val
290                 295                 300

Glu Met Glu Arg Asp Ser Ala His Ile Ser Arg Leu Ser Lys Arg Leu
305                 310                 315                 320

Leu Asn Gly Leu Gln Ser Arg Leu Pro His Ile Thr Val Asn Gly Asp
                325                 330                 335

Leu Glu Lys Arg Tyr Pro Gly Asn Leu Asn Ile Ser Phe Ser Cys Val
                340                 345                 350

Glu Gly Glu Ser Leu Leu Met Gly Met Lys Asn Val Ala Val Ser Ser
            355                 360                 365

Gly Ser Ala Cys Thr Ser Ala Ser Leu Glu Pro Ser Tyr Val Leu Arg
370                 375                 380

Ala Leu Gly Ile Asp Ala Glu Asn Ala His Thr Ser Ile Arg Phe Gly
385                 390                 395                 400

Ile Gly Arg Phe Thr Thr Glu Arg Glu Ile Asp Val Thr Ile Glu Glu
                405                 410                 415

Cys Val Arg Asn Val Glu Arg Leu Arg Glu Met Ser Pro Leu Trp Asp
            420                 425                 430

Leu Leu Gln Glu Gly Lys Ser Leu Ala Asp Val Glu Trp Arg
            435                 440                 445

<210> SEQ ID NO 67
<211> LENGTH: 450
<212> TYPE: PRT
<213> ORGANISM: Trypanosoma cruzi

<400> SEQUENCE: 67

Met Asn Ser Arg Val Ile Leu Val Phe Gly Glu Asn Cys Met Lys Arg
1               5                   10                  15

Arg Arg Ala Asp Glu Thr Lys Lys Ile Ile Ala Ala Leu Arg Ala Gly
                20                  25                  30

Val Ala Ala Leu Ser Val Ser Ser Thr Ala Ala Lys Glu Leu Thr
            35                  40                  45

Cys Arg Asp Ala His Leu Ser Ala Ile Val Glu Phe Leu Asn Asp Ser
    50                  55                  60

Val His Pro Val Met Gln Ile Phe Gly Met Pro Gly Thr Gly Lys Thr

-continued

```
                 65                  70                  75                  80
Ala Ser Val Asn His Ala Leu Thr Leu Leu Ala Gln Ser Ala Pro Pro
                         85                  90                  95

Gly Arg Lys Pro Thr Ala Val Phe Leu Asn Gly Tyr Val Ile Gln Lys
            100                 105                 110

Asn Ser Asp Ile Tyr Trp Thr Leu Asn Ser His Leu Ser Lys Ala Arg
            115                 120                 125

Leu Gly His Thr Glu Asn Cys Leu Pro Asp Gln Cys Ala Ala Leu Ile
            130                 135                 140

Glu Lys Arg Phe Arg Gln Gly Trp Gly Gly Ala Ser Thr Pro Leu Cys
145                 150                 155                 160

Val Ile Val Ile Asp Glu Val Asp Lys Val Leu Lys Arg His Asn Lys
                        165                 170                 175

Ala Phe Phe Arg Ile Val Asp Trp Leu Ser Phe Pro Phe Ala Phe Cys
                    180                 185                 190

Lys Leu Val Thr Ile Ser Asn Ser Met Glu Leu Ala Ala Asp Ala Lys
                    195                 200                 205

Thr Arg Ser Arg Leu Asp Ile Thr Lys Arg Leu Val Phe Glu Pro Tyr
            210                 215                 220

Ser Phe Ser Glu Leu Lys Glu Ile Leu Leu Arg Arg Val Gly Lys Ile
225                 230                 235                 240

Lys Pro Thr Leu Phe Ala Glu Lys Ala Ile Asn Tyr Leu Cys Asn Gln
                245                 250                 255

Thr Ala Ser His Tyr Gly Asp Val Arg Arg Leu Leu Gln Ser Ala Ser
            260                 265                 270

Ser Ala Val Cys Gly Leu Met Met Lys Leu Glu Glu Gly Tyr Arg Val
            275                 280                 285

Pro Glu Ala Gln Asp Val Leu Leu Thr Val Lys Asp Val His Ala Val
            290                 295                 300

Val Arg Gln Ile Phe His Asp Arg Phe Val Glu Phe Ile Gln Thr Ile
305                 310                 315                 320

Arg Leu Pro Ile Leu Phe Ile Ser Val Ala Val Val Ala His Glu Thr
                325                 330                 335

Asn Lys Leu Phe Arg Ser Asn Pro Gly Asp Cys Arg Leu Ser Leu Asp
            340                 345                 350

Gly Leu Phe Leu Ser Thr Lys Arg Ala Gln Gln Ile Tyr Ser Ala Ser
            355                 360                 365

Leu Gly Glu Pro His Thr Val Asp Leu Thr Tyr Gly Ala Tyr Leu Asp
            370                 375                 380

Ile Val Glu Met Leu Arg Glu Val Ala Leu Ile Asp Val Ser Ile Gly
385                 390                 395                 400

Glu Glu Arg Ile Pro Val Lys Thr Thr Gln Asn Leu Leu Glu Ala Thr
                405                 410                 415

Glu Lys Ala Tyr Val Ser Met Leu Gln Pro Phe Pro Thr Val Leu Asp
            420                 425                 430

Ala Cys Gln Leu His Asp Val Phe Gly Glu Gly Ile Asn Pro Leu Phe
            435                 440                 445

Lys Thr
    450

<210> SEQ ID NO 68
<211> LENGTH: 655
<212> TYPE: PRT
<213> ORGANISM: Trypanosoma cruzi
```

<400> SEQUENCE: 68

```
Met Phe Ala Arg Arg Leu Cys Gly Ala Gly Ser Leu Ala Ala Ala Ser
1               5                   10                  15

Leu Ala Arg Trp Gln Ser Ser Lys Val Thr Gly Asp Val Ile Gly Ile
            20                  25                  30

Asp Leu Gly Thr Thr Tyr Ser Cys Val Ala Val Met Glu Gly Asp Lys
        35                  40                  45

Pro Arg Val Leu Glu Asn Thr Glu Gly Phe Arg Thr Thr Pro Ser Val
    50                  55                  60

Val Ala Phe Lys Gly Gln Glu Lys Leu Val Gly Leu Ala Ala Lys Arg
65                  70                  75                  80

Gln Ala Ile Thr Asn Pro Gln Ser Thr Phe Phe Ala Val Lys Arg Leu
                85                  90                  95

Ile Gly Arg Arg Phe Glu Asp Ser Asn Ile Gln His Asp Ile Lys Asn
            100                 105                 110

Val Pro Tyr Lys Ile Val Arg Ser Ser Asn Gly Asp Ala Trp Val Gln
        115                 120                 125

Asp Ala Asn Gly Lys Gln Tyr Ser Pro Ser Gln Val Gly Ala Phe Val
    130                 135                 140

Leu Glu Lys Met Lys Glu Thr Ala Glu Asn Phe Leu Gly Arg Lys Val
145                 150                 155                 160

Ser Asn Ala Val Val Thr Cys Pro Ala Tyr Phe Asn Asp Ala Gln Arg
                165                 170                 175

Gln Ala Thr Lys Asp Ala Gly Thr Ile Ala Gly Leu Asn Val Ile Arg
            180                 185                 190

Val Val Asn Glu Pro Thr Ala Ala Ala Leu Ala Tyr Gly Leu Asp Lys
        195                 200                 205

Thr Lys Asp Ser Met Ile Ala Val Tyr Asp Leu Gly Gly Gly Thr Phe
    210                 215                 220

Asp Ile Ser Val Leu Glu Ile Ala Gly Gly Val Phe Glu Val Lys Ala
225                 230                 235                 240

Thr Asn Gly Asp Thr His Leu Gly Gly Glu Asp Phe Asp Leu Cys Leu
                245                 250                 255

Ser Asp Tyr Ile Leu Thr Glu Phe Lys Lys Ser Thr Gly Ile Asp Leu
            260                 265                 270

Ser Asn Glu Arg Met Ala Leu Gln Arg Ile Arg Glu Ala Ala Glu Lys
        275                 280                 285

Ala Lys Cys Glu Leu Ser Thr Thr Met Glu Thr Glu Val Asn Leu Pro
    290                 295                 300

Phe Ile Thr Ala Asn Gln Asp Gly Ala Gln His Val Gln Met Thr Val
305                 310                 315                 320

Ser Arg Ser Lys Phe Glu Ser Leu Ala Glu Lys Leu Val Gln Arg Ser
                325                 330                 335

Leu Gly Pro Cys Lys Gln Cys Ile Lys Asp Ala Ala Val Asp Leu Lys
            340                 345                 350

Glu Ile Ser Glu Val Val Leu Val Gly Gly Met Thr Arg Met Pro Lys
        355                 360                 365

Val Ile Glu Ala Val Lys Gln Phe Phe Gly Arg Asp Pro Phe Arg Gly
    370                 375                 380

Val Asn Pro Asp Glu Ala Val Ala Leu Gly Ala Ala Thr Leu Gly Gly
385                 390                 395                 400

Val Leu Arg Gly Asp Val Lys Gly Leu Val Leu Leu Asp Val Thr Pro
```

-continued

```
            405                 410                 415
Leu Ser Leu Gly Ile Glu Thr Leu Gly Gly Val Phe Thr Arg Met Ile
            420                 425                 430

Pro Lys Asn Thr Thr Ile Pro Thr Lys Lys Ser Gln Thr Phe Ser Thr
            435                 440                 445

Ala Ala Asp Asn Gln Thr Gln Val Gly Ile Lys Val Phe Gln Gly Glu
            450                 455                 460

Arg Glu Met Ala Ala Asp Asn Gln Met Met Gly Gln Phe Asp Leu Val
465                 470                 475                 480

Gly Ile Pro Pro Ala Pro Arg Gly Val Pro Gln Ile Glu Val Thr Phe
            485                 490                 495

Asp Ile Asp Ala Asn Gly Ile Cys His Val Thr Ala Lys Asp Lys Ala
            500                 505                 510

Thr Gly Lys Thr Gln Asn Ile Thr Ile Thr Ala Ser Gly Gly Leu Ser
            515                 520                 525

Lys Glu Gln Ile Glu Arg Met Ile Arg Asp Ser Glu Ser His Ala Glu
            530                 535                 540

Ser Asp Arg Leu Lys Arg Glu Leu Val Glu Val Arg Asn Asn Ala Glu
545                 550                 555                 560

Thr Gln Ala Asn Thr Ala Glu Arg Gln Leu Thr Glu Trp Lys Tyr Val
            565                 570                 575

Ser Asp Ala Glu Lys Glu Asn Val Arg Thr Leu Leu Ala Glu Leu Arg
            580                 585                 590

Lys Ser Met Glu Asn Pro Asn Val Thr Lys Asp Glu Leu Ser Ala Ala
            595                 600                 605

Thr Asp Lys Leu Gln Lys Ala Val Met Glu Cys Gly Arg Thr Glu Tyr
            610                 615                 620

Gln Gln Ala Ala Ala Asn Ser Ser Ser Ser Gly Asn Thr Asp
625                 630                 635                 640

Ser Ser Gln Gly Glu Gln Gln Gln Gly Asp Gln Lys Gln
            645                 650                 655

<210> SEQ ID NO 69
<211> LENGTH: 898
<212> TYPE: PRT
<213> ORGANISM: Trypanosoma cruzi

<400> SEQUENCE: 69

Met Phe Arg Ser Thr Ser Ala Ser Arg Thr Gly Asn Pro Gln Leu Asn
1               5                   10                  15

Pro Phe Ile Lys Tyr Val Ala Thr Met Ala Ala Asp Gly Gly Glu Ala
            20                  25                  30

Lys Tyr Phe Lys Leu His Glu Ile Asp Pro Arg Tyr Glu Thr Leu Pro
            35                  40                  45

Phe Ser Ile Arg Val Leu Leu Glu Ser Ala Val Arg Asn Cys Asp Glu
            50                  55                  60

Phe Asp Ile Thr Ser Lys Met Val Asp Asn Ile Phe Asn Trp Lys Glu
65                  70                  75                  80

Thr Cys His Lys Asn Ile Glu Ile Pro Phe Lys Pro Ala Arg Val Val
            85                  90                  95

Leu Gln Asp Phe Thr Gly Val Pro Cys Val Val Asp Leu Ala Ala Met
            100                 105                 110

Arg Glu Ala Thr Lys Arg Leu Gly Gly Asp Leu Asn Lys Ile Asn Pro
            115                 120                 125
```

-continued

```
Gln Ile Pro Val Glu Leu Val Asp His Ser Val Gln Asp Lys
    130                 135                 140

Ala Gly Thr Pro Thr Ala Val Lys Glu Asn Gln Asp Met Glu Met Gln
145                 150                 155                 160

Arg Asn Arg Glu Arg Phe Glu Phe Leu Arg Trp Gly Ser Lys Ala Phe
                165                 170                 175

Asp Asn Leu Leu Ile Val Pro Pro Gly Ser Gly Ile Val His Gln Val
            180                 185                 190

Asn Leu Glu Tyr Leu Ala Arg Val Phe Asn Asn Lys Gly Leu Leu
        195                 200                 205

Tyr Pro Asp Ser Val Val Gly Thr Asp Ser His Thr Thr Met Val Asn
    210                 215                 220

Gly Val Gly Val Val Gly Trp Gly Val Gly Ile Glu Ala Glu Ala
225                 230                 235                 240

Gly Met Leu Gly Gln Ser Leu Ser Met Val Leu Pro Gln Val Leu Gly
                245                 250                 255

Tyr Arg Phe Thr Gly Lys Leu Ala Glu Gly Cys Thr Ala Thr Asp Leu
            260                 265                 270

Val Leu Thr Val Ala Lys Asn Leu Arg Lys Phe Gly Val Val Gly Lys
        275                 280                 285

Phe Val Glu Phe Tyr Gly Pro Gly Val Asp Asn Leu Ser Leu Pro Asp
    290                 295                 300

Arg Ala Thr Leu Ala Asn Met Ala Pro Glu Tyr Gly Ala Thr Thr Gly
305                 310                 315                 320

Phe Phe Pro Ile Asp Arg Glu Thr Ile Asn Tyr Leu Arg Cys Thr Asn
                325                 330                 335

Arg Ser Val Glu Gln Leu Glu Arg Ile Glu Ala Tyr Ala Lys Ala Val
            340                 345                 350

Lys Met Phe Arg Thr Gly Asp Glu Lys Ile Glu Tyr Ser His His Leu
        355                 360                 365

Glu Leu Asp Leu Ser Thr Val Glu Pro Cys Val Ala Gly Pro Lys Arg
    370                 375                 380

Pro Gln Asp His Val Pro Leu Lys Asn Met Lys Glu Asp Phe Ala Ala
385                 390                 395                 400

Cys Leu Gln Ala Lys Ser Gly Phe Lys Gly Phe Gly Ile Pro Ala Lys
                405                 410                 415

Asp Val Asn Lys Thr Lys Asn Tyr Met Val Asp Gly Gln Glu Ala Val
            420                 425                 430

Met Arg His Gly Ser Val Val Ile Ala Ala Ile Thr Ser Cys Thr Asn
        435                 440                 445

Thr Ser Asn Pro His Val Leu Val Ala Ala Gly Leu Val Ala Lys Lys
    450                 455                 460

Ala Leu Glu Lys Gly Leu Lys Val Pro Pro Gly Ile Lys Thr Ser Leu
465                 470                 475                 480

Ser Pro Gly Ser His Val Val Thr Arg Tyr Leu Glu Ala Ala Gly Leu
                485                 490                 495

Gln Ser Ser Leu Asp Ala Leu Gly Phe Asn Thr Thr Gly Tyr Gly Cys
            500                 505                 510

Met Thr Cys Ile Gly Asn Ser Gly Asp Ile His Ala Glu Val Ser Lys
        515                 520                 525

Cys Ile Ser Glu Asn Asn Phe Val Ala Ala Val Leu Ser Gly Asn
    530                 535                 540

Arg Asn Phe Glu Ala Arg Ile His Pro Leu Thr Ala Ala Asn Tyr Leu
```

-continued

```
            545                 550                 555                 560
Ala Ser Pro Pro Leu Val Val Ala Tyr Ala Leu Ser Gly Arg Val Asp
                565                 570                 575

Ile Asp Phe Asn Glu Glu Pro Ile Ala Lys Gly Val Phe Leu Arg Asp
                580                 585                 590

Ile Trp Pro Arg Asn Glu Glu Val Gln Glu Ile Val Ser Arg Tyr Val
                595                 600                 605

Thr Pro Glu Leu Phe Lys Ser Val Tyr Ser Asn Ile Thr Thr Ile Asn
                610                 615                 620

Glu Gln Trp Asn Ala Leu Gln Val Asn Glu Gly Lys Leu Tyr Glu Trp
625                 630                 635                 640

Gln Pro Asn Ser Thr Tyr Ile His His Pro Pro Tyr Phe Glu Ser Met
                645                 650                 655

Thr Met Glu Pro Thr Pro Asn Thr Val Ile Lys Asp Ala Ala Cys Leu
                660                 665                 670

Ala Leu Phe Gly Asp Ser Ile Thr Thr Asp His Ile Ser Pro Ala Gly
                675                 680                 685

Thr Ile Ala Lys Asp Ser Pro Ala Ala Lys Phe Leu Gln Asp His Gly
                690                 695                 700

Val Glu Arg Lys Asp Phe Asn Thr Tyr Gly Ser Arg Arg Gly Asn Asp
705                 710                 715                 720

Leu Val Met Val Arg Gly Thr Phe Ala Asn Thr Arg Leu Gly Asn Arg
                725                 730                 735

Leu Val Gly Glu Gly Gln Thr Gly Pro Phe Thr Ile Tyr Phe Pro Thr
                740                 745                 750

Asn Glu Lys Met Tyr Ile Phe Asp Ala Ala Met Lys Tyr Gln Gln Glu
                755                 760                 765

Asn Ile Pro Leu Val Ile Ile Ala Gly Lys Glu Tyr Gly Ser Gly Ser
                770                 775                 780

Ser Arg Asp Trp Ala Ala Lys Gly Pro Phe Met Gln Gly Ile Lys Val
785                 790                 795                 800

Val Ile Ala Glu Ser Phe Glu Arg Ile His Arg Ser Asn Leu Val Gly
                805                 810                 815

Met Gly Ile Val Pro Leu Gln Phe Lys Pro Gly Glu Ser Ala Gln Ser
                820                 825                 830

Leu Gly Leu Thr Gly Lys Glu Arg Tyr Ser Phe Asp Phe Ser Gly Gly
                835                 840                 845

Leu Arg Pro Gly Gln Glu Ala Thr Val Gln Lys Gly Asp Gly Ser Ser
                850                 855                 860

Phe Ser Thr Ile Leu Arg Ile Asp Thr Glu Met Glu Val Lys Tyr Val
865                 870                 875                 880

Glu Asn Gly Gly Ile Leu Gln Tyr Val Leu Arg Glu Lys Ile Arg Gly
                885                 890                 895

Ala Leu
```

<210> SEQ ID NO 70
<211> LENGTH: 1531
<212> TYPE: PRT
<213> ORGANISM: Trypanosoma cruzi

<400> SEQUENCE: 70

```
Met Pro Gln Ser Ala Gln Ser Glu Glu Gly Arg Ile Thr Val Cys Val
1               5                   10                  15

Arg Ala Arg Pro Leu Asn Glu Arg Glu Lys Arg Leu Lys Ser Pro Ser
```

-continued

```
                     20                  25                  30
Cys Leu Thr Phe His Glu Gly Lys Lys Val Gln Ile Phe Arg Lys Gly
             35                  40                  45

Phe Ala Ala Asp Gly Val Glu Gly Leu Asp Glu Ser Phe Val Gly Lys
         50                  55                  60

Val Phe Ala Phe Asp His Ala Tyr Asp Thr Asp Val Pro Gln Ser Ser
 65                  70                  75                  80

Leu Tyr Glu Asp Leu Gly Leu Pro Val Leu Asp Ser Ser Phe Lys Gly
                 85                  90                  95

Phe Asn Thr Cys Ile Phe Ala Tyr Gly Gln Thr Gly Ser Gly Lys Ser
                100                 105                 110

Tyr Ser Met Met Gly Pro Ser Gly Arg Asp Val Phe Val Asp Pro
             115                 120                 125

Gly Ile Ile Pro Arg Leu Ser Lys Gly Leu Phe Ala Met Leu Arg Glu
         130                 135                 140

Arg Gln Ala Lys Asn Gln Ser Asp Arg Glu Ala Ala Arg Ala Asn Ala
145                 150                 155                 160

Val Glu Glu His Ala Leu Pro Pro Glu Val Asn Val Ile Val Leu Val
                 165                 170                 175

Ser Tyr Leu Glu Ile Tyr Gln Glu Arg Val Asn Cys Leu Leu Asn Ser
             180                 185                 190

Lys Leu Asp Asn Leu Lys Val Arg Glu His Pro Val Leu Gly Val Tyr
         195                 200                 205

Val Glu Gly Leu Arg Glu Val Lys Val Ser Ser Glu Glu Glu Ile Met
210                 215                 220

Gln Ile Met Glu Arg Gly Asn Gln Cys Arg His Thr Ala Ala Thr Lys
225                 230                 235                 240

Met Asn Asp Arg Ser Ser Arg Ser His Ala Ile Phe Ala Ile Ser Leu
                 245                 250                 255

Ile Gln Glu Arg Lys Ser Ile Thr Lys Asp Gly Lys Val Thr Ser Thr
             260                 265                 270

Met Leu Arg Ala Lys Ile Asn Leu Val Asp Leu Ala Gly Ser Glu Arg
         275                 280                 285

Ala Lys Ser Thr Gly Ala Glu Gly Asp Thr Leu Arg Glu Gly Ala Asn
290                 295                 300

Ile Asn Arg Ser Leu Thr Val Leu Gly Gln Val Ile Ser Ala Leu Ala
305                 310                 315                 320

Gln Ala Ser Lys Gln Lys Pro Asp Ala Ala Gly Leu Lys His Val Pro
                 325                 330                 335

Tyr Arg Asp Ser Thr Leu Thr Phe Ile Leu Lys Glu Ser Leu Gly Gly
             340                 345                 350

Asn Ser Lys Thr Phe Met Leu Ser Thr Leu Ser Pro Ala Ala Ala Asn
         355                 360                 365

Tyr Asp Glu Thr Leu Ser Thr Leu Arg Tyr Ala Asp Arg Ala Lys Ala
370                 375                 380

Ile Leu Thr Arg Ala Val Ile Asn Glu Ser Ala Gly Asp Lys Lys Ile
385                 390                 395                 400

Arg Glu Leu Glu Asp Glu Val Arg Leu Leu Arg Glu Lys Met Arg His
                 405                 410                 415

Tyr Glu Glu Met Ile Ala Arg Gly Glu Val Met Ser Gln Met Ser Ile
             420                 425                 430

Ser Gly Ser Pro Gln Leu Arg Asp Lys Ile Gly Lys Asp Gly Glu Ser
         435                 440                 445
```

```
Lys Ala Ile Val Glu Asp Asp Met Val Tyr Ala Asn Ala Lys Thr Pro
    450                 455                 460

Arg Gln Ala Gly Asp Ala Ala Val Leu Glu Arg Glu Leu His Arg Ala
465                 470                 475                 480

Glu Ser Leu Val Gln Asn Leu Val Ala Asn Lys Gly Ile Ser Leu Glu
                485                 490                 495

Ser Phe Ile Met Pro Ala Phe His Arg Asn Thr Ser Thr Ile Arg Val
            500                 505                 510

Asn Gly Asn Asp Pro Phe Ile Leu Asn Leu Asp Gly Ala Gly Asp Trp
        515                 520                 525

Val Val Glu Tyr Ile Val Ala Gly Ile Thr Tyr Leu Gly Val Glu Ala
    530                 535                 540

Ser Ala Thr Gly Asn Asp Ala Arg Tyr Ile Val Ser Gly Ser Gln
545                 550                 555                 560

Thr Ala Gly Ile Ala Pro Gln His Cys Cys Phe Val Arg Lys Asp Gly
                565                 570                 575

Gly Gln Val Leu Leu Arg Pro Leu Gly Gly Asn Arg Thr Tyr Ile Asp
            580                 585                 590

Asp Asp Pro Asp Pro Val Asp Gly Asp Thr Pro Met Lys Ser Gly Thr
        595                 600                 605

Val Leu Cys Leu Gly Asp Glu Tyr Val Gln Phe Lys Phe Ile Asp Pro
    610                 615                 620

Ser Ala Pro Gln Ser Ala Val Arg Arg Thr Val Arg Asn Ser Glu
625                 630                 635                 640

Ser Ile Pro Met Gln Ser Leu Ser Ile Asp Ala Lys Ser Ser Ser Ser
                645                 650                 655

Asn Ser Asn His Ser Leu Lys Ser Ser Pro Leu Leu Ile Gly Ala Gly
            660                 665                 670

Ser Gly Asn Ala Gly His Pro Pro Val Pro Ala Leu Lys Leu Lys Glu
        675                 680                 685

Ala Leu Gln Arg Met Gln Ser Asn Ser Ala Arg Thr Lys Lys Ala His
    690                 695                 700

Arg Asp Pro Met Thr Pro Thr Gly Ser Ser Leu Thr Ser Ala Pro His
705                 710                 715                 720

Gly Ile Ser Val Val Gly Ile Thr Pro Arg Thr Thr Arg Thr Ala Gly
                725                 730                 735

Lys Val Val Ile Ser Pro Ser Asp Glu Leu Thr Val Ile Tyr Arg His
            740                 745                 750

Thr Phe Leu Phe Leu Gly Ala Cys Asn Ser Gly Lys Ser Ala Leu Arg
        755                 760                 765

Glu Asn Leu Gln Lys Pro Asp Arg Trp Tyr Ser Met Phe Ala Asn Asp
    770                 775                 780

Lys Leu His Val Arg Pro Thr Phe Gly Val Asp Ser Ser Leu Ile Glu
785                 790                 795                 800

Thr Phe Ala Gly Asn Gln Pro Val Gln Met Asn Leu Met Glu Leu Ser
                805                 810                 815

Gly Asn Arg Cys Phe Ser Phe Glu Ser Leu Leu Pro Thr Arg His
            820                 825                 830

Val Ser Tyr Val Leu Cys Phe Ser Leu Arg Glu Leu Pro Thr Leu Glu
        835                 840                 845

Thr Leu Gln Pro Leu Leu Glu Phe Ile Leu Cys Arg Thr Phe Asn Arg
    850                 855                 860
```

-continued

```
Asp Ala Thr Val Ile Leu Ile Gly Thr His Leu Asp Glu Ile Ser Leu
865                 870                 875                 880

Asp Glu Ile Lys Leu Ala His Leu Phe Ala Ile Glu Thr Glu Ile
            885                 890                 895

Asn Asn Tyr Phe Phe Leu Val Gln Ala Ile Pro Glu Lys Arg Pro Ser
        900                 905                 910

Ile Leu Gly Arg Phe Ala Val Asp Asn Val Gly Arg Val Val Ser
        915                 920                 925

Pro Gly Phe Ser Lys Phe Lys Lys Phe Pro Glu Leu Leu Cys Trp Phe
930                 935                 940

Ser Asp Gln Ala Leu Gln Arg Cys Arg Asn Asp Val Glu Phe Pro Asn
945                 950                 955                 960

Ala Gln Val Pro Leu Arg Ala Val Ala Leu Ser Lys Lys Ile Arg Glu
            965                 970                 975

Ile Asn Arg Glu Gly Gln Trp Tyr Leu Thr Ser Ala Asn Tyr Lys Ala
                980                 985                 990

Ile Ala Lys Ala Val Asp Ala Arg Tyr Gly Leu Ser Arg His Asp Leu
        995                 1000                1005

His Arg His Thr Gln Leu Leu Val Gly Trp Gly Val Leu His His
    1010                1015                1020

His Phe Arg His Leu Thr Met Lys Lys Tyr Val Val Ile Asp Val
    1025                1030                1035

Gln Trp Val Phe Arg Val Val Ala Val Leu Ala Cys Cys Met Tyr
    1040                1045                1050

Ser Arg Gly Tyr Gly Thr Glu Asn Asn Ser Leu Leu Gln Pro Val
    1055                1060                1065

Pro Leu Leu Phe Cys Arg Lys Thr Met Glu Asp Met Gln Asn Val
    1070                1075                1080

Ile Pro Phe Asp Val Lys Thr Val Met Ala Ser Asp Leu Cys Cys
    1085                1090                1095

Val Phe Asn Gln Gly Val Val Ser Met Lys Thr Ala Met Ser Leu
    1100                1105                1110

Phe Arg Gly Val Leu Gly Glu Lys Gly Leu Asp Ser Cys His Leu
    1115                1120                1125

Thr Gly Ile Leu Glu Leu Leu Arg Ser Tyr Asp Leu Ile Ile Met
    1130                1135                1140

Gly Ser Arg Leu Lys Phe Ser Phe Met Gly Glu Leu Arg Glu
    1145                1150                1155

Asn Lys Ser His Gly Met Met Asp Thr Ser Val Leu His Gly Asn
    1160                1165                1170

His Pro Val Glu Asn Asp Asp Asp Glu Glu Glu Glu Glu Glu
    1175                1180                1185

Glu Glu Glu Glu Glu Thr Ala Gly Ala Ser Val Leu Ser Ser
    1190                1195                1200

Glu Phe Phe Met Leu Ile Pro Ala Cys Phe Thr Cys Gln Pro Pro
    1205                1210                1215

Ser Ala Phe Asn Leu His Leu Pro Ser Phe Leu Phe Gly Pro Phe
    1220                1225                1230

Tyr Arg Phe Thr Leu Asn Ile Val Pro His Asn Phe Phe Ala Arg
    1235                1240                1245

Val Met Ser Arg Val Ala His Phe Ala Glu Lys Ile Tyr Leu Gly
    1250                1255                1260

Pro Val Ser Ala Arg Leu Val Leu Val Glu Asn Leu Val Ser Asp
```

```
                    1265                1270                1275

Asp Cys Ser Asn Ile Thr Ile Arg Gly Ser Ile Cys His Ala Phe
        1280                1285                1290

Gly Asp His Asp Ser Arg Asn Val Ser Val Gly Thr Met Glu Gly
        1295                1300                1305

Arg Arg Ala Gly Lys Ser Gln Glu Lys Thr Ser Met Val Gly Lys
        1310                1315                1320

Ser His Phe Trp Gly Ser Thr Ala Trp Val Ile Ser Ser Ala Arg
        1325                1330                1335

Ser Arg Ala Leu Ile Arg Met Val His His Ser Leu Leu Ile Thr
        1340                1345                1350

Phe His Asp Leu Asp Asp Asp Glu Glu Phe Tyr Asn Gly Leu Arg
        1355                1360                1365

His Val Val Arg Asn Leu Val Tyr Glu Ser Pro Gly Val Lys Cys
        1370                1375                1380

Glu Glu Ser Ile Leu Cys Ser Arg Asp Phe Met Glu Glu Gly Glu
        1385                1390                1395

Lys Ala Ser Glu Val His Gly Asp Lys Val Tyr Trp His Asp Val
        1400                1405                1410

Asp Glu Asn Leu Asn Ser Leu Glu Lys Ile Arg Gln Arg Glu Gln
        1415                1420                1425

Phe Ala Leu Met Thr Ala Arg Ser Ser Thr Ser Arg Thr Leu Ser
        1430                1435                1440

Gly Gly Ala Glu Gly Arg Ser Asn Ile Asp Ala Leu Met Glu Glu
        1445                1450                1455

Glu Asp Asp Asn Met Val Ile Pro Phe Val Arg Asn Arg Thr Glu
        1460                1465                1470

Cys Val Asp Val Glu Ala Ser Val Arg Arg Val Cys Glu Asp Ser
        1475                1480                1485

Leu Leu Thr Asp Asp Val Leu His Gly Val Arg Glu Ala Leu His
        1490                1495                1500

Ala Met Asn Lys Ala Arg Arg Arg Gly Ser Gly Ala Gly Gln Cys
        1505                1510                1515

Arg Ala Met Asp Arg Leu Val Asp Val Leu Ala Gln Ala
        1520                1525                1530

<210> SEQ ID NO 71
<211> LENGTH: 437
<212> TYPE: PRT
<213> ORGANISM: Trypanosoma brucei

<400> SEQUENCE: 71

Met Phe Ser Gly Val Arg Val Leu Leu Cys Ala Ala Cys Gly Ser Ala
1               5                   10                  15

Ser Ala Ile Ser Gln Gly Val Ser Val Gly Gly Ser Ala Gly Arg
                20                  25                  30

Pro Phe Lys Arg Asp Pro Arg Pro Leu Tyr Leu Asp Leu Gln Ser Thr
            35                  40                  45

Thr Pro Leu Asp Pro Arg Val Leu Asp Lys Met Leu Pro Tyr Met Thr
        50                  55                  60

Glu Met Tyr Gly Asn Pro His Ser Arg Thr His Ser Tyr Gly Trp Thr
65                  70                  75                  80

Ala Glu Glu Ala Val Glu Lys Ala Arg Thr Gln Val Ala Asp Leu Ile
                85                  90                  95
```

```
Arg Ala Ser Pro Lys Gly Val Phe Phe Thr Ser Gly Ala Thr Glu Ser
            100                 105                 110

Asn Asn Ile Ala Ile Lys Gly Val Ala Asn Tyr Asn Lys Glu Lys Lys
        115                 120                 125

Asn His Leu Ile Thr Leu Gln Thr Glu His Lys Cys Val Leu Asp Ser
    130                 135                 140

Cys Arg Tyr Leu Glu Met Glu Gly Phe Glu Val Thr Tyr Leu Pro Val
145                 150                 155                 160

Glu Lys Asn Gly Ile Val Asn Leu Gln Lys Leu Glu Ala Ile Arg
                165                 170                 175

Pro Thr Thr Ala Leu Val Ser Cys Met Tyr Val Asn Asn Glu Ile Gly
                180                 185                 190

Val Ile Gln Pro Ile Gly Glu Ile Gly Lys Ile Cys Arg Lys Lys Lys
        195                 200                 205

Val Leu Phe His Thr Asp Ala Ala Gln Ala Val Gly Lys Leu Asp Ile
    210                 215                 220

Asp Val Asp Arg Asp Asn Ile Asp Leu Met Ser Val Ser Ser His Lys
225                 230                 235                 240

Ile Tyr Gly Pro Lys Gly Cys Gly Ala Leu Tyr Met Arg Arg Arg Pro
                245                 250                 255

Arg Val Arg Val Arg Ser Pro Val Ser Gly Gly Gln Glu Arg Gly
                260                 265                 270

Val Arg Ser Gly Thr Ile Ala Thr Pro Leu Ala Val Gly Leu Gly Ala
                275                 280                 285

Ala Cys Glu Leu Ala Lys Val Glu Met Lys Arg Asp Ser Glu Arg Ile
290                 295                 300

Ala Gln Leu Ser Lys Arg Leu Trp Glu Gly Leu Gln Lys Arg Leu Thr
305                 310                 315                 320

His Ile Thr Leu Asn Gly Asp Val Glu Arg Arg Phe His Gly Asn Leu
                325                 330                 335

Asn Ile Ser Phe Ala Cys Val Glu Gly Glu Ser Leu Leu Met Gly Met
                340                 345                 350

Lys Lys Val Ala Val Ser Ser Gly Ser Ala Cys Thr Ser Ala Ser Leu
            355                 360                 365

Glu Pro Ser Tyr Val Leu Arg Ala Leu Gly Ile Asp Ala Glu Asn Ala
    370                 375                 380

His Thr Ser Ile Arg Phe Gly Ile Gly Arg Phe Thr Thr Glu Arg Glu
385                 390                 395                 400

Val Asp Val Thr Val Glu Glu Cys Ala Arg Thr Val Glu Arg Leu Arg
                405                 410                 415

Glu Met Ser Pro Leu Trp Asp Leu Leu Met Glu Gly Lys Ser Leu Lys
            420                 425                 430

Asp Val Glu Trp Arg
        435

<210> SEQ ID NO 72
<211> LENGTH: 436
<212> TYPE: PRT
<213> ORGANISM: Trypanosoma brucei

<400> SEQUENCE: 72

Met Lys Arg Arg Arg Asp Ser Asn Gly Lys Ser Ile Ala Ala Leu Arg
1               5                   10                  15

Ala Gly Val Ala Ala Leu Ser Val Ser Ser Asn Ile Ala Ser Arg Glu
            20                  25                  30
```

```
Leu Thr Cys Arg Asp Ser His Val Lys Ala Ile Leu Asp Phe Leu Asn
        35                  40                  45

Asp Lys Val His Pro Val Met Gln Val Phe Gly Met Pro Gly Thr Gly
 50                  55                  60

Lys Thr Ala Ser Val Asn His Ala Leu Ala Leu Ala Ser Ser Ser
 65                  70                  75                  80

Pro Ala Gly Ser Lys Pro Thr Ala Val Phe Leu Asn Gly Tyr Ile Ile
                 85                  90                  95

Gln Lys Thr Ser Asp Ile Tyr Trp Thr Leu Asn Ser His Leu Ser Lys
                100                 105                 110

Thr Arg Leu Lys His Ala Glu Asn Cys Leu Pro Glu Gln Cys Pro Ala
                115                 120                 125

Leu Ile Glu Lys Arg Phe Lys Gln Gly Trp Gly Ser Ser Thr Thr Pro
        130                 135                 140

Leu Cys Val Ile Val Asp Glu Val Asp Lys Val Leu Lys Lys His
145                 150                 155                 160

Asn Lys Ala Phe Phe Arg Ile Val Asp Trp Leu Ser Leu Pro Tyr Ala
                165                 170                 175

Phe Cys Lys Leu Ile Thr Ile Ser Asn Ser Met Glu Leu Ala Ala Asp
                180                 185                 190

Ala Lys Thr Arg Ser Arg Leu Asp Ile Thr Lys Arg Leu Val Phe Glu
        195                 200                 205

Pro Tyr Ser Leu Pro Glu Leu Lys Glu Ile Ile Leu Arg Arg Val Ser
        210                 215                 220

His Ile Lys Pro Thr Leu Phe Ala Glu Lys Ala Ile Asn Tyr Leu Cys
225                 230                 235                 240

Asn Gln Thr Ala Ser His Tyr Gly Asp Val Arg Arg Leu Leu Gln Ser
                245                 250                 255

Ala Ser Ser Ala Ile Cys Gly Leu Met Met Arg Ile Glu Glu Gly Tyr
                260                 265                 270

Lys Leu Pro Glu Lys His Asp Gly Leu Leu Thr Val Lys Asp Val His
        275                 280                 285

Ser Val Val Arg Gln Ile Phe His Asp Arg Phe Val Glu Phe Ile Gln
        290                 295                 300

Thr Ile Arg Leu Pro Val Phe Ile Ser Val Ala Val Ile Ala Val
305                 310                 315                 320

Glu Thr Ala Arg Leu Phe Arg Ala Asn Cys Glu Asp Ser Arg Leu Pro
                325                 330                 335

Ile Asp Ser Leu Phe Thr Ala Thr Lys Arg Ala Gln Glu Arg Phe Gly
                340                 345                 350

Ser Val Phe Ala Asp Leu His Ala Val Thr Leu Asn Tyr Gly Ala Tyr
        355                 360                 365

Leu Glu Ile Val Glu Met Leu Arg Glu Val Ala Leu Ile Asp Val Ser
        370                 375                 380

Val Gly Glu Glu Arg Ile Pro Val Lys Thr Val Gln Ser Leu Leu Glu
385                 390                 395                 400

Ala Thr Glu Arg Ala His Ala Ser Met Leu Gln Pro Phe Gln Thr Val
                405                 410                 415

Val Asp Ala Cys Lys Leu His Asp Asp Phe Gly Thr Gly Ile Cys Pro
                420                 425                 430

Leu Phe Ser Ile
        435
```

-continued

```
<210> SEQ ID NO 73
<211> LENGTH: 657
<212> TYPE: PRT
<213> ORGANISM: Trypanosoma brucei

<400> SEQUENCE: 73
```

| | | | | | | | | | | | | | | |
|---|---|---|---|---|---|---|---|---|---|---|---|---|---|---|
| Met | Leu | Ala | Arg | Arg | Val | Cys | Ala | Pro | Met | Cys | Leu | Ala | Ser | Ala | Pro |
| 1 | | | | 5 | | | | | 10 | | | | | 15 | |

Phe Ala Arg Trp Gln Ser Ser Lys Val Thr Gly Asp Val Ile Gly Ile
                20                  25                  30

Asp Leu Gly Thr Thr Tyr Ser Cys Val Ala Val Met Glu Gly Asp Arg
            35                  40                  45

Pro Arg Val Leu Glu Asn Thr Glu Gly Phe Arg Thr Thr Pro Ser Val
50                  55                  60

Val Ala Phe Lys Gly Gln Glu Lys Leu Val Gly Leu Ala Ala Lys Arg
65                  70                  75                  80

Gln Ala Ile Thr Asn Pro Gln Ser Thr Phe Phe Ala Val Lys Arg Leu
                85                  90                  95

Ile Gly Arg Arg Phe Asp Asp Glu His Ile Gln His Asp Ile Lys Asn
            100                 105                 110

Val Pro Tyr Lys Ile Ile Arg Ser Asn Asn Gly Asp Ala Trp Val Gln
        115                 120                 125

Asp Gly Asn Gly Lys Gln Tyr Ser Pro Ser Gln Val Gly Ala Phe Val
    130                 135                 140

Leu Glu Lys Met Lys Glu Thr Ala Glu Asn Phe Leu Gly Arg Lys Val
145                 150                 155                 160

Ser Asn Ala Val Val Thr Cys Pro Ala Tyr Phe Asn Asp Ala Gln Arg
                165                 170                 175

Gln Ala Thr Lys Asp Ala Gly Thr Ile Ala Gly Leu Asn Val Ile Arg
            180                 185                 190

Val Val Asn Glu Pro Thr Ala Ala Ala Leu Ala Tyr Gly Leu Asp Lys
        195                 200                 205

Thr Lys Asp Ser Leu Ile Ala Val Tyr Asp Leu Gly Gly Gly Thr Phe
    210                 215                 220

Asp Ile Ser Val Leu Glu Ile Ala Gly Gly Val Phe Glu Val Lys Ala
225                 230                 235                 240

Thr Asn Gly Asp Thr His Leu Gly Gly Glu Asp Phe Asp Leu Cys Leu
                245                 250                 255

Ser Asp His Ile Leu Glu Glu Phe Arg Lys Thr Ser Gly Ile Asp Leu
            260                 265                 270

Ser Lys Glu Arg Met Ala Leu Gln Arg Ile Arg Glu Ala Ala Glu Lys
        275                 280                 285

Ala Lys Cys Glu Leu Ser Thr Thr Met Glu Thr Glu Val Asn Leu Pro
    290                 295                 300

Phe Ile Thr Ala Asn Gln Asp Gly Ala Gln His Val Gln Met Met Val
305                 310                 315                 320

Ser Arg Ser Lys Phe Glu Ser Leu Ala Asp Lys Leu Val Gln Arg Ser
                325                 330                 335

Leu Gly Pro Cys Lys Gln Cys Ile Lys Asp Ala Ala Val Asp Leu Lys
            340                 345                 350

Glu Ile Ser Glu Val Val Leu Val Gly Gly Met Thr Arg Met Pro Lys
        355                 360                 365

Val Val Glu Ala Val Lys Gln Phe Phe Gly Arg Glu Pro Phe Arg Gly
    370                 375                 380

```
Val Asn Pro Asp Glu Ala Val Ala Leu Gly Ala Ala Thr Leu Gly Gly
385                 390                 395                 400

Val Leu Arg Gly Asp Val Lys Gly Leu Val Leu Asp Val Thr Pro
            405                 410                 415

Leu Ser Leu Gly Ile Glu Thr Leu Gly Gly Val Phe Thr Arg Met Ile
                420                 425                 430

Pro Lys Asn Thr Thr Ile Pro Thr Lys Lys Ser Gln Thr Phe Ser Thr
            435                 440                 445

Ala Ala Asp Asn Gln Thr Gln Val Gly Ile Lys Val Phe Gln Gly Glu
    450                 455                 460

Arg Glu Met Ala Ser Asp Asn Gln Met Met Gly Gln Phe Asp Leu Val
465                 470                 475                 480

Gly Ile Pro Pro Ala Pro Arg Gly Val Pro Gln Ile Glu Val Thr Phe
                485                 490                 495

Asp Ile Asp Ala Asn Gly Ile Cys His Val Thr Ala Lys Asp Lys Ala
            500                 505                 510

Thr Gly Lys Thr Gln Asn Ile Thr Ile Thr Ala His Gly Gly Leu Thr
        515                 520                 525

Lys Glu Gln Ile Glu Asn Met Ile Arg Asp Ser Glu Met His Ala Glu
530                 535                 540

Ala Asp Arg Val Lys Arg Glu Leu Val Glu Val Arg Asn Asn Ala Glu
545                 550                 555                 560

Thr Gln Ala Asn Thr Ala Glu Arg Gln Leu Thr Glu Trp Lys Tyr Val
                565                 570                 575

Thr Asp Ala Glu Lys Glu Asn Val Arg Thr Leu Leu Ala Glu Leu Arg
            580                 585                 590

Lys Val Met Glu Asn Pro Asn Val Thr Lys Asp Glu Leu Ser Ala Ser
        595                 600                 605

Thr Asp Lys Leu Gln Lys Ala Val Met Glu Cys Gly Arg Thr Glu Tyr
    610                 615                 620

Gln Gln Ala Ala Ala Ala Asn Ser Gly Ser Ser Gly Ser Ser Ser Thr
625                 630                 635                 640

Glu Gly Gln Gly Glu Gln Gln Gln Gln Ala Ser Gly Glu Lys Lys
                645                 650                 655

Glu
```

<210> SEQ ID NO 74
<211> LENGTH: 897
<212> TYPE: PRT
<213> ORGANISM: Trypanosoma brucei

<400> SEQUENCE: 74

```
Met Leu Ser Thr Met Lys Leu Leu Lys Ala Ser Leu Pro Ser Asn Asn
1               5                   10                  15

Pro Phe Leu Lys Tyr Ile Ala Thr Leu Ser Val Asp Gly Gly Gln Ala
                20                  25                  30

Gln Tyr Phe Lys Leu His Glu Ile Asp Pro Arg Tyr Asp Gly Leu Pro
            35                  40                  45

Phe Ser Ile Arg Val Leu Leu Glu Ser Ala Val Arg Asn Cys Asp Glu
    50                  55                  60

Phe Asp Ile Thr Ser Lys Ala Val Glu Asn Ile Leu Ser Trp Ser Glu
65                  70                  75                  80

Asn Cys His Lys Ser Ile Glu Ile Pro Phe Lys Pro Ala Arg Val Val
                85                  90                  95
```

```
Leu Gln Asp Phe Thr Gly Val Pro Cys Val Val Asp Leu Ala Ala Met
            100                 105                 110

Arg Asp Ala Thr Lys Arg Leu Gly Gly Asp Val Asp Lys Ile Asn Pro
            115                 120                 125

Gln Ile Pro Val Glu Leu Val Val Asp His Ser Val Gln Val Asp Ser
            130                 135                 140

Tyr Gly Thr Pro Glu Ala Ala Lys Leu Asn Gln Asp Ile Glu Met Gln
145                 150                 155                 160

Arg Asn Arg Glu Arg Phe Glu Phe Leu Lys Trp Gly Ser Glu Ala Phe
            165                 170                 175

His Asn Leu Leu Ile Val Pro Pro Gly Ser Gly Ile Val His Gln Val
            180                 185                 190

Asn Leu Glu Tyr Leu Ala Arg Val Phe Asn Asn Asp Gly Val Leu
            195                 200                 205

Tyr Pro Asp Ser Val Val Gly Thr Asp Ser His Thr Thr Met Val Asn
            210                 215                 220

Gly Val Gly Val Ile Gly Trp Gly Val Gly Gly Ile Glu Ala Glu Ala
225                 230                 235                 240

Gly Met Leu Gly Gln Ser Leu Ser Met Val Leu Pro Glu Val Val Gly
            245                 250                 255

Tyr Arg Phe Thr Gly Lys Leu Ser Glu Gly Cys Thr Ala Thr Asp Leu
            260                 265                 270

Val Leu Thr Val Val Arg Asn Leu Arg Lys Leu Gly Val Val Gly Lys
            275                 280                 285

Phe Val Glu Phe Tyr Gly Pro Gly Val Asp Thr Leu Ser Leu Pro Asp
290                 295                 300

Arg Ala Thr Leu Ala Asn Met Ala Pro Glu Tyr Gly Ala Thr Thr Gly
305                 310                 315                 320

Phe Phe Pro Ile Asp Gln Glu Thr Leu Asn Tyr Leu Arg Cys Thr Gly
            325                 330                 335

Arg Asp Ala Glu His Leu Ala Arg Ile Glu Lys Tyr Thr Lys Ala Thr
            340                 345                 350

Lys Met Phe Arg Thr Gly Asp Glu Lys Ile Ser Tyr Ser Gln Asn Ile
            355                 360                 365

Glu Leu Asp Leu Ser Thr Val Glu Pro Ser Leu Ala Gly Pro Lys Arg
            370                 375                 380

Pro His Asp His Ile Leu Leu Arg Asn Met Lys Gln Asp Phe Glu Ala
385                 390                 395                 400

Cys Leu Gly Ala Lys Thr Gly Phe Lys Gly Phe Gly Ile Pro Asp Gly
            405                 410                 415

Glu His Lys Lys Glu Val Lys Tyr Thr Val Asp Gly Lys Glu Ala Val
            420                 425                 430

Met Arg His Gly Ser Val Val Ile Ala Ala Ile Thr Ser Cys Thr Asn
            435                 440                 445

Thr Ser Asn Pro Asn Val Leu Ile Ala Ala Gly Leu Leu Ala Lys Lys
            450                 455                 460

Ala Val Glu Lys Gly Leu Lys Val Pro Ala Gly Val Lys Thr Ser Leu
465                 470                 475                 480

Ser Pro Gly Ser His Val Val Thr Lys Tyr Leu Glu Asn Ser Gly Leu
            485                 490                 495

Gln Ser Phe Leu Asp Glu Leu Arg Phe His Thr Thr Gly Tyr Gly Cys
            500                 505                 510
```

```
Met Thr Cys Ile Gly Asn Ala Gly Asp Val Asp Pro Ala Val Ser Lys
            515                 520                 525

Cys Ile Asn Asp Asn Asn Phe Val Ala Ala Val Leu Ser Gly Asn
        530                 535                 540

Arg Asn Phe Glu Ala Arg Ile His Pro Gln Thr Ala Ala Asn Tyr Leu
545                 550                 555                 560

Ala Ser Pro Pro Leu Val Val Ala Tyr Ala Leu Ala Gly Arg Val Asn
                565                 570                 575

Ile Asp Phe Ala Thr Glu Pro Ile Ala Asn Asp Val Tyr Leu Arg Asp
                580                 585                 590

Ile Trp Pro Thr Asn Asp Glu Val Ser Ala Val Val Arg Glu His Val
                595                 600                 605

Thr Pro Asp Leu Phe Lys Thr Val Tyr Lys Ser Ile Thr Thr Leu Asn
        610                 615                 620

Glu Gln Trp Asn Gly Leu Lys Val Lys Gly Gly Thr Gln Tyr Glu Trp
625                 630                 635                 640

Gln Glu Ser Thr Tyr Ile His Lys Pro Pro Tyr Phe Glu Lys Met Thr
                645                 650                 655

Met Glu Val Thr Pro Asn Val Val Phe Lys Asn Ala Ala Cys Leu Ala
                660                 665                 670

Val Phe Gly Asp Ser Ile Thr Thr Asp His Ile Ser Pro Ala Gly Asn
        675                 680                 685

Ile Ala Lys Asp Ser Pro Ala Ala Gln Phe Leu Gln Gly Leu Gly Val
        690                 695                 700

Ala Arg Lys Asp Phe Asn Thr Tyr Gly Ala Arg Gly Asn Asp Met
705                 710                 715                 720

Val Met Val Arg Gly Thr Phe Ala Asn Thr Arg Leu Gly Asn Arg Ile
                725                 730                 735

Val Gly Glu Gly Gln Thr Gly Pro Phe Thr Ile His Trp Pro Thr Asn
                740                 745                 750

Glu Lys Val Tyr Ile Phe Asp Ala Ala Met Arg Tyr Ala Glu Glu Asn
        755                 760                 765

Thr Pro Leu Val Ile Leu Ala Gly Lys Glu Tyr Gly Ser Gly Ser Ser
770                 775                 780

Arg Asp Trp Ala Ala Lys Gly Pro Phe Leu Gln Gly Val Lys Val Val
785                 790                 795                 800

Ile Ala Glu Ser Phe Glu Arg Ile His Arg Ser Asn Leu Val Gly Met
                805                 810                 815

Gly Ile Val Pro Leu Gln Phe Arg Gln Gly Glu Ser Val Glu Ser Leu
                820                 825                 830

Gly Leu Thr Gly Arg Glu Arg Phe Asn Phe Asp Phe Ser Gly Gly Ile
        835                 840                 845

His Pro Gly Gln Glu Val Thr Val Gln Lys Asp Asp Gly Ser Ser Phe
        850                 855                 860

Ser Ala Ile Leu Arg Ile Asp Thr Glu Met Glu Val Lys Tyr Val Glu
865                 870                 875                 880

His Gly Gly Ile Leu Gln Tyr Val Leu Arg Glu Lys Ile Lys Gly Asn
                885                 890                 895

Leu

<210> SEQ ID NO 75
<211> LENGTH: 430
<212> TYPE: PRT
<213> ORGANISM: Trypanosoma brucei
```

<400> SEQUENCE: 75

```
Met Glu Leu Gln Ser Leu Ile Asp Thr Val Ser Leu Gln Lys Leu Leu
1               5                   10                  15

Leu Leu Gly Ala Leu Leu Arg Leu Ile Leu Ile Ala Tyr Ala Phe Phe
            20                  25                  30

His Asp Gln Trp Phe Arg Val Lys Tyr Thr Asp Ile Asp Tyr Met Ile
        35                  40                  45

Val Val Asp Gly Ala Arg His Met Trp Asn Gly Gly Ser Pro Phe Asp
    50                  55                  60

Arg Thr Thr Phe Arg Tyr Thr Pro Leu Leu Ala Ala Leu Val Met Pro
65                  70                  75                  80

Ser Ile Trp Ile Ala Asn Pro Met Gly Lys Leu Ile Phe Ala Ser Ser
                85                  90                  95

Asp Leu Gly Ala Ala Trp Tyr Cys Tyr Gly Val Leu Lys Ser Phe Ala
            100                 105                 110

Lys Glu Arg Ser Ala Lys Trp Met Val Ser Leu Phe Ile Leu Phe Asn
        115                 120                 125

Pro Ile Val Leu Ser Val Ser Thr Arg Gly Asn Ser Asp Met Leu Val
    130                 135                 140

Thr Phe Met Ser Leu Met Val Leu Ser Lys Phe Ala Arg Arg Lys Cys
145                 150                 155                 160

Tyr Gln Ala Ala Ala Val Leu Gly Phe Ala Val His Phe Lys Ile Tyr
                165                 170                 175

Pro Ile Ile Tyr Ala Leu Pro Leu Thr Leu Gly Val Trp Glu Gln Ser
            180                 185                 190

Val Ala Ala Ser Thr Asn Thr Trp Arg Arg Val Val Lys Thr Ala Val
        195                 200                 205

Val Val Ser Ile Cys Ala Leu Met Ala Ala Ile Ser Phe Ala Val Pro
    210                 215                 220

Thr Val Leu Cys Tyr Met Lys Tyr Gly Gln Gln Tyr Leu Asn Glu Ala
225                 230                 235                 240

Phe Ile Tyr His Val Tyr Arg Glu Asp His Arg His Asn Phe Ser Pro
                245                 250                 255

Tyr Trp Leu Leu Met Tyr Leu Asn Met Ala Arg Arg His Leu Gly Gln
            260                 265                 270

Gly Val Asp Phe Ser Pro Arg Leu Val Ala Phe Ala Pro Gln Ala Val
        275                 280                 285

Val Leu Ser Phe Val Ser Tyr Lys Leu Arg Arg Asn Thr Ala His Ala
    290                 295                 300

Cys Cys Val Gln Thr Val Leu Phe Val Ala Phe Asn Lys Val Cys Thr
305                 310                 315                 320

Val Gln Tyr Phe Val Trp Phe Ile Pro Phe Leu Ala Phe Leu Phe Cys
                325                 330                 335

Glu Pro Lys Glu Val Glu Asp Glu Ser Gly Gly Ser Gly Ala Phe
            340                 345                 350

Lys Phe Phe Ser Trp Val Lys Ala Leu Gly Val Val Leu Met Trp Ala
        355                 360                 365

Ala Thr Ile Pro Leu Trp Val Thr Thr Ala Val Pro Leu Glu Phe His
    370                 375                 380

Gly Tyr Ser Asp Phe Ala Gln Leu Trp Ile Val Ser Cys Leu Phe Phe
385                 390                 395                 400

Leu Ala Met Val Val Leu Ala Ser Met Leu Ala Arg Ile Ala Tyr Arg
```

```
                    405                 410                 415
Val Gln Cys Thr Lys Cys Ser Ala Lys Ser Ile Lys Val Ala
            420                 425                 430

<210> SEQ ID NO 76
<211> LENGTH: 634
<212> TYPE: PRT
<213> ORGANISM: Leishmania major

<400> SEQUENCE: 76

Met Phe Ala Arg Arg Val Cys Gly Ser Ala Ala Ser Ala Ala Cys
1               5                   10                  15

Leu Ala Arg His Glu Ser Gln Lys Val Gln Gly Asp Val Ile Gly Val
            20                  25                  30

Asp Leu Gly Thr Thr Tyr Ser Cys Val Ala Thr Met Asp Gly Asp Lys
        35                  40                  45

Ala Arg Val Leu Glu Asn Ser Glu Gly Phe Arg Thr Thr Pro Ser Val
    50                  55                  60

Val Ala Phe Lys Gly Ser Glu Lys Leu Val Gly Leu Ala Ala Lys Arg
65                  70                  75                  80

Gln Ala Ile Thr Asn Pro Gln Ser Thr Phe Tyr Ala Val Lys Arg Leu
                85                  90                  95

Ile Gly Arg Arg Phe Glu Asp Glu His Ile Gln Lys Asp Ile Lys Asn
            100                 105                 110

Val Pro Tyr Lys Ile Val Arg Ala Gly Asn Gly Asp Ala Trp Val Gln
        115                 120                 125

Asp Gly Asn Gly Lys Gln Tyr Ser Pro Ser Gln Ile Gly Ala Phe Val
    130                 135                 140

Leu Glu Lys Met Lys Glu Thr Ala Glu Asn Phe Leu Gly His Lys Val
145                 150                 155                 160

Ser Asn Ala Val Val Thr Cys Pro Ala Tyr Phe Asn Asp Ala Gln Arg
                165                 170                 175

Gln Ala Thr Lys Asp Ala Gly Thr Ile Ala Gly Leu Asn Val Ile Arg
            180                 185                 190

Val Val Asn Glu Pro Thr Ala Ala Ala Leu Ala Tyr Gly Met Asp Lys
        195                 200                 205

Thr Lys Asp Ser Leu Ile Ala Val Tyr Asp Leu Gly Gly Gly Thr Phe
    210                 215                 220

Asp Ile Ser Val Leu Glu Ile Ala Gly Gly Val Phe Glu Val Lys Ala
225                 230                 235                 240

Thr Asn Gly Asp Thr His Leu Gly Gly Glu Asp Phe Asp Leu Ala Leu
                245                 250                 255

Ser Asp Tyr Ile Leu Glu Glu Phe Arg Lys Thr Ser Gly Ile Asp Leu
            260                 265                 270

Ser Lys Glu Arg Met Ala Leu Gln Arg Val Arg Glu Ala Ala Glu Lys
        275                 280                 285

Ala Lys Cys Glu Leu Ser Ser Ala Met Glu Thr Glu Val Asn Leu Pro
    290                 295                 300

Phe Ile Thr Ala Asn Ala Asp Gly Ala Gln His Ile Gln Met Arg Ile
305                 310                 315                 320

Ser Arg Ser Lys Phe Glu Gly Ile Thr Gln Arg Leu Ile Glu Arg Ser
                325                 330                 335

Ile Ala Pro Cys Lys Gln Cys Met Lys Asp Ala Gly Val Glu Leu Lys
            340                 345                 350
```

```
Glu Ile Asn Asp Val Val Leu Val Gly Gly Met Thr Arg Ile Arg Ser
        355                 360                 365

Gly Gly Gly Gly Glu Val Leu Pro Glu Gly Pro Val Arg Gly Val
370                 375                 380

Asn Pro Asp Glu Ala Val Ala Leu Gly Ala Ala Thr Leu Gly Gly Val
385                 390                 395                 400

Leu Arg Gly Lys Ala Ser Asp Leu Ile Leu Val Asp Val Thr Pro Leu
                405                 410                 415

Ser Leu Gly Thr Ser Val Val Gly Asp Val Phe Val Pro Ile Ile Pro
            420                 425                 430

Lys Asn Thr Thr Ile Pro Cys Met Arg Ser His Ile Phe Thr Thr Val
        435                 440                 445

Asp Asp Gly Gln Thr Ala Ile Lys Phe Lys Val Phe Gln Gly Glu Arg
450                 455                 460

Glu Ile Ala Ser Glu Asn Gln Ile Arg Gly Glu Phe Asp Leu Ser Gly
465                 470                 475                 480

Ile Pro Pro Ala Pro Arg Gly Val Pro Gln Val Glu Val Thr Phe Asp
                485                 490                 495

Ile Asp Ala Asn Gly Ile Cys His Val Thr Ala Lys Asp Lys Ala Thr
            500                 505                 510

Gly Lys Thr Gln Asn Ile Thr Ile Thr Ala Asn Gly Gly Leu Ser Lys
        515                 520                 525

Glu Gln Ile Glu Gln Met Ile Arg Asp Ser Glu Gln His Ala Glu Ala
530                 535                 540

Asp Arg Val Lys Arg Glu Leu Val Glu Val Arg Asn Asn Ala Glu Thr
545                 550                 555                 560

Gln Leu Thr Thr Ala Glu Arg Gln Leu Gly Glu Trp Lys Tyr Val Ser
                565                 570                 575

Asp Ala Glu Lys Glu Asn Val Lys Thr Leu Val Ala Glu Leu Arg Lys
            580                 585                 590

Ala Met Glu Asn Pro Asn Val Ala Lys Asp Asp Leu Ala Ala Ala Thr
        595                 600                 605

Asp Lys Leu Gln Lys Ala Val Met Glu Cys Gly Arg Thr Glu Tyr Gln
610                 615                 620

Gln Ala Ala Ala Ala Asn Ser Gly Gln Cys
625                 630

<210> SEQ ID NO 77
<211> LENGTH: 187
<212> TYPE: PRT
<213> ORGANISM: Leishmania major

<400> SEQUENCE: 77

Met Arg Phe Val Ala Val Leu Ala Val Val Leu Cys Ala Leu Ser Phe
1               5                   10                  15

Leu Asn Val Ala Ala Glu Pro Glu Val Thr Ala Lys Val Tyr Phe Asp
                20                  25                  30

Val Met Ile Asp Ser Glu Pro Leu Gly Arg Ile Thr Ile Gly Leu Phe
            35                  40                  45

Gly Lys Asp Ala Pro Leu Thr Thr Glu Asn Phe Arg Gln Leu Cys Thr
50                  55                  60

Gly Glu His Gly Phe Gly Tyr Lys Asp Ser Ile Phe His Arg Val Ile
65                  70                  75                  80

Gln Asn Phe Met Ile Gln Gly Gly Asp Phe Thr Asn Phe Asp Gly Thr
                85                  90                  95
```

-continued

```
Gly Gly Lys Ser Ile Tyr Gly Glu Lys Phe Ala Asp Glu Asn Leu Asn
            100                 105                 110

Val Lys His Phe Val Gly Ala Leu Ser Met Ala Asn Ala Gly Pro Asn
        115                 120                 125

Thr Asn Gly Ser Gln Phe Phe Ile Thr Thr Ala Pro Thr Pro Trp Leu
    130                 135                 140

Asp Gly Arg His Val Val Phe Gly Lys Val Leu Asp Gly Met Asp Val
145                 150                 155                 160

Val Leu Arg Ile Glu Lys Thr Lys Thr Asn Ser His Asp Arg Pro Val
                165                 170                 175

Lys Pro Val Lys Ile Val Ala Ser Gly Glu Leu
            180                 185

<210> SEQ ID NO 78
<211> LENGTH: 859
<212> TYPE: PRT
<213> ORGANISM: Leishmania major

<400> SEQUENCE: 78

Met His Pro Ser Thr Val Arg Arg Glu Ala Glu Arg Val Lys Val Ser
1               5                   10                  15

Val Arg Val Arg Pro Leu Asn Glu Arg Glu Asn Asn Ala Pro Glu Gly
            20                  25                  30

Thr Lys Val Thr Val Ala Ala Lys Gln Ala Ala Val Val Thr Val
        35                  40                  45

Lys Val Leu Gly Gly Ser Asn Asn Ser Gly Ala Ala Glu Ser Met Gly
    50                  55                  60

Thr Ala Arg Arg Val Ala Gln Asp Phe Gln Phe Asp His Val Phe Trp
65                  70                  75                  80

Ser Val Glu Thr Pro Asp Ala Cys Gly Ala Thr Pro Ala Thr Gln Ala
                85                  90                  95

Asp Val Phe Arg Thr Ile Gly Tyr Pro Leu Val Gln His Ala Phe Asp
            100                 105                 110

Gly Phe Asn Ser Cys Leu Phe Ala Tyr Gly Gln Thr Gly Ser Gly Lys
        115                 120                 125

Met Tyr Thr Met Met Gly Ala Asp Val Ser Ala Leu Ser Gly Glu Gly
    130                 135                 140

Asn Gly Val Thr Pro Arg Ile Cys Leu Glu Ile Phe Ala Arg Lys Ala
145                 150                 155                 160

Ser Val Glu Ala Gln Gly His Ser Arg Trp Ile Val Glu Leu Gly Tyr
                165                 170                 175

Val Glu Val Tyr Asn Glu Arg Val Ser Asp Leu Leu Gly Lys Arg Lys
            180                 185                 190

Lys Gly Val Lys Gly Gly Gly Glu Glu Val Tyr Val Asp Val Arg Glu
        195                 200                 205

His Pro Ser Arg Gly Val Phe Leu Glu Gly Gln Arg Leu Val Glu Val
    210                 215                 220

Gly Ser Leu Asp Asp Val Val Arg Leu Ile Glu Ile Gly Asn Gly Val
225                 230                 235                 240

Arg His Thr Ala Ser Thr Lys Met Asn Asp Arg Ser Ser Arg Ser His
                245                 250                 255

Ala Ile Ile Met Leu Leu Leu Arg Glu Glu Arg Thr Met Thr Thr Lys
            260                 265                 270

Ser Gly Glu Thr Ile Arg Thr Ala Gly Lys Ser Ser Arg Met Asn Leu
```

-continued

```
                275                 280                 285
Val Asp Leu Ala Gly Ser Lys Arg Val Ala Gln Ser Gln Val Glu Gly
            290                 295                 300
Gln Gln Phe Lys Glu Ala Thr His Ile Asn Leu Ser Leu Thr Thr Leu
305                 310                 315                 320
Gly Arg Val Ile Asp Val Leu Ala Asp Met Ala Thr Lys Gly Ala Lys
                325                 330                 335
Ala Gln Tyr Ser Val Ala Pro Phe Arg Asp Ser Lys Leu Thr Phe Ile
            340                 345                 350
Leu Lys Asp Ser Leu Gly Gly Asn Ser Lys Thr Phe Met Ile Ala Thr
            355                 360                 365
Val Ser Pro Ser Ala Leu Asn Tyr Glu Glu Thr Leu Ser Thr Leu Arg
370                 375                 380
Tyr Ala Ser Arg Ala Arg Asp Ile Val Asn Val Ala Gln Val Asn Glu
385                 390                 395                 400
Asp Pro Arg Ala Arg Arg Ile Arg Glu Leu Glu Glu Gln Met Glu Asp
            405                 410                 415
Met Arg Gln Ala Met Ala Gly Gly Asp Pro Ala Tyr Val Ser Glu Leu
            420                 425                 430
Lys Lys Lys Leu Ala Leu Leu Glu Ser Glu Ala Gln Lys Arg Ala Ala
            435                 440                 445
Asp Leu Gln Ala Leu Glu Arg Glu Arg Glu His Asn Gln Val Gln Glu
            450                 455                 460
Arg Leu Leu Arg Ala Thr Glu Ala Glu Lys Ser Glu Leu Glu Ser Arg
465                 470                 475                 480
Ala Ala Ala Leu Gln Glu Glu Met Thr Ala Thr Arg Arg Gln Ala Asp
            485                 490                 495
Lys Met Gln Ala Leu Asn Leu Arg Leu Lys Glu Gln Ala Arg Lys
            500                 505                 510
Glu Arg Glu Leu Leu Lys Glu Met Ala Lys Lys Asp Ala Ala Leu Ser
            515                 520                 525
Lys Val Arg Gln Arg Lys Asp Ala Glu Ile Ala Ser Glu Arg Glu Lys
530                 535                 540
Leu Glu Ser Thr Val Ala Gln Leu Glu Arg Glu Gln Arg Glu Arg Glu
545                 550                 555                 560
Val Ala Leu Asp Ala Leu Gln Thr His Gln Arg Lys Leu Gln Glu Ala
            565                 570                 575
Leu Glu Ser Ser Glu Arg Thr Ala Ala Glu Arg Asp Gln Leu Leu Gln
            580                 585                 590
Gln Leu Thr Glu Leu Gln Ser Glu Arg Thr Gln Leu Ser Gln Val Val
            595                 600                 605
Thr Asp Arg Glu Arg Leu Thr Arg Asp Leu Gln Arg Ile Gln Tyr Glu
            610                 615                 620
Tyr Gly Glu Thr Glu Leu Ala Arg Asp Val Ala Leu Cys Ala Ala Gln
625                 630                 635                 640
Glu Met Glu Ala Arg Tyr His Ala Ala Val Phe His Leu Gln Thr Leu
            645                 650                 655
Leu Glu Leu Ala Thr Glu Trp Glu Asp Ala Leu Arg Glu Arg Ala Leu
            660                 665                 670
Ala Glu Arg Asp Glu Ala Ala Ala Glu Leu Asp Ala Ala Ala Ser
            675                 680                 685
Thr Ser Gln Asn Ala Arg Glu Ser Ala Cys Glu Arg Leu Thr Ser Leu
            690                 695                 700
```

-continued

```
Glu Gln Gln Leu Arg Asp Ser Glu Glu Arg Ala Ala Glu Leu Met Arg
705                 710                 715                 720

Lys Leu Glu Ala Thr Ala Ala Lys Ser Ser Ala Glu Gln Asp Arg
            725                 730                 735

Glu Asn Thr Arg Ala Thr Leu Glu Gln Gln Leu Arg Glu Ser Glu Glu
            740                 745                 750

His Ala Ala Glu Leu Lys Ala Gln Leu Glu Ser Thr Ala Ala Ala Lys
        755                 760                 765

Thr Ser Ala Glu Gln Asp Arg Glu Asn Thr Arg Ala Ala Leu Glu Gln
    770                 775                 780

Arg Leu Arg Glu Ser Glu Glu Arg Ala Ala Glu Leu Ala Ser Gln Leu
785                 790                 795                 800

Glu Ala Thr Ala Ala Ala Lys Ser Ser Ala Glu Gln Asp Arg Glu Asn
                805                 810                 815

Thr Arg Ala Thr Leu Glu Gln Gln Leu Arg Glu Ser Glu Ala Arg Ala
            820                 825                 830

Ala Glu Leu Ala Ser Gln Leu Glu Ser Thr Ala Ala Ala Lys Ser Ser
        835                 840                 845

Ala Glu Gln Asp Arg Glu Asn Thr Arg Ala Thr
850                 855
```